(12) United States Patent
Takahashi et al.

(10) Patent No.: US 12,404,247 B2
(45) Date of Patent: Sep. 2, 2025

(54) 3, 5-DISUBSTITUTED PYRIDINE AND 3, 5-DISUBSTITUTED PYRIDAZINE DERIVATIVES AND PHARMACEUTICAL USE OF SAME

(71) Applicant: MITSUBISHI TANABE PHARMA CORPORATION, Osaka (JP)

(72) Inventors: Taichi Takahashi, Osaka (JP); Hisayuki Takamatsu, Osaka (JP); Daisuke Iijima, Osaka (JP); Shuzo Takeda, Osaka (JP)

(73) Assignee: MITSUBISHI TANABE PHARMA CORPORATION, Osaka (JP)

( * ) Notice: Subject to any disclaimer, the term of this patent is extended or adjusted under 35 U.S.C. 154(b) by 0 days.

(21) Appl. No.: 18/603,405

(22) Filed: Mar. 13, 2024

(65) Prior Publication Data

US 2024/0239756 A1 Jul. 18, 2024

Related U.S. Application Data

(62) Division of application No. 17/258,682, filed as application No. PCT/JP2019/029366 on Jul. 26, 2019, now Pat. No. 11,958,812.

(30) Foreign Application Priority Data

Jul. 27, 2018 (JP) .................................. 2018-141254

(51) Int. Cl.
| | |
|---|---|
| C07D 237/14 | (2006.01) |
| A61P 11/00 | (2006.01) |
| C07D 213/89 | (2006.01) |
| C07D 237/08 | (2006.01) |
| C07D 401/04 | (2006.01) |
| C07D 413/04 | (2006.01) |

(52) U.S. Cl.
CPC ............ *C07D 237/14* (2013.01); *A61P 11/00* (2018.01); *C07D 213/89* (2013.01); *C07D 237/08* (2013.01); *C07D 401/04* (2013.01); *C07D 413/04* (2013.01)

(58) Field of Classification Search
CPC .................................................. C07D 237/14
See application file for complete search history.

(56) References Cited

U.S. PATENT DOCUMENTS

| | | | |
|---|---|---|---|
| 8,754,097 B2 | 6/2014 | Schiemann et al. | |
| 8,791,111 B2 | 7/2014 | Schiemann et al. | |
| 9,000,025 B2 | 4/2015 | Roppe et al. | |
| 9,006,246 B2 | 4/2015 | Ohata et al. | |
| 9,273,011 B2 | 3/2016 | Gibson et al. | |
| 11,958,812 B2* | 4/2024 | Takahashi ............... | A61P 43/00 |
| 2010/0222341 A1 | 9/2010 | Schiemann et al. | |
| 2012/0316162 A1 | 12/2012 | Schiemann et al. | |
| 2013/0109699 A1 | 5/2013 | Ohata et al. | |
| 2013/0150326 A1 | 6/2013 | Roppe et al. | |
| 2013/0345426 A1 | 12/2013 | Ohata et al. | |
| 2014/0275100 A1 | 9/2014 | Gibson et al. | |
| 2014/0303140 A1 | 10/2014 | Desroy et al. | |
| 2015/0111872 A1 | 4/2015 | Desroy et al. | |
| 2015/0164861 A1 | 6/2015 | Roppe et al. | |
| 2015/0231118 A1 | 8/2015 | Ohata et al. | |
| 2015/0299123 A1 | 10/2015 | Peng et al. | |
| 2016/0031884 A1 | 2/2016 | Ohata et al. | |
| 2016/0214986 A1 | 7/2016 | Desroy et al. | |
| 2016/0244443 A1 | 8/2016 | Desroy et al. | |
| 2016/0287584 A1 | 10/2016 | Gibson et al. | |
| 2017/0044133 A1 | 2/2017 | Takahashi et al. | |
| 2017/0189386 A1 | 7/2017 | Ohata et al. | |
| 2017/0362227 A1 | 12/2017 | Desroy et al. | |
| 2018/0127425 A1 | 5/2018 | Desroy et al. | |

FOREIGN PATENT DOCUMENTS

| | | |
|---|---|---|
| JP | 2010-540579 A | 12/2010 |
| JP | 2013-536200 A | 9/2013 |
| JP | 2014-530902 A | 11/2014 |
| JP | 2016-512208 A | 4/2016 |
| JP | 2016-525072 A | 8/2016 |
| JP | 2016-164154 A | 9/2016 |
| JP | 2017-78039 A | 4/2017 |
| WO | WO 2009/046841 A2 | 4/2009 |
| WO | WO 2012/005227 A1 | 1/2012 |

(Continued)

OTHER PUBLICATIONS

International Search Report issued Oct. 8, 2019 in PCT/JP2019/029366 filed Jul. 26, 2019, 3 pages.
Ji Woong Choi, et al., "LPA Receptors: Subtypes and Biological Actions" Annual Review of Pharmacology and Toxicology, vol. 50, 2010, pp. 157-186.
Anna J. S. Houben, et al. "Autotaxin and LPA Receptor Signaling in Cancer" Cancer Metastasis Rev., vol. 30, No. 3-4, 2011, pp. 557-565.
Matthew G. K. Benesch, et al., "Autotaxin in the Crosshairs: Taking Aim at Cancer and other Inflammatory Conditions" FEBS Letters, vol. 588, 2014, pp. 2712-2727.
Makoto Inoue, et al., "Autotaxin, a Synthetiuc Enzyme of Lysophosphatidic Acid (LPA), Mediates the Induction of Nerve-Injured Neuropathic Pain" Molecular Pain, vol. 4, No. 6, 2008, pp. 1-5.

(Continued)

*Primary Examiner* — Golam M Shameem
(74) *Attorney, Agent, or Firm* — Finnegan, Henderson, Farabow, Garrett & Dunner, LLP

(57) ABSTRACT

A method for treating or preventing a disease involving autotaxin including administering a carboxylic acid compound of formula (1)

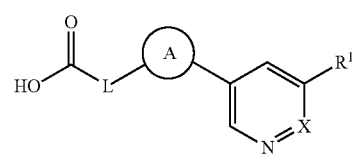

or a pharmacologically acceptable salt thereof to a patient in need thereof.

22 Claims, 4 Drawing Sheets

(56) References Cited

FOREIGN PATENT DOCUMENTS

| WO | WO 2012/024620 A2 | 2/2012 |
|---|---|---|
| WO | WO 2013/061297 A1 | 5/2013 |
| WO | WO 2014/081756 A1 | 5/2014 |
| WO | WO 2014/139882 A1 | 9/2014 |
| WO | WO 2014/202458 A1 | 12/2014 |
| WO | WO 2015/163435 A1 | 10/2015 |
| WO | WO 2017/033966 A1 | 3/2017 |

OTHER PUBLICATIONS

Ioanna Nikitopoulou, et al., "Autotaxin Expression from Synovial Fibroblasts is Essential for the Pathogenesis of Modeled Arthritis" J. Exp. Med., vol. 209, No. 5, 2012, pp. 925-933.

Wolfgang Siess, et al., "Lysophosphatidic Acid Mediates the Rapid Activation of Platelets and Endothelial Cells by Mildly Oxidized Low Density Lipoprotein and Accumulates in Human Atherosclerotic Lesions" Proc. Natl. Acad. Sci USA., vol. 96, Jun. 1999, pp. 6931-6936.

Zhe Zhou, et al., "Lipoprotein-Derived Lysophosphatidic Acid Promotes Atherosclerosis by Releasing CXCL1 from the Endothelium" Cell Metabolism, vol. 13, No. 5, May 4, 2011, pp. 592-600.

"Translational Research on Autotaxin-LPA-LPA Receptors and Drug Discovery" Clinical Lipidology, 2015; vol. 10, No. 2, pp. 177-190.

Silvia Anahi Valdés-Rives, et al., "Autotaxin-Lysophosphatidic Acid: From Inflammation to Cancer Development" Mediators of Inflammation, vol. 2017, Article ID 9173090, 2017, pp. 1-15.

Kenneth D'Souza, et al., "Lysophosphatidic Acid Signaling in Obesity and Insulin Resistance" Nutrients. vol. 10, E399, 2018, pp. 1-20.

Andreas E. Kremer, et al., "Serum Autotaxin is Increased in Pruritus of Cholestasis, but Not of Other Origin, and Responds to Therapeutic Interventions" Hepatology, vol. 56, No. 4, Oct. 2012, pp. 1391-1400.

Vinod S. Hegade, et al., "A Systematic Approach to the Management of Cholestatic Pruritus in Primary Biliary Cirrhosis" Frontline Gastroenterol., vol. 7, No. 3, 2016, pp. 158-166.

Xiangpeng Chu, et al., "Autotaxin-LPA Receptor Axis in the Pathogenesis of Lung Diseases" Int. J. Clin. Exp. Med., vol. 8, No. 10, 2015, pp. 17117-17122.

Andrew M. Tager, et al., "The Lysophosphatidic Acid Receptor LPA1 Links Pulmonary Fibrosis to Lung Injury by Mediating Fibroblast Recruitment and Vascular Leak" Nature Medicine, vol. 14, No. 1, Jan. 2008, pp. 45-54.

Nikos Oikonomou, et al., "Pulmonary Autotaxin Expression Contributes to the Pathogenesis of Pulmonary Fibrosis" Am. J. Respir. Cell. Mol. Biol. vol. 47, No. 5, 2012, pp. 566-574.

Hitoshi Ikeda, et al., "Effects of Lysophosphatidic Acid on Proliferation of Stellate Cells and Hepatocytes in Culture" Biochemical and Biophysical Research Communications, vol. 248, No. 2, 1998, pp. 436-440.

Mikio Yanase, et al., "Lysophosphatidic Acid Enhances Collagen Gel Contraction by Hepatic Stellate Cells: Association with Rho-Kinase" Biochemical Biophysical Research Communications, vol. 277, No. 1, 2000, pp. 72-78.

Hitoshi Ikeda, et al., "Involvement of Rho/Rho Kinase Pathway in Regulation of Apoptosis in Rat Hepatic Stellate Cells" Am. J. Physiol. Gastrointest. Liver Physiol., vol. 285, No. 5, 2003, pp. G880-G886.

Jean-Philippe Pradere, et al., "LPA1 Receptor Activation Promotes Renal Interstitial Fibrosis" J. Am. Soc. Nephrol., vol. 18, No. 12, 2007, pp. 3110-3118.

Flavia V Castelino, et al., "An Autotaxin/Lysophosphatidic Acid/Interleukin-6 Amplification Loop Drives Scleroderma Fibrosis" Arthritis Rheumatol. vol. 68, No. 12, Dec. 2016, pp. 2964-2974.

Hiroshi Saga, et al., "A Novel Highly Potent Autotaxin/ENPP2 Inhibitor Produces Prolonged Decreases in Plasma Lysophosphatidic Acid Formation In Vivo and Regulates Urethral Tension" PLoS One, vol. 9, No. 4, e93230, Apr. 2014, pp. 1-9.

Megumi Honjo, et al., "Autotaxin-Lysophosphatidic Acid Pathway in Intraocular Pressure Regulation and Glaucoma Subtypes" Invest. Ophthalmol. Vis. Sci. IOVS, vol. 59, No. 2, Feb. 2018, pp. 693-701.

Padma Iyer, et al., "Autotaxin-Lysophosphatidic Acid Axis Is a Novel Molecular Target for Lowering Intraocular Pressure" PLoS One. vol. 7, No. 8, e42627, Aug. 2012, pp. 1-14.

Makoto Inoue, et al., "Initiation of Neuropathic Pain Requires Lysophosphatidic Acid Receptor Signaling" Nature Medicine, vol. 10, No. 7, Jul. 2004, pp. 712-718.

Yasutaka Kakiuchi, et al., "Antinociceptive Effect Of Cyclic Phosphatidic Acid and its Derivative on Animal Models of Acute and Chronic Pain" Molecular Pain, vol. 7, No. 33, 2011, pp. 1-11.

Thomas Pleli, et al., "Serum Autotaxin Is a Parameter for the Severity of Liver Cirrhosis and Overall Survival in Patients with Liver Cirrhosis—A Prospective Cohort Study" PLoS One, vol. 9, No. 7, e103532, Jul. 2014, pp. 1-9.

Gretchen Bain, et al., "Selective Inhibition of Autotaxin Is Efficacious in Mouse Models of Liver Fibrosis" J. Pharmacol. Exp. Ther., vol. 360, No. 1, Jan. 2017, pp. 1-13.

A Kehlen, et al., "IL-1β- and IL-4-Induced Down-Regulation of Autotaxin mRNA and PC-1 in Fibroblast-Like Synoviocytes of Patients with Rheumatoid Arthritis (RA)" Clin. Exp. Immunol., vol. 123, No. 1, 2001, pp. 147-154.

Ioanna Nikitopoulou, et al., "A Metabolically-Stabilized Phosphonate Analog of Lysophosphatidic Acid Attenuates Collagen-Induced Arthritis" PLoS One, vol. 8, No. 7, e70941, Jul. 2013, pp. 1-11.

Thomas Mabey, et al., "Plasma and Synovial Fluid Autotaxin Correlate with Severity in Knee Osteoarthritis" Clinica Chimica Acta, vol. 444, 2015, pp. 72-77.

K. Thirunavukkarasu, et al., "Identification and Pharmacological Characterization of a Novel Inhibitor of Autotaxin in Rodent Models of Joint Pain" Osteoarthritis and Cartilage, vol. 25, No. 6, 2017, pp. 935-942.

Peng Cui, et al., "Synthesis and Biological Evaluation of Phosphonate Derivatives as Autotaxin (ATX) Inhibitors" Bioorganic & Medicinal Chemistry Letters, vol. 17, 2007, pp. 1634-1640.

* cited by examiner

3,5-DISUBSTITUTED PYRIDINE AND 3,5-DISUBSTITUTED PYRIDAZINE DERIVATIVES AND PHARMACEUTICAL USE OF SAME

CROSS-REFERENCE TO RELATED APPLICATIONS

This application is a divisional of U.S. application Ser. No. 17/258,682, filed Jan. 7, 2021, which is a national stage application of International Application No. PCT/JP2019/029366, filed Jul. 26, 2019, which is based upon and claims the benefit of priority to Japanese Patent Application No. 2018-141254, filed Jul. 27, 2018. The entire contents of these applications are incorporated herein by reference. The present application claims the benefit of priority to U.S. Application Ser. No. 17/258,682, International Application No. PCT/JP2019/029366 and Japanese Application No. 2018-141254.

TECHNICAL FIELD OF THE INVENTION

The present invention relates to novel 3,5-disubstituted pyridine and 3,5-disubstituted pyridazine derivatives or a pharmacologically acceptable salt thereof, having an autotaxin inhibitory action and effective for the prophylaxis or treatment of a disease caused by autotoxin in mammals inclusive of human.

BACKGROUND OF THE INVENTION

Autotaxin (hereinafter sometimes to be indicated as ATX) was isolated from a culture supernatant of human malignant melanoma cell line A2058 and identified as a cell migration stimulating factor. ATX is also called secreted lysophospholipase D (lysophospholipase D; hereinafter to be indicated as lysoPLD) and ENPP2 (Ectonucleotide Pyrophosphatase/Phosphodiesterase 2), and mainly affords lysoPLD activity. It hydrolyzes lysophosphatidylcholine (LPC) and produces lysophosphatidic acid (hereinafter to be indicated as LPA) which is a lipid mediator having various physiological activities.

LPA produced by ATX binds to a G-protein-coupled receptor (GPCR) and intracellularly transmits signals, whereby various physiological actions are shown. As LPA receptor, 6 kinds of subtypes of from LPA1 to LPA6 are known. LPA receptor subtypes are distributed everywhere in the body, at different tissues to be localized in depending on the subtypes, and various receptor subtypes are involved in respective biological functions depending on the tissue. LPA receptor is classified into two subfamilies. LPA1 to LPA3 are classified into the endothelial differentiation gene (Edg) family. LPA4 to LPA6 are non-Edg family LPA receptors, and are receptors similar to the purinergic receptor family (non-patent documents 1 and 2). LPA is physiologically (both homeostasis maintenance and pathology) involved in a wide variety of life phenomena via these LPA receptors.

On the other hand, in relation to diseases, it has been clarified that the intracellular signal pathway via ATX and LPA receptors is involved in various carcinomas and various inflammatory diseases. Specifically, it is related to various diseases including cancer, tumor, neoplasm, various carcinomas such as malignant melanoma, brain tumor, neuroblastoma, glioblastoma multiforme, EBV positive Hodgkin lymphoma, glioblastoma, non-small cell lung cancer, lung tumor, breast tumor, ovary tumor, pancreas tumor, prostatic intraepithelial neoplasia, prostate tumor, thyroid tumor, follicular lymphoma, liver tumor, renal cell carcinoma and the like, various fibroses such as lung fibrosis, scleroderma, hepatic fibrosis, renal fibrosis, diabetic nephropathy, atherosclerosis and the like, various inflammatory diseases such as asthma, COPD, rheumatoid arthritis, arthritis deformans, NASH, NAFLD, type II diabetes-related obesity, acute coronary syndrome, inflammatory bowel disease, Crohn's disease, ulcerative colitis, neuropathic pain, pruritus and the like, ophthalmic diseases such as glaucoma and the like, urological diseases such as prostatomegaly and the like, and the like (non-patent documents 2-13).

Furthermore, it has been clarified that intracellular signal pathway via ATX and LPA receptors is involved in various fibrosis diseases.

In relation to the involvement in the aforementioned diseases, it is shown as regards pulmonary fibrosis that LPA concentration increases in alveolar lavage fluid of idiopathic pulmonary fibrosis patients and ATX concentration increases in lung tissue of bleomycin-induced pulmonary fibrosis model. Furthermore, it has been shown that progression of bleomycin-induced pulmonary fibrosis and death were markedly suppressed in LPA1 deficient mouse (non-patent documents 14 and 15).

As for hepatic fibrosis, it has been shown that LPA promotes contraction and growth of hepatic stellate cells that play a key role in hepatic fibrosis, thus suppressing apoptosis, and serum autotaxin activity and plasma LPA levels are promoted along with the progression of hepatic fibrosis in chronic hepatitis C patients (non-patent documents 16-18).

As for renal fibrosis, it has been shown that production of LPA and expression of LPA1 are promoted in a lateral ureteral ligation model, LPA1 deficient mouse shows resistance to fibrosis, and LPA receptor antagonists suppress progression of fibrosis (non-patent document 19).

As for scleroderma, expression of ATX is promoted in the skin of scleroderma patients. In bleomycin-induced scleroderma models, moreover, it has been shown that ATX expression in the skin is promoted, and ATX inhibitors suppress IL-6 production and CD3 positive cell infiltration in the skin, and suppress skin sclerosis and hydroxyproline production (non-patent document 20).

As for urine discharge disorder in prostatomegaly which is one of the urological diseases, it has been shown that urethral contraction is caused by action of LPA on isolated urinary tract of rat. Furthermore, it has been shown that the urethral pressure can be decreased by administration of an ATX inhibitor to a rat (non-patent document 21).

As for glaucoma, it has been shown that the ATX concentration and LPA concentration of the aqueous humor of respective patients with normal intraocular pressure glaucoma, primary open angle glaucoma, secondary open angle glaucoma and exfoliation glaucoma increase, and that the LPA concentration, ATX concentration and LysoPLD activity are each positively correlated with intraocular pressure. Furthermore, it has been shown that an ATX inhibitor decreases intraocular pressure in a rabbit intraocular pressure test (Dutch belted rabbits) (non-patent documents 22 and 23).

As for neuropathic pain, it has been shown that spinal and intrathecal administration of LPA to a mouse induces hyperalgesic response and allodynia (non-patent document 24). Furthermore, it has been shown that an ATX inhibitor shows an analgesic action and an anti-allodynic action in a rat chronic constriction injury (CCI) model (non-patent document 25).

As for COPD, an ATX inhibitor suppressed gene expression of CCL2, SSA3, TIMP1, SLC26A4, LCN2, MMP12 in the lung in a cigarette smoke exposed mouse COPD model (patent documents 6 and 7).

As for inflammatory diseases such as NASH, NAFLD and the like, it has been shown that serum ATX concentration increases in cirrhosis patients, and serum ATX concentration is positively correlated with Child-Pugh stage and MELD score (non-patent document 26). In a mouse STAM-NASH model for which streptozotocin (STZ) administration is combined with a high-fat diet loading, moreover, an ATX inhibitor improved NAS score by an anti-inflammatory action and a suppressive action on balloon hypertrophy of hepatocytes. It is further shown that ATX inhibitors suppress liver fibrosis in a mouse NASH model on a choline-deficient high-fat diet (CDAHFD) (non-patent document 27).

As for rheumatoid arthritis, it has been shown that ATX concentration increases in fibroblast-like synoviocytes (SFC) of rheumatoid arthritis patients (non-patent document 28). It is further shown that ATX concentration of synovium increases (non-patent document 5) in a collagen-induced arthritis model, and ATX inhibitors improve articular pathology score (non-patent document 29).

As for arthritis deformans, it has been shown that ATX concentration increases in the synovial fluid of arthritis deformans patients. It is further shown that Western Ontario McMaster Universities Osteoarthritis Index (WOMAC) is positively correlated with ATX concentration of synovial fluid (non-patent document 30). Furthermore, it has been shown that ATX inhibitors suppress pain in a monoiodoacetate-induced arthritis deformans model (non-patent document 31).

As ATX inhibitors, a particular lipid analog (non-patent document 32), a tetrahydrocarboline derivative (patent document 1), a 1H-indole compound (patent document 2), a piperidine or piperazine derivative (patent document 3), a pyridazine derivative (patent document 4) and 2-aminopyridine and 2-amino-pyrimidine derivatives (patent document 5) are known. These have structures different from that of 3,5-disubstituted pyridine and 3,5-disubstituted pyridazine derivatives which are the compounds of the present invention.

Document List

Patent Documents

[patent document 1] WO 2012/005227
[patent document 2] WO 2012/024620
[patent document 3] WO 2009/046841
[patent document 4] WO 2013/061297
[patent document 5] WO 2015/163435
[patent document 6] WO 2014/139882
[patent document 7] WO 2014/202458

Non-Patent Documents

[non-patent document 1] Choi et al., Annu Rev Pharmacol Toxicol. 2010, 50:157-186
[non-patent document 2] Houben et al., Cancer Metastasis Rev. 2011, 30 (3-4): 557-565
[non-patent document 3] Benesch et al., FEBS Lett. 2014; 588: 2712-2727
[non-patent document 4] Inoue et al., Mol Pain. 2008; 4:6
[non-patent document 5] Nikitopoulou et al., J Exp Med. 2012; 209(5):925-933
[non-patent document 6] Siess et al., Proc Natl Acad Sci USA. 1999; 96(12):6931-6936
[non-patent document 7] Zhou et al., Cell Metab. 2011; 13(5):592-600
[non-patent document 8] Im et al., Clinical Lipidology 2015; 10(2):177-190
[non-patent document 9] Valdes-Rives et al., Mediators Inflamm. 2017; 2017:9173090
[non-patent document 10] D'Souza et al., Nutrients. 2018; 10 (4):E399
[non-patent document 11] Kremer et al., Hepatology 2012; 56(4):1391-1400
[non-patent document 12] Hegade et al., Frontline Gastroenterol. 2016; 7(3):158-166
[non-patent document 13] Chu et al., Int J Clin Exp Med. 2015; 8(10):17117-17122
[non-patent document 14] Tager et al., Nat Med. 2008; 14(1):45-54
[non-patent document 15] Oikonomou et al., Am J Respir Cell Mol Biol. 2012; 47(5):566-574
[non-patent document 16] Ikeda et al., Biochem Biophys Res Commun. 1998; 248(2):436-440
[non-patent document 17] Yanase et al., Biochem Biophys Res Commun. 2000; 277(1):72-78
[non-patent document 18] Ikeda et al., Am J Physiol Gastrointest Liver Physiol. 2003; 285 (5):G880-G886
[non-patent document 19] Pradere et al., J Am Soc Nephrol. 2007; 18(12):3110-3118
[non-patent document 20] Castelino et al., Arthritis Rheumatol. 2016; 68(12):2964-2974
[non-patent document 21] Saga et al., PLoS One 2014; 9(4):e93230
[non-patent document 22] Honjo et al., Invest Ophthalmol Vis Sci. 2018; 59(2):693-701
[non-patent document 23] Iyer et al., PLoS One. 2012; 7 (8):e42627
[non-patent document 24] Inoue et al., Nat Med. 2004; 10(7):712-718
[non-patent document 25] Kakiuchi et al., Mol Pain. 2011; 7:33
[non-patent document 26] Pleli, PLoS One. 2014; 9 (7):e103532
[non-patent document 27] Bain, J Pharmacol Exp Ther. 2017; 360(1):1-13
[non-patent document 28] Kehlen et al., Clin Exp Immunol. 2001; 123(1):147-154
[non-patent document 29] Nikitopoulou et al., PLoS One 2013; 8(7):e70941
[non-patent document 30] Mabey et al., Clin Chim Acta. 2015; 444 72-77
[non-patent document 31] Thirunavukkarasu et al., Osteoarthritis Cartilage. 2017; 25(6):935-942
[non-patent document 32] Peng et al., Bioorganic & Medicinal Chemistry Letters 2007, 17:1634-1640

SUMMARY OF THE INVENTION

Problems to be Solved by the Invention

The present invention aims to provide a compound superior in an ATX inhibitory action and useful for the prophylaxis or treatment of a disease involving ATX.

Means of Solving the Problems

The present inventors have conducted intensive studies in an attempt to solve the aforementioned problems and found a compound that inhibits ATX and found that a prophylactic or therapeutic drug for a disease involving ATX can be provided, which resulted in the completion of the present invention.

That is, the gist of the present invention relates to the following [1]-[24] but is not limited to these. [1] A carboxylic acid compound represented by the following formula (1) or a pharmacologically acceptable salt thereof (sometimes to be abbreviated as "Compound (1)" in the present specification)

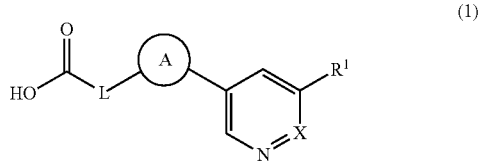
(1)

wherein, $R^1$ is

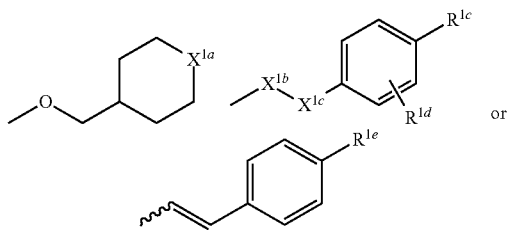
or wherein $X^{1a}$ is —$C(R^{1a})_2$— wherein plural symbols $R^{1a}$ are the same or different and each is a hydrogen atom, a halogen atom, $C_1$-$C_2$ perfluoroalkyl, $C_1$-$C_2$ perfluoroalkoxy or $C_1$-$C_6$ alkyl, or plural symbols $R^{1a}$ are bonded to form 1,1-$C_3$-$C_6$ cycloalkylene or —$NR^{1b}$— wherein $R^{1b}$ is a hydrogen atom or $C_1$-$C_2$ perfluoroalkyl, $X^{1b}$ and $X^{1c}$ are the same or different and each is —O— or —$CH_2$-provided $X^{1b}$ and $X^{1c}$ are not simultaneously —O—, $R^{1c}$ is a hydrogen atom, a halogen atom, $C_1$-$C_2$ perfluoroalkyl, $C_1$-$C_2$ perfluoroalkoxy, $C_1$-$C_6$ alkyl or $C_1$-$C_2$ perfluoroalkylthio, $R^{1d}$ is a hydrogen atom, a halogen atom or $C_1$-$C_6$ alkyl, and $R^{1e}$ is a hydrogen atom, $C_1$-$C_2$ perfluoroalkyl or $C_1$-$C_2$ perfluoroalkoxy, X is —N= or —CH=, ring A is

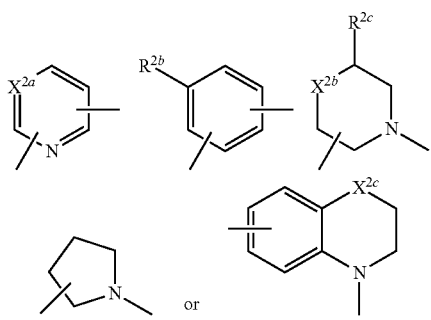

wherein $X^{2a}$ is —N= or —$CR^{2a}$= wherein $R^{2a}$ is a hydrogen atom, a halogen atom, $C_1$-$C_6$ alkyl or $C_1$-$C_6$ alkoxy, $R^{2b}$ is a hydrogen atom, a halogen atom, $C_1$-$C_6$ alkyl or $C_1$-$C_6$ alkoxy, $R^{2c}$ is a hydrogen atom or $C_1$-$C_6$ alkyl, $X^{2b}$ is —O—, —$NR^{2d}$— wherein $R^{2d}$ is a hydrogen atom or $C_1$-$C_2$ perfluoroalkyl or —$CHR^{2e}$— wherein $R^{2e}$ is a hydrogen atom or $C_1$-$C_6$ alkyl, $X^{2c}$ is —$(CH_2)_{n'}$— wherein n' is 0 or 1 or —O—, L is —$(CHR^{3a})_n$— wherein n is 0, 1, 2 or 3, plural symbols $R^{3a}$ are the same or different and each is a hydrogen atom or a $C_1$-$C_6$ alkyl, —$(CH_2)_m$—O—$(CH_2)_{m'}$, wherein m and m' are the same or different and each is 0, 1 or 2, $C_2$-$C_3$ alkenylene,

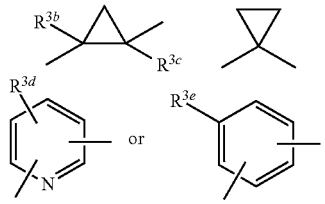
or wherein $R^{3b}$ and $R^{3c}$ are the same or different and each is a hydrogen atom or $C_1$-$C_6$ alkyl, $R^{3d}$ is a hydrogen atom, $C_1$-$C_6$ alkoxy, $C_1$-$C_6$ alkyl or $C_1$-$C_2$ perfluoroalkyl, $R^{3e}$ is a hydrogen atom, $C_1$-$C_6$ alkoxy, $C_1$-$C_6$ alkyl or $C_1$-$C_2$ perfluoroalkyl.

[2] The carboxylic acid compound of the aforementioned [1] wherein $R^1$ is

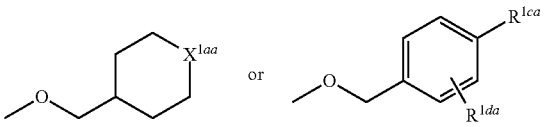

wherein $X^{1aa}$ is —$C(R^{1aa})_2$— wherein plural symbols $R^{1aa}$ are the same or different and each is a hydrogen atom, $C_1$-$C_2$ perfluoroalkyl or $C_1$-$C_6$ alkyl, or plural symbols $R^{1aa}$ are bonded to form 1,1-$C_3$-$C_6$ cycloalkylene, or —$NR^{1ba}$— wherein $R^{1ba}$ is a hydrogen atom or $C_1$-$C_2$ perfluoroalkyl, $R^{1ca}$ is $C_1$-$C_2$ perfluoroalkyl, $C_1$-$C_2$ perfluoroalkoxy or $C_1$-$C_2$ perfluoroalkylthio, and $R^{1da}$ is a halogen atom or $C_1$-$C_6$ alkyl, or a pharmacologically acceptable salt thereof.

[3] The carboxylic acid compound of the aforementioned [1] or [2] wherein ring A is

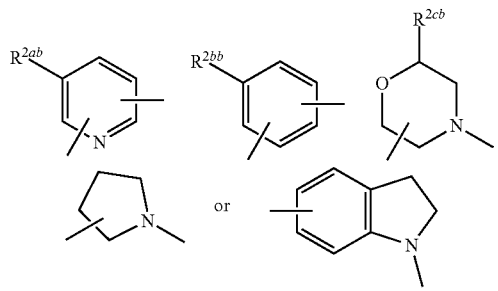

wherein $R^{2ab}$ is a hydrogen atom, $C_1$-$C_6$ alkoxy or $C_1$-$C_6$ alkyl, $R^{2bb}$ is a hydrogen atom, $C_1$-$C_6$ alkoxy or $C_1$-$C_6$ alkyl, and $R^{2cb}$ is a hydrogen atom or $C_1$-$C_6$ alkyl, or a pharmacologically acceptable salt thereof.

[4] The carboxylic acid compound of any of the aforementioned [1] to [3] wherein the ring A is

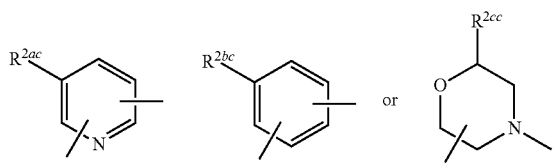

wherein $R^{2ac}$ is a hydrogen atom, $C_1$-$C_6$ alkoxy or $C_1$-$C_6$ alkyl, $R^{2bc}$ is a hydrogen atom, $C_1$-$C_6$ alkoxy or $C_1$-$C_6$ alkyl, and $R^2CC$ is a hydrogen atom or $C_1$-$C_6$ alkyl, or a pharmacologically acceptable salt thereof.

[5] The carboxylic acid compound of any of the aforementioned [1] to [4] wherein the ring A is

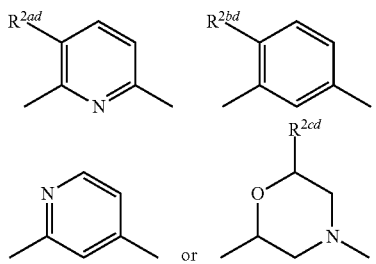

wherein $R^{2ad}$ is a hydrogen atom, $C_1$-$C_6$ alkoxy or $C_1$-$C_6$ alkyl, $R^{2bd}$ is a hydrogen atom, $C_1$-$C_6$ alkoxy or $C_1$-$C_6$ alkyl, and $R^{2cd}$ is a hydrogen atom or $C_1$-$C_6$ alkyl, or a pharmacologically acceptable salt thereof.

[6] The carboxylic acid compound of any of the aforementioned [1] to [5], wherein L is —(CH$_2$)$_n$— wherein n is 1 or 2 or

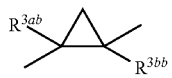

wherein $R^{3a}b$ and $R^{3bb}$ are the same or different and each is a hydrogen atom or $C_1$-$C_6$ alkyl, or a pharmacologically acceptable salt thereof.

[7] The carboxylic acid compound of any of the aforementioned [6] to [6], wherein X is —N═, or a pharmacologically acceptable salt thereof.

[8] The carboxylic acid compound of the aforementioned [1], wherein the compound represented by the formula (1) is any of the following, or a pharmacologically acceptable salt thereof:

trans-2-[2-methoxy-5-(5-{[4-(trifluoromethoxy)benzyl]oxy}pyridin-3-yl)phenyl]cyclopropanecarboxylic acid, trans-2-[2-methoxy-5-(6-{[4-(trifluoromethoxy)benzyl]oxy}pyridazin-4-yl)phenyl]cyclopropanecarboxylic acid, (1S,2S)-2-[2-methoxy-5-(6-{[trans-4-(trifluoromethyl)cyclohexyl]methoxy}pyridazin-4-yl)phenyl]cyclopropanecarboxylic acid, (1R,2R)-2-[2-methoxy-5-(6-{[trans-4-(trifluoromethyl)cyclohexyl]methoxy}pyridazin-4-yl)phenyl]cyclopropanecarboxylic acid, (1S,2S)-2-(5-methoxy-5'-{[4-(trifluoromethoxy)benzyl]oxy}-2,3'-bipyridin-6-yl)cyclopropanecarboxylic acid, (1S,2S)-2-[3-methoxy-6-(6-{[4-(trifluoromethoxy)benzyl]oxy}pyridazin-4-yl)pyridin-2-yl]cyclopropanecarboxylic acid, (1S,2S)-2-[3-methoxy-6-(6-{[trans-4-(trifluoromethyl)cyclohexyl]methoxy}pyridazin-4-yl)pyridin-2-yl]cyclopropanecarboxylic acid, (1S,2S)-2-(5-{[4-(trifluoromethoxy)benzyl]oxy}-3,4'-bipyridin-2'-yl)cyclopropanecarboxylic acid, (1R,2R)-2-(5-{[4-(trifluoromethoxy)benzyl]oxy}-3,4'-bipyridin-2'-yl)cyclopropanecarboxylic acid, (1S,2S)-2-(5-{[trans-4-(trifluoromethyl)cyclohexyl]methoxy}-3,4'-bipyridin-2'-yl)cyclopropanecarboxylic acid, (1R,2R)-2-(5-{[trans-4-(trifluoromethyl)cyclohexyl]methoxy}-3,4'-bipyridin-2'-yl)cyclopropanecarboxylic acid, (1S,2S)-2-[4-(6-{[trans-4-(trifluoromethyl)cyclohexyl]methoxy}pyridazin-4-yl)pyridin-2-yl]cyclopropanecarboxylic acid, (1R,2R)-2-[4-(6-{[trans-4-(trifluoromethyl)cyclohexyl]methoxy}pyridazin-4-yl)pyridin-2-so yl]cyclopropanecarboxylic acid, (1S,2S)-2-(5'-{[trans-4-(trifluoromethyl)cyclohexyl]methoxy}-2,3'-bipyridin-6-yl)cyclopropanecarboxylic acid, (1R,2R)-2-(5'-{[trans-4-(trifluoromethyl)cyclohexyl]methoxy}-2,3'-bipyridin-6-yl)cyclopropanecarboxylic acid, (1S,2S)-2-[3-methoxy-6-(6-{[trans-4-(trifluoromethyl)cyclohexyl]methoxy}pyridazin-4-yl)pyridin-2-yl]-1-methylcyclopropanecarboxylic acid, (1R,2R)-2-[3-methoxy-6-(6-{[trans-4-(trifluoromethyl)cyclohexyl]methoxy}pyridazin-4-yl)pyridin-2-yl]-1-methylcyclopropanecarboxylic acid, (1S,2S)-2-[2-ethoxy-5-(6-{[1-(2,2,2-trifluoroethyl)piperidin-4-yl]methoxy}pyridazin-4-yl)phenyl]cyclopropanecarboxylic acid, 3-[(2S)-4-(5-{[4-(trifluoromethoxy)benzyl]oxy}pyridin-3-yl)morpholin-2-yl]propanoic acid, 3-[(2S)-4-(5-{[trans-4-(trifluoromethyl)cyclohexyl]methoxy}pyridin-3-yl)morpholin-2-yl]propanoic acid, 3-[(2S)-4-(5-{[3-fluoro-4-(trifluoromethoxy)benzyl]oxy}pyridin-3-yl)morpholin-2-yl]propanoic acid, 3-[(2S)-4-(5-{[2-fluoro-4-(trifluoromethoxy)benzyl]oxy}pyridin-3-yl)morpholin-2-yl]propanoic acid, 3-[(2S)-4-(5-{[2-methyl-4-(trifluoromethoxy)benzyl]oxy}pyridin-3-yl)morpholin-2-yl]propanoic acid, 3-[(2S)-4-(5-{[3-chloro-4-(trifluoromethoxy)benzyl]oxy}pyridin-3-yl)morpholin-2-yl]propanoic acid, 3-[(2S,6R)-6-methyl-4-(5-{[4-(trifluoromethoxy)benzyl]oxy}pyridin-3-yl)morpholin-2-yl]propanoic acid, (1S,2S)-2-[(2S)-4-(5-{[trans-4-(trifluoromethyl)cyclohexyl]methoxy}pyridin-3-yl)morpholin-2-yl]cyclopropanecarboxylic acid, (1R,2R)-2-[(2S)-4-(5-{[trans-4-(trifluoromethyl)cyclohexyl]methoxy}pyridin-3-yl)morpholin-2-yl]cyclopropanecarboxylic acid, (1R,2R)-2-[(2R)-4-(5-{[trans-4-(trifluoromethyl)cyclohexyl]methoxy}pyridin-3-yl)morpholin-2-yl]cyclopropanecarboxylic acid, or (1S,2S)-2-[(2R)-4-(5-{[trans-4-(trifluoromethyl)cyclohexyl]methoxy}pyridin-3-yl)morpholin-2-yl]cyclopropanecarboxylic acid.

[9] A pharmaceutical composition comprising the carboxylic acid compound of any of the aforementioned [1] to [8], or a pharmacologically acceptable salt thereof, and a pharmaceutically acceptable carrier.

[10] The pharmaceutical composition of the aforementioned [9], which is used as an autotaxin inhibitor.

[11] The pharmaceutical composition of the aforementioned [9], which is used for the treatment or prophylaxis of a disease involving autotaxin.

[12] The pharmaceutical composition of the aforementioned [11], wherein the disease involving autotaxin is cancer or tumor, a fibrotic disease, an inflammatory disease, an ophthalmic disease, a urological disease, type II diabetes-related obesity or an acute coronary syndrome.

[13] The pharmaceutical composition of the aforementioned [12], wherein the cancer or tumor is malignant melanoma, brain tumor, neuroblastoma, glioblastoma multiforme, EBV positive Hodgkin lymphoma, glioblastoma, non-small cell lung cancer, lung tumor, breast tumor, ovary tumor, pancreas tumor, prostate intraepithelial tumor, prostate tumor, thyroid gland tumor, follicular lymphoma, liver tumor or renal cell carcinoma.

[14] The pharmaceutical composition of the aforementioned [12], wherein the fibrotic disease is lung fibrosis, scleroderma, hepatic fibrosis, renal fibrosis, diabetic nephropathy or atherosclerosis.

[15] The pharmaceutical composition of the aforementioned [14], wherein the fibrotic disease is lung fibrosis, scleroderma, hepatic fibrosis or renal fibrosis.

[16] The pharmaceutical composition of the aforementioned [12], wherein the inflammatory disease is asthma, COPD, rheumatoid arthritis, arthritis deformans, NASH, NAFLD, inflammatory bowel disease, Crohn's disease, ulcerative colitis, neuropathic pain or pruritus.

[17] The pharmaceutical composition of the aforementioned [16], wherein the inflammatory disease is asthma or COPD.

[18] The pharmaceutical composition of the aforementioned [16], wherein the inflammatory disease is rheumatoid arthritis or arthritis deformans.

[19] The pharmaceutical composition of the aforementioned [16], wherein the inflammatory disease is NASH or NAFLD.

[20] The pharmaceutical composition of the aforementioned [16], wherein the inflammatory disease is an inflammatory bowel disease, a Crohn's disease or ulcerative colitis.

[21] The pharmaceutical composition of the aforementioned [16], wherein the inflammatory disease is neuropathic pain or pruritus.

[22] The pharmaceutical composition of the aforementioned [12], wherein the acute coronary syndrome is angina pectoris or myocardial infarction.

[23] The pharmaceutical composition of the aforementioned [12], wherein the ophthalmic disease is glaucoma.

[24] The pharmaceutical composition of the aforementioned [12], wherein the urological disease is prostatomegaly.

[25] A method for treating or preventing a disease involving autotaxin in a test subject comprising administering an effective amount of the carboxylic acid compound of any of the aforementioned [1] to [8] or a pharmacologically acceptable salt thereof to the test subject.

[26] The method of the aforementioned [25], wherein the disease involving autotaxin is cancer or tumor, a fibrotic disease, an inflammatory disease, an ophthalmic disease, a urological disease, type II diabetes-related obesity or an acute coronary syndrome.

[27] Use of the carboxylic acid compound of any of the aforementioned [1] to [8] or a pharmacologically acceptable salt thereof in the production of an agent for treating or preventing a disease involving autotaxin.

[28] The use of the aforementioned [27], wherein the disease involving autotaxin is cancer or tumor, a fibrotic disease, an inflammatory disease, an ophthalmic disease, a urological disease, type II diabetes-related obesity or acute coronary syndrome.

Effect of the Invention

The compound of the present invention has a superior autotaxin inhibitory action and is useful as a prophylactic or therapeutic drug for a disease caused by autotaxin, for example, cancer, tumor, fibrotic disease, inflammatory disease, ophthalmic disease, urological disease, type II diabetes-related obesity or acute coronary syndrome.

DESCRIPTION OF EMBODIMENTS

Figure 1:
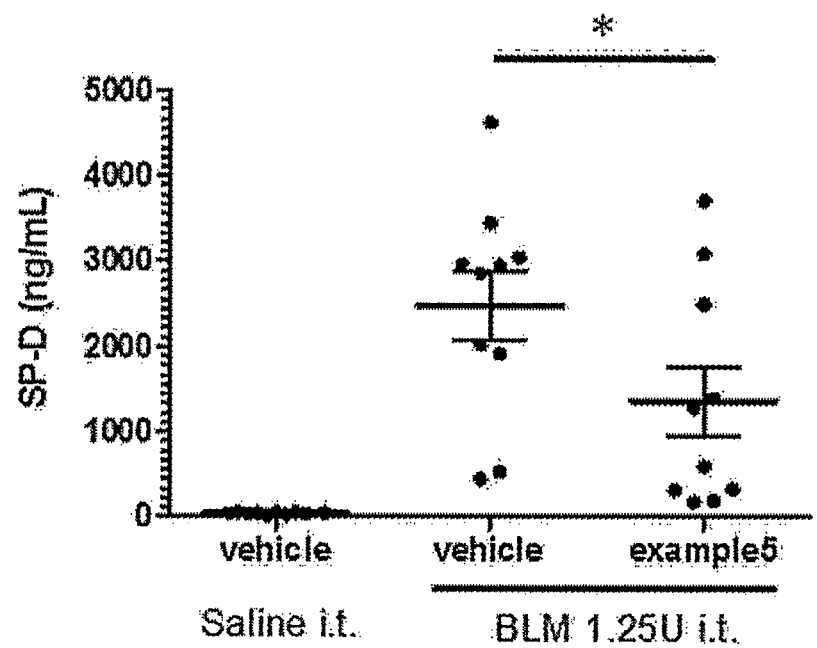
FIG. 1 is a graph showing the SP-D level in plasma as the result of Experimental Example 3.

The definition of each group in the present specification can be freely combined unless particularly indicated.

The definition of each symbol in the present specification is as follows.

The $C_1$-$C_6$ alkyl for $R^{1a}$, $R^{1c}$, $R^{1d}$, $R^{2a}$, $R^{2b}$, $R^{2c}$, $R^{2e}$, $R^{3a}$, $R^{3b}$, $R^{3c}$, $R^{3d}$, $R^{3e}$, $R^{1aa}$, $R^{1da}$, $R^{2ab}$, $R^{2bb}$, $R^{2cb}$, $R^{2ac}$, $R^{2bc}$, $R^{2cc}$, $R^{2ad}$, $R^{2bd}$, $R^{2cd}$, $R^{3bb}$ or $R^{3bc}$ is a linear or branched chain saturated hydrocarbon group having 1-6 carbon atoms. Particularly, the group having 1-4 carbon atoms ($C_1$-$C_4$) is preferable. Specifically, methyl, ethyl, propyl, isopropyl, butyl, isobutyl, sec-butyl, tert-butyl, pentyl, hexyl and the like can be mentioned. Particularly, methyl, ethyl, isopropyl or tert-butyl is preferable.

The halogen atom for $R^{1a}$, $R^{1c}$, $R^{1d}$, $R^{2a}$, $R^{2b}$ or $R^{1da}$ is a fluorine atom, a chlorine atom, a bromine atom or an iodine atom. Particularly, a fluorine atom or a chlorine atom is preferable.

The $C_1$-$C_2$ perfluoroalkyl for $R^{1a}$, $R^{1b}$, $R^{1c}$, $R^{1e}$, $R^{2d}$, $R^{3d}$, $R^{3e}$, $R^{1aa}$, $R^{1ba}$ or $R^{1ca}$ is methyl or ethyl substituted with 1 to 5 fluorines. Specifically, it is fluoromethyl, difluoromethyl, trifluoromethyl, 2,2,2-trifluoroethyl or the like. Particularly, trifluoromethyl or 2,2,2-trifluoroethyl is preferable.

The $C_1$-$C_2$ perfluoroalkoxy for $R^{1a}$, $R^{1c}$, $R^{1e}$ or $R^{1ca}$ is a monovalent group in which the aforementioned perfluoroalkyl is bonded to an oxygen, and perfluoroalkyl-O— having 1-2 ($C_1$-$C_2$) carbon atoms can be mentioned. Specifically, it is fluoromethoxy, difluoromethoxy, trifluoromethoxy, 2,2,2-trifluoroethoxy or the like. Particularly, trifluoromethoxy or 2,2,2-trifluoroethoxy is preferable.

The 1,1-$C_3$-$C_6$ cycloalkylene for $R^{1a}$ or $R^{1aa}$ is 1,1-cycloalkylene having 3-6 carbon atoms such as 1,1-cyclopropylene, 1,1-cyclobutylene, 1,1-cyclopentylene, 1,1-cyclohexylene or the like.

The $C_1$-$C_2$ perfluoroalkylthio for $R^{1c}$ or $R^{1ca}$ is a monovalent group in which the aforementioned perfluoroalkyl is bonded to sulfur, and perfluoroalkyl-S— having 1-2 ($C_1$-$C_2$) carbon atoms can be mentioned. Specifically, it is fluoromethylthio, difluoromethylthio, trifluoromethylthio, 2,2,2-trifluoroethylthio or the like. Particularly, trifluoromethylthio or 2,2,2-trifluoroethylthio is preferable.

The $C_1$-$C_6$ alkoxy for $R^{2a}$, $R^{2b}$, $R^{3d}$, $R^{3e}$, $R^{2ab}$, $R^{2bb}$, $R^{2ac}$, $R^{2bc}$, $R^{2ad}$ or $R^{2bd}$ is a monovalent group in which $C_1$-$C_6$ alkyl for $R^{1a}$ is bonded to oxygen, and straight chain or branched chain alkyl-O-having 1-6 ($C_1$-$C_6$) carbon atoms can be mentioned.
Particularly, alkyl-O— having 1-4 ($C_1$-$C_4$) carbon atoms is preferable, and alkyl-O— having 1-2 ($C_1$-$C_2$) carbon atoms is preferable. Specifically, methoxy, ethoxy, n-propoxy, i-propoxy, n-butoxy, t-butoxy and the like can be mentioned. Particularly, methoxy or ethoxy is preferable.

The $C_2$-$C_3$ alkenylene for L is a linear divalent hydrocarbon group having 2-3 ($C_2$-$C_3$) carbon atoms and having at least one double bond. Specifically, vinylene or propenylene can be mentioned.

The disease involving autotaxin includes, for example, cancer or tumor, fibrotic diseases, inflammatory diseases, ophthalmic diseases, urological diseases, type II diabetes-related obesity and acute coronary syndrome. Examples of the cancer or tumor include malignant melanoma, brain tumor, neuroblastoma, glioblastoma multiforme, EBV positive Hodgkin lymphoma, glioblastoma, non-small cell lung cancer, lung tumor, breast tumor, ovary tumor, pancreas tumor, prostate intraepithelial tumor, prostate tumor, thyroid gland tumor, follicular lymphoma, liver tumor, renal cell carcinoma and the like. Examples of the fibrotic disease include lung fibrosis, scleroderma, hepatic fibrosis, renal fibrosis, diabetic nephropathy, atherosclerosis and the like, examples of the inflammatory disease include asthma, COPD, rheumatoid arthritis, arthritis deformans, NASH, NAFLD, acute coronary syndrome, inflammatory bowel disease, Crohn's disease, ulcerative colitis, neuropathic pain, pruritus and the like, examples of the ophthalmic disease include glaucoma and the like, and examples of the urological disease include prostatomegaly and the like, but the examples are not limited to these. Preferably, the disease involving autotaxin is selected from the group consisting of fibrotic diseases such as lung fibrosis, scleroderma, hepatic fibrosis, renal fibrosis and the like, inflammatory diseases such as asthma, COPD, rheumatoid arthritis, arthritis deformans, NASH, NAFLD, neuropathic pain or pruritus and the like and ophthalmic diseases such as glaucoma. More preferably, the disease involving autotaxin is selected from the group consisting of fibrotic diseases such as lung fibrosis, scleroderma, hepatic fibrosis, renal fibrosis and the like.

$R^1$ in the formula (1) is preferably any group represented by the following formula:

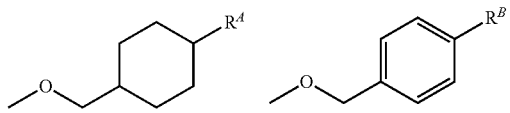

-continued

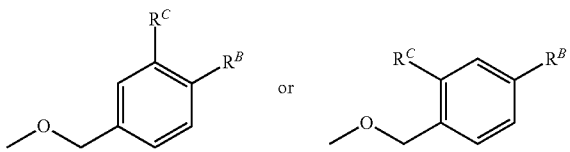

wherein $R^A$ is preferably a hydrogen atom, $C_1$-$C_2$ perfluoroalkyl or $C_1$-$C_6$ alkyl, more preferably, $C_1$-$C_2$ perfluoroalkyl or $C_1$-$C_6$ alkyl, $R^B$ is preferably $C_1$-$C_2$ perfluoroalkyl, $C_1$-$C_2$ perfluoroalkoxy or $C_1$-$C_2$ perfluoroalkylthio, more preferably, $C_1$-$C_2$ perfluoroalkyl or $C_1$-$C_2$ perfluoroalkoxy, $R^C$ is preferably a halogen atom or $C_1$-$C_6$ alkyl, more preferably, $C_1$-$C_6$ alkyl.

In another embodiment of the present invention, $R^1$ in the formula (1) is preferably

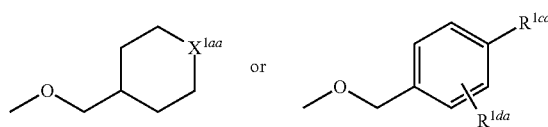

wherein $X^{1aa}$ is —$C(R^{1a}a)_2$— wherein plural symbols $R^{1aa}$ are the same or different and each is a hydrogen atom, $C_1$-$C_2$ perfluoroalkyl or $C_1$-$C_6$ alkyl, or plural symbols $R^{1aa}$ are bonded to form 1,1-$C_3$-$C_6$ cycloalkylene, or —$NR^{1ba}$— wherein $R^{1ba}$ is a hydrogen atom or $C_1$-$C_2$ perfluoroalkyl, $R^{1ca}$ is $C_1$-$C_2$ perfluoroalkyl, $C_1$-$C_2$ perfluoroalkoxy or $C_1$-$C_2$ perfluoroalkylthio, and $R^{1da}$ is a halogen atom or $C_1$-$C_6$ alkyl.

The following substituent containing ring A in the formula (1)

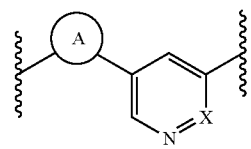

is preferably any group represented by the following formula:

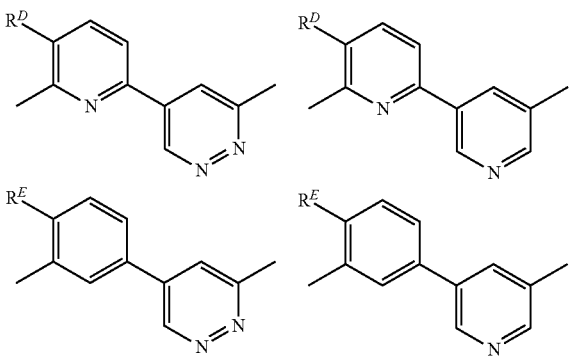

-continued

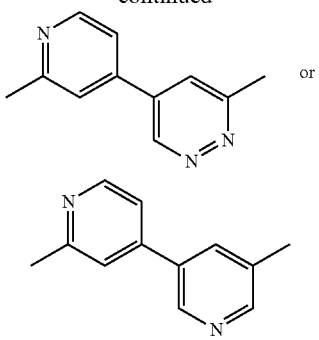

or wherein $R^D$ is preferably a hydrogen atom, $C_1$-$C_6$ alkoxy or $C_1$-$C_6$ alkyl, more preferably, a hydrogen atom or $C_1$-$C_6$ alkoxy, $R^E$ is preferably a hydrogen atom, $C_1$-$C_6$ alkoxy or $C_1$-$C_6$ alkyl, more preferably, a hydrogen atom or $C_1$-$C_6$ alkoxy, more preferably any group represented by the following formula:

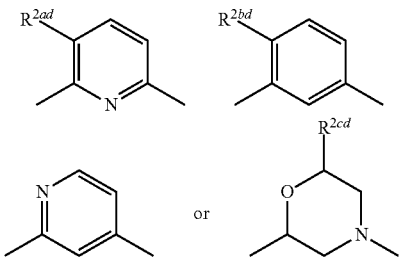

or wherein $R^D$ and $R^E$ are as defined above.

In another embodiment of the present invention, ring A in the formula (1) is preferably

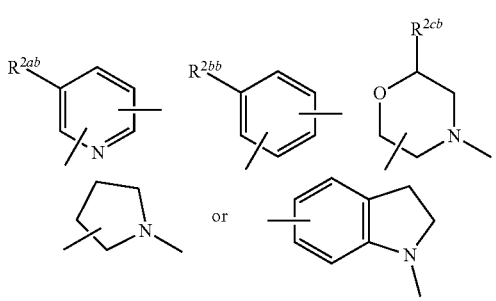

wherein $R^{2ab}$ is a hydrogen atom, $C_1$-$C_6$ alkoxy or $C_1$-$C_6$ alkyl, $R^{2bb}$ is a hydrogen atom, $C_1$-$C_6$ alkoxy or $C_1$-$C_6$ alkyl, and $R^{2cb}$ is a hydrogen atom or $C_1$-$C_6$ alkyl, more preferably,

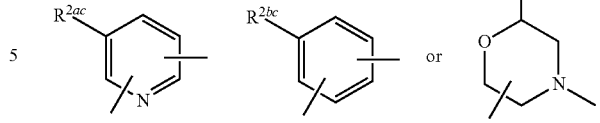

or wherein $R^{2ac}$ is a hydrogen atom, $C_1$-$C_6$ alkoxy or $C_1$-$C_6$ alkyl, $R^{2bc}$ is a hydrogen atom, $C_1$-$C_6$ alkoxy or $C_1$-$C_6$ alkyl, and $R^{2CC}$ is a hydrogen atom or $C_1$-$C_6$ alkyl, further preferably

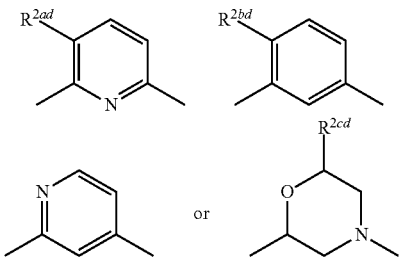

or wherein $R^{2ad}$ is a hydrogen atom, $C_1$-$C_6$ alkoxy or $C_1$-$C_6$ alkyl, $R^{2bd}$ is a hydrogen atom, $C_1$-$C_6$ alkoxy or $C_1$-$C_6$ alkyl, and $R^{2cd}$ is a hydrogen atom or $C_1$-$C_6$ alkyl.

In another embodiment of the present invention, X in the formula (1) is preferably —N=.

L in the formula (1) is preferably —(CH$_2$)$_n$— wherein n is 1 or 2 or

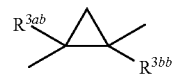

wherein $R^{3ab}$ and $R^{3bb}$ are the same or different and each is a hydrogen atom or $C_1$-$C_6$ alkyl, more preferably,

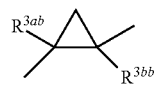

wherein $R^{3ab}$ and $R^{3bb}$ are as defined above.

Preferable examples of Compound (1) include the following compounds.

[Compound 1-A]

Compound (1) wherein $R^1$ is

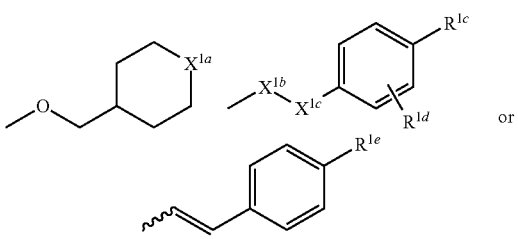

or wherein $X^{1a}$ is —C($R^{1a}$)$_2$— wherein plural symbols $R^{1a}$ are the same or different and each is a hydrogen atom, a halogen atom (e.g., fluorine atom), $C_1$-$C_2$ perfluoroalkyl (e.g., trifluoromethyl) or $C_1$-$C_6$ alkyl (e.g., methyl), or plural symbols $R^{1a}$ are bonded to form 1,1-$C_3$-$C_6$ cycloalkylene (e.g., 1,1-cyclopropylene, 1,1-cyclobutylene) or —$NR^{1b}$— wherein $R^{1b}$ is $C_1$-$C_2$ perfluoroalkyl (e.g., trifluoroethyl), $X^{1b}$ and $X^{1c}$ are the same or different and each is —O— or —$CH_2$-(provided that $X^{1b}$ and $X^{1c}$ are not simultaneously —O—), $R^{1c}$ is a hydrogen atom, a halogen atom (e.g., fluorine atom, chlorine atom), $C_1$-$C_2$ perfluoroalkyl (e.g., trifluoromethyl), $C_1$-$C_2$ perfluoroalkoxy (e.g., trifluoromethoxy) or $C_1$-$C_2$ perfluoroalkylthio (e.g., trifluoromethylthio), $R^{1d}$ is a hydrogen atom, a halogen atom (e.g., fluorine atom, chlorine atom) or $C_1$-$C_6$ alkyl (e.g., methyl), $R^{1e}$ is $C_1$-$C_2$ perfluoroalkoxy (e.g., trifluoromethoxy);

X is —N= or —CH=;

ring A is

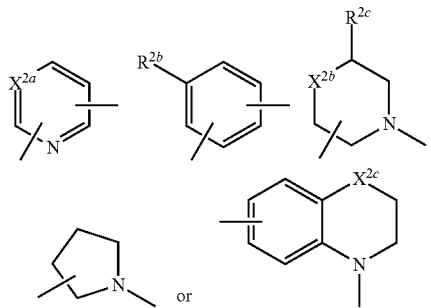

wherein $X^{2a}$ is —$CR^{2a}$= wherein $R^{2a}$ is a hydrogen atom or $C_1$-$C_6$ alkoxy (e.g., methoxy), $R^{2b}$ is a hydrogen atom or $C_1$-$C_6$ alkoxy (e.g., methoxy, ethoxy), $R^{2c}$ is a hydrogen atom or $C_1$-$C_6$ alkyl (e.g., methyl), $X^{2b}$ is —O—, —$NR^{2d}$— wherein $R^{2d}$ is $C_1$-$C_2$ perfluoroalkyl (e.g., trifluoroethyl) or —$CHR^{2e}$— wherein $R^{2e}$ is a hydrogen atom, $X^{2c}$ is —$(CH_2)_{n'}$— wherein n' is 0 or 1 or —O—;

L is —$(CHR^{3a})_n$— wherein n is 0, 1, 2 or 3, plural symbols $R^{3a}$ are the same or different and each is a hydrogen atom or $C_1$-$C_6$ alkyl (e.g., methyl), —$(CH_2)_m$—O—$(CH_2)_{m'}$ wherein m and m' are each 1, $C_2$-$C_3$ alkenylene (e.g., vinylene, propenylene),

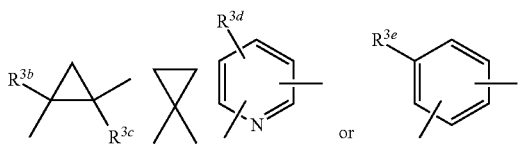

wherein $R^{3b}$ and $R^{3c}$ are the same or different and each is a hydrogen atom or $C_1$-$C_6$ alkyl (e.g., methyl), $R^{3d}$ is a hydrogen atom, $C_1$-$C_6$ alkoxy (e.g., methoxy), $C_1$-$C_6$ alkyl (e.g., methyl) or $C_1$-$C_2$ perfluoroalkyl (e.g., trifluoromethyl), $R^{3e}$ is a hydrogen atom or $C_1$-$C_6$ alkoxy (e.g., methoxy).

Specific examples of Compound (1) include the below-mentioned compounds of Examples 1-101, preferably, trans-2-[2-methoxy-5-(5-{[4-(trifluoromethoxy)benzyl]oxy}pyridin-3-yl)phenyl]cyclopropanecarboxylic acid, trans-2-[2-methoxy-5-(6-{[4-(trifluoromethoxy)benzyl]oxy}pyridazin-4-yl)phenyl]cyclopropanecarboxylic acid, trans-2-[2-methoxy-5-(6-{[trans-4-(trifluoromethyl)cyclohexyl]methoxy}pyridazin-4-yl)phenyl]cyclopropanecarboxylic acid, trans-2-(5-methoxy-5'-{[4-(trifluoromethoxy)benzyl]oxy}-2,3'-bipyridin-6-yl)cyclopropanecarboxylic acid, trans-2-[3-methoxy-6-(6-{[4-(trifluoromethoxy)benzyl]oxy}pyridazin-4-yl)pyridin-2-yl]cyclopropanecarboxylic acid, trans-2-[3-methoxy-6-(6-{[trans-4-(trifluoromethyl)cyclohexyl]methoxy}pyridazin-4-yl)pyridin-2-yl]cyclopropanecarboxylic acid, trans-2-(5-methoxy-5'-{[4-(trifluoromethyl)phenoxy]methyl}-2,3'-bipyridin-6-yl)cyclopropanecarboxylic acid, trans-2-(5-methoxy-5'-{2-[4-(trifluoromethoxy)phenyl]ethyl}-2,3'-bipyridin-6-yl)cyclopropanecarboxylic acid, trans-2-(5-{[4-(trifluoromethoxy)benzyl]oxy}-3,4'-bipyridin-2'-yl)cyclopropanecarboxylic acid, trans-2-(5-{[trans-4-(trifluoromethyl)cyclohexyl]methoxy}-3,4'-bipyridin-2'-yl)cyclopropanecarboxylic acid, trans-2-[4-(6-{[trans-4-(trifluoromethyl)cyclohexyl]methoxy}pyridazin-4-yl)pyridin-2-yl]cyclopropanecarboxylic acid, trans-2-(5'-{[trans-4-(trifluoromethyl)cyclohexyl]methoxy}-2,3'-bipyridin-6-yl)cyclopropanecarboxylic acid, trans-2-[3-methoxy-6-(6-{[trans-4-(trifluoromethyl)cyclohexyl]methoxy}pyridazin-4-yl)pyridin-2-yl]-1-methylcyclopropanecarboxylic acid, trans-2-[2-ethoxy-5-(6-{[1-(2,2,2-trifluoroethyl)piperidin-4-yl]methoxy}pyridazin-4-yl)phenyl]cyclopropanecarboxylic acid, 1-(5-{[trans-4-(trifluoromethyl)cyclohexyl]methoxy}pyridin-3-yl)-2,3-dihydro-1H-indole-5-carboxylic acid, 1-(5-{[1-(2,2,2-trifluoroethyl)piperidin-4-yl]methoxy}pyridin-3-yl)-2,3-dihydro-1H-indole-5-carboxylic acid, 4-[4-(5-{[trans-4-(trifluoromethyl)cyclohexyl]methoxy}pyridin-3-yl)morpholin-2-yl]benzoic acid, 3-[4-(5-{[trans-4-(trifluoromethyl)cyclohexyl]methoxy}pyridin-3-yl)morpholin-2-yl]benzoic acid, 2-methoxy-4-[4-(5-{[trans-4-(trifluoromethyl)cyclohexyl]methoxy}pyridin-3-yl)morpholin-2-yl]benzoic acid, 3-[(2S)-4-(5-{[4-(trifluoromethoxy)benzyl]oxy}pyridin-3-yl)morpholin-2-yl]propanoic acid, 3-[(2S)-4-(5-{[trans-4-(trifluoromethyl)cyclohexyl]methoxy}pyridin-3-yl)morpholin-2-yl]propanoic acid, 3-[(2S)-4-(5-{[4-(trifluoromethyl)benzyl]oxy}pyridin-3-yl)morpholin-2-yl]propanoic acid, 3-[(2S)-4-(5-{[3-fluoro-4-(trifluoromethoxy)benzyl]oxy}pyridin-3-yl)morpholin-2-yl]propanoic acid, 3-[(2S)-4-(5-{[2-fluoro-4-(trifluoromethoxy)benzyl]oxy}pyridin-3-yl)morpholin-2-yl]propanoic acid, 3-[(2S)-4-(5-{[2-methyl-4-(trifluoromethoxy)benzyl]oxy}pyridin-3-yl)morpholin-2-yl]propanoic acid, 3-[(2S)-4-(5-{[3-chloro-4-(trifluoromethoxy)benzyl]oxy}pyridin-3-yl)morpholin-2-yl]propanoic acid, 3-[(2S, 6R)-6-methyl-4-(5-{[4-(trifluoromethoxy)benzyl]oxy}pyridin-3-yl)morpholin-2-yl]propanoic acid, 3-[1-(2,2,2-trifluoroethyl)-4-(5-{[4-(trifluoromethoxy)benzyl]oxy}pyridin-3-yl)piperazin-2-yl]propanoic acid,

[1-(5-{[4-(trifluoromethoxy)benzyl]oxy}pyridin-3-yl)piperidin-3-yl]acetic acid,

4-[1-(5-{[4-(trifluoromethoxy)benzyl]oxy}pyridin-3-yl)pyrrolidin-2-yl]butanoic acid,
(1S,2S)-2-[(2S)-4-(5-{[trans-4-(trifluoromethyl)cyclohexyl]methoxy}pyridin-3-yl)morpholin-2-yl]cyclopropanecarboxylic acid,
(1R,2R)-2-[(2S)-4-(5-{[trans-4-(trifluoromethyl)cyclohexyl]methoxy}pyridin-3-yl)morpholin-2-yl]cyclopropanecarboxylic acid,
(1R,2R)-2-[(2R)-4-(5-{[trans-4-(trifluoromethyl)cyclohexyl]methoxy}pyridin-3-yl)morpholin-2-yl]cyclopropanecarboxylic acid, or,
(1S,2S)-2-[(2R)-4-(5-{[trans-4-(trifluoromethyl)cyclohexyl]methoxy}pyridin-3-yl)morpholin-2-yl]cyclopropanecarboxylic acid, more preferably,
trans-2-[2-methoxy-5-(5-{[4-(trifluoromethoxy)benzyl]oxy}pyridin-3-yl)phenyl]cyclopropanecarboxylic acid,
trans-2-[2-methoxy-5-(6-{[4-(trifluoromethoxy)benzyl]oxy}pyridazin-4-yl)phenyl]cyclopropanecarboxylic acid,
(1S,2S)-2-[2-methoxy-5-(6-{[trans-4-(trifluoromethyl)cyclohexyl]methoxy}pyridazin-4-yl)phenyl]cyclopropanecarboxylic acid,
(1R,2R)-2-[2-methoxy-5-(6-{[trans-4-(trifluoromethyl)cyclohexyl]methoxy}pyridazin-4-yl)phenyl]cyclopropanecarboxylic acid,
(1S,2S)-2-(5-methoxy-5'-{[4-(trifluoromethoxy)benzyl]oxy}-2,3'-bipyridin-6-yl)cyclopropanecarboxylic acid,
(1S,2S)-2-[3-methoxy-6-(6-{[4-(trifluoromethoxy)benzyl]oxy}pyridazin-4-yl)pyridin-2-yl]cyclopropanecarboxylic acid,
(1S,2S)-2-[3-methoxy-6-(6-{[trans-4-(trifluoromethyl)cyclohexyl]methoxy}pyridazin-4-yl)pyridin-2-yl]cyclopropanecarboxylic acid,
(1S,2S)-2-(5-{[4-(trifluoromethoxy)benzyl]oxy}-3,4'-bipyridin-2'-yl)cyclopropanecarboxylic acid,
(1R,2R)-2-(5-{[4-(trifluoromethoxy)benzyl]oxy}-3,4'-bipyridin-2'-yl)cyclopropanecarboxylic acid,
(1S,2S)-2-(5-{[trans-4-(trifluoromethyl)cyclohexyl]methoxy}-3,4'-bipyridin-2'-yl)cyclopropanecarboxylic acid,
(1R,2R)-2-(5-{[trans-4-(trifluoromethyl)cyclohexyl]methoxy}-3,4'-bipyridin-2'-yl)cyclopropanecarboxylic acid,
(1S,2S)-2-[4-(6-{[trans-4-(trifluoromethyl)cyclohexyl]methoxy}pyridazin-4-yl)pyridin-2-yl]cyclopropanecarboxylic acid,
(1R,2R)-2-[4-(6-{[trans-4-(trifluoromethyl)cyclohexyl]methoxy}pyridazin-4-yl)pyridin-2-yl]cyclopropanecarboxylic acid,
(1S,2S)-2-(5'-{[trans-4-(trifluoromethyl)cyclohexyl]methoxy}-2,3'-bipyridin-6-yl)cyclopropanecarboxylic acid,
(1R,2R)-2-(5'-{[trans-4-(trifluoromethyl)cyclohexyl]methoxy}-2,3'-bipyridin-6-yl)cyclopropanecarboxylic acid,
(1S,2S)-2-[3-methoxy-6-(6-{[trans-4-(trifluoromethyl)cyclohexyl]methoxy}pyridazin-4-yl)pyridin-2-yl]-1-methylcyclopropanecarboxylic acid,
(1R,2R)-2-[3-methoxy-6-(6-{[trans-4-(trifluoromethyl)cyclohexyl]methoxy}pyridazin-4-yl)pyridin-2-yl]-1-methylcyclopropanecarboxylic acid,
(1S,2S)-2-[2-ethoxy-5-(6-{[1-(2,2,2-trifluoroethyl)piperidin-4-yl]methoxy}pyridazin-4-yl)phenyl]cyclopropanecarboxylic acid,
3-[(2S)-4-(5-{[4-(trifluoromethoxy)benzyl]oxy}pyridin-3-yl)morpholin-2-yl]propanoic acid,
3-[(2S)-4-(5-{[trans-4-(trifluoromethyl)cyclohexyl]methoxy}pyridin-3-yl)morpholin-2-yl]propanoic acid,
3-[(2S)-4-(5-{[3-fluoro-4-(trifluoromethoxy)benzyl]oxy}pyridin-3-yl)morpholin-2-yl]propanoic acid,
3-[(2S)-4-(5-{[2-fluoro-4-(trifluoromethoxy)benzyl]oxy}pyridin-3-yl)morpholin-2-yl]propanoic acid,
3-[(2S)-4-(5-{[2-methyl-4-(trifluoromethoxy)benzyl]oxy}pyridin-3-yl)morpholin-2-yl]propanoic acid,
3-[(2S)-4-(5-{[3-chloro-4-(trifluoromethoxy)benzyl]oxy}pyridin-3-yl)morpholin-2-yl]propanoic acid,
3-[(2S, 6R)-6-methyl-4-(5-{[4-(trifluoromethoxy)benzyl]oxy}pyridin-3-yl)morpholin-2-yl]propanoic acid,
(1S,2S)-2-[(2S)-4-(5-{[trans-4-(trifluoromethyl)cyclohexyl]methoxy}pyridin-3-yl)morpholin-2-yl]cyclopropanecarboxylic acid,
(1R,2R)-2-[(2S)-4-(5-{[trans-4-(trifluoromethyl)cyclohexyl]methoxy}pyridin-3-yl)morpholin-2-yl]cyclopropanecarboxylic acid,
(1R,2R)-2-[(2R)-4-(5-{[trans-4-(trifluoromethyl)cyclohexyl]methoxy}pyridin-3-yl)morpholin-2-yl]cyclopropanecarboxylic acid, or
(1S,2S)-2-[(2R)-4-(5-{[trans-4-(trifluoromethyl)cyclohexyl]methoxy}pyridin-3-yl)morpholin-2-yl]cyclopropanecarboxylic acid, further preferably,
trans-2-[2-methoxy-5-(5-{[4-(trifluoromethoxy)benzyl]oxy}pyridin-3-yl)phenyl]cyclopropanecarboxylic acid,
trans-2-[2-methoxy-5-(6-{[4-(trifluoromethoxy)benzyl]oxy}pyridazin-4-yl)phenyl]cyclopropanecarboxylic acid,
(1S,2S)-2-[2-methoxy-5-(6-{[trans-4-(trifluoromethyl)cyclohexyl]methoxy}pyridazin-4-yl)phenyl]cyclopropanecarboxylic acid,
(1R,2R)-2-[2-methoxy-5-(6-{[trans-4-(trifluoromethyl)cyclohexyl]methoxy}pyridazin-4-yl)phenyl]cyclopropanecarboxylic acid,
(1S,2S)-2-(5-methoxy-5'-{[4-(trifluoromethoxy)benzyl]oxy}-2,3'-bipyridin-6-yl)cyclopropanecarboxylic acid,
(1S,2S)-2-[3-methoxy-6-(6-{[4-(trifluoromethoxy)benzyl]oxy}pyridazin-4-yl)pyridin-2-yl]cyclopropanecarboxylic acid,
(1S,2S)-2-[3-methoxy-6-(6-{[trans-4-(trifluoromethyl)cyclohexyl]methoxy}pyridazin-4-yl)pyridin-2-yl]cyclopropanecarboxylic acid,
(1S,2S)-2-(5-{[4-(trifluoromethoxy)benzyl]oxy}-3,4'-bipyridin-2'-yl)cyclopropanecarboxylic acid,
(1R,2R)-2-(5-{[4-(trifluoromethoxy)benzyl]oxy}-3,4'-bipyridin-2'-yl)cyclopropanecarboxylic acid,
(1S,2S)-2-(5-{[trans-4-(trifluoromethyl)cyclohexyl]methoxy}-3,4'-bipyridin-2'-yl)cyclopropanecarboxylic acid,
(1R,2R)-2-(5-{[trans-4-(trifluoromethyl)cyclohexyl]methoxy}-3,4'-bipyridin-2'-yl)cyclopropanecarboxylic acid,
(1S,2S)-2-[4-(6-{[trans-4-(trifluoromethyl)cyclohexyl]methoxy}pyridazin-4-yl)pyridin-2-yl]cyclopropanecarboxylic acid,
(1R,2R)-2-[4-(6-{[trans-4-(trifluoromethyl)cyclohexyl]methoxy}pyridazin-4-yl)pyridin-2-yl]cyclopropanecarboxylic acid,
(1S,2S)-2-(5'-{[trans-4-(trifluoromethyl)cyclohexyl]methoxy}-2,3'-bipyridin-6-yl)cyclopropanecarboxylic acid,
(1R,2R)-2-(5'-{[trans-4-(trifluoromethyl)cyclohexyl]methoxy}-2,3'-bipyridin-6-yl)cyclopropanecarboxylic acid,
(1S,2S)-2-[3-methoxy-6-(6-{[trans-4-(trifluoromethyl)cyclohexyl]methoxy}pyridazin-4-yl)pyridin-2-yl]-1-methylcyclopropanecarboxylic acid, (1R,2R)-2-[3-methoxy-6-(6-{[trans-4-(trifluoromethyl)cyclohexyl]methoxy}pyridazin-4-yl)pyridin-2-yl]-1-methylcyclopropanecarboxylic acid, or (1S,2S)-2-[2-ethoxy-5-(6-{[1-(2,2,2-trifluoroethyl)piperidin-4-yl]methoxy}pyridazin-4-yl)phenyl]cyclopropanecarboxylic acid.

Prophylaxis means the act of administering the compound of the present invention or a pharmaceutical composition containing the compound to an individual who has not developed a sickness, a disease or a symptom. Treatment means the act of administering the compound of the present invention or a pharmaceutical composition containing the compound to an individual who has already developed a sickness, a disease or a symptom. Therefore, the act of administration to an individual who has already developed a sickness, a disease or a symptom, for the purpose of preventing exacerbation of the symptom and the like or preventing seizure or preventing recurrence is one embodiment of treatment.

When the compound of the present invention is used as a medicament, the compound of the present invention can be administered orally or parenterally in the form of a pharmaceutical composition or preparation (oral preparation, injection and the like) obtained by mixing with a pharmaceutically acceptable carrier (excipient, binder, disintegrant, corrigent, flavor, emulsifier, diluent, solubilizing agent and the like). The pharmaceutical composition can be formulated according to a general method.

Examples of the preparation suitable for oral administration include tablet, capsule, powder, fine granules, granules, liquid, syrup and the like. Examples of the preparation suitable for parenteral administration include injection, drip transfusion, suppository and the like. Excipient, disintegrant, binder, lubricant, coating agent, base and the like can be used as additives for the preparation suitable for oral administration. When the compound of the present invention is administered to a patient to be the subject of treatment, other appropriate agents and the compound of the present invention may be used in combination for the treatment of the target disease.

Parenteral administration includes subcutaneous injection, intravenous injection, intramuscular injection, intraperitoneal injection, drip method or topical administration (transdermal administration, transocular administration, pulmonary and bronchial administration, transnasal administration, rectal administration and the like) and the like.

The compound of the present invention can be used in combination with other medicaments and the like in some cases. The timing of administration of the compound of the present invention or a pharmacologically acceptable salt thereof or a solvate thereof, and a concomitant drug is not limited, and these may be administered simultaneously or may be administered at different times to the subject of administration. Furthermore, the compound of the present invention and the concomitant drug may be administered as two kinds of preparations containing each active ingredient or as a single preparation containing the both active ingredients.

The dose of the compound of the present invention is determined according to age, body weight, general health condition, sex, administration time, administration method, clearance rate, level of disease state of patients under treatment at that time, or in consideration of other factors. The daily dose of the compound of the present invention varies depending on the condition and body weight of patients, the kind of compound, administration route and the like. For parenteral administration, for example, it is administered subcutaneously, intravenously, intramuscularly, transdermally, transocularly, pulmonarily and bronchially, transnasally or intrarectally at about 0.0001-500 mg/person/day and, for oral administration, it is administered at about 0.001-5000 mg/person/day.

Compound (1) of the present invention can be produced according to, for example, the following Production Methods 1-29.

Production Method 1 (when a is Aryl or Heteroaryl Such as Phenyl, Pyridyl or the Like)

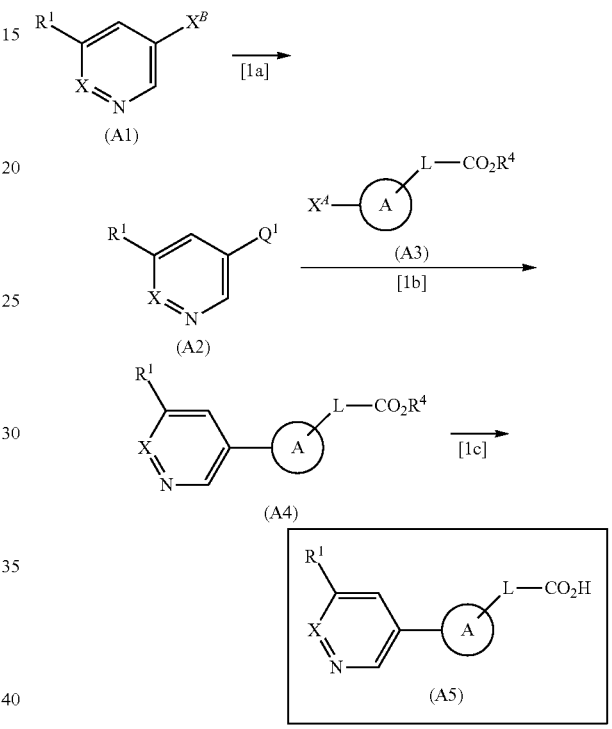

wherein $R^4$ is alkyl, $X^A$ and $X^B$ are halogen atoms, $Q^1$ is borate, and other symbols are as defined above.

Step 1a

Compound (A2) can be produced by reacting compound (A1) with bis(pinacolato)diborane in a solvent in the presence of a transition metal complex and a base. As the solvent, toluene, benzene, xylene, tetrahydrofuran, 1,2-dimethoxyethane, 1,4-dioxane, acetonitrile, ethyl acetate, N,N-dimethylformamide, dimethyl sulfoxide, N-methylpyrrolidone and the like can be appropriately used.

As the transition metal complex, a 0 valent palladium complex such as tetrakis(triphenylphosphine)palladium(0), tris(dibenzylideneacetone)dipalladium(0), bis(dibenzylideneacetone)palladium(0), bis(tri-tert-butylphosphine)palladium(0) or bis(tricyclohexylphosphine)palladium(0), or a divalent palladium complex such as palladium(II) acetate, bis(triphenylphosphine)palladium(II) dichloride, bis(tri-O-tolylphosphine)palladium(II) dichloride, bis(tricyclohexylphosphine)palladium(II) dichloride, bis(benzonitrile)palladium(II) dichloride, bis(acetonitrile)palladium(II) dichloride, [1,1'-bis(diphenylphosphino)ferrocene]palladium(II) dichloride or bis(di-tert-butyl(4-dimethylaminophenyl)phosphine)dichloropalladium(II) is used.

In addition, a suitable ligand may be added to the transition metal complex. Examples of a suitable ligand include tri-tert-butylphosphine, tri-cyclohexylphosphine, 1,1'-bis(diphenylphosphino)ferrocene, (±)-2,2'-bis(diphenylphosphino)-1,1'-binaphthyl, tri(ortho-tolyl)phosphine, 1,2,3,4,5-pentaphenyl-1'-(di-tert-butylphosphino)ferrocene, 4,5-bis(diphenylphosphino)-9,9-dimethylxanthene, di(1-adamantyl)-n-butylphosphine, (2-biphenyl)di-tert-butylphosphine, (S)-1-[(1R)-2-(diphenylphosphino)ferrocenyl]ethyldicyclohexylphosphine, 2-dicyclohexylphosphino-2',6'-diisopropoxybiphenyl, 2-dicyclohexylphosphino-2',6'-dimethoxybiphenyl, 2-dicyclohexylphosphino-2'-(N,N-dimethylamino)biphenyl, 2-dicyclohexylphosphino-2',4',6'-triisopropylbiphenyl, 2-di-tert-butylphosphino-2',4',6'-triisopropyl-1,1'-biphenyl, 2-(dicyclohexylphosphino)-3,6-dimethoxy-2',4',6'-triisopropyl-1,1'-biphenyl and the like.

Examples of the base include sodium hydrogen carbonate, sodium carbonate, potassium carbonate, cesium carbonate, sodium acetate, potassium acetate, tripotassium phosphate, dipotassium hydrogen phosphate, potassium dihydrogen phosphate and the like. The amount of the transition metal complex to be used may be 0.01-0.5 equivalents, preferably 0.03-0.1 equivalents, relative to compound (A1). The amount of the base to be used may be 1-10 equivalents, preferably 2-7 equivalents, relative to compound (A1). Particularly, it can be preferably produced by a method using reaction conditions such as those described in J. Org. Chem., 1995, 60, 7508-7510.

Step 1b

Compound (A4) can be produced by reacting compound (A2) with compound (A3) in a solvent in the presence of a transition metal complex and a base. As the solvent, toluene, benzene, xylene, tetrahydrofuran, 1,2-dimethoxyethane, 1,4-dioxane, acetonitrile, ethyl acetate, N,N-dimethylformamide, dimethyl sulfoxide, N-methylpyrrolidone, methanol, ethanol, 2-propanol, tert-butyl alcohol, water or a mixed solvent can be appropriately used. As the transition metal complex, a 0 valent palladium complex such as tetrakis(triphenylphosphine)palladium(0), tris(dibenzylideneacetone)dipalladium(0), bis(dibenzylideneacetone)palladium(0), bis(tri-tert-butylphosphine)palladium(0) or bis(tricyclohexylphosphine)palladium(0), or a divalent palladium complex such as palladium(II) acetate, bis(triphenylphosphine)palladium(II) dichloride, bis(tri-O-tolylphosphine)palladium(II) dichloride, bis(tricyclohexylphosphine)palladium(II) dichloride, bis(benzonitrile)palladium(II) dichloride, bis(acetonitrile)palladium(II) dichloride, [1,1'-bis(diphenylphosphino)ferrocene]palladium(II) dichloride or bis(di-tert-butyl(4-dimethylaminophenyl)phosphine)dichloropalladium(II) is used.

In addition, a suitable ligand may be added to the transition metal complex. Examples of a suitable ligand include tri-tert-butylphosphine, tri-cyclohexylphosphine, 1,1'-bis(diphenylphosphino)ferrocene, (±)-2,2'-bis(diphenylphosphino)-1,1'-binaphthyl, tri(ortho-tolyl)phosphine, 1,2,3,4,5-pentaphenyl-1'-(di-tert-butylphosphino)ferrocene, 4,5-bis(diphenylphosphino)-9,9-dimethylxanthene, di(1-adamantyl)-n-butylphosphine, (2-biphenyl)di-tert-butylphosphine, (S)-1-[(1R)-2-(diphenylphosphino)ferrocenyl]ethyldicyclohexylphosphine, 2-dicyclohexylphosphino-2',6'-diisopropoxybiphenyl, 2-dicyclohexylphosphino-2',6'-dimethoxybiphenyl, 2-dicyclohexylphosphino-2'-(N,N-dimethylamino)biphenyl, 2-dicyclohexylphosphino-2',4',6'-triisopropylbiphenyl, 2-di-tert-butylphosphino-2',4',6'-triisopropyl-1,1'-biphenyl, 2-(dicyclohexylphosphino)-3,6-dimethoxy-2',4',6'-triisopropyl-1,1'-biphenyl and the like.

Examples of the base include sodium carbonate, potassium carbonate, cesium carbonate, tripotassium phosphate, dipotassium hydrogen phosphate and the like. The amount of the transition metal complex to be used is 0.01-0.5 equivalents, preferably 0.03-0.1 equivalents, relative to compound (A3). The amount of the base to be used is 1-10 equivalents, preferably 2-7 equivalents, relative to compound (A3). Particularly, it can be preferably produced by a method using reaction conditions such as those described in Acc. Chem. Res., 2008, 41, 1461-1473. In addition, it can be preferably produced by a method using a palladium catalyst precursor containing a suitable ligand such as the one described in J. Am. Chem. Soc., 2010, 132, 14073-14075.

Step 1c

Compound (A5) can be produced by hydrolyzing compound (A4) by a method used generally. It can be produced by hydrolyzing in a suitable mixed aqueous solution in the presence of a base. As the solvent, for example, a mixed aqueous solution of methanol, ethanol, tetrahydrofuran and the like can be preferably used. As the base, lithium hydroxide, sodium hydroxide and potassium hydroxide can be preferably used.

Production Method 2 (when A is Aryl or Heteroaryl Such as Phenyl, Pyridyl or the Like)

Scheme 2

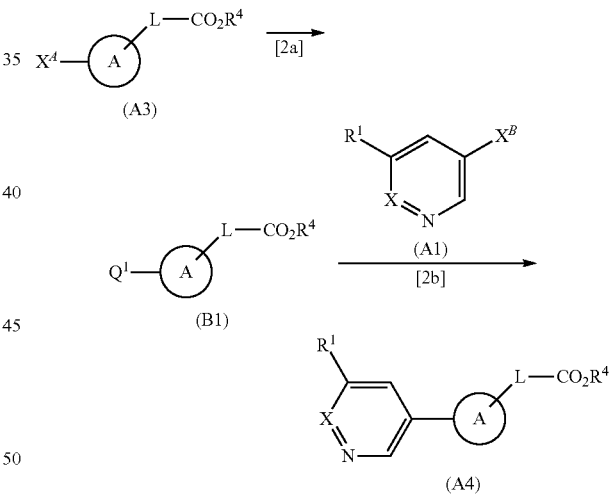

wherein $R^4$ is alkyl, $X^A$ and $X^B$ is a halogen atom, $Q^1$ is borate, and other symbols are as defined above.

Step 2a

Compound (B1) can be produced by reacting compound (A3) with bis(pinacolato)diborane by a method similar to [Step 1a].

Step 2b

Compound (A4) can be produced by reacting compound (B1) with compound (A1) by a method similar to [Step 1b].

Production Method 3 (when A is aryl or heteroaryl such as phenyl, pyridyl or the like)

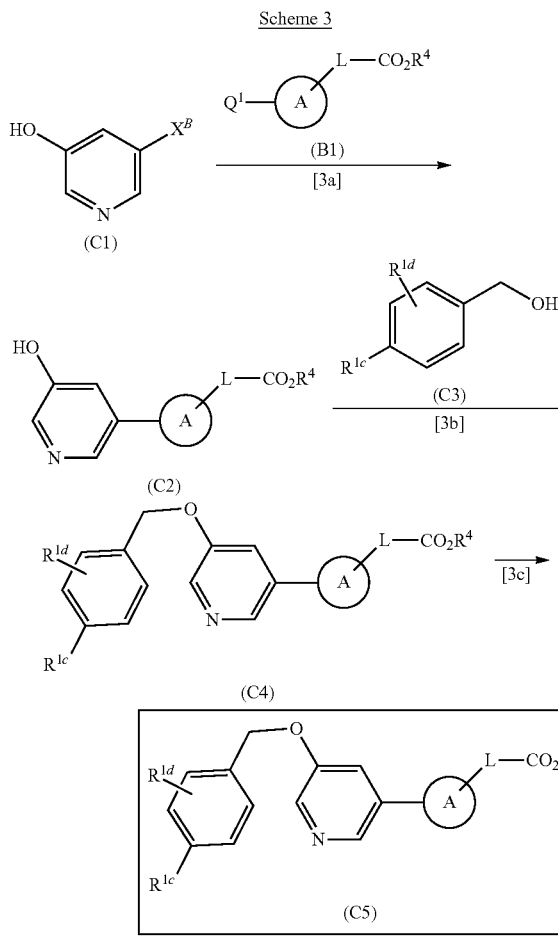

wherein $R^4$ is alkyl, $X^B$ is a halogen atom, $Q^1$ is borate, and other symbols are as defined above.

Step 3a

Compound ($C_2$) can be produced by reacting compound ($C_1$) with compound (B1) by a method similar to [Step 1b].

Step 3b

Compound ($C_4$) can be produced by reacting compound ($C_2$) with compound ($C_3$) in a solvent in the presence of a Mitsunobu reagent and a phosphine reagent. Examples of the Mitsunobu reagent include diethyl azodicarboxylate, diisopropyl azodicarboxylate, di-tert-butyl azodicarboxylate, 1,1'-(azodicarbonyl)dipiperidine, di-p-nitrobenzyl azodicarboxylate, 1,1'-azobis(N,N'-diisopropylformamide), 1,6-dimethyl-1,5,7-hexahydro-1,4,6,7-tetrazocine-2,5-dione, N,N,N',N'-tetramethylazodicarboxamide, di-p-chlorobenzyl azodicarboxylate, di-2-methoxyethyl azodicarboxylate and the like. Examples of the phosphine reagent include triphenylphosphine, tri-n-butylphosphine, tri-n-octylphosphine, tricyclohexylphosphine, diphenyl-2-pyridylphosphine and the like. When a Tsunoda reagent such as cyanomethylenetributylphosphorane, cyanomethylenetrimethylphosphorane and the like is used, this reaction also preferably proceeds even in the absence of a phosphine reagent. Examples of the solvent include toluene, benzene, xylene, dichloromethane, 1,2-dichloroethane, chloroform, tetrahydrofuran, 1,2-dimethoxyethane, 1,4-dioxane, diethyl ether, acetonitrile, ethyl acetate, N,N-dimethylformamide, dimethyl sulfoxide, N-methylpyrrolidone and the like. This reaction preferably proceeds at −40° C. to 100° C., preferably 0° C. to 70° C.

Step 3c

Compound (C5) can be produced by hydrolyzing compound (C4) by a method similar to [Step 1c].

Production Method 4 (when a is Aryl or Heteroaryl Such as Phenyl, Pyridyl or the Like)

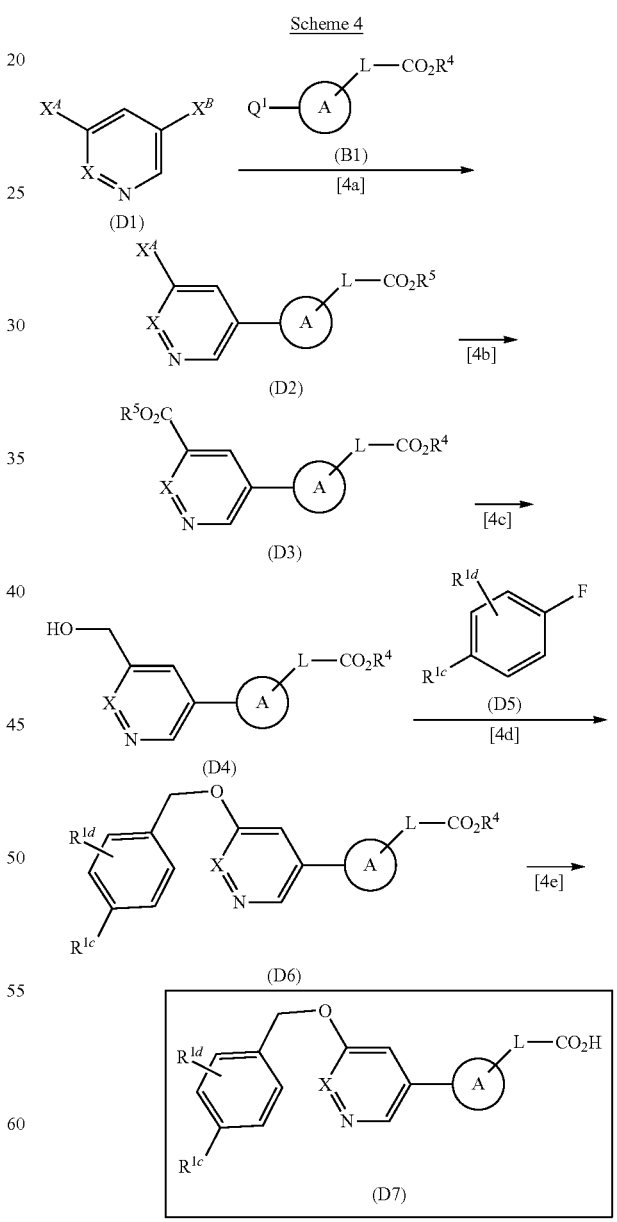

wherein $R^4$ and $R^5$ are alkyl, $X^A$ and $X^B$ are halogen atoms, $Q^1$ is borate, and other symbols are as defined above.

Step 4a

Compound (D2) can be produced by reacting compound (D1) with compound (B1) by a method similar to [Step 1b].

Step 4b

Compound (D3) can be produced by reacting compound (D2) in a solvent in the presence of a transition metal complex and a base under carbon monoxide atmosphere. Examples of the solvent include alcohol solvents such as methanol, ethanol, 2-propanol, tert-butyl alcohol and the like, and a mixed solvent with toluene, benzene, xylene, tetrahydrofuran, 1,2-dimethoxyethane, 1,4-dioxane, acetonitrile, ethyl acetate, N,N-dimethylformamide, dimethyl sulfoxide, N-methylpyrrolidone may also be used. As the transition metal complex, a 0 valent palladium complex such as
tetrakis(triphenylphosphine)palladium(0), tris(dibenzylideneacetone)dipalladium(0), bis(dibenzylideneacetone)palladium(0), bis(tri-tert-butylphosphine)palladium(0) or bis(tricyclohexylphosphine)palladium(0), or a divalent palladium complex such as palladium(II) acetate, bis(triphenylphosphine)palladium(II) dichloride, bis(tri-O-tolylphosphine)palladium(II) dichloride, bis(tricyclohexylphosphine)palladium(II) dichloride, bis(benzonitrile)palladium(II) dichloride, bis(acetonitrile)palladium(II) dichloride, [1,1'-bis(diphenylphosphino)ferrocene]palladium(II) dichloride or bis(di-tert-butyl(4-dimethylaminophenyl)phosphine)dichloropalladium(II) is used.

In addition, a suitable ligand may be added to the transition metal complex. Examples of a suitable ligand include tri-tert-butylphosphine, tri-cyclohexylphosphine, 1,1'-bis(diphenylphosphino)ferrocene, (±)-2,2'-bis(diphenylphosphino)-1,1'-binaphthyl, tri(ortho-tolyl)phosphine, 1,2,3,4,5-pentaphenyl-1'-(di-tert-butylphosphino)ferrocene, 4,5-bis(diphenylphosphino)-9,9-dimethylxanthene, di(1-adamantyl)-n-butylphosphine, (2-biphenyl)di-tert-butylphosphine, (S)-1-[(1R)-2-(diphenylphosphino)ferrocenyl]ethyldicyclohexylphosphine, 2-dicyclohexylphosphino-2',6'-diisopropoxybiphenyl, 2-dicyclohexylphosphino-2',6'-dimethoxybiphenyl, 2-dicyclohexylphosphino-2'-(N,N-dimethylamino)biphenyl, 2-dicyclohexylphosphino-2',4',6'-triisopropylbiphenyl, 2-di-tert-butylphosphino-2',4',6'-triisopropyl-1,1'-biphenyl, 2-(dicyclohexylphosphino)-3,6-dimethoxy-2',4',6'-triisopropyl-1,1'-biphenyl and the like. Examples of the base include sodium hydrogen carbonate, sodium carbonate, potassium carbonate, cesium carbonate, sodium acetate, potassium acetate, tripotassium phosphate, dipotassium hydrogen phosphate, potassium dihydrogen phosphate, triethylamine, diisopropylethylamine, 1,8-diazabicyclo[5.4.0]undecene, 1,4-diazabicyclo[2.2.2]octane and the like. The amount of the transition metal complex to be used is 0.01-0.3 equivalents, preferably 0.03-0.1 equivalents, relative to compound (D2). The amount of the base to be used is 1-10 equivalents, preferably 2-7 equivalents, relative to compound (D2). Particularly, it can be preferably produced by a method using reaction conditions such as those described in Organometallics, 2008, 27, 5402-5422.

Step 4c

Compound (D4) can be produced by treating compound (D3) with a reducing agent in a solvent. Examples of the solvent include toluene, benzene, xylene, dichloromethane, 1,2-dichloroethane, tetrahydrofuran, 1,2-dimethoxyethane, 1,4-dioxane, diethyl ether and the like, and a mixed solvent with an alcohol solvent such as methanol, ethanol, 2-propanol and the like may also be used. As the reducing agent, sodium borohydride, lithium borohydride, lithium aluminum hydride, diisobutylaluminum hydride and the like are used. This reaction preferably proceeds at −78° C. to 100° C., preferably −10° C. to room temperature.

Step 4d

Compound (D6) can be produced by reacting compound (D4) with compound (D5) in a solvent in the presence of a base and in the presence or absence of a phase-transfer catalyst. Examples of the solvent include toluene, benzene, xylene, tetrahydrofuran, 1,2-dimethoxyethane, 1,4-dioxane, diethyl ether, acetone, acetonitrile, N,N-dimethylformamide, dimethyl sulfoxide and N-methylpyrrolidone. Examples of the base include sodium carbonate, potassium carbonate, cesium carbonate, sodium hydride, sodium tert-butoxide, potassium tert-butoxide, lithium bis(trimethylsilyl)amide, sodium bis(trimethylsilyl)amide, potassium bis(trimethylsilyl)amide, lithium diisopropylamide, butyllithium and the like. Examples of the phase-transfer catalyst include halogenated quaternary ammonium salt, crown ether and the like. This reaction preferably proceeds at 0° C. to 200° C., preferably room temperature to 100° C.

Step 4e

Compound (D7) can be produced by hydrolyzing compound (D6) by a method similar to [Step 1c].

Production Method 5 (when A is Aryl or Heteroaryl Such as Phenyl, Pyridyl or the Like)

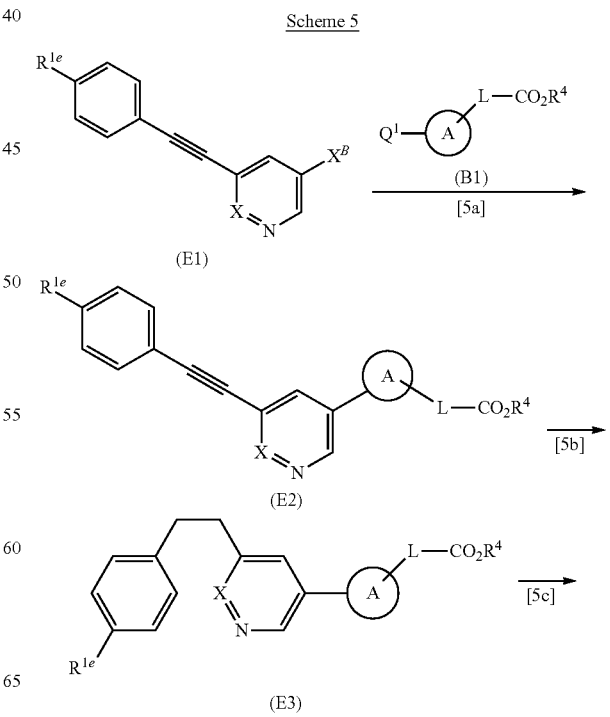

Scheme 5

-continued

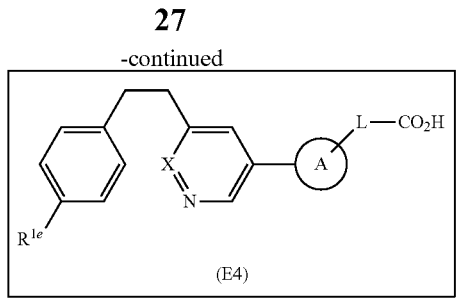

(E4)

wherein $R^4$ is alkyl, $X^B$ is a halogen atom, $Q^1$ is borate, and other symbols are as defined above.

Step 5a

Compound (E2) can be produced by reacting compound (E1) with compound (B1) by a method similar to [Step 1b].

Step 5b

Compound (E3) can be produced by a contact hydrogenation reaction of compound (E2) in a solvent in the presence of a transition metal catalyst under a hydrogen atmosphere. As the solvent, any solvent that does not disturb the reaction is suitable and, for example, methanol, ethanol, ethyl acetate, tetrahydrofuran and the like can be mentioned. As the transition metal catalyst, palladium carbon (Pd/C), palladium hydroxide carbon (Pd(OH)$_2$/C) and the like are used. This reaction preferably proceeds at 0° C. to 100° C., preferably at room temperature.

Step 5c

Compound (E4) can be produced by hydrolyzing compound (E3) by a method similar to [Step 1c].
Production Method 6 (when A is Aryl or Heteroaryl Such as Phenyl, Pyridyl or the Like)

Scheme 6

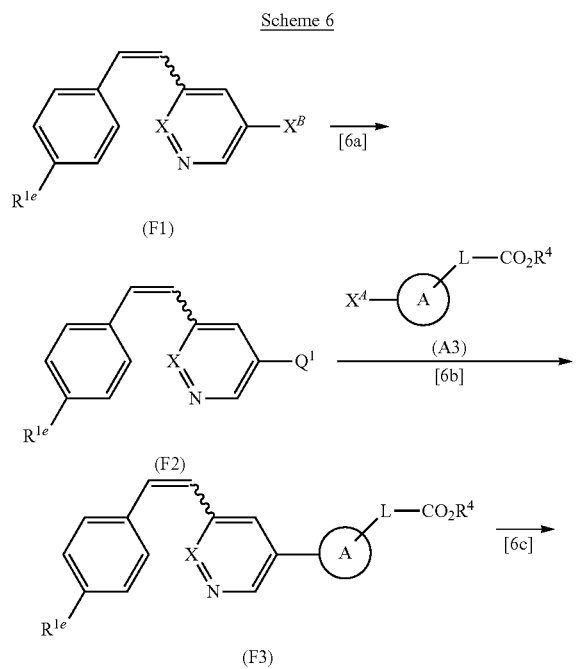

-continued

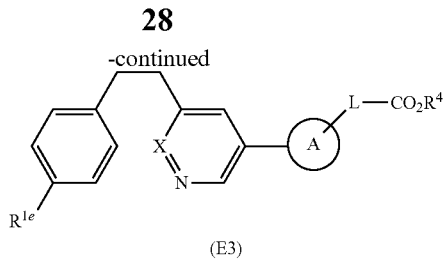

(E3)

wherein $R^4$ is alkyl, $X^A$ and $X^B$ is a halogen atom, $Q^1$ is borate, and other symbols are as defined above.

Step 6a

Compound (F2) can be produced by reacting compound (F1) with bis(pinacolato)diborane by a method similar to [Step 1a].

Step 6b

Compound (F3) can be produced by reacting compound (F2) with compound (A3) by a method similar to [Step 1b].

Step 6c

Compound (E3) can be produced by reacting compound (F3) by a method similar to [Step 5b].
Production Method 7 (when A is a heterocyclic group such as morpholinyl, pyrrolidinyl, indolinyl or the like)

Scheme 7

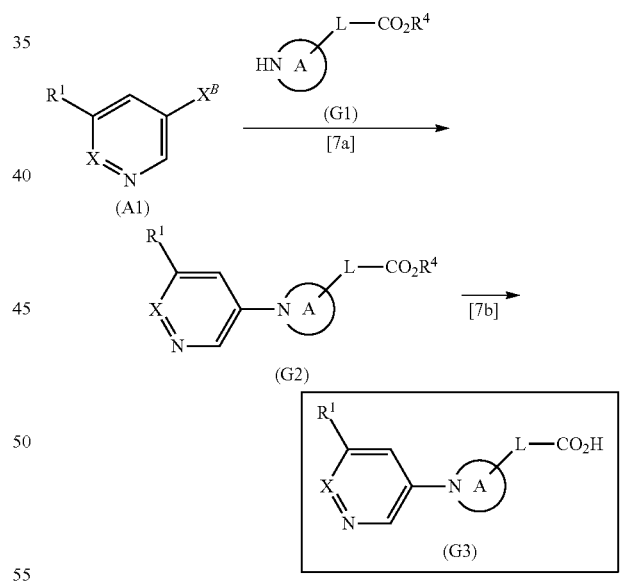

wherein $R^4$ is alkyl, $X^B$ is a halogen atom, and other symbols are as defined above.

Step 7a

Compound (G2) can be produced by reacting compound (G1) with (A1) in a suitable solvent in the presence of a transition metal complex and a base. As the solvent, toluene, benzene, xylene, tetrahydrofuran, 1,2-dimethoxyethane, 1,4-dioxane, acetonitrile, N,N-dimethylformamide, dimethyl sulfoxide, N-methylpyrrolidone and the like can be appropriately used. As the transition metal complex, a 0 valent palladium complex such as tetrakis(triphenylphosphine)palladium(0), tris(dibenzylideneacetone)dipalladium (0), bis(dibenzylideneacetone)palladium(0), bis(tri-tert-butylphosphine)palladium(0) or bis(tricyclohexylphosphine)palladium(0), or a divalent palladium complex such as palladium(II) acetate, bis(triphenylphosphine)palladium(II) dichloride, bis(tri-O-tolylphosphine)palladium(II) dichloride, bis(tricyclohexylphosphine)palladium (II) dichloride, bis(benzonitrile)palladium(II) dichloride, bis(acetonitrile)palladium(II) dichloride, [1,1'-bis(diphenylphosphino)ferrocene]palladium(II) dichloride or bis(di-tert-butyl(4-dimethylaminophenyl)phosphine)dichloropalladium(II) is used. In addition, a suitable ligand may be added to the transition metal complex. Examples of a suitable ligand include tri-tert-butylphosphine, tri-cyclohexylphosphine, 1,1'-bis(diphenylphosphino)ferrocene, (±)-2,2'-bis(diphenylphosphino)-1,1'-binaphthyl, tri(ortho-tolyl)phosphine, 1,2,3,4,5-pentaphenyl-1'-(di-tert-butylphosphino)ferrocene, 4,5-bis(diphenylphosphino)-9,9-dimethylxanthene, di(1-adamantyl)-n-butylphosphine, (2-biphenyl)di-tert-butylphosphine, (S)-1-[(1R)-2-(diphenylphosphino)ferrocenyl]ethyldicyclohexylphosphine, 2-dicyclohexylphosphino-2',6'-diisopropoxybiphenyl, 2-dicyclohexylphosphino-2',6'-dimethoxybiphenyl, 2-dicyclohexylphosphino-2'-(N,N-dimethylamino)biphenyl, 2-dicyclohexylphosphino-2',4',6'-triisopropylbiphenyl, 2-di-tert-butylphosphino-2',4',6'-triisopropyl-1,1'-biphenyl, 2-(dicyclohexylphosphino)-3,6-dimethoxy-2',4',6'-triisopropyl-1,1'-biphenyl and the like.

Examples of the base include sodium carbonate, potassium carbonate, cesium carbonate, lithium tert-butoxide, sodium tert-butoxide, potassium tert-butoxide, tripotassium phosphate, lithium bis(trimethylsilyl)amide, sodium bis(trimethylsilyl)amide, potassium bis(trimethylsilyl)amide, 1,8-diazabicyclo[5.4.0]undecene, 1,4-diazabicyclo[2.2.2]octane, 7-methyl-1,5,7-triazabicyclo[4.4.0]dec-5-ene and the like. The amount of the transition metal complex to be used may be 0.01-0.5 equivalents, preferably 0.03-0.1 equivalents, relative to compound (A1). The amount of the base to be used may be 1-10 equivalents, preferably 2-5 equivalents, relative to compound (A1). Particularly, it can be preferably produced under reaction conditions such as those described in Angew. Chem. Int. Ed., 2008, 47, 6338-6361. In addition, it can be preferably produced by a method using a palladium catalyst precursor containing a suitable ligand such as the one described in Chemical Science, 2013, 4, 916-920.

Step 7b

Compound (G3) can be produced by hydrolyzing compound (G2) by a method similar to [Step 1c].

Production Method 8 (when A is a Heterocyclic Group Such as Morpholinyl, Pyrrolidinyl, Indolinyl or the Like)

Scheme 8

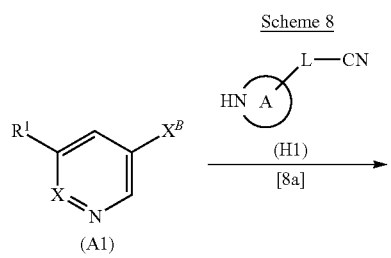

-continued

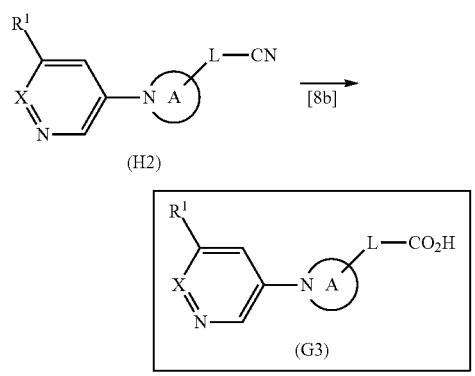

wherein $X^B$ is a halogen atom, and other symbols are as defined above.

Step 8a

Compound (H2) can be produced by reacting compound (H1) with compound (A1) by a method similar to [Step 7a].

Step 8b

Compound (G3) can be produced by hydrolyzing compound (H2) in a suitable mixed aqueous solution in the presence of a base. As the solvent, a mixed aqueous solution of 1,4-dioxane, ethylene glycol and the like can be preferably used. As the base, lithium hydroxide, sodium hydroxide and potassium hydroxide can be preferably used. This reaction preferably proceeds at 0° C. to 200° C., preferably room temperature to 120° C.

Production Method 9 (when A is a Heterocyclic Group Such as Piperidinyl, Piperazinyl, Morpholinyl or the Like)

Scheme 9

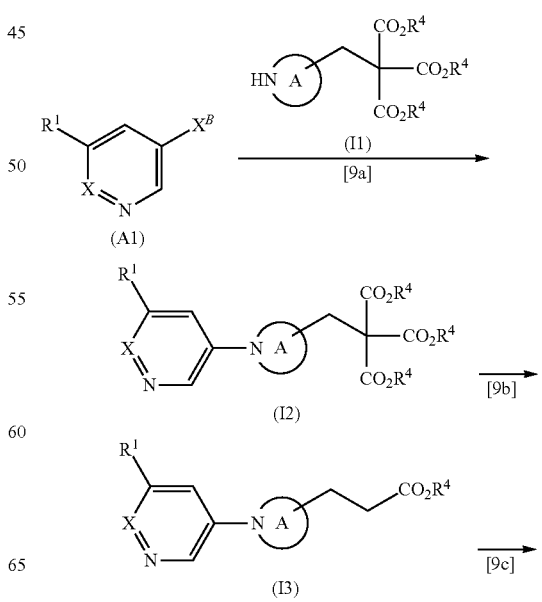

-continued

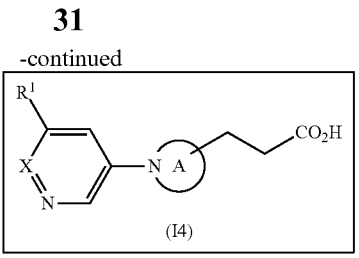

wherein R⁴ is alkyl, $X^B$ is a halogen atom, and other symbols are as defined above.

Step 9a

Compound (I2) can be produced by reacting compound (I1) with compound (A1) by a method similar to [Step 7a].

Step 9b

Compound (I3) can be produced by reacting compound (I2) in a suitable solvent in the presence of 2 equivalents of a base. As the solvent, alcohol solvents such as methanol, ethanol and the like can be used. As the base, lithium hydroxide, potassium hydroxide, sodium hydroxide and the like can be used. This reaction preferably proceeds at 0° C. to 100° C., preferably 0° C. to room temperature.

Step 9c

Compound (I4) can be produced by hydrolyzing compound (I3) by a method similar to [Step 1c].

Production Method 10 (when A is a Heterocyclic Group Such as Piperidinyl, Piperazinyl, Morpholinyl or the Like)

Scheme 10

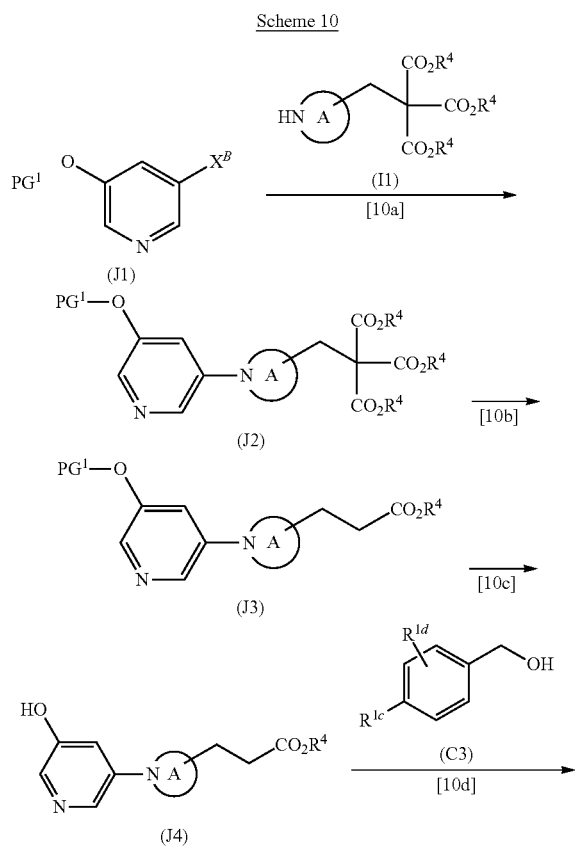

-continued

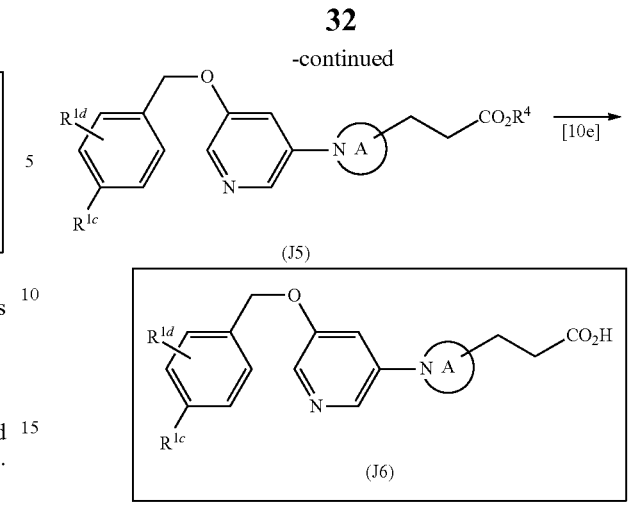

wherein R⁴ is alkyl, $X^B$ is a halogen atom, PG¹ is a hydroxyl-protecting group and other symbols are as defined above.

Step 10a

Compound (J2) can be produced by reacting compound (J1) with compound (I1) by a method similar to [Step 7a].

Step 10b

Compound (J3) can be produced by reacting compound (J2) by a method similar to [Step 9b].

Step 10c

Compound (J4) can be produced by removing PG¹ of compound (J3) by a general method.

Step 10d

Compound (J5) can be produced by reacting compound (J4) with compound (C₃) by a method similar to [Step 3b].

Step 10e

Compound (J6) can be produced by hydrolyzing compound (J5) by a method similar to [Step 1c].

Production Method 11 (when A is a Heterocyclic Group Such as Piperidinyl, Piperazinyl, Morpholinyl or the Like)

Scheme 11

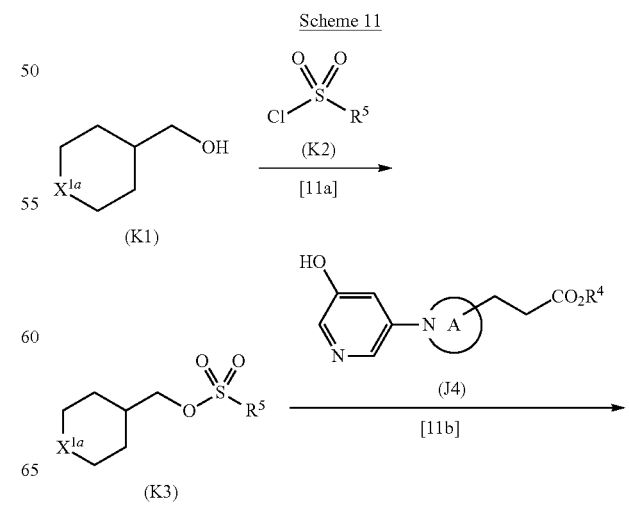

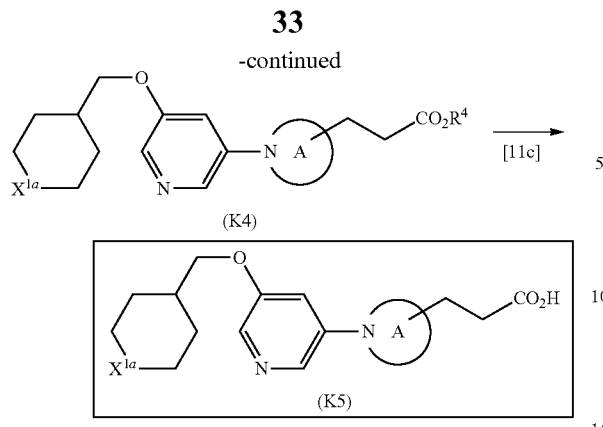

(K4)

(K5)

wherein R⁴ is alkyl, R⁵ is alkyl or aryl, and other symbols are as defined above.

Step 11a

Compound (K3) can be produced by reacting compound (K1) with compound (K2) in a solvent in the presence of a base. Examples of the solvent include toluene, benzene, xylene, dichloromethane, 1,2-dichloroethane, tetrahydrofuran, 1,2-dimethoxyethane, 1,4-dioxane, acetone, acetonitrile, N,N-dimethylformamide, dimethyl sulfoxide, N-methylpyrrolidone. Examples of the base include sodium hydrogen carbonate, sodium carbonate, potassium carbonate, sodium acetate, potassium acetate, tripotassium phosphate, dipotassium hydrogen phosphate, potassium dihydrogen phosphate, triethylamine, diisopropylethylamine, pyridine, 4-dimethylaminopyridine and the like. This reaction preferably proceeds at −40° C. to 100° C., preferably 0° C. to room temperature.

Step 11b

Compound (K4) can be produced by reacting compound (K3) with compound (J4) in a solvent in the presence of a base and in the presence or absence of a phase-transfer catalyst. Examples of the solvent include toluene, benzene, xylene, tetrahydrofuran, 1,2-dimethoxyethane, 1,4-dioxane, diethyl ether, acetone, acetonitrile, N,N-dimethylformamide, dimethyl sulfoxide and N-methylpyrrolidone. Examples of the base include sodium carbonate, potassium carbonate, cesium carbonate, sodium hydride, sodium tert-butoxide, potassium tert-butoxide, lithium bis(trimethylsilyl)amide, sodium bis(trimethylsilyl)amide, potassium bis(trimethylsilyl)amide, butyllithium and the like. Examples of the phase-transfer catalyst include halogenated quaternary ammonium salt, crown ether and the like. This reaction preferably proceeds at −40° C. to 120° C., preferably 0° C. to room temperature.

Step 11c

Compound (K5) can be produced by hydrolyzing compound (K4) by a method similar to [Step 1c].

Production Method 12 (when A is a Heterocyclic Group Such as Piperidinyl, Piperazinyl, Morpholinyl or the Like)

Scheme 12

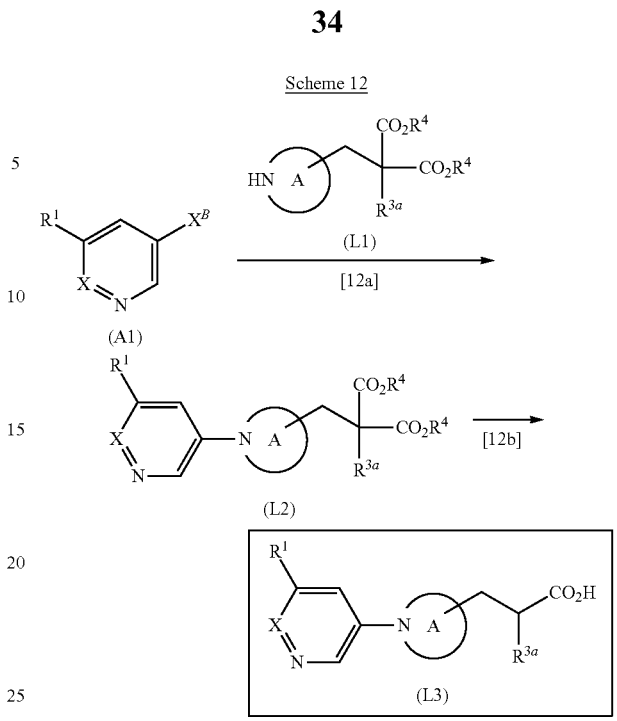

wherein R⁴ is alkyl, X^B is a halogen atom, and other symbols are as defined above.

Step 12a

Compound (L2) can be produced by reacting compound (L1) with compound (A1) by a method similar to [Step 7a].

Step 12b

Compound (L3) can be produced by reacting compound (L2) in a suitable solvent in the presence of a base and heating in the presence of an acid. As the solvent, alcohol solvents such as methanol, ethanol and the like can be appropriately used. As the base, lithium hydroxide, potassium hydroxide, sodium hydroxide and the like can be appropriately used. As the acid, acetic acid, hydrochloric acid, sulfuric acid and the like can be appropriately used. This reaction preferably proceeds by reacting in the presence of a base at 0° C. to room temperature and heating to room temperature to 100° C. in the presence of acid.

Production Method 13 (when A is a Heterocyclic Group Such as Morpholinyl, Pyrrolidinyl, Indolinyl or the Like)

Scheme 13

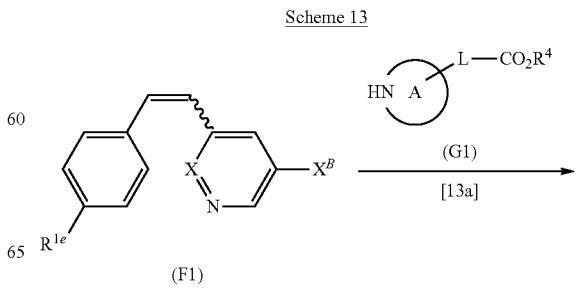

(F1)

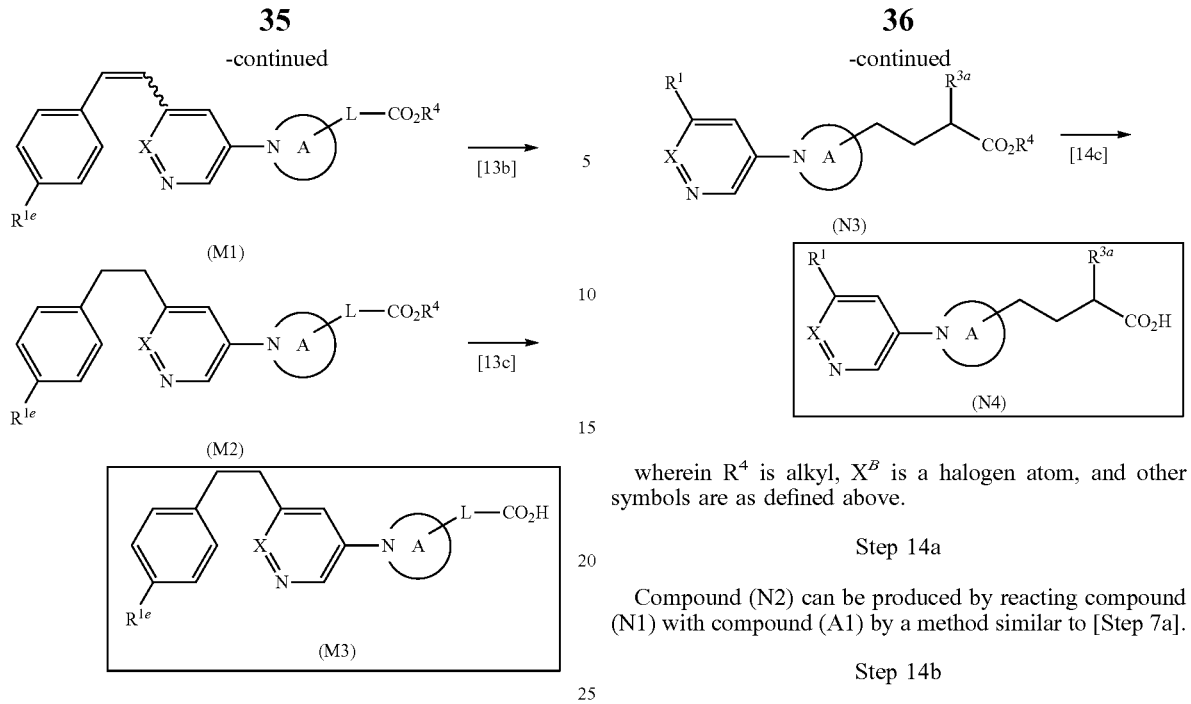

(M1)

(M2)

(M3)

wherein R⁴ is alkyl, $X^B$ is a halogen atom, and other symbols are as defined above.

Step 13a

Compound (M1) can be produced by reacting compound (G1) with compound (F1) by a method similar to [Step 7a].

Step 13b

Compound (M2) can be produced by reacting compound (M1) by a method similar to [Step 5b].

Step 13c

Compound (M3) can be produced by hydrolyzing compound (M2) by a method similar to [Step 1c].

Production Method 14 (when A is a Heterocyclic Group Such as Morpholinyl, Pyrrolidinyl, Indolinyl or the Like)

Scheme 14

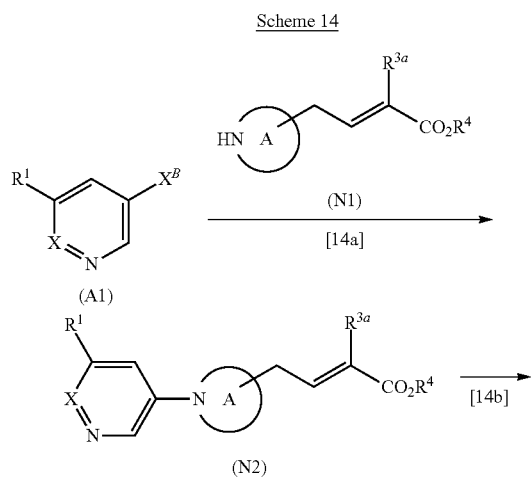

(A1)

(N2)

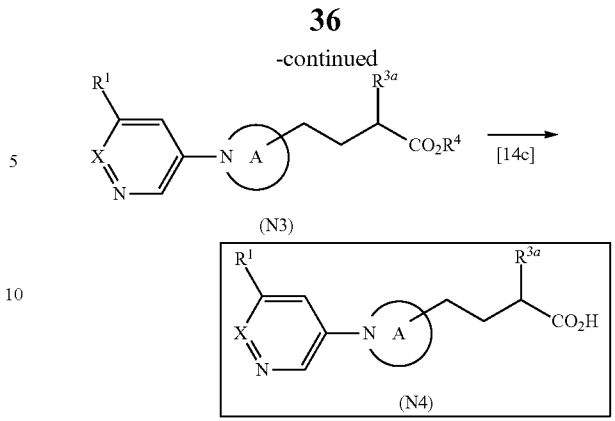

(N3)

(N4)

wherein R⁴ is alkyl, $X^B$ is a halogen atom, and other symbols are as defined above.

Step 14a

Compound (N2) can be produced by reacting compound (N1) with compound (A1) by a method similar to [Step 7a].

Step 14b

Compound (N3) can be produced by reacting compound (N2) by a method similar to [Step 5b].

Step 14c

Compound (N4) can be produced by hydrolyzing compound (N3) by a method similar to [Step 1c].

Production Method 15 (when A is a Heterocyclic Group Such as Morpholinyl, Pyrrolidinyl, Indolinyl or the Like)

Scheme 15

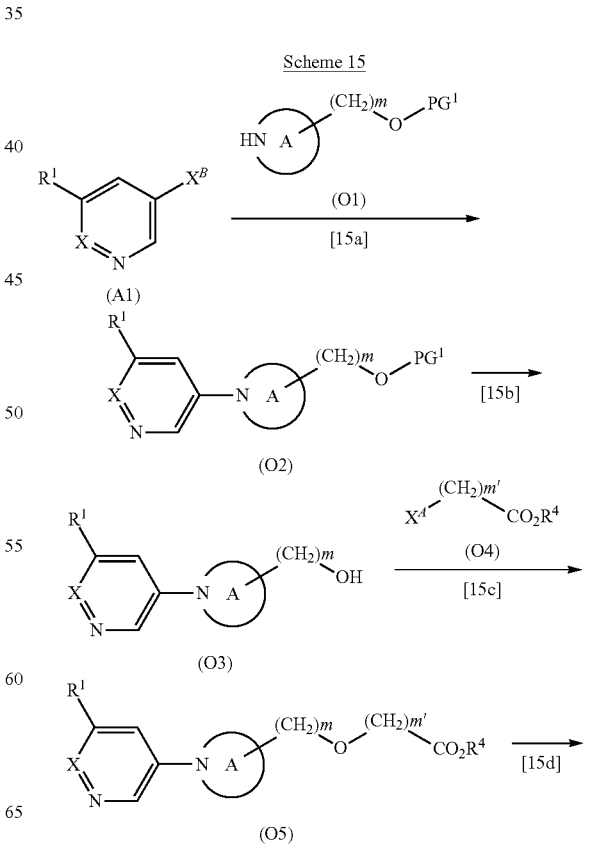

(A1)

(O2)

(O3)

(O5)

-continued

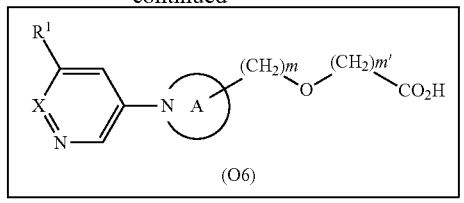

wherein $R^4$ is alkyl, $X^A$ and $X^B$ are halogen atoms, $PG^1$ is a hydroxyl-protecting group, and other symbols are as defined above.

Step 15a

Compound (O2) can be produced by reacting compound (O1) with compound (A1) by a method similar to [Step 7a].

Step 15b

Compound (O3) can be produced by removing $PG^1$ of compound (O2) by a general method.

Step 15c

Compound (O5) can be produced by reacting compound (O3) with compound (O4) in a solvent in the presence of a base and in the presence or absence of a phase-transfer catalyst. Examples of the solvent include toluene, benzene, xylene, tetrahydrofuran, 1,2-dimethoxyethane, 1,4-dioxane, acetone, acetonitrile, N,N-dimethylformamide, dimethyl sulfoxide and N-methylpyrrolidone. Examples of the base include sodium carbonate, potassium carbonate, cesium carbonate, sodium hydride, sodium tert-butoxide, potassium tert-butoxide, lithium bis(trimethylsilyl)amide, sodium bis(trimethylsilyl)amide, potassium bis(trimethylsilyl)amide, butyllithium and the like. Examples of the phase-transfer catalyst include halogenated quaternary ammonium salt, crown ether and the like. This reaction preferably proceeds at −40° C. to 120° C., preferably 0° C. to room temperature.

Step 15d

Compound (O6) can be produced by hydrolyzing compound (O5) by a method similar to [Step 1c].

Production Method 16 (when A is a Heterocyclic Group Such as Morpholinyl, Pyrrolidinyl, Indolinyl or the Like)

Scheme 16

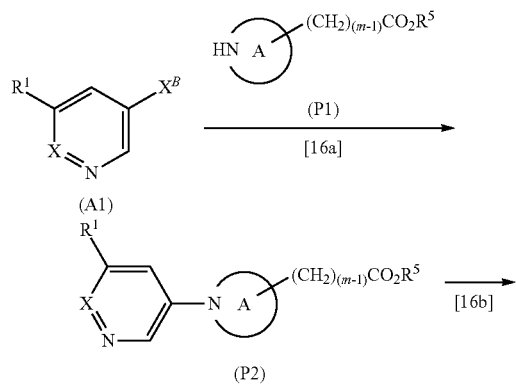

-continued

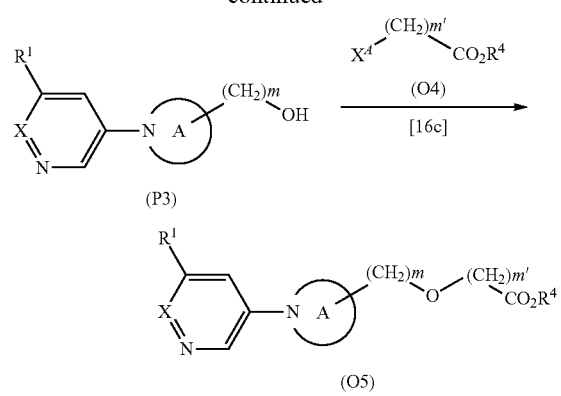

wherein $R^4$ and $R^5$ are alkyl, $X^A$ and $X^B$ are halogen atoms, and other symbols are as defined above.

Step 16a

Compound (P2) can be produced by reacting compound (P1) with compound (A1) by a method similar to [Step 7a].

Step 16b

Compound (P3) can be produced by reducing compound (P2) by a method similar to [Step 4c].

Step 16c

Compound (O5) can be produced by reacting compound (P3) with compound (O4) by a method similar to [Step 15c].

Production Method 17 (when A is a heterocyclic group such as morpholinyl, pyrrolidinyl, indolinyl or the like)

Scheme 17

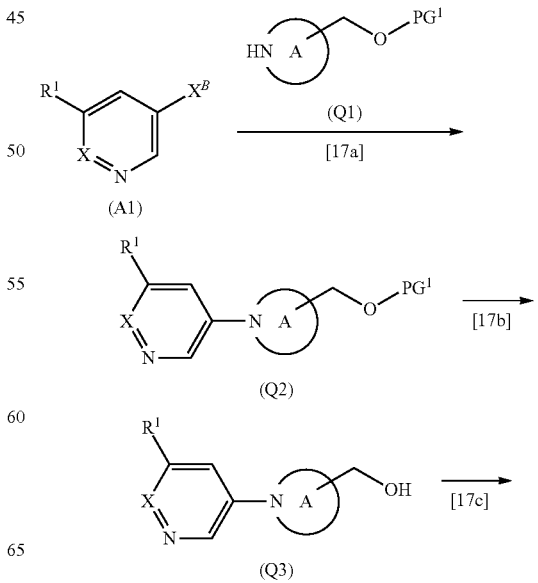

-continued

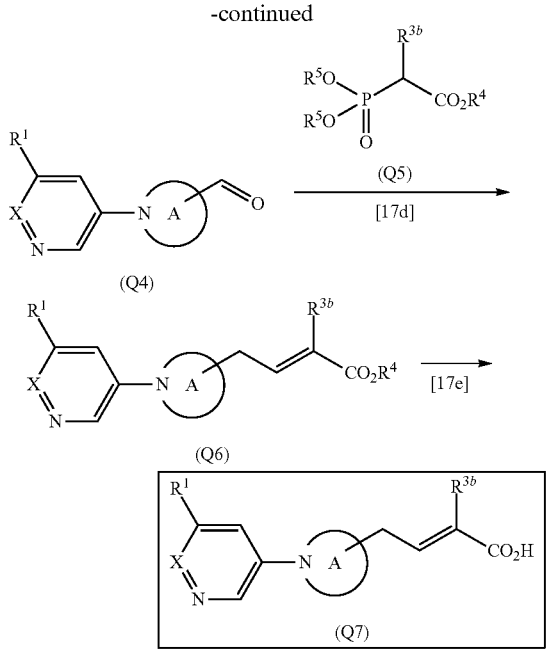

wherein $R^4$ and $R^5$ are alkyl, $X^B$ is a halogen atom, $PG^1$ is a hydroxyl-protecting group, and other symbols are as defined above.

Step 17a

Compound (Q2) can be produced by reacting compound (Q1) with compound (A1) by a method similar to [Step 7a].

Step 17b

Compound (Q3) can be produced by removing $PG^1$ of compound (Q2) by a general method.

Step 17c

Compound (Q4) can be produced by oxidizing primary alcohol of compound (Q3) into aldehyde by a general method. Particularly, it can be preferably produced under oxidation reaction conditions using dimethyl sulfoxide as described in Tetrahedron, 1978, 34, 1651-1660 or under oxidation reaction conditions using 2,2,6,6-tetramethyl-1-piperidinyloxy free radical as described in Org. Synth., 1990, 69, 212-217, or under oxidation reaction conditions using Dess-Martin periodinane as described in J. Org. Chem., 1983, 48, 4155-4156 and the like.

Step 17d

Compound (Q6) can be produced by reacting compound (Q4) with Wittig-Horner reagent (Q5) in a solvent in the presence of a base. Examples of the solvent include toluene, benzene, xylene, tetrahydrofuran, 1,2-dimethoxyethane, 1,4-dioxane, diethyl ether, N,N-dimethylformamide, dimethyl sulfoxide, N-methylpyrrolidone and the like. Examples of the base include sodium hydride, lithium tert-butoxide, sodium tert-butoxide, potassium tert-butoxide, lithium bis(trimethylsilyl)amide, sodium bis(trimethylsilyl)amide, potassium bis(trimethylsilyl)amide and the like. This reaction preferably proceeds at −20° C. to 100° C., especially 0° C. to 60° C.

Step 17e

Compound (Q7) can be produced by hydrolyzing compound (Q6) by a method similar to [Step 1c].

Production Method 18 (when A is Aryl or Heteroaryl Such as Phenyl, Pyridyl or the Like)

Scheme 18

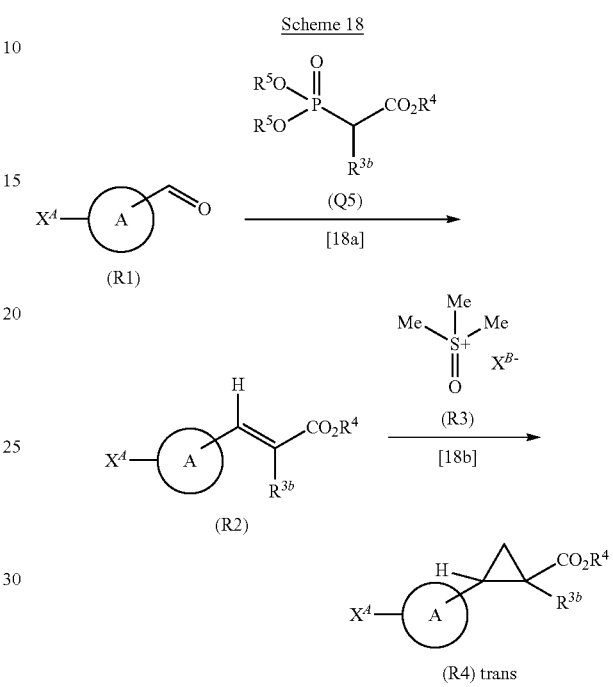

wherein $R^4$ and $R^5$ are alkyl, $X^A$ and $X^B$ are halogen atoms, and other symbols are as defined above.

Step 18a

Compound ($R^2$) can be produced by reacting compound ($R^1$) with Wittig-Horner reagent (Q5) by a method similar to [Step 17d].

Step 18b

Compound ($R^4$) can be produced by a Corey-Chaykovsky reaction of compound ($R^2$) and compound ($R^3$). Particularly, it can be preferably produced by a method using reaction conditions such as those described in J. Am. Chem. Soc., 1965, 87, 1353-1364.

Production Method 19 (when A is Aryl or Heteroaryl Such as Phenyl, Pyridyl or the Like)

Scheme 19

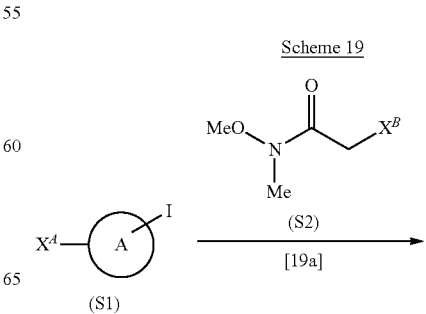

-continued

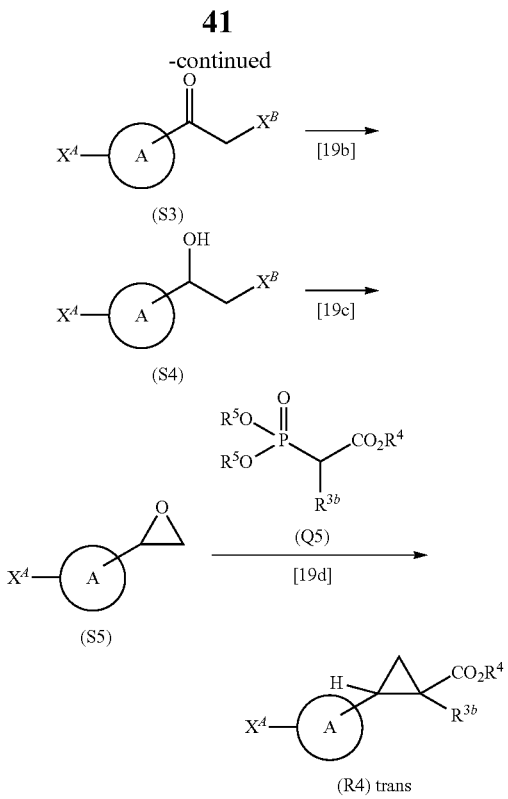

wherein $R^4$ and $R^5$ are alkyl, $X^A$ and $X^B$ are halogen atoms, and other symbols are as defined above.

Step 19a

Compound (S3) can be produced by reacting compound (S1) with compound (S2) in a solvent in the presence of a base. As the solvent, ether solvents such as tetrahydrofuran can be used. As the base, alkyl metals such as butyllithium, isopropylmagnesium chloride and the like can be used. This reaction preferably proceeds at −78° C. to 100° C., preferably 0° C. to room temperature.

Step 19b

Compound (S4) can be produced by treating compound (S3) with a reducing agent in a solvent. As the solvent, a mixed solvent of ether solvents such as tetrahydrofuran, and alcohol solvents such as methanol, ethanol, 2-propanol and the like can be used. As the reducing agent, sodium borohydride and the like is used. This reaction preferably proceeds at −78° C. to 100° C., preferably −10° C. to room temperature. In addition, an optically active form can be preferably produced by using a Noyori asymmetric hydrogen transfer reaction described in J. Am. Chem. Soc., 1996, 118, 2521-2522.

Step 19c

Compound (S5) can be produced by reacting compound (S4) in a solvent in the presence of a base in the presence or absence of a phase-transfer catalyst. Examples of the solvent include toluene, benzene, xylene, dichloromethane, 1,2-dichloroethane, tetrahydrofuran, 1,2-dimethoxyethane, 1,4-dioxane, diethyl ether, acetone, acetonitrile, N,N-dimethylformamide, dimethyl sulfoxide and N-methylpyrrolidone. Examples of the base include sodium carbonate, potassium carbonate, cesium carbonate, sodium hydride, sodium tert-butoxide, potassium tert-butoxide, lithium hexamethyl disilazide, sodium hexamethyl disilazide, potassium hexamethyl disilazide, lithium diisopropylamide, lithium hydroxide, sodium hydroxide, potassium hydroxide and the like. Examples of the phase-transfer catalyst include halogenated quaternary ammonium salt, crown ether and the like. This reaction preferably proceeds at −40° C. to 120° C., preferably 0° C. to room temperature.

Step 19d

Compound ($R^4$) can be produced by reacting compound (S5) with Wittig-Horner reagent (Q5) in a solvent in the presence of a base. Examples of the solvent include toluene, benzene, xylene, tetrahydrofuran, 1,2-dimethoxyethane, 1,4-dioxane, diethyl ether, N,N-dimethylformamide, dimethyl sulfoxide, N-methylpyrrolidone and the like. Examples of the base include sodium hydride, lithium tert-butoxide, sodium tert-butoxide, potassium tert-butoxide, lithium bis(trimethylsilyl)amide, sodium bis(trimethylsilyl)amide, potassium bis(trimethylsilyl)amide and the like. This reaction preferably proceeds at 0° C. to 120° C., preferably room temperature to 60° C.

Production Method 20 (when A is Aryl or Heteroaryl Such as Phenyl, Pyridyl or the Like)

Scheme 20

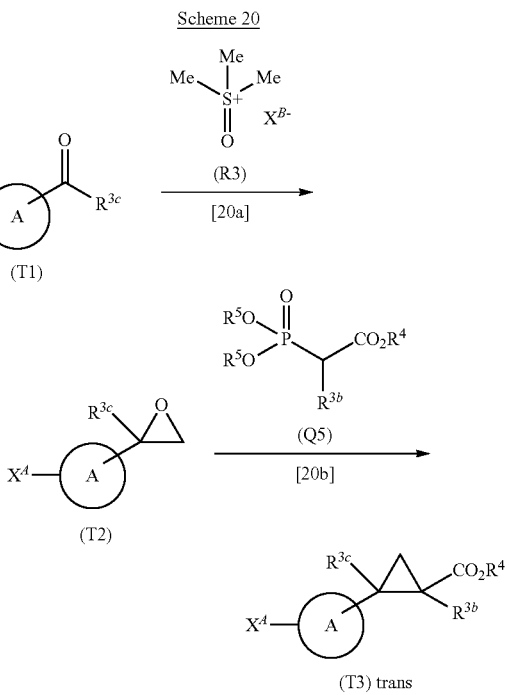

wherein $R^4$ and $R^5$ are alkyl, $X^A$ and $X^B$ are halogen atoms, and other symbols are as defined above.

Step 20a

Compound (T2) can be produced by a Corey-Chaykovsky reaction of compound (T1) and compound (R3). Particularly, it can be preferably produced by a method using reaction conditions such as those described in J. Am. Chem. Soc., 1965, 87, 1353-1364.

Step 20b

Compound (T3) can be produced by reacting compound (T2) with Wittig-Horner reagent (Q5) by a method similar to [Step 19d].

Production Method 21 (when A is a Heterocyclic Group Such as Morpholinyl or the Like)

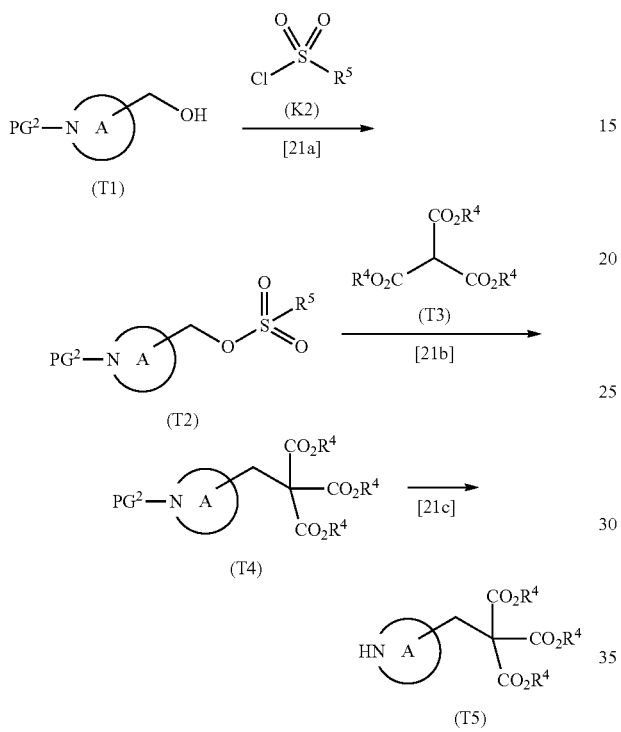

Scheme 21

(T1)

(T2)

(T4)

(T5)

wherein $R^4$ is alkyl, $R^5$ is alkyl or aryl, $PG^2$ is an amino-protecting group, and other symbols are as defined above.

Step 21a

Compound (T2) can be produced by reacting compound (T1) with compound (K2) by a method similar to [Step 11a].

Step 21b

Compound (T4) can be produced by reacting compound (T2) with compound (T3) in a solvent in the presence of a base. Examples of the solvent include toluene, benzene, xylene, tetrahydrofuran, 1,2-dimethoxyethane, 1,4-dioxane, diethyl ether, acetone, acetonitrile, N,N-dimethylformamide, dimethyl sulfoxide and N-methylpyrrolidone. Examples of the base include sodium carbonate, potassium carbonate, cesium carbonate, sodium hydride, sodium tert-butoxide, potassium tert-butoxide, lithium hexamethyl disilazide, sodium hexamethyl disilazide, potassium hexamethyl disilazide, lithium diisopropylamide and the like. To accelerate the reaction, sodium iodide, potassium iodide, cesium iodide and the like may also be added. This reaction preferably proceeds at 0° C. to 120° C., preferably room temperature to 100° C.

Step 21c

Compound (T5) can be produced by removing $PG^2$ of compound (T4) by a general method.

Production Method 22 (when A is a Heterocyclic Group Such as Morpholinyl or the Like)

Scheme 22

(U1)

(U2)

(U3)

(U4)

(U5)

(U6)

(U7)

(U8)

wherein $R^4$ and $R^5$ are alkyl, $PG^1$ is a hydroxyl-protecting group, $PG^2$ is an amino-protecting group, and other symbols are as defined above.

Step 22a

Compound (U2) can be produced by reacting compound (U1) by a method similar to step [4c].

Step 22b

Compound (U3) can be produced by protecting the hydroxyl group of compound (U2) with $PG^1$ by a general method.

Step 22c

Compound (U4) can be produced by a Simmons-Smith reaction of compound (U3). Particularly, it can be preferably produced by a method using reaction conditions such as those described in Tetrahedron Lett., 1966, 28, 3353-3354.

Step 22d

Compound (U5) can be produced by removing PG$^1$ of compound (U4) by a general method.

Step 22e

Compound (U6) can be produced by oxidizing the primary alcohol of compound (U5) into carboxylic acid by a general method. Particularly, it can be preferably produced under oxidation reaction conditions using 2,2,6,6-tetramethyl-1-piperidinyloxy free radical such as those described in Org. Synth., 2005, 81, 195-203 or oxidation reaction conditions using ruthenium (IV) oxide such as those described in Tetrahedron, 1972, 28, 4259-4266.

Step 22f

Compound (U7) can be produced by a general method of converting carboxylic acid into an ester such as a method of reacting compound (U6) with alcohol in the presence of a condensing agent, a method of reacting compound (U6) with an alkylating agent in the presence of a base and the like.

Step 22g

Compound (U8) can be produced by removing PG$^2$ of compound (U7) by a general method.

Production Method 23 (when A is a Heterocyclic Group Such as Morpholinyl or the Like)

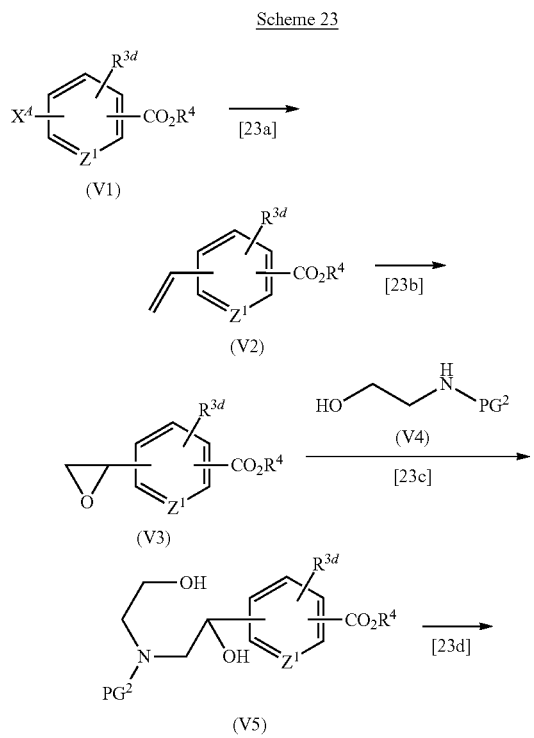

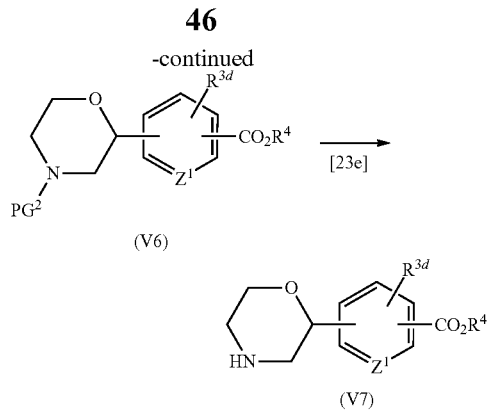

wherein $Z^1$ is —N= or —CH=, $R^4$ is alkyl, $X^4$ is a halogen atom, PG$^2$ is an amino-protecting group, and other symbols are as defined above.

Step 23a

Compound (V2) can be produced by reacting compound (V1) with vinylboronic acid ester by a method similar to [Step 1b].

Step 23b

Compound (V3) can be produced by reacting compound (V2) with a halogenating reagent in a solvent, and treating with a base. As the solvent, a mixed aqueous solution of tetrahydrofuran, 1,2-dimethoxyethane, 1,4-dioxane, acetonitrile, N,N-dimethylformamide, dimethyl sulfoxide, N-methylpyrrolidone, acetone, tert-butyl alcohol and the like can be preferably used. Examples of the halogenating reagent include N-iodosuccinimide, N-bromosuccinimide and the like. Examples of the base include sodium carbonate, potassium carbonate, cesium carbonate, sodium hydride, lithium tert-butoxide, sodium tert-butoxide, potassium tert-butoxide, tripotassium phosphate, lithium hydroxide, sodium hydroxide, potassium hydroxide and the like. This reaction preferably proceeds at −20° C. to 100° C., preferably 0° C. to 60° C.

Step 23c

Compound (V5) can be produced by reacting compound (V3) with compound (V4) in a solvent in the presence or absence of a base. Examples of the solvent include toluene, benzene, xylene, tetrahydrofuran, 1,2-dimethoxyethane, 1,4-dioxane, diethyl ether, acetonitrile, N,N-dimethylformamide, dimethyl sulfoxide and N-methylpyrrolidone. Examples of the base include sodium carbonate, potassium carbonate, cesium carbonate, sodium hydride, sodium tert-butoxide, potassium tert-butoxide, lithium bis(trimethylsilyl)amide, sodium bis(trimethylsilyl)amide, potassium bis(trimethylsilyl)amide and the like. This reaction preferably proceeds at 0° C. to 180° C., preferably room temperature to 100° C.

Step 23d

Compound (V6) can be produced by reacting compound (V5) in a solvent in the presence of a Mitsunobu reagent and a phosphine reagent. Examples of the Mitsunobu reagent include diethyl azodicarboxylate, diisopropyl azodicarboxylate, di-tert-butyl azodicarboxylate, 1,1'-(azodicarbonyl)

dipiperidine, di-p-nitrobenzyl azodicarboxylate, 1,1'-azobis (N,N'-diisopropylformamide), 1,6-dimethyl-1,5,7-hexahydro-1,4,6,7-tetrazocine-2,5-dione, N,N,N',N'-tetramethylazodicarboxamide, di-p-chlorobenzyl azodicarboxylate, di-2-methoxyethyl azodicarboxylate and the like. Examples of the phosphine reagent include triphenylphosphine, tri-n-butylphosphine, tri-n-octylphosphine, tricyclohexylphosphine, diphenyl-2-pyridylphosphine and the like. When a Tsunoda reagent such as cyanomethylenetributylphosphorane, cyanomethylenetrimethylphosphorane and the like is used, this reaction also preferably proceeds even in the absence of a phosphine reagent. Examples of the solvent include toluene, benzene, xylene, dichloromethane, dichloroethane, chloroform, tetrahydrofuran, 1,2-dimethoxyethane, 1,4-dioxane, diethyl ether, acetonitrile, ethyl acetate, N,N-dimethylformamide, dimethyl sulfoxide, N-methylpyrrolidone and the like. This reaction preferably proceeds at −40° C. to 100° C., preferably 0° C. to 70° C.

Step 23e

Compound (V7) can be produced by removing $PG^2$ of compound (V6) by a general method.

Production Method 24 (when A is a Heterocyclic Group Such as Morpholinyl or the Like)

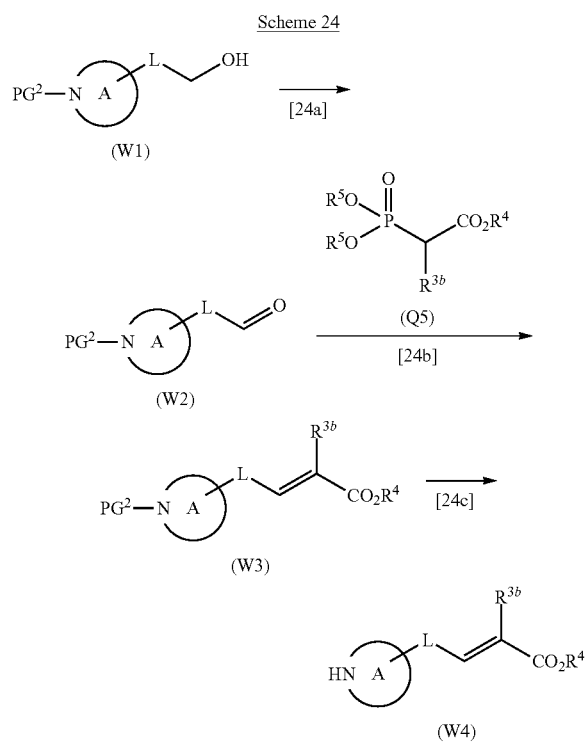

wherein $R^4$ and $R^5$ are alkyl, $PG^2$ is an amino-protecting group, and other symbols are as defined above.

Step 24a

Compound (W2) can be produced by reacting compound (W1) by a method similar to [Step 17c].

Step 24b

Compound (W3) can be produced by reacting compound (W2) with a Wittig-Horner reagent (Q5) by a method similar to [Step 17d].

Step 24c

Compound (W4) can be produced by removing $PG^2$ of compound (W3) by a general method.

Production Method 25

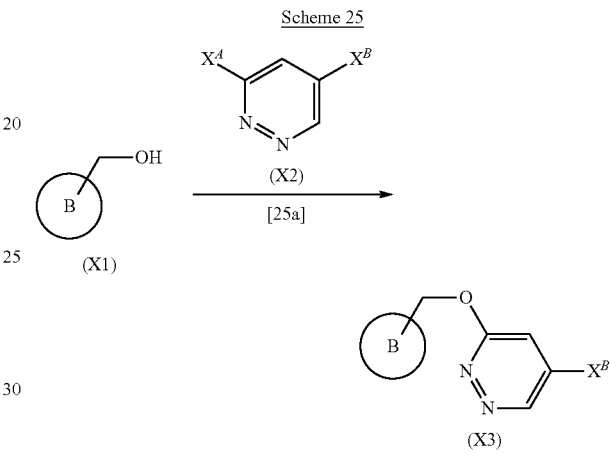

wherein $X^A$ and $X^B$ are halogen atoms, ring B is

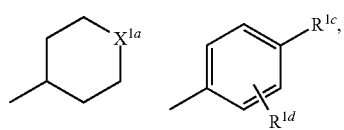

and other symbols are as defined above.

Step 25a

Compound (X3) can be produced by reacting compound (X1) with compound (X2) in a solvent in the presence of a base and in the presence or absence of a phase-transfer catalyst. Examples of the solvent include toluene, benzene, xylene, dichloromethane, dichloroethane, chloroform, tetrahydrofuran, 1,2-dimethoxyethane, 1,4-dioxane, diethyl ether, acetone, acetonitrile, N,N-dimethylformamide, dimethyl sulfoxide, N-methylpyrrolidone can be mentioned. Examples of the base include sodium carbonate, potassium carbonate, cesium carbonate, sodium hydride, sodium tert-butoxide, potassium tert-butoxide, lithium bis(trimethylsilyl)amide, sodium bis(trimethylsilyl)amide, potassium bis(trimethylsilyl)amide, butyllithium and the like. This reaction particularly preferably proceeds using sodium hydride, butyllithium. Examples of the phase-transfer catalyst include halogenated quaternary ammonium salt, crown ether and the like. This reaction preferably proceeds at 0° C. to 120° C., preferably room temperature to 60° C.

Production Method 26

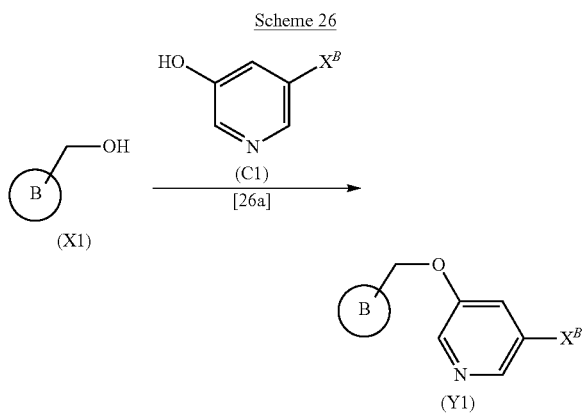

wherein $X^B$ is a halogen atom, ring B is

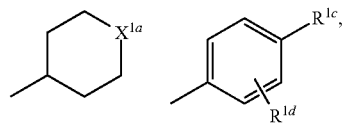

and other symbols are as defined above.

Step 26a

Compound (Y1) can be produced by reacting compound (X1) with compound (C1) by a method similar to [Step 3b].

Production Method 27

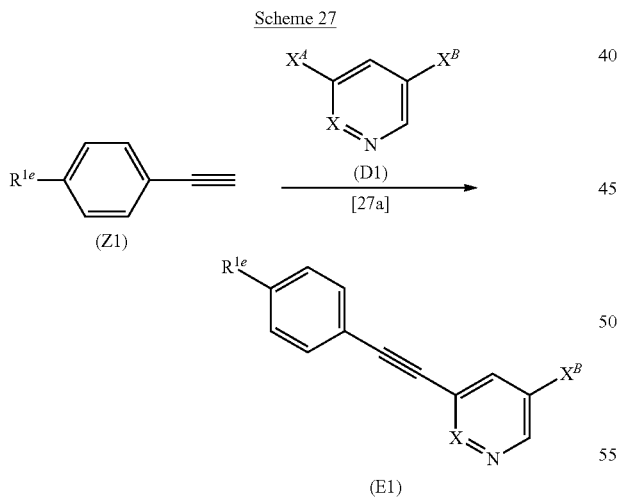

wherein $X^A$ and $X^B$ are halogen atoms, and other symbols are as defined above.

Step 27a

Compound (E1) can be produced by reacting compound (Z1) with compound (D1) in a solvent in the presence or absence of a catalytic amount of copper iodide in the presence of a transition metal complex and a base. As the solvent, toluene, benzene, xylene, tetrahydrofuran, 1,2-dimethoxyethane, 1,4-dioxane, acetonitrile, ethyl acetate, N,N-dimethylformamide, dimethyl sulfoxide, N-methylpyrrolidone and the like can be appropriately used. As the transition metal complex, a 0 valent palladium complex such as tetrakis(triphenylphosphine)palladium(0), tris(dibenzylideneacetone)dipalladium(0), bis(dibenzylideneacetone) palladium(0), bis(tri-tert-butylphosphine)palladium(0) or bis(tricyclohexylphosphine)palladium(0), or a divalent palladium complex such as palladium(II) acetate, bis(triphenylphosphine)palladium(II) dichloride, bis(tri-O-tolylphosphine)palladium(II) dichloride, bis(tricyclohexylphosphine)palladium(II) dichloride, bis(benzonitrile)palladium(II) dichloride, bis(acetonitrile)palladium(II) dichloride, [1,1'-bis(diphenylphosphino)ferrocene]palladium(II) dichloride or bis(di-tert-butyl(4-dimethylaminophenyl)phosphine)dichloropalladium(II) is used.

In addition, a suitable ligand may be added to the transition metal complex. Examples of a suitable ligand include tri-tert-butylphosphine, tri-cyclohexylphosphine, 1,1'-bis(diphenylphosphino)ferrocene, (±)-2,2'-bis(diphenylphosphino)-1,1'-binaphthyl, tri(ortho-tolyl)phosphine, 1,2,3,4,5-pentaphenyl-1'-(di-tert-butylphosphino)ferrocene, 4,5-bis(diphenylphosphino)-9,9-dimethylxanthene, di(1-adamantyl)-n-butylphosphine, (2-biphenyl)di-tert-butylphosphine, (S)-1-[(1R)-2-(diphenylphosphino)ferrocenyl]ethyldicyclohexylphosphine, 2-dicyclohexylphosphino-2',6'-diisopropoxybiphenyl, 2-dicyclohexylphosphino-2',6'-dimethoxybiphenyl, 2-dicyclohexylphosphino-2'-(N,N-dimethylamino)biphenyl, 2-dicyclohexylphosphino-2',4',6'-triisopropylbiphenyl, 2-di-tert-butylphosphino-2',4',6'-triisopropyl-1,1'-biphenyl, 2-(dicyclohexylphosphino)-3,6-dimethoxy-2',4',6'-triisopropyl-1,1'-biphenyl and the like. Examples of the base include sodium hydrogen carbonate, sodium carbonate, potassium carbonate, cesium carbonate, sodium acetate, potassium acetate, tripotassium phosphate, dipotassium hydrogen phosphate, potassium dihydrogen phosphate, triethylamine, diisopropylethylamine, diisopropylamine and the like. The amount of the transition metal complex to be used is 0.01-0.5 equivalents, preferably 0.03-0.1 equivalents, relative to compound (Z1). The amount of the base to be used is 1-10 equivalents, preferably 2-7 equivalents, relative to compound (Z1). Particularly, it can be preferably produced by a method using reaction conditions such as those described in J. Organomet. Chem., 2002, 653, 46-49.

Production Method 28

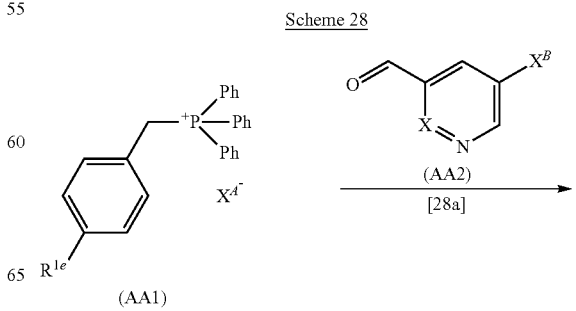

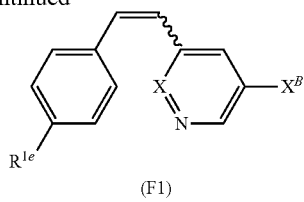

(F1)

wherein $X^A$ and $X^B$ are halogen atoms, and other symbols are as defined above.

Step 28a

Compound (F1) can be produced by reacting compound (AA1) with compound (AA2) in a solvent in the presence of a base. As the solvent, ether solvents such as tetrahydrofuran and amide solvents such as N,N-dimethylformamide can be appropriately used. Examples of the base include sodium hydride, lithium bis(trimethylsilyl)amide, sodium bis(trimethylsilyl)amide, potassium bis(trimethylsilyl)amide, butyllithium and the like. This reaction preferably proceeds at −78° C. to 60° C., preferably −10° C. to room temperature.

Production Method 29

Scheme 29

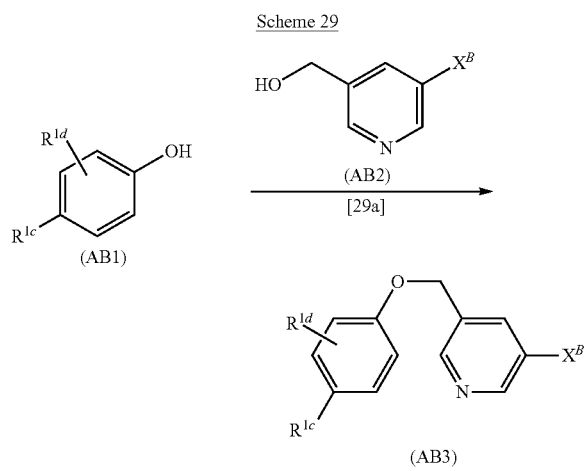

wherein $X^B$ is a halogen atom, and other symbols are as defined above.

Step 29a

Compound (AB3) can be produced by reacting compound (AB1) with compound (AB2) by a method similar to [Step 3b].

The thus-obtained compound of the present invention can be isolated and purified by a separation means known per se, for example, concentration, concentration under reduced pressure, solvent extraction, crystallization, recrystallization, chromatography and the like. When the compound of the present invention is obtained as a free form, it can be converted to an object salt by a method known per se or a method analogous thereto. When the compound is obtained as a salt, it can be converted to a free form or other object salt by a method known per se or a method analogous thereto.

The compound of the present invention has a basic group and an acidic group in a molecule. Thus, examples of the pharmacologically acceptable salt thereof include metal salt, ammonium salt, salts with organic bases, salts with inorganic acids, salts with organic acids, salts with basic amino acids, salts with acidic amino acids and the like.

Preferable examples of the metal salt include alkali metal salts such as sodium salt, potassium salt and the like; alkaline earth metal salts such as calcium salt, magnesium salt, barium salt and the like; aluminum salt, barium salt and the like.

Preferable examples of the salts with organic bases include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like.

Preferable examples of the salts with inorganic acids include salts with hydrochloric acid, hydrobromic acid, nitric acid, sulfuric acid, phosphoric acid and the like.

Preferable examples of the salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salts with basic amino acids include salts with arginine, lysine, ornithine and the like.

Preferable examples of the salts with acidic amino acid include salts with aspartic acid, glutamic acid and the like.

The compound of the present invention also encompasses, besides the above-mentioned Compound (1) and a pharmacologically acceptable salt thereof, hydrates and solvates thereof.

When the compound of the present invention has an isomer such as optical isomer, stereoisomer, regio isomer, rotamer and the like, all these isomers and mixtures are encompassed in the compound of the present invention. For example, when the compound of the present invention contains an optical isomer, an optical isomer resolved from a racemate is also encompassed in the compound of the present invention. These isomers can be obtained as respective single products by a synthesis method, a separation method (e.g., concentration, solvent extraction, column chromatography, recrystallization) known per se.

Furthermore, enantiometric excess (% ee) can be determined using chiral HPLC against a standard substance. The enantiometric excess can be calculated as follows:

$$[(R\ mol - S\ mol)/(R\ mol + S\ mol)] \times 100\%$$

In the formula, R mol and S mol are R and S mol fractions in the mixture such that R mol+S mol=1. Alternatively, enantiometric excess can also be calculated from the specific optical rotation of the desired enantiomer and the prepared mixture as follows:

$$ee = ([\alpha\text{-}Obs]/[\alpha\text{-max}]) \times 100\%$$

The compound of the present invention may be a crystal, which is encompassed in the compound of the present invention whether it has a single crystal form or it is a crystal form mixture. The crystal can be produced by crystallization by applying a crystallization method known per se. In addition, the compound of the present invention may be a pharmaceutically acceptable cocrystal or co-crystal salt. As used herein, the cocrystal or co-crystal salt means a crystalline substance consisting of two or more particular solids at room temperature, wherein each has different physical properties (e.g., structure, melting point, melting heat, hygroscopicity, stability). The cocrystal or co-crystal salt can be produced by cocrystallization method known per se.

A compound labeled with an isotope (e.g., $^2H$, $^3H$, $^{13}C$, $^{14}C$, $^{15}N$, $^{35}S$) and the like are also encompassed in the compound of the present invention.

EXAMPLES

The present invention is explained in detail in the following by referring to Examples and Experimental Examples, which are not to be construed as limitative.

In the Examples, the following abbreviations are used.
Me: methyl
Et: ethyl
iPr: isopropyl
tBu: tert-butyl
Ph: phenyl
Bn: benzyl
Boc: tert-butoxycarbonyl
TBDPS: tert-butyldiphenylsilyl
Ms: methanesulfonyl
Tf: trifluoromethanesulfonyl
Ts: 4-toluenesulfonyl
HPLC: high performance liquid chromatography

Example 1

(1S,2S)-2-[2-methoxy-5-(6-{[trans-4-(trifluoromethyl)cyclohexyl]methoxy}pyridazin-4-yl)phenyl]cyclopropanecarboxylic acid, (1R,2R)-2-[2-methoxy-5-(6-{[trans-4-(trifluoromethyl)cyclohexyl]methoxy}pyridazin-4-yl)phenyl]cyclopropanecarboxylic acid

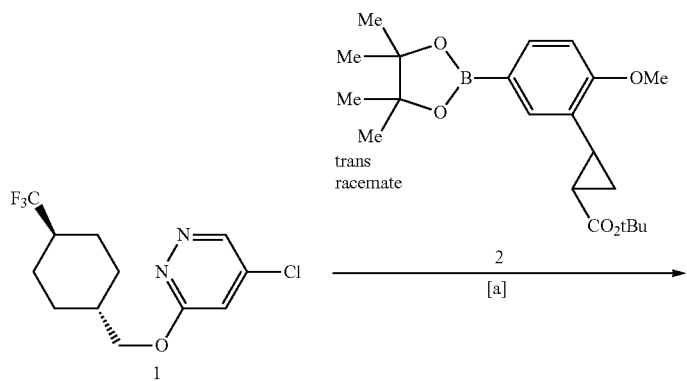

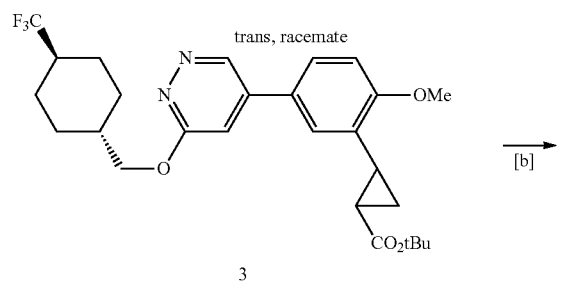

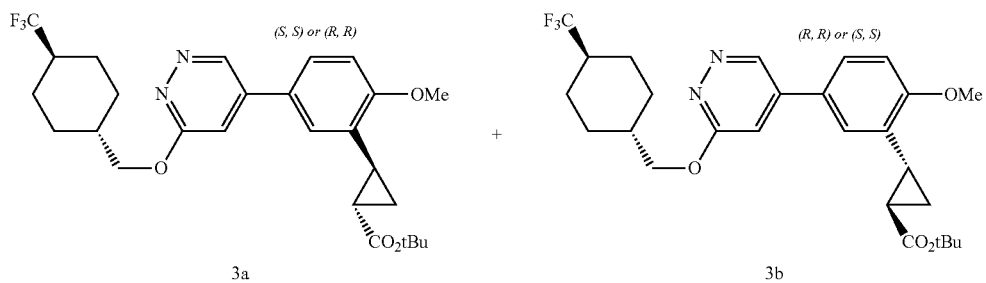

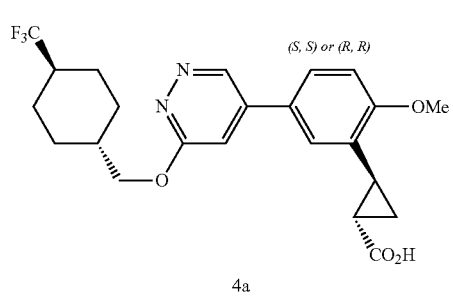

4a (S, S) or (R, R)

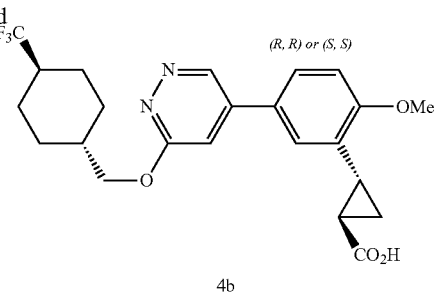

4b (R, R) or (S, S)

Step a

To a solution of compound 1 (200 mg, 679 μmol) obtained in Reference Example 44, Step a, and compound 2 (508 mg, 1.36 mmol) obtained in Reference Example 1, Step c, in 1,4-dioxane (10 mL) were added a solution of potassium carbonate (188 mg, 1.36 mmol) in water (1.0 mL), tris(dibenzylideneacetone)dipalladium(0) (62 mg, 68 μmol) and 2-dicyclohexylphosphino-2',4',6'-triisopropylbiphenyl (129 mg, 271 μmol), and the mixture was stirred in a nitrogen atmosphere with heating under reflux overnight. The reaction mixture was allowed to cool to room temperature, diluted with ethyl acetate, and filtered through celite. The filtrate was washed with water and saturated brine, dried over anhydrous sodium sulfate, filtered and concentrated. The residue was purified by NH silica gel chromatography and silica gel chromatography to give compound 3 (207 mg, 60.2%). MS(ESI) m/z: 507 (M+1)$^+$.

Step b

Chiral resolution of compound 3 (170 mg) by chiral HPLC (CHIRAL PAK IA, 30×250, tert-butyl methyl ether:methanol:diethylamine=95:5:0.1, 20 mL/min) gave compound 3a (82.4 mg, 99.9% ee, peak at retention time 17 min) and compound 3b (81.1 mg, 99.3% ee, peak at retention time 23 min).

Step c

To a solution of compound 3a (82.4 mg, 160 μmol) in dichloromethane (2.0 mL) was added trifluoroacetic acid (249 μL), and the mixture was stirred at room temperature for 4 hr. The reaction solution was concentrated under reduced pressure, and the residue was purified by silica gel chromatography to give compound 4a (54.3 mg, 74.1%). This enantiomer was used as Example 1-1. MS(ESI) m/z: 451 (M+1)$^+$.

Step d

To a solution of compound 3b (81.1 mg, 160 μmol) in dichloromethane (2.0 mL) was added trifluoroacetic acid (245 μL), and the mixture was stirred at room temperature for 4 hr. To the reaction solution was further added trifluoroacetic acid (122 μL), and the mixture was stirred at room temperature for 4 hr. The reaction solution was concentrated under reduced pressure, and the residue was purified by silica gel chromatography to give compound 4b (56.1 mg, 77.8%). This enantiomer was used as Example 1-2. MS(ESI) m/z: 451 (M+1)$^+$.

Example 2 trans-2-[2-methoxy-5-(5-{[4-(trifluoromethoxy)benzyl]oxy}pyridin-3-yl)phenyl]cyclopropanecarboxylic acid

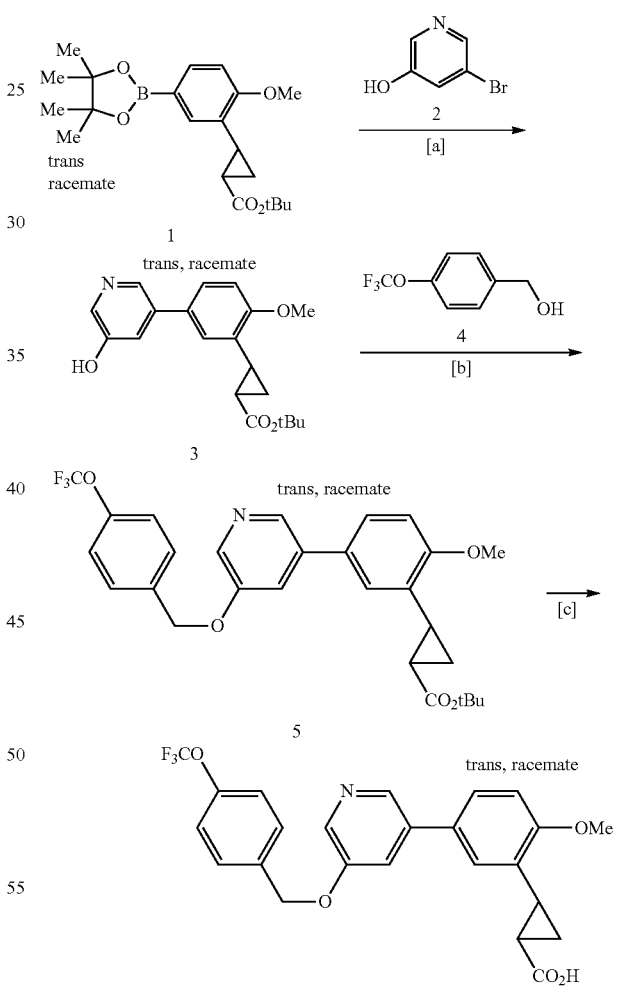

Step a

To a solution of compound 1 (2.37 g, 6.33 mmol) obtained in Reference Example 1, Step c, and compound 2 (1.00 g, 5.75 mmol) in 1,4-dioxane (20 mL) were added a solution of tripotassium phosphate (3.66 g, 17.2 mmol) in water (2 mL) and bis(di-tert-butyl (4-dimethylaminophenyl)phosphine) dichloropalladium(II) (204 mg, 287 μmol), and the mixture was stirred in a nitrogen atmosphere under heating at 80° C. overnight. The reaction mixture was neutralized with 1 M-hydrochloric acid and extracted with ethyl acetate. The organic layer was washed with saturated brine, dried over anhydrous sodium sulfate, filtered and concentrated. The residue was purified by silica gel chromatography to give compound 3 (894 mg, 45.6%).

MS (APCI) m/z: 342 (M+1)+.

Step b

To a solution of compound 3 (60.0 mg, 176 μmol) and compound 4 (64.0 μL, 439 μmol) in tetrahydrofuran (1.0 mL) were added triphenylphosphine (115 mg, 439 μmol) and bis(2-methoxyethyl) azodicarboxylate (103 mg, 439 μmol), and the mixture was stirred at room temperature for 2 days. The reaction mixture was concentrated under reduced pressure, and the residue was purified by silica gel chromatography to give compound 5 (46.2 mg, 51.0%). MS(ESI) m/z: 516 (M+1)+.

Step c

To a solution of compound 5 (44.0 mg, 85.4 μmol) in dichloromethane (1.0 mL) was added trifluoroacetic acid (653 μL), and the mixture was stirred at room temperature overnight. The reaction solution was concentrated under reduced pressure, and the residue was subjected to solid phase extraction purification using cation exchange resin column (Waters, PoraPak™, RxnCX) and purified by silica gel chromatography to give compound 6 (23.9 mg, 61.0%). MS(APCI) m/z: 460 (M+1)+

Example 3 trans-2-[2-methoxy-5-(6-{[4-(trifluoromethyl)phenoxy]methyl}pyridazin-4-yl)phenyl]cyclopropanecarboxylic acid

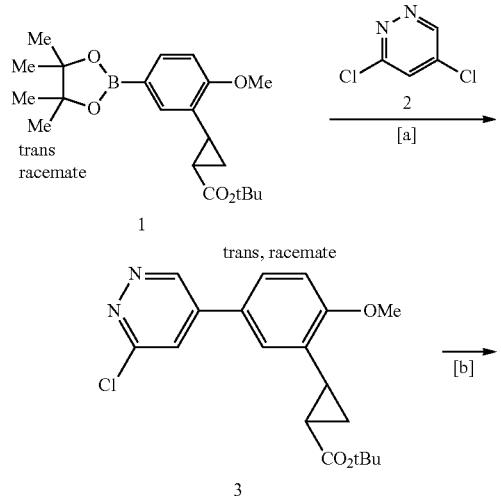

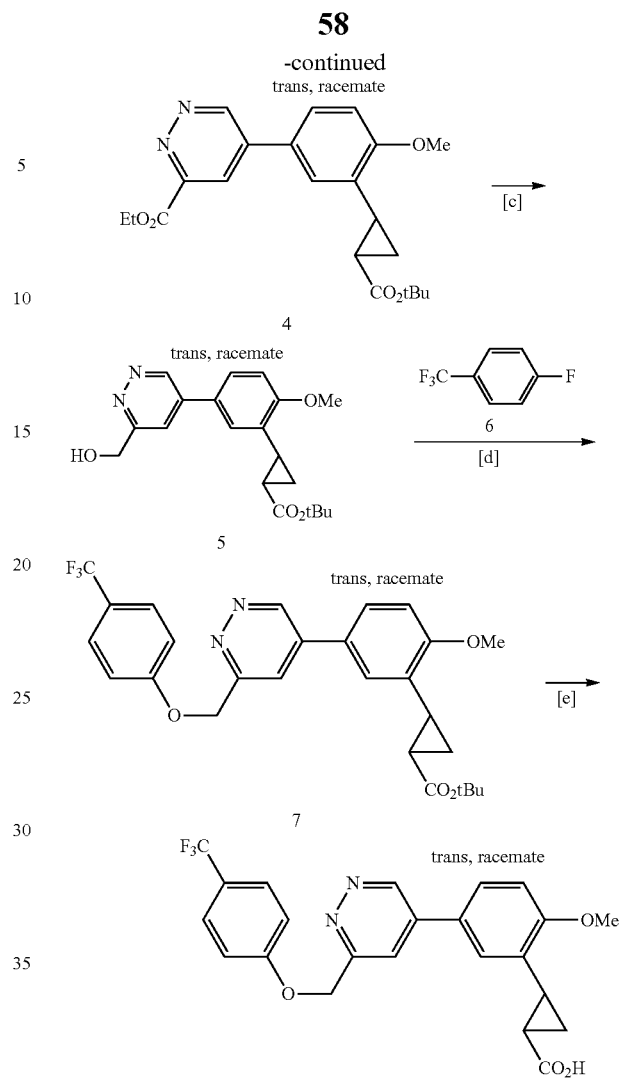

Step a

To a solution of compound 1 (1.26 g, 3.36 mmol) obtained in Reference Example 1, Step c, compound 2 (500 mg, 3.36 mmol) in toluene (13 mL) were added a solution of potassium fluoride (487 mg, 8.39 mmol) in water (3.4 mL), palladium(II) acetate (37.7 mg, 168 μmol) and 1,2,3,4,5-pentaphenyl-1'-(di-tert-butylphosphino) ferrocene (119 mg, 168 μmol), and the mixture was stirred in an nitrogen atmosphere under heating at 70° C. for 19 hr. The reaction mixture was allowed to cool to room temperature, filtered through celite, and washed with ethyl acetate (50 mL). The filtrate was concentrated under reduced pressure, and the residue was purified by silica gel chromatography to give compound 3 (398 mg, 32.9%).

MS (ESI) m/z: 361, 363 (M+1)+.

Step b

To a mixed solution of compound 3 (370 mg, 1.03 mmol) in N,N-dimethylformamide (4.0 mL) and ethanol (1.0 mL) were added sodium acetate (168 mg, 2.05 mmol) and [1,1'-bis(diphenylphosphino)ferrocene]palladium(II) dichloride (83.7 mg, 103 μmol), and the mixture was stirred in a carbon monoxide atmosphere under heating at 90° C. for 4 hr. To the reaction mixture were further added ethanol (1.0 mL) and [1,1'-bis(diphenylphosphino)ferrocene]palladium (II) dichloride (83.7 mg, 103 μmol), and the mixture was stirred in a carbon monoxide atmosphere under heating at 90° C. overnight. The reaction mixture was allowed to cool to room temperature, water (30 mL) and ethyl acetate (30 mL) were added, and the mixture was filtered through celite. The filtrate was phase separated, and the organic layer was washed with water (30 mL) and saturated brine (30 mL), dried over anhydrous sodium sulfate, filtered and concentrated. The residue was purified by NH silica gel chromatography to give compound 4 (98.3 mg, 24.1%).

MS (ESI) m/z: 399 (M+1)+.

Step c

To a mixed suspension of compound 4 (95.0 mg, 239 μmol) in ethanol (3.0 mL) and tetrahydrofuran (0.50 mL) was added sodium borohydride (18.0 mg, 477 μmol) under ice-cooling and the mixture was stirred for 1.5 hr while warming to room temperature. Water was added to the reaction mixture, and the mixture was extracted with chloroform. The organic layer was dried over anhydrous sodium sulfate, filtered and concentrated. The residue was purified by silica gel chromatography to give compound 5 (45.5 mg, 53.5%). MS(ESI) m/z: 357 (M+1)+.

Step d

To a solution of compound 5 (68.6 mg, 160 μmol) and compound 6 (66.3 mg, 404 μmol) in N,N-dimethylformamide (2.1 mL) was added sodium hydride (60 wt %, 41.2 mg, 1.03 mmol), and the mixture was stirred under heating at 100° C. for 2 hr. The reaction mixture was allowed to cool to room temperature, water was added, and the mixture was extracted with ethyl acetate. The organic layer was washed with water and saturated brine, dried over anhydrous sodium sulfate, filtered and concentrated. The residue was purified by silica gel chromatography to give compound 7 (14.6 mg, 28.9%). MS(ESI) m/z: 501 (M+1)+.

Step e

To a solution of compound 7 (14.6 mg, 29.2 μmol) in dichloromethane (1.0 mL) was added trifluoroacetic acid (100 μL), and the mixture was stirred at room temperature for 5 hr. The reaction solution was concentrated under reduced pressure, and the residue was purified by silica gel chromatography to give compound 8 (11.2 mg, 86.4%). MS(ESI) m/z: 445 (M+1)+.

Example 4 trans-2-[2-methoxy-5-(6-{2-[4-(trifluoromethoxy)phenyl]ethyl}pyridazin-4-yl)phenyl]cyclopropanecarboxylic acid

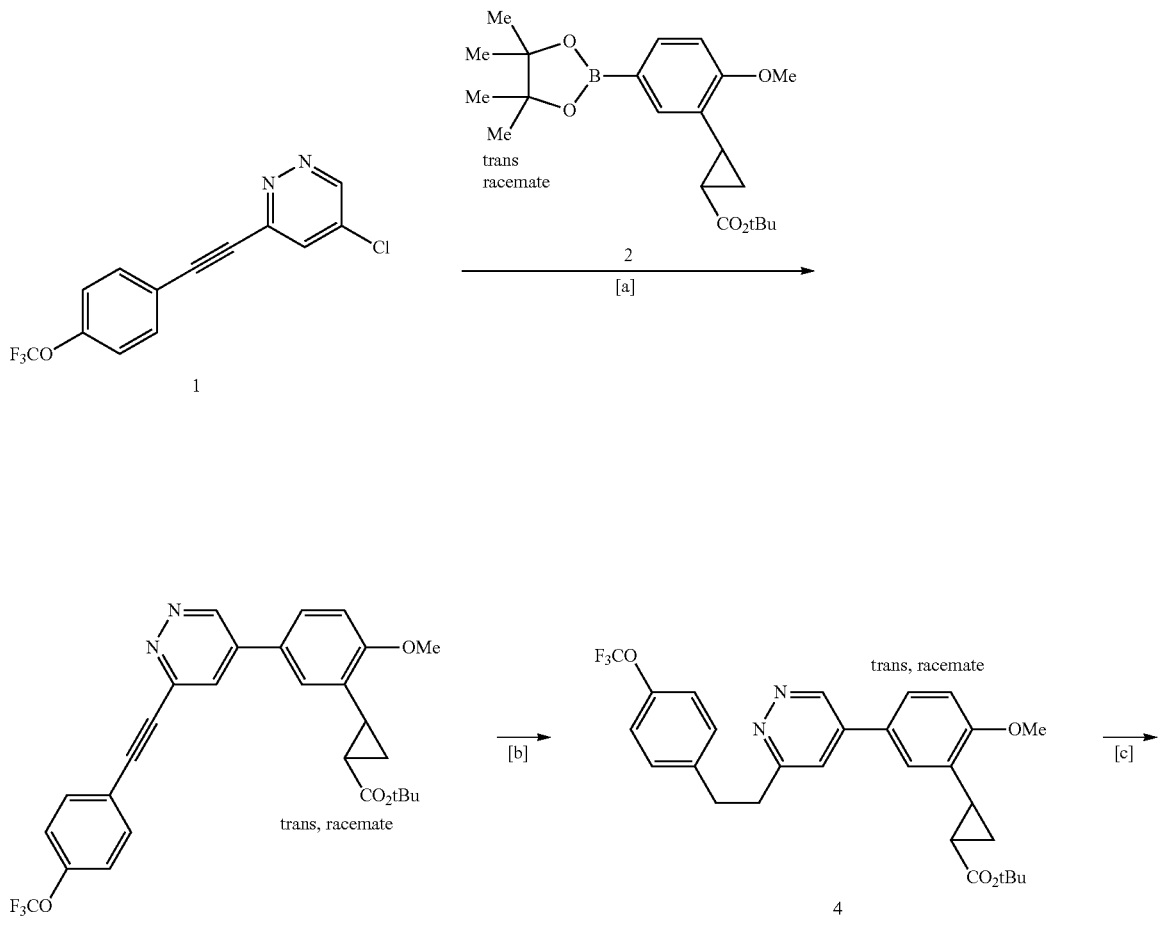

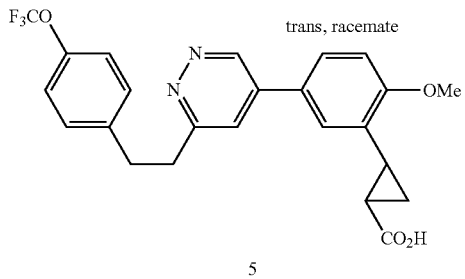

5

Step a

To a solution of compound 1 (80.0 mg, 268 μmol) obtained in Reference Example 46, Step a, and compound 2 (201 mg, 536 μmol) obtained in Reference Example 1, Step c, in 1,4-dioxane (2.4 mL) were added a solution of potassium carbonate (74.1 mg, 536 μmol) in water (0.24 mL), tris(dibenzylideneacetone)dipalladium(0) (25 mg, 27 μmol) and 2-dicyclohexylphosphino-2',4',6'-triisopropylbiphenyl (51.1 mg, 107 μmol), and the mixture was stirred in a nitrogen atmosphere with heating under reflux overnight. The reaction mixture was allowed to cool to room temperature and purified by NH silica gel chromatography to give compound 3 (52.2 mg, 38.2%). MS (ESI) m/z: 511 (M+1)+.

Step b

To a solution of compound 3 (50 mg, 98 μmol) in methanol (3.0 mL) was added 10%-palladium/carbon (10 mg), and the mixture was stirred in a hydrogen atmosphere at room temperature overnight. The reaction solution was diluted with chloroform, filtered through celite, and the filtrate was concentrated under reduced pressure. The residue was dissolved in methanol (3.0 mL), 10%-palladium/carbon (10 mg) was added and the mixture was stirred in a hydrogen atmosphere at room temperature overnight. The reaction mixture was diluted with chloroform and filtered through celite. The filtrate was concentrated under reduced pressure to give compound 4 (44 mg, 88%). MS(ESI) m/z: 515 (M+1)+.

Step c

To a solution of compound 4 (40 mg, 78 μmol) in dichloromethane (1.6 mL) was added trifluoroacetic acid (0.80 mL), and the mixture was stirred at room temperature for 3 days. The reaction solution was purified by silica gel chromatography to give compound 5 (36 mg). MS(ESI) m/z: 459 (M+1)+.

Example 5

(1S,2S)-2-[3-methoxy-6-(6-{[trans-4-(trifluoromethyl)cyclohexyl]methoxy}pyridazin-4-yl)pyridin-2-yl]cyclopropanecarboxylic acid

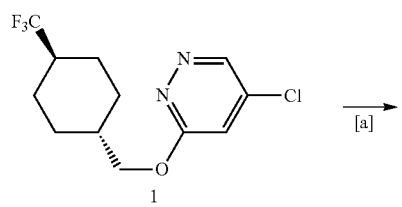

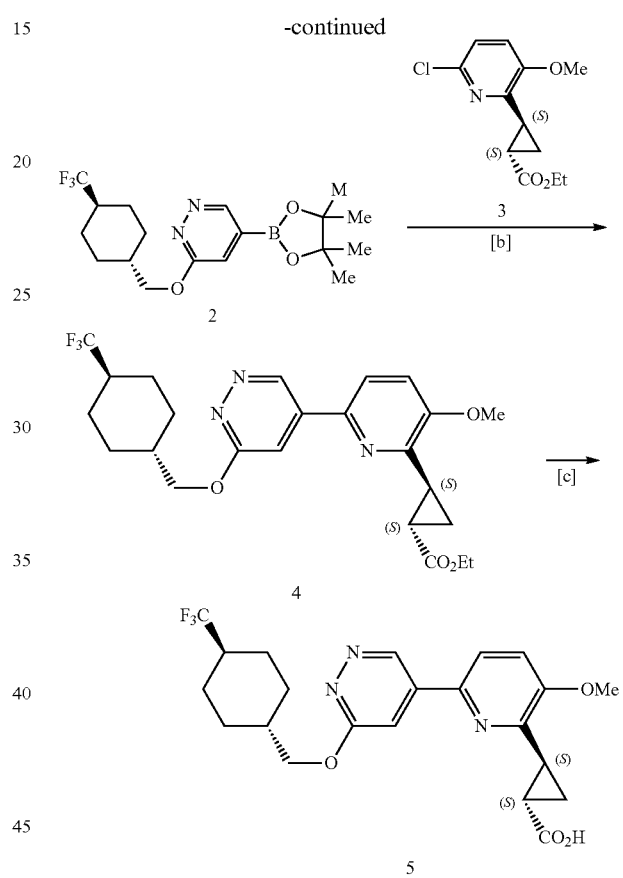

Step a

To a solution of compound 1 (1.81 g, 6.14 mmol) obtained in Reference Example 44, Step a, and bis(pinacolato)diborane (2.49 g, 9.82 mmol) in 1,4-dioxane (61 mL) were added potassium acetate (1.81 g, 18.4 mmol), tris(dibenzylideneacetone)dipalladium(0) (337 mg, 368 μmol) and 2-dicyclohexylphosphino-2',4',6'-triisopropylbiphenyl (351 mg, 736 μmol), and the mixture was stirred in a nitrogen atmosphere under heating at 100° C. for 3 hr. The reaction mixture was ice-cooled, and the resulting solid was diluted with water and washed with water. The obtained solid was washed with hexane to give compound 2 (1.78 g, 75.2%). MS (APCI) m/z: 387 (M+1)+.

Step b

To a solution of compound 3 (384 mg, 1.50 mmol) obtained in Reference Example 2, Step d, and compound 2

(645 mg, 1.67 mmol) in tetrahydrofuran (15 mL) were added a solution of tripotassium phosphate (1.95 g, 9.19 mmol) in water (3.0 mL) and X-Phos aminobiphenyl palladium chloride precatalyst (66 mg, 84 µmol), and the mixture was stirred in a nitrogen atmosphere under heating at 80° C. for 4 hr. To the reaction mixture was further added a X-Phos aminobiphenyl palladium chloride precatalyst (65.7 mg, 83.5 µmol), and the mixture was stirred in a nitrogen atmosphere under heating at 80° C. for 2.5 hr. The reaction mixture was allowed to cool to room temperature, water (25 mL) was added, and the mixture was extracted with ethyl acetate. The organic layer was washed with saturated brine, dried over anhydrous sodium sulfate, filtered and concentrated. The residue was purified by NH silica gel chromatography to give compound 4 (380 mg, 38.0%). MS(ESI) m/z: 480 (M+1)$^+$.

Step c

To a mixed solution of compound 4 (73.0 mg, 152 µmol) in tetrahydrofuran (2.0 mL) and methanol (2.0 mL) was added 4 M-aqueous sodium hydroxide solution (0.50 mL, 2.0 mmol), and the mixture was stirred at room temperature overnight. The reaction mixture was diluted with water (4 mL), neutralized with 1 M-hydrochloric acid (2 mL), and the resulting solid was collected by filtration and washed with water to give compound (57.0 mg, 82.9%). MS(ESI) m/z: 452 (M+1)$^+$.

Example 6

(1S,2S)-2-(5-methoxy-5'-{2-[4-(trifluoromethoxy)phenyl]ethyl}-2,3'-bipyridin-6-yl)cyclopropanecarboxylic acid

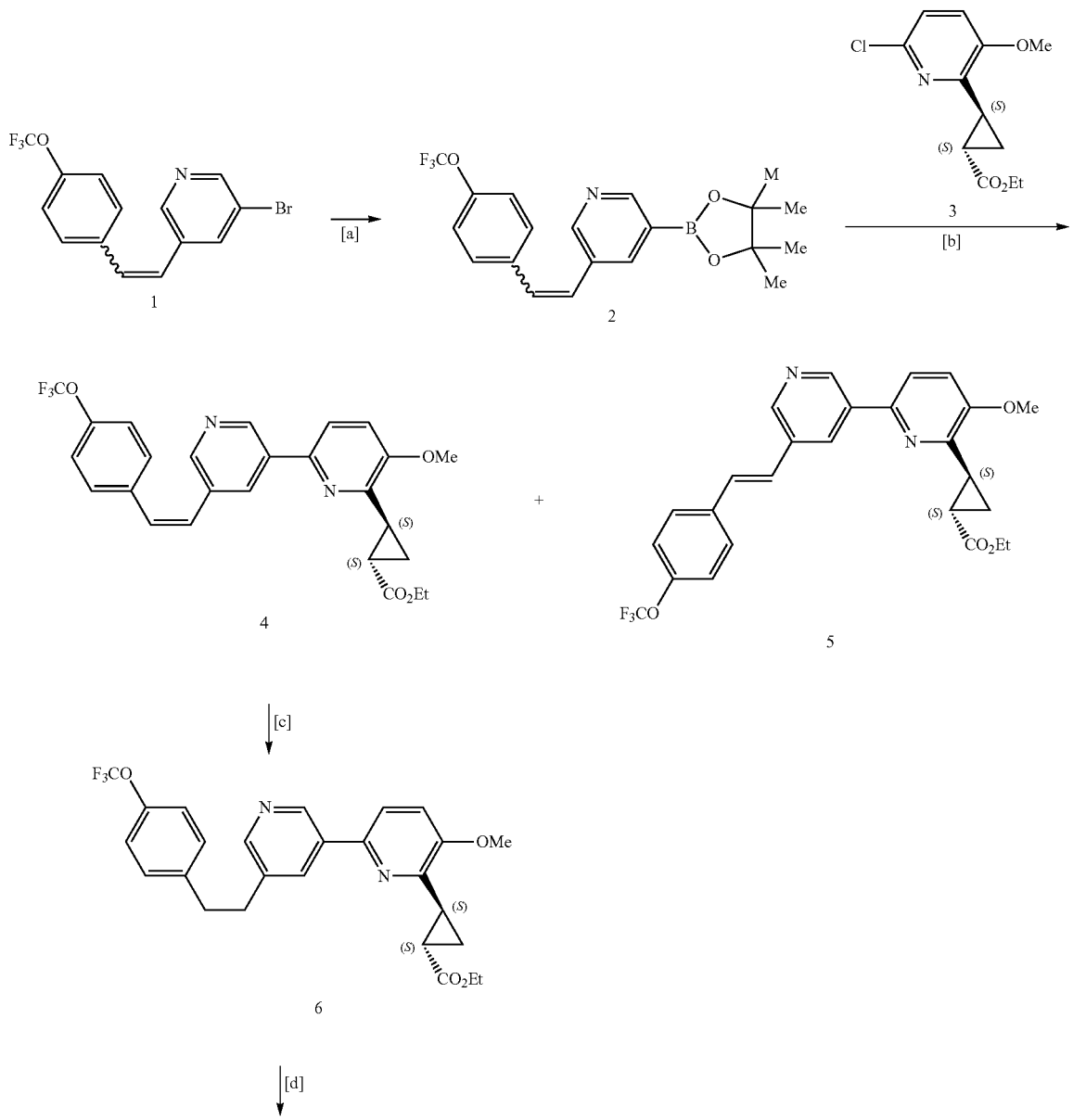

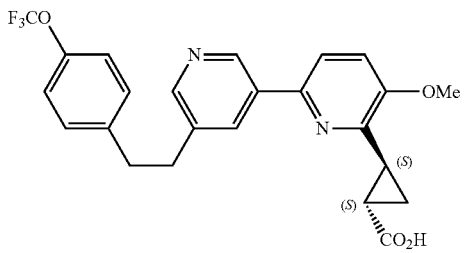

-continued

Step a

To a solution of compound 1 (600 mg, 1.74 mmol) obtained in Reference Example 45, Step b, and bis(pinacolato)diborane (487 mg, 1.92 mmol) in 1,4-dioxane (12 mL) were added potassium acetate (513 mg, 5.23 mmol) and [1,1'-bis(diphenylphosphino)ferrocene]palladium(II) dichloride (64 mg, 87 μmol), and the mixture was stirred in a nitrogen atmosphere under heating at 100° C. for 6 hr. The reaction mixture was allowed to cool to room temperature, water (40 mL) was added and the mixture was extracted twice with ethyl acetate (40 mL). The organic layer was washed with water (20 mL) and saturated brine (20 mL), dried over anhydrous sodium sulfate, filtered and concentrated. The residue was purified by silica gel column chromatography to give compound 2 (746 mg) as a cis/trans mixture. MS(ESI) m/z: 310 (M+1)$^+$.

Step b

To a solution of compound 3 (196 mg, 767 μmol) obtained in Reference Example 2, Step d, and compound 2 (300 mg, 767 μmol) in 1,4-dioxane (5.4 mL) were added a solution of tripotassium phosphate (488 mg, 2.30 mmol) in water (0.60 mL), and bis(di-tert-butyl(4-dimethylaminophenyl)phosphine)dichloropalladium(II) (27 mg, 37 μmol), and the mixture was stirred in a nitrogen atmosphere under heating at 100° C. for 4 hr. The reaction mixture was allowed to cool to room temperature, water was added, and the mixture was extracted with chloroform. The organic layer was dried over anhydrous sodium sulfate, filtered and concentrated. The residue was purified by silica gel chromatography and further subjected to solid phase extraction purification using cation exchange resin column (Waters, PoraPak™, RxnCX) to give compound 4 (125 mg, 33.7%) and compound 5 (75 mg, 20%). MS(ESI) m/z: 485 (M+1)$^+$. 485 (M+1)$^+$.

Step c

To a solution of compound 4 (120 mg, 248 μmol) in methanol (2.4 mL) was added 10%-palladium/carbon (24 mg), and the mixture was stirred in a hydrogen atmosphere at room temperature for one day. The reaction mixture was filtered through celite, washed with chloroform, and the filtrate was concentrated under reduced pressure. The residue was purified by silica gel chromatography to give compound 6 (87.5 mg, 72.6%). MS(APCI) m/z: 487 (M+1)$^+$.

Step d

To a mixed solution of compound 6 (85.0 mg, 175 μmol) in tetrahydrofuran (1.7 mL) and methanol (1.7 mL) was added 4 M-aqueous sodium hydroxide solution (218 μL, 0.87 mmol), and the mixture was stirred at room temperature overnight. The reaction mixture was neutralized with 1 M-hydrochloric acid (0.88 mL) and diluted with water (10 mL). The resulting solid was collected by filtration and washed with water (15 mL). The obtained solid was washed with ethyl acetate (5.0 mL) to give compound 7 (42.5 mg, 53.1%). MS(ESI) m/z: 459 (M+1)$^+$.

Example 7

(1S,2S)-2-[3-methoxy-6-(6-{[trans-4-(trifluoromethyl)cyclohexyl]methoxy}pyridazin-4-yl)pyridin-2-yl]-1-methylcyclopropanecarboxylic acid (1R,2R)-2-[3-methoxy-6-(6-{[trans-4-(trifluoromethyl)cyclohexyl]methoxy}pyridazin-4-yl)pyridin-2-yl]-1-methylcyclopropanecarboxylic acid

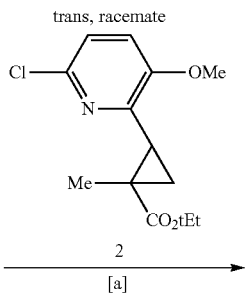

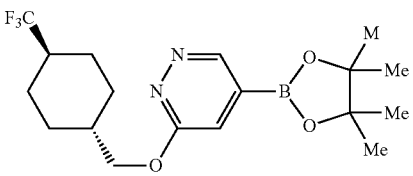

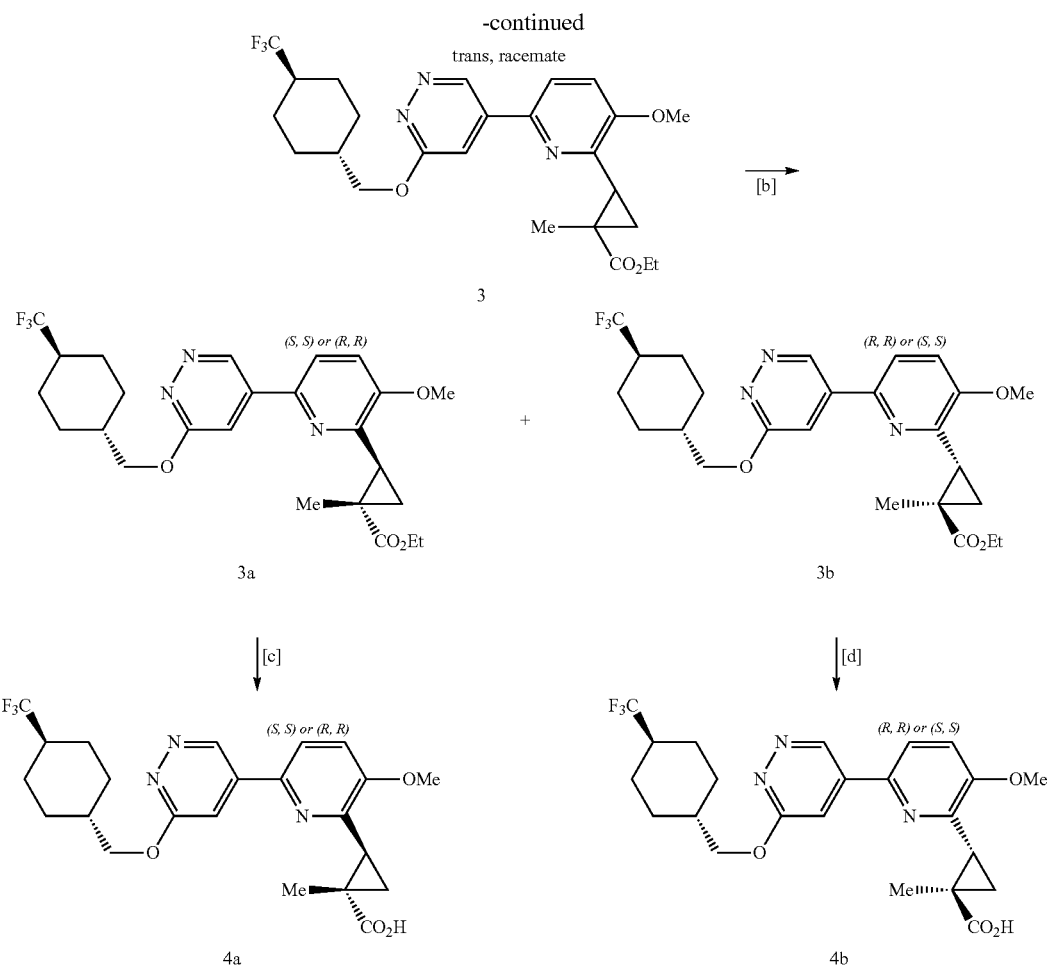

Step a

To a solution of compound 1 (200 mg, 440 μmol) obtained in Example 5, Step a, and compound 2 (119 mg, 440 μmol, Reference Example 5) in 1,4-dioxane (4.0 mL) were added a solution of tripotassium phosphate (93.4 mg, 440 μmol) in water (0.40 mL), tris(dibenzylideneacetone)dipalladium(0) (20 mg, 22 μmol) and tricyclohexylphosphine (18.5 mg, 66 μmol), and the mixture was stirred in a nitrogen atmosphere under heating at 105° C. for 4 hr. The reaction mixture was allowed to cool to room temperature, water and ethyl acetate were added and the mixture was filtered through celite. The filtrate was phase separated, and the organic layer was washed with saturated brine, dried over anhydrous sodium sulfate, filtered and concentrated. The residue was purified by silica gel chromatography to give compound 3 (35 mg, 16%).

MS (ESI) m/z: 494 (M+1)$^+$.

Step b

Chiral resolution of compound 3 (35 mg) by chiral HPLC (CHIRAL PAK IF, 30×250, tert-butyl methyl ether:methanol:diethylamine=96:4:0.1, 20 mL/min) gave compound 3a (13 mg, 99.9% ee, peak at retention time 15 min) and compound 3b (13 mg, 99.3% ee, peak at retention time 22 min).

Step c

To a mixed solution of compound 3a (13 mg, 26 μmol) in tetrahydrofuran (1.0 mL) and methanol (0.50 mL) was added 2 M-aqueous sodium hydroxide solution (0.50 mL, 1.0 mmol), and the mixture was stirred at room temperature overnight. The reaction solution was neutralized with 0.5 M-hydrochloric acid (2.1 mL) and diluted with water (8 mL). The organic solvent was evaporated from the reaction mixture under reduced pressure, and the resulting solid was collected by filtration and washed with water to give compound 4a (11 mg, 90%). This enantiomer was used as Example 7-1. MS(ESI) m/z: 466 (M+1)$^+$.

Step d

To a mixed solution of compound 3b (13 mg, 26 μmol) in tetrahydrofuran (1.0 mL) and methanol (0.50 mL) was added 2 M-aqueous sodium hydroxide solution (0.50 mL, 1.0 mmol), and the mixture was stirred at room temperature overnight. The reaction solution was neutralized with 0.5 M-hydrochloric acid (2.1 mL) and diluted with water (8 mL). The organic solvent was evaporated from the reaction mixture under reduced pressure, and the resulting solid was collected by filtration and washed with water to give compound 4b (9.0 mg, 73%). This enantiomer was used as Example 7-2. MS(ESI) m/z: 466 (M+1)$^+$.

Example 8

(1S,2S)-2-(5'-{[trans-4-(trifluoromethyl)cyclohexyl]methoxy}-2,3'-bipyridin-6-yl) cyclopropanecarboxylic acid (1R,2R)-2-(5'-{[trans-4-(trifluoromethyl)cyclohexyl]methoxy}-2,3'-bipyridin-6-yl) cyclopropanecarboxylic acid mmol) and [1,1'-bis(diphenylphosphino) ferrocene]palladium(II) dichloride (41.1 mg, 56.2 µmol), and the mixture was stirred in a nitrogen atmosphere under heating at 80° C. overnight. The reaction mixture was allowed to cool to room temperature, diluted with ethyl acetate and filtered through celite. The filtrate was washed with water and saturated brine, dried over anhydrous sodium sulfate, filtered and concentrated under reduced pressure to give compound 2 (727 mg). MS(ESI) m/z: 304 (M+1 of boronic acid)$^+$.

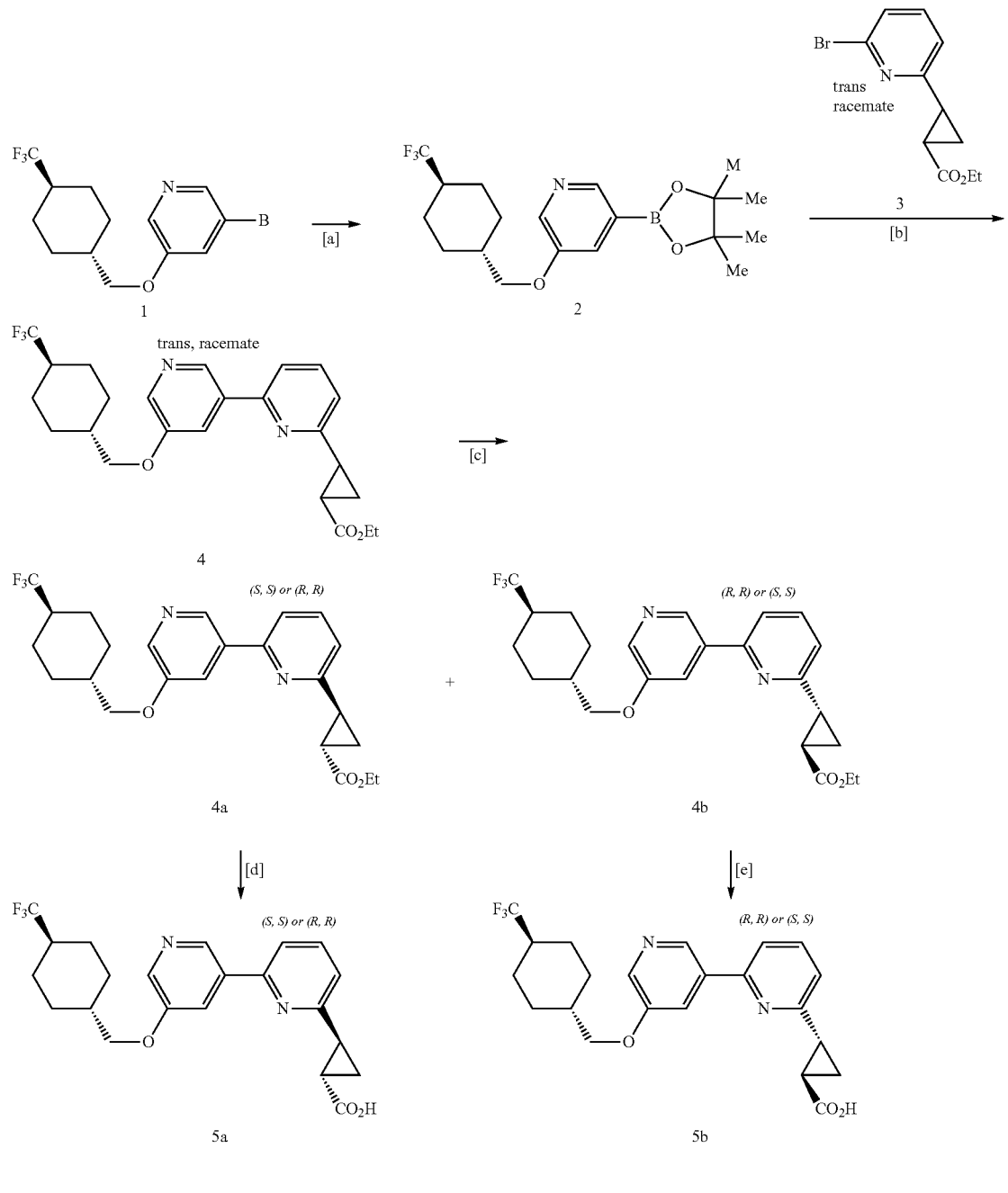

Step a

To a solution of compound 1 (380 mg, 1.12 mmol) obtained in Reference Example 42, Step b, and bis(pinacolato)diborane (342 mg, 1.35 mmol) in dimethyl sulfoxide (2.7 mL) were added potassium acetate (331 mg, 3.37

Step b

To a solution of compound 3 (180 mg, 666 µmol) obtained in Reference Example 3, Step b, and compound 2 (1.44 g, 2.02 mmol) in 1,4-dioxane (6.0 mL) were added a solution of tripotassium phosphate (424 mg, 2.00 mmol) in water (1.2 mL) and bis(di-tert-butyl(4-dimethylaminophenyl)phosphine)dichloropalladium(II) (42 mg, 67 µmol), and the mixture was stirred in a nitrogen atmosphere under heating at 105° C. for 3 hr. The reaction mixture was allowed to cool to room temperature, water was added, and the mixture was extracted with ethyl acetate. The organic layer was washed with saturated brine, dried over anhydrous sodium sulfate, filtered and concentrated. The residue was purified by silica gel chromatography and NH silica gel chromatography to give compound 4 (400 mg, 100%). MS(ESI) m/z: 449 (M+1)+.

Step c

Chiral resolution of compound 4 (400 mg) by chiral HPLC (CHIRAL PAK IF, 30×250, ethanol:diethylamine=100:0.1, 15 mL/min) gave compound 4a (119 mg, 99.8% ee, peak at retention time 22 min) and compound 4b (128 mg, 99.9% ee, peak at retention time 18 min).

Step d

To a mixed solution of compound 4a (119 mg, 265 µmol) in tetrahydrofuran (3.0 mL) and methanol (1.5 mL) was added 2 M-aqueous sodium hydroxide solution (1.5 mL, 3.0 mmol), and the mixture was stirred at room temperature for 3 hr. The reaction solution was neutralized with 0.2 M-hydrochloric acid (15 mL), and the mixture was extracted with ethyl acetate. The organic layer was washed with saturated brine, dried over anhydrous sodium sulfate, filtered and concentrated. The resulting solid was washed with diethyl ether-hexane to give compound 5a (92.0 mg, 82.5%). This enantiomer was used as Example 8-1.

MS (ESI) m/z: 421 (M+1)+.

Step e

To a mixed solution of compound 4b (128 mg, 285 µmol) in tetrahydrofuran (3.0 mL) and methanol (1.5 mL) was added 2 M-aqueous sodium hydroxide solution (1.5 mL, 3.0 mmol), and the mixture was stirred at room temperature for 3 hr. The reaction solution was neutralized with 0.2 M-hydrochloric acid (15 mL), and the mixture was extracted with ethyl acetate. The organic layer was washed with saturated brine, dried over anhydrous sodium sulfate, filtered and concentrated. The resulting solid was washed with diethyl ether-hexane to give compound 5b (95.0 mg, 79.2%). This enantiomer was used as Example 8-2.

MS (ESI) m/z: 421 (M+1)+.

Example 9

(1S,2S)-2-(5-{[trans-4-(trifluoromethyl)cyclohexyl]methoxy}-3,4'-bipyridin-2'-yl)cyclopropanecarboxylic acid (1R,2R)-2-(5-{[trans-4-(trifluoromethyl)cyclohexyl]methoxy}-3,4'-bipyridin-2'-yl)cyclopropanecarboxylic acid

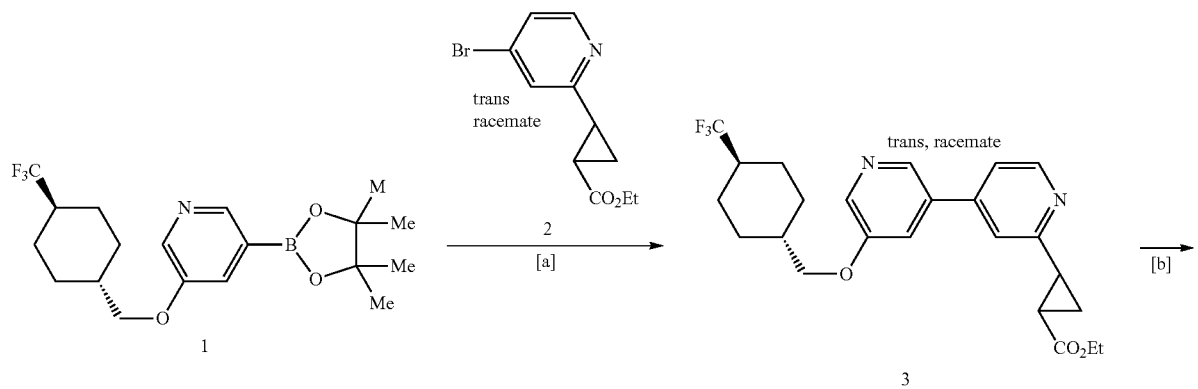

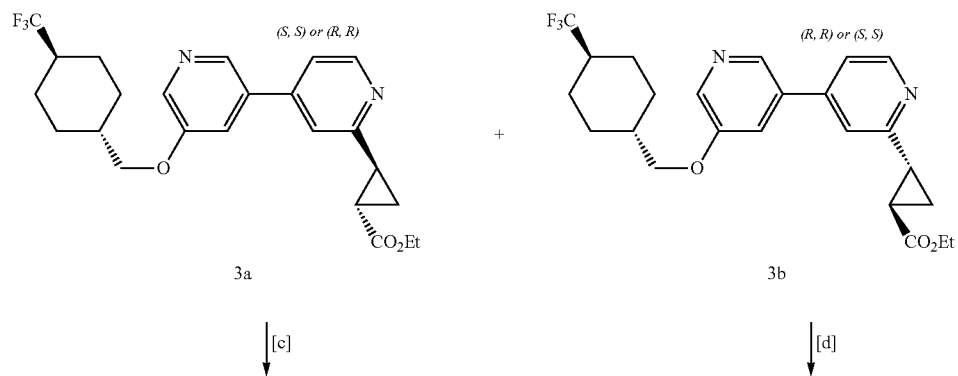

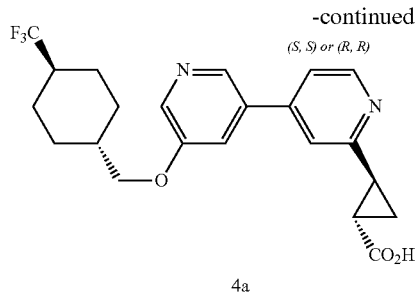

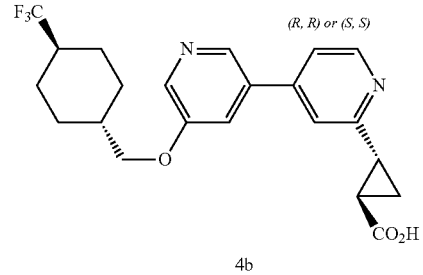

4a

4b

Step a

To a solution of compound 1 (719 mg, 1.11 mmol) obtained in Example 8, Step a, and compound 2 (200 mg, 740 μmol, Reference Example 6) in 1,4-dioxane (3.6 mL) were added a solution of tripotassium phosphate (472 mg, 2.22 mol) in water (0.40 mL), and bis(di-tert-butyl(4-dimethylaminophenyl)phosphine)dichloropalladium(II) (52 mg, 74 μmol), and the mixture was stirred in a nitrogen atmosphere with heating under reflux for 3 hr. The reaction mixture was allowed to cool to room temperature, water was added, and the mixture was extracted with chloroform. The organic layer was washed with saturated brine, dried over anhydrous sodium sulfate, filtered and concentrated. The residue was purified by NH silica gel chromatography and silica gel chromatography to give compound 3 (115 mg, 34.5%). MS(ESI) m/z: 449 (M+1)$^+$.

Step b

Chiral resolution of compound 3 (110 mg) by chiral HPLC (CHIRAL PAK IA, 30×250, methanol:tetrahydrofuran:diethylamine=90:10:0.1, 20 mL/min) gave compound 3a (54 mg, 99.9% ee, peak at retention time 18 min) and compound 3b (54 mg, 99.8% ee, peak at retention time 13 min).

Step c

To a mixed solution of compound 3a (54 mg, 122 μmol) in tetrahydrofuran (2.0 mL) and methanol (1.0 mL) was added 2 M-aqueous sodium hydroxide solution (1.0 mL, 2.0 mmol), and the mixture was stirred at room temperature overnight. The reaction solution was neutralized with 1 M-hydrochloric acid (2.2 mL), diluted with saturated brine (10 mL), and extracted with chloroform. The organic layer was washed with saturated brine, dried over anhydrous sodium sulfate, filtered and concentrated. The residue was washed with diethyl ether to give compound 4a (28 mg, 54%). This enantiomer was used as Example 9-1. MS(ESI) m/z: 421 (M+1)$^+$.

Step d

To a mixed solution of compound 3b (54 mg, 122 μmol) in tetrahydrofuran (2.0 mL) and methanol (1.0 mL) was added 2 M-aqueous sodium hydroxide solution (1.0 mL, 2.0 mmol), and the mixture was stirred at room temperature overnight. The reaction solution was neutralized with 1 M-hydrochloric acid (2.0 mL) and diluted with water (10 mL). The organic solvent was evaporated from the reaction mixture under reduced pressure and the resulting solid was collected by filtration and washed with water to give compound 4b (16 mg, 33%). This enantiomer was used as Example 9-2. MS(ESI) m/z: 421 (M+1)$^+$.

Example 10

(1S,2S)-2-[4-(6-{[trans-4-(trifluoromethyl)cyclohexyl]methoxy}pyridazin-4-yl)pyridin-2-yl]cyclopropanecarboxylic acid (1R, 2R)-2-[4-(6-{[trans-4-(trifluoromethyl)cyclohexyl]methoxy}pyridazin-4-yl)pyridin-2-yl]cyclopropanecarboxylic acid

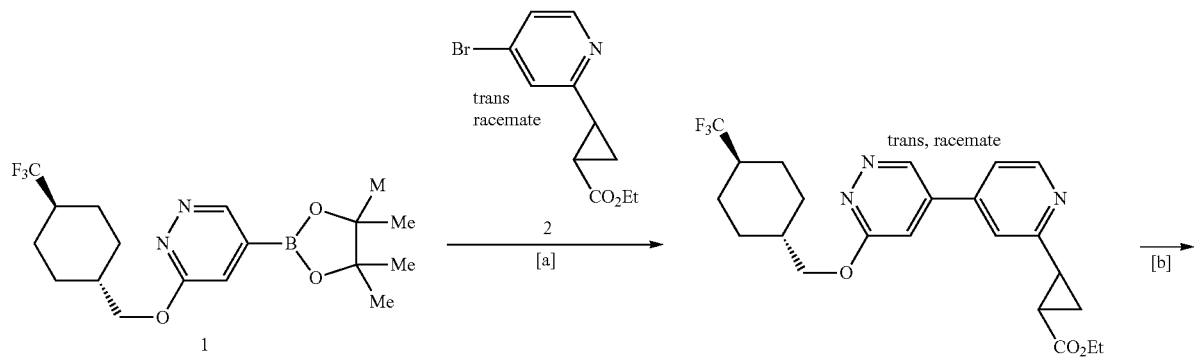

-continued

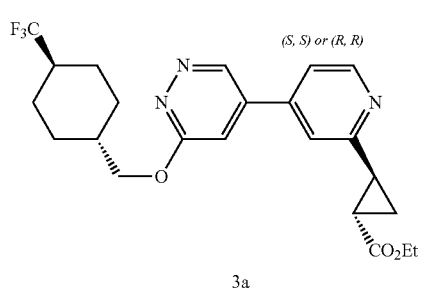

3a

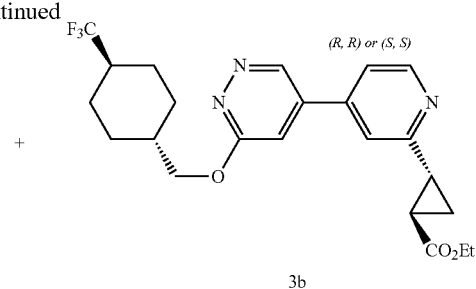

3b

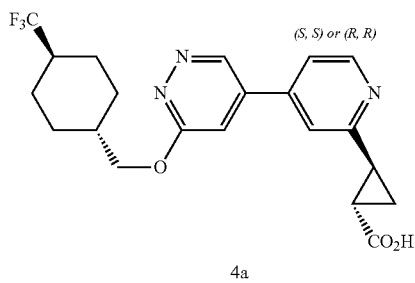

4a

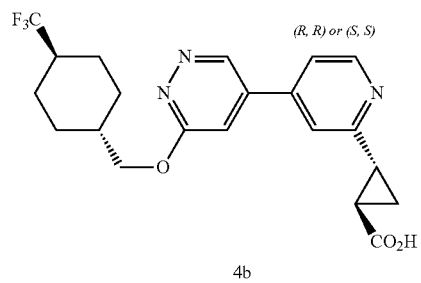

4b

Step a

Compound 3 was obtained from compound 1 obtained in Example 5, Step a, and compound 2 by a method similar to Example 7, Step a. MS(ESI) m/z: 450 (M+1)$^+$.

Step b

Chiral resolution of compound 3 (30 mg) by chiral HPLC (CHIRAL PAK IF, 30×250, tert-butyl methyl ether: 2-propanol:diethylamine=93:7:0.1, 20 mL/min, separated after one recycle) gave compound 3a (9.0 mg, 99.9% ee, peak at retention time 38 min) and compound 3b (9.0 mg, 99.3% ee, peak at retention time 58 min).

Step c

Compound 4a was obtained from compound 3a by a method similar to Example 7, Step c. This enantiomer was used as Example 10-1. MS(ESI) m/z: 422 (M+1)$^+$.

Step d

Compound 4b was obtained from compound 3b by a method similar to Example 7, Step c. This enantiomer was used as Example 10-2. MS(ESI) m/z: 422 (M+1)$^+$.

Example 11

(1S,2S)-2-(5-{[4-(trifluoromethoxy)benzyl]oxy}-3,4'-bipyridin-2'-yl)cyclopropanecarboxylic acid (1R,2R)-2-(5-{[4-(trifluoromethoxy)benzyl]oxy}-3,4'-bipyridin-2'-yl)cyclopropanecarboxylic acid

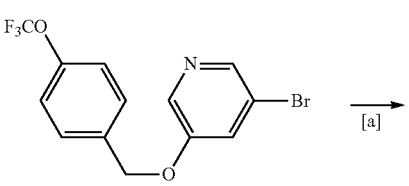

1

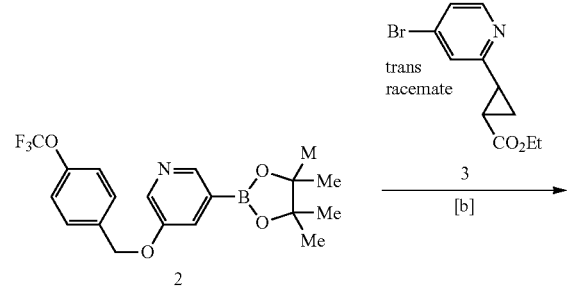

77
-continued

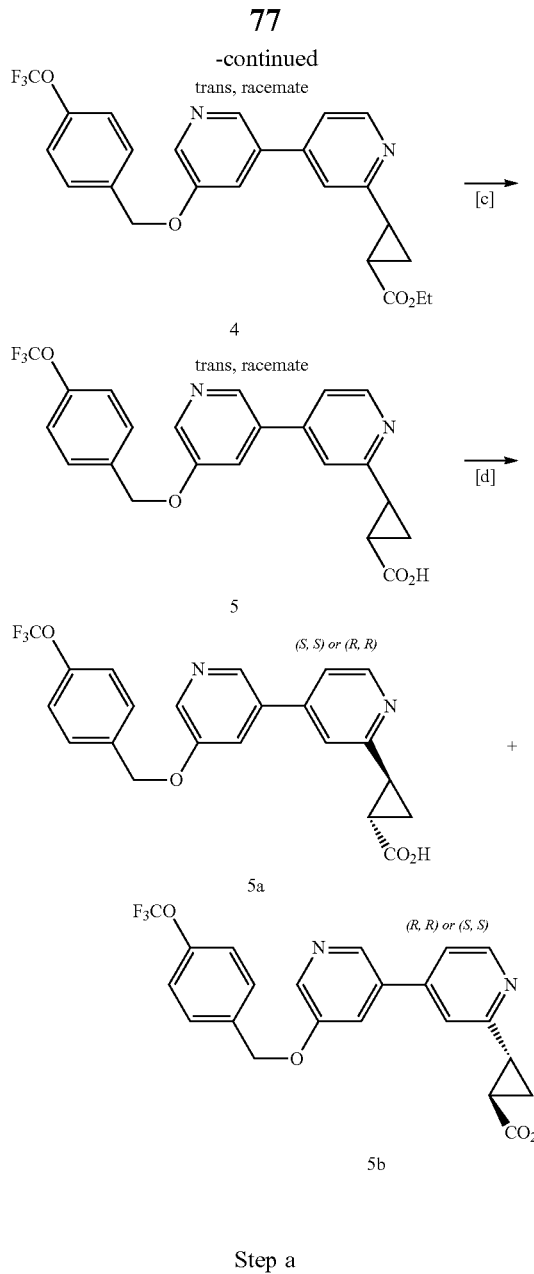

78

Step c

Compound 5 was obtained from compound 4 by a method similar to Example 7, Step c. MS(ESI) m/z: 431 (M+1)+.

Step d

Chiral resolution of compound 5 (60 mg) by chiral HPLC (CHIRAL PAK IA, 30×250, ethanol:acetic acid=100:0.1, 10 mL/min) gave compound 5a (25 mg, 99.9% ee, peak at retention time 38 min) and compound 5b (25 mg, 99.9% ee, peak at retention time 23 min). Compound 5a was used as Example 11-1 and compound 5b was used as Example 11-2.

Example 11-1: MS(ESI) m/z: 431 (M+1)+

Example 11-2: MS(ESI) m/z: 431 (M+1)+

Example 12

1-(5-{[[trans-4-(trifluoromethyl)cyclohexyl]methoxy}pyridin-3-yl)-2,3-dihydro-1H-indole-5-carboxylic acid

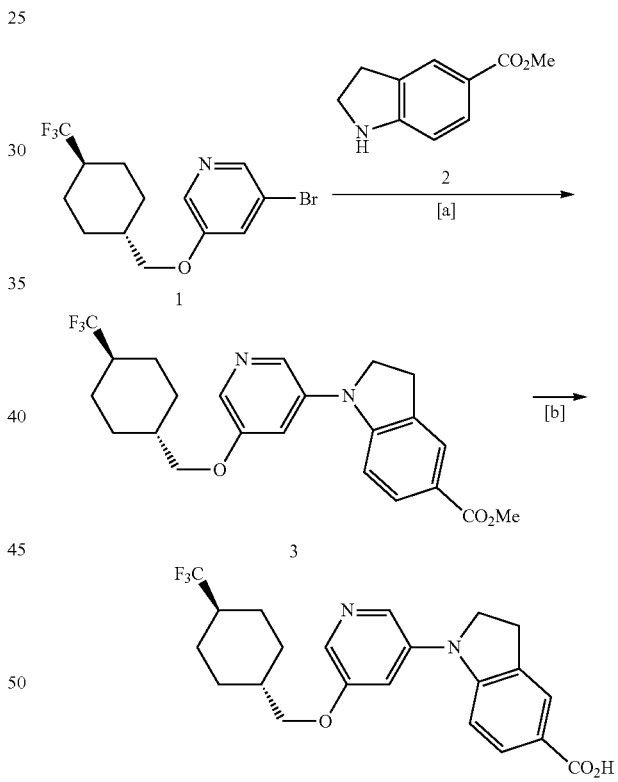

Step a

To a solution of compound 1 (3.00 g, 8.62 mmol, Reference Example 49) and bis(pinacolato)diborane (2.85 g, 11.2 mmol) in 1,4-dioxane (30 mL) were added potassium acetate (2.11 g, 21.6 mmol) and [1,1'-bis(diphenylphosphino) ferrocene]palladium(II) dichloride (352 mg, 431 μmol), and the mixture was stirred in a nitrogen atmosphere under heating at 110° C. for 3 hr. The reaction mixture was allowed to cool to room temperature, diluted with ethyl acetate and filtered through celite. The filtrate was washed with water and saturated brine, dried over anhydrous sodium sulfate, filtered and concentrated under reduced pressure to give compound 2 (5.64 g). MS(ESI) m/z: 314 (M+1 of boronic acid)+.

Step b

Compound 4 was obtained from compound 2 and compound 3 by a method similar to Example 9, Step a. MS(ESI) m/z: 459 (M+1)+.

Step a

To a solution of compound 1 (100 mg, 296 μmol) obtained in Reference Example 42, Step b, and compound 2 (78.6 mg, 444 μmol) in 1,4-dioxane (3.0 mL) were added cesium carbonate (289 mg, 887 μmol), palladium(II) acetate (3.3 mg, 15 μmol) and 2-dicyclohexylphosphino-2',6'-diisopropoxybiphenyl (14 mg, 30 μmol), and the mixture was stirred in a nitrogen atmosphere with heating under reflux for 5 hr. The reaction mixture was allowed to cool to room temperature, filtered through celite, and the filtrate was concentrated. The residue was purified by silica gel chromatography to give compound 3 (109 mg, 84.9%). MS (ESI) m/z: 435 (M+1)⁺.

Step b

To a mixed solution of compound 3 (109 mg, 251 μmol) in tetrahydrofuran (3 mL) and methanol (1.0 mL) was added 4 M-aqueous sodium hydroxide solution (0.20 mL, 0.80 mmol), and the mixture was stirred at room temperature for 15 hr and stirred under heating at 60° C. for 4 hr. The reaction mixture was allowed to cool to room temperature, neutralized with 1 M-hydrochloric acid (0.8 mL), water was added, and the resulting solid was collected by filtration and washed with 50% aqueous methanol solution to give compound 4 (85.0 mg, 80.6%). MS (ESI) m/z: 421 (M+1)⁺.

Example 13

3-[4-(5-{[trans-4-(trifluoromethyl)cyclohexyl]methoxy}pyridin-3-yl)morpholin-2-yl]benzoic acid

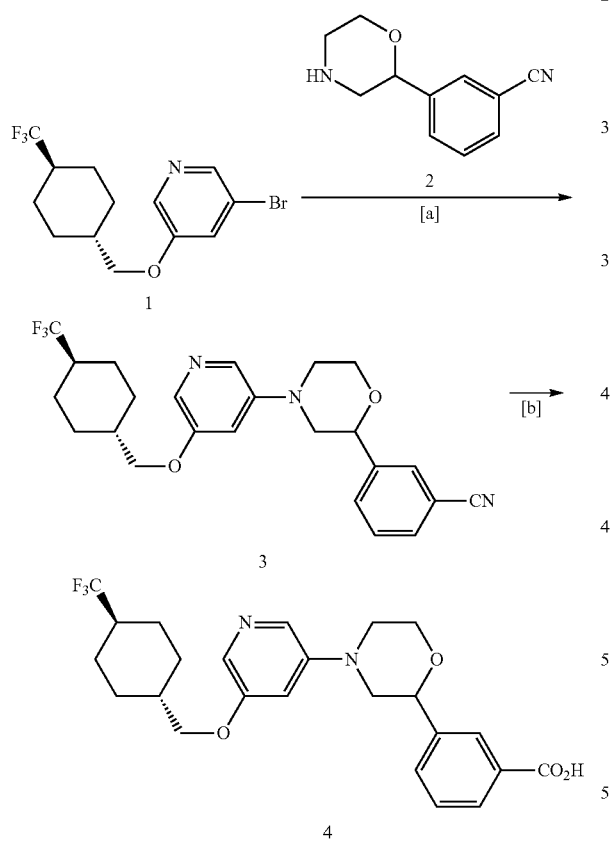

Step a

To compound 2 hydrochloride (133 mg, 591 μmol, Reference Example 15) were added saturated aqueous sodium hydrogen carbonate and chloroform and the mixture was stirred. The organic phase was separated and concentrated under reduced pressure. The residue was dissolved in 1,4-dioxane (3.0 mL), compound 1 (100 mg, 296 μmol) obtained in Reference Example 42, Step b, cesium carbonate (289 mg, 887 μmol), palladium(II) acetate (3.3 mg, 15 μmol) and 2-dicyclohexylphosphino-2',6'-diisopropoxybiphenyl (14 mg, 30 μmol) were added, and the mixture was stirred in a nitrogen atmosphere under heating at 100° C. for 3 hr. The reaction mixture was allowed to cool to room temperature, filtered through celite, and the filtrate was concentrated. The residue was purified by silica gel chromatography to give compound 3 (100 mg, 75.9%).

MS (ESI) m/z: 446 (M+1)⁺.

Step b

To a solution of compound 3 (100 mg, 225 μmol) in ethylene glycol (3.0 mL) was added potassium hydroxide (85 wt %, 74 mg, 1.1 mmol), and the mixture was stirred under heating at 150° C. for 3.5 hr. The reaction solution was allowed to cool to room temperature, neutralized with 1 M-hydrochloric acid and extracted with chloroform. The organic layer was washed with saturated brine, dried over anhydrous sodium sulfate, filtered and concentrated. The resulting solid was washed with ethyl acetate-hexane to give compound 4 (80 mg, 76.7%).

MS (ESI) m/z: 465 (M+1)⁺.

Example 14

3-[(2S)-4-(5-{[4-(trifluoromethoxy)benzyl]oxy}pyridin-3-yl)morpholin-2-yl]propanoic acid

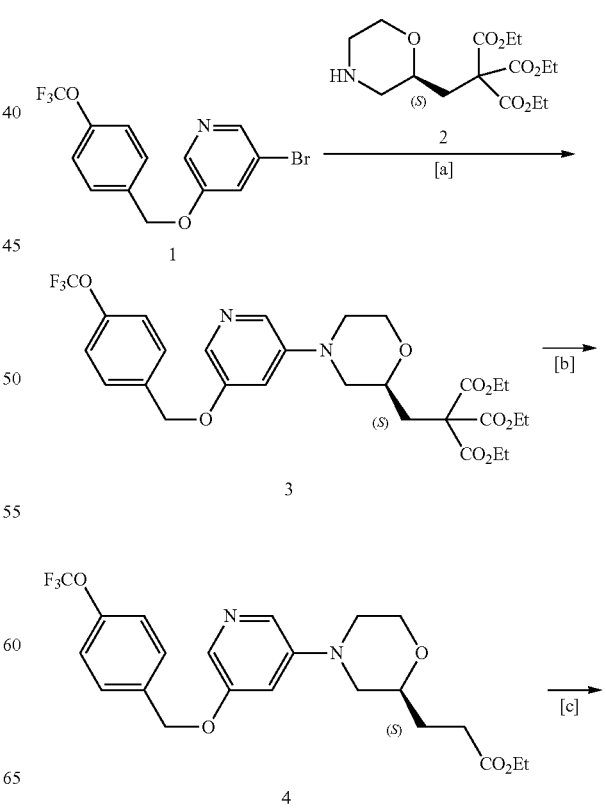

-continued

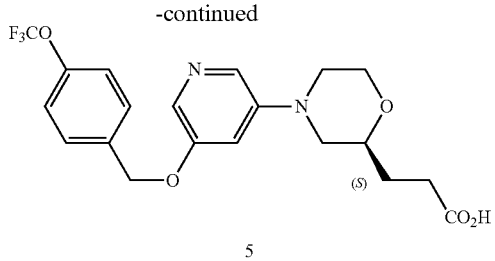

5

Step a

To a solution of compound 2 (1.39 g, 4.19 mmol) obtained in Reference Example 9, Step c, and compound 1 (1.81 g, 5.45 mmol, Reference Example 49) in 1,4-dioxane (28 mL) were added cesium carbonate (3.42 g, 10.5 mmol), palladium(II) acetate (141 mg, 629 µmol) and 2-dicyclohexylphosphino-2',6'-diisopropoxybiphenyl (587 mg, 1.26 mmol), and the mixture was stirred in a nitrogen atmosphere with heating under reflux for 4 hr. The reaction mixture was allowed to cool to room temperature, water was added, and the mixture was extracted with chloroform. The organic layer was dried over anhydrous sodium sulfate, filtered and concentrated. The residue was purified by silica gel chromatography to give compound 3 (1.93 g, 76.4%). MS(ESI) m/z: 599 (M+1)$^+$.

Step b

To a solution of compound 3 (1.93 g, 3.15 mmol) in ethanol (39 mL) was added potassium hydroxide (85 wt %, 415 mg, 6.29 mmol), and the mixture was stirred at room temperature for 4 days. The reaction solution was neutralized with 1 M-hydrochloric acid (6.29 mL), water (100 mL) was added and the mixture was extracted with chloroform (150 mL). The organic layer was dried over anhydrous sodium sulfate, filtered and concentrated. The residue was dissolved in toluene (35 mL), diisopropylethylamine (545 µL, 3.15 mmol) was added and the mixture was stirred with heating under reflux for 2 hr. The reaction solution was concentrated under reduced pressure, and the residue was purified by silica gel chromatography to give compound 4 (1.34 g, 90.2%). MS(ESI) m/z: 455 (M+1)$^+$.

Step c

To a mixed solution of compound 4 (1.34 g, 2.83 mmol) in tetrahydrofuran (8.0 mL) and methanol (2.7 mL) was added 4 M-aqueous sodium hydroxide solution (2.83 mL, 11.3 mmol), and the mixture was stirred at room temperature overnight. The reaction solution was neutralized with 10% aqueous citric acid solution (25 mL), and the organic solvent was evaporated under reduced pressure. The residue was left standing and the resulting solid was collected by filtration and washed with water to give compound 5 (1.13 g, 93.3%). MS(ESI) m/z: 427 (M+1)$^+$.

Example 15

3-[(2S)-4-(5-{[4-(trifluoromethyl)benzyl]oxy}pyridin-3-yl)morpholin-2-yl]propanoic acid

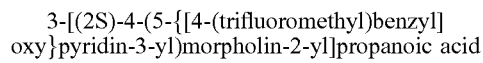

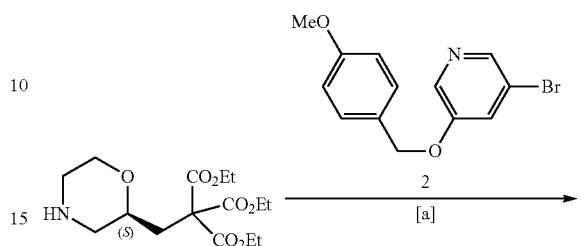

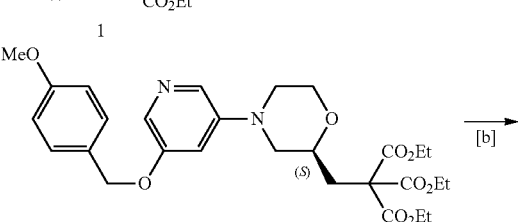

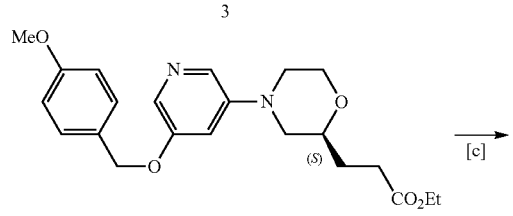

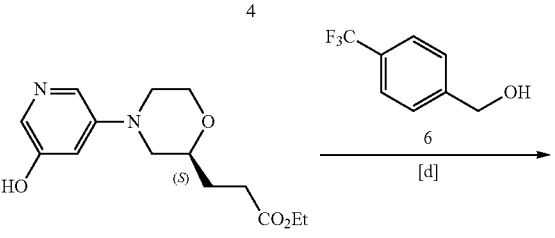

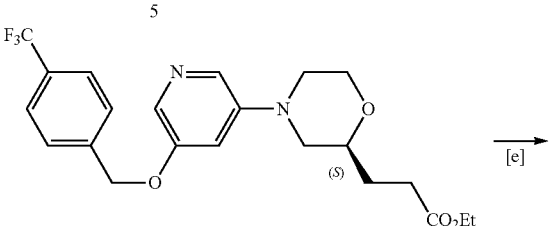

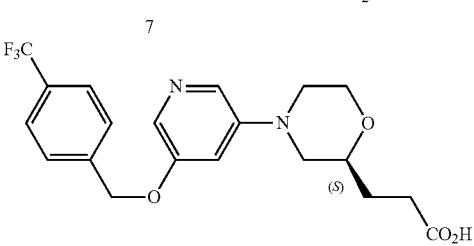

Step a

To a solution of compound 1 (4.80 g, 11.6 mmol) obtained in Reference Example 9, Step c, and compound 2 (4.09 g, 13.9 mmol) in 1,4-dioxane (120 mL) were added cesium carbonate (9.44 g, 29.0 mmol), palladium(II) acetate (390 mg, 1.74 mmol) and 2-dicyclohexylphosphino-2',6'-diisopropoxybiphenyl (1.62 g, 3.48 mmol), and the mixture was stirred in a nitrogen atmosphere with heating under reflux for 3 hr. The reaction mixture was allowed to cool to room temperature and filtered through celite. The filtrate was washed with water and saturated brine, dried over anhydrous sodium sulfate, filtered and concentrated. The residue was purified by silica gel chromatography to give compound 3 (5.46 g, 86.5%). MS(ESI) m/z: 545 (M+1)$^+$.

Step b

To a solution of compound 3 (5.46 g, 10.0 mmol) in ethanol (150 mL) was added potassium hydroxide (85 wt %, 1.32 g, 20.1 mmol), and the mixture was stirred at room temperature for 14 hr. The reaction solution was concentrated under reduced pressure, and the residue was dissolved in water (500 mL), neutralized with 1 M-hydrochloric acid (20 mL) and extracted 6 times with chloroform (100 mL). The organic layer was dried over anhydrous sodium sulfate, filtered and concentrated. The residue was suspended in toluene (150 mL), diisopropylethylamine (1.62 mL, 9.36 mmol) was added and the mixture was stirred with heating under reflux for 1 hr. The reaction solution was concentrated under reduced pressure, and the residue was purified by silica gel chromatography to give compound 4 (2.88 g, 76.8%). MS(ESI) m/z: 401 (M+1)$^+$.

Step c

To a solution of compound 4 (2.88 g, 7.19 mmol) in dichloromethane (150 mL) was added trifluoroacetic acid (10.0 mL), and the mixture was stirred at room temperature overnight. The reaction solution was concentrated under reduced pressure, and the residue was purified by silica gel chromatography to give compound 5 (1.33 g, 66.0%). MS(ESI) m/z: 281 (M+1)$^+$.

Step d

To a solution of compound 5 (80.0 mg, 285 μmol) and compound 6 (65.4 mg, 371 μmol) in tetrahydrofuran (2.4 mL) were added tributylphosphine (75.1 mg, 371 μmol) and 1,1'-(azodicarbonyl)dipiperidine (93.6 mg, 371 μmol), and the mixture was stirred at room temperature overnight. The reaction suspension was diluted with tetrahydrofuran (6.0 mL) and hexane (12 mL), and the insoluble material was filtered off and the filtrate was concentrated. The residue was purified by silica gel chromatography and subjected to solid phase extraction purification using cation exchange resin column (Waters, PoraPak™, RxnCX) to give compound 7 (66.9 mg, 53.5%). MS (ESI) m/z: 439 (M+1)$^+$.

Step e

To a mixed solution of compound 7 (60.0 mg, 137 μmol) in tetrahydrofuran (1.8 mL) and methanol (1.8 mL) was added 4 M-aqueous sodium hydroxide solution (0.17 mL, 0.68 mmol), and the mixture was stirred at room temperature overnight. The reaction solution was neutralized with 1 M-hydrochloric acid (0.78 mL) and diluted with water (12 mL). The resulting solid was collected by filtration and washed with water to give compound 8 (46.3 mg, 82.4%). MS(ESI) m/z: 411 (M+1)$^+$.

Example 16

3-[(2S)-4-(5-{[trans-4-(trifluoromethyl)cyclohexyl]methoxy}pyridin-3-yl)morpholin-2-yl]propanoic acid

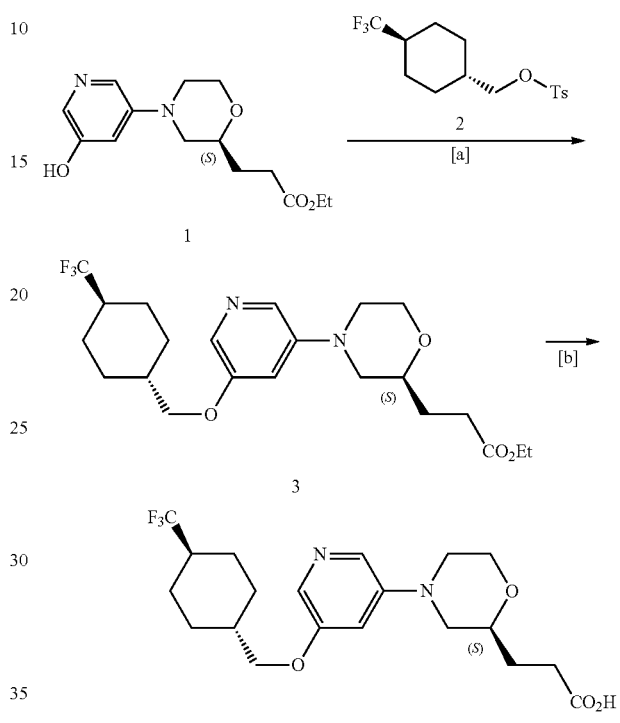

Step a

To a solution of compound 1 (60.0 mg, 214 μmol) obtained in Example 15, Step c, and compound 2 (72.0 mg, 214 μmol) obtained in Reference Example 48, Step a, in N,N-dimethylformamide (1.8 mL) was added potassium carbonate (59.2 mg, 428 μmol), and the mixture was stirred under heating at 80° C. for 5 hr. The reaction mixture was allowed to cool to room temperature, diluted with ethyl acetate, washed with water and saturated brine, dried over anhydrous sodium sulfate, filtered and concentrated. The residue was purified by silica gel chromatography to give compound 3 (63.0 g, 66.2%). MS (ESI) m/z: 445 (M+1)$^+$.

Step b

To a mixed solution of compound 3 (60.0 mg, 135 μmol) in tetrahydrofuran (1.5 mL) and methanol (1.5 mL) was added 4 M-aqueous sodium hydroxide solution (0.17 mL, 0.68 mmol), and the mixture was stirred at room temperature for 2 days. The reaction solution was neutralized with 1 M-hydrochloric acid (0.68 mL) and diluted with water (20 mL). The resulting solid was collected by filtration and washed with water to give compound 4 (44.2 mg, 78.6%). MS(ESI) m/z: 417 (M+1)$^+$.

Example 17

2-methyl-3-[(2S)-4-(5-{[4-(trifluoromethoxy)benzyl]oxy}pyridin-3-yl)morpholin-2-yl]propanoic acid

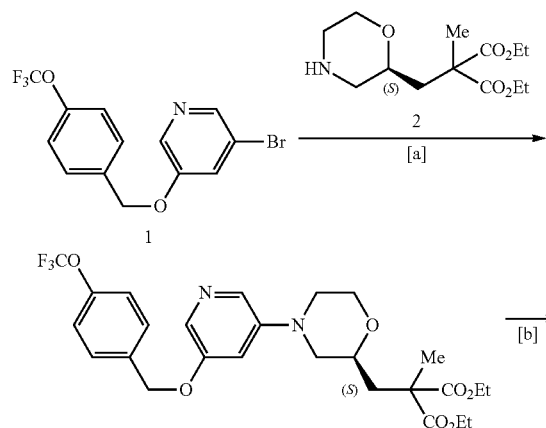

Step a

To a solution of compound 1 (270 mg, 775 μmol, Reference Example 49) and compound 2 (230 mg, 547 μmol, Reference Example 33) in 1,4-dioxane (5.0 mL) were added cesium carbonate (530 mg, 1.63 mmol), palladium(II) acetate (12 mg, 55 μmol) and 2-dicyclohexylphosphino-2′,6′-diisopropoxybiphenyl (51.0 mg, 109 μmol), and the mixture was stirred in a nitrogen atmosphere under heating at 105° C. for 7 hr. The reaction mixture was allowed to cool to room temperature, water was added, and the mixture was extracted with ethyl acetate. The organic layer was washed with saturated brine, dried over anhydrous sodium sulfate, filtered and concentrated. The residue was purified by silica gel chromatography to give compound 3 (300 mg, 87.2%) MS (ESI) m/z: 541 (M+1)+.

Step b

To a solution of compound 3 (100 mg, 160 μmol) in ethanol (1.0 mL) was added 4 M-aqueous sodium hydroxide solution (0.50 mL, 2.0 mmol), and the mixture was stirred under heating at 85° C. for 2.5 hr. The reaction solution was allowed to cool to room temperature, neutralized with acetic acid (114 μL, 2.0 mmol) and concentrated under reduced pressure. The residue was dissolved in acetic acid (3.0 mL) and the mixture was stirred under heating at 125° C. for 5.5 hr. The reaction solution was allowed to cool to room temperature and subjected to solid phase extraction purification using cation exchange resin column (Waters, PoraPak™, RxnCX) to give compound 4 (65.0 g, 92.5%). MS(ESI) m/z: 441 (M+1)+.

Example 18

3-[(2S)-4-(5-{2-[4-(trifluoromethoxy)phenyl]ethyl}pyridin-3-yl)morpholin-2-yl]propanoic acid

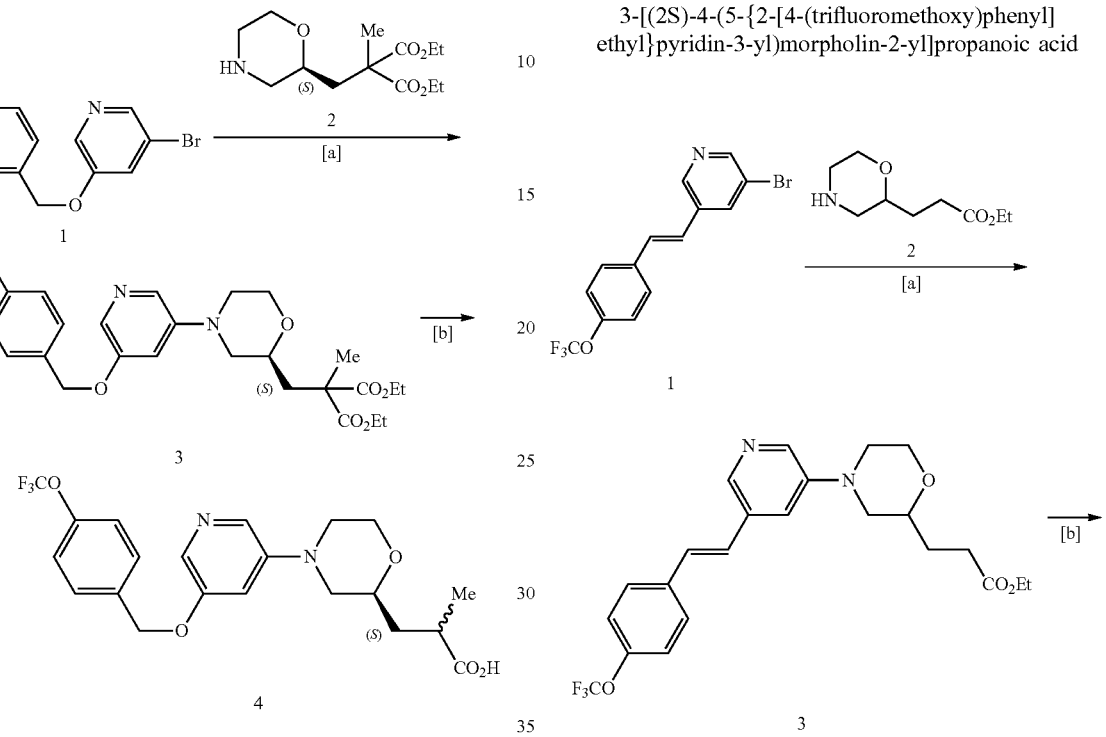

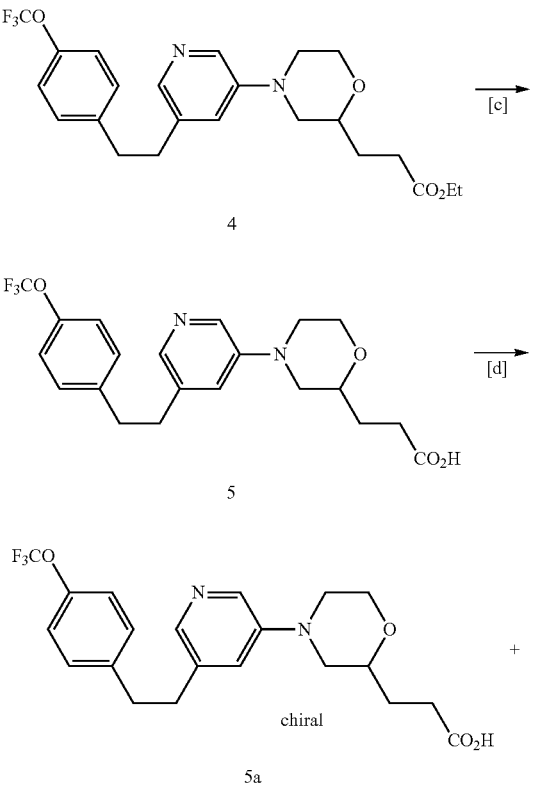

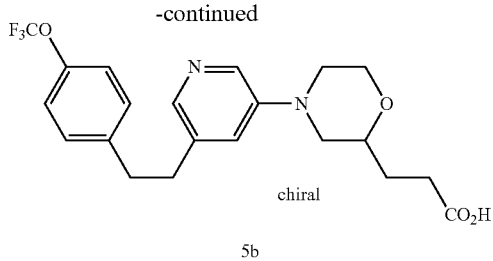

5b

Step a

To a solution of compound 1 (190 mg, 552 μmol) obtained in Reference Example 45, Step b, and compound 2 (50.0 mg, 267 μmol, Reference Example 39) in 1,4-dioxane (5.0 mL) were added cesium carbonate (220 mg, 675 μmol), palladium(II) acetate (7.0 mg, 31 μmol) and 2-(dicyclohexylphosphino)-3,6-dimethoxy-2',4',6'-triisopropyl-1,1'-biphenyl (25 mg, 54 μmol), and the mixture was stirred under microwave radiation with heating at 160° C. for 30 min. The reaction mixture was allowed to cool to room temperature, water was added and the mixture was extracted with ethyl acetate. The organic layer was washed with saturated brine, dried over anhydrous sodium sulfate, filtered and concentrated. The residue was purified by silica gel chromatography to give compound 3 (155 mg).

MS (ESI) m/z: 451 (M+1)$^+$.

Step b

To a solution of compound 3 (150 mg, 267 μmol) in ethanol (6.0 mL) was added 10%-palladium/carbon (100 mg), and the mixture was stirred in a hydrogen atmosphere at room temperature overnight. The reaction mixture was diluted with chloroform, filtered through celite, and washed with chloroform. The filtrate was concentrated under reduced pressure to give compound 4 (135 mg). MS(ESI) m/z: 453 (M+1)$^+$.

Step c

To a mixed solution of compound 4 (135 mg, 267 μmol) in tetrahydrofuran (3.0 mL) and methanol (1.5 mL) was added 2 M-aqueous sodium hydroxide solution (1.5 mL, 3.0 mmol), and the mixture was stirred at room temperature for 3 hr. The reaction solution was neutralized wit 0.5 M-hydrochloric acid (6.5 mL) and extracted with chloroform. The organic layer was washed with saturated brine, dried over anhydrous sodium sulfate, filtered and concentrated. The residue was subjected to solid phase extraction purification using cation exchange resin column (Waters, PoraPak™, RxnCX) to give compound 5 (70 mg, 61%). MS(ESI) m/z: 425 (M+1)$^+$.

Step d

Chiral resolution of compound 5 (170 mg) by chiral HPLC (CHIRAL PAK IA, 30×250, hexane:methanol:tetrahydrofuran:acetic acid=70:15:15:0.5, 20 mL/min) gave compound 5a (28 mg, 99.8% ee, peak at retention time 17 min) and compound 5b (27 mg, 99.9% ee, peak at retention time 13 min). Compound 5a was used as Example 18-1 and compound 5b was used as Example 18-2.

Example 18-1: MS(ESI) m/z: 425 (M+1)$^+$

Example 18-2: MS(ESI) m/z: 425 (M+1)$^+$

Example 19

(1S,2S)-2-[(2S)-4-(5-{[trans-4-(trifluoromethyl)cyclohexyl]methoxy}pyridin-3-yl)morpholin-2-yl]cyclopropanecarboxylic acid (1R,2R)-2-[(2S)-4-(5-{[trans-4-(trifluoromethyl)cyclohexyl]methoxy}pyridin-3-yl)morpholin-2-yl]cyclopropanecarboxylic acid (1R,2R)-2-[(2R)-4-(5-{[trans-4-(trifluoromethyl)cyclohexyl]methoxy}pyridin-3-yl)morpholin-2-yl]cyclopropanecarboxylic acid (1S,2S)-2-[(2R)-4-(5-{[trans-4-(trifluoromethyl)cyclohexyl]methoxy}pyridin-3-yl)morpholin-2-yl]cyclopropanecarboxylic acid

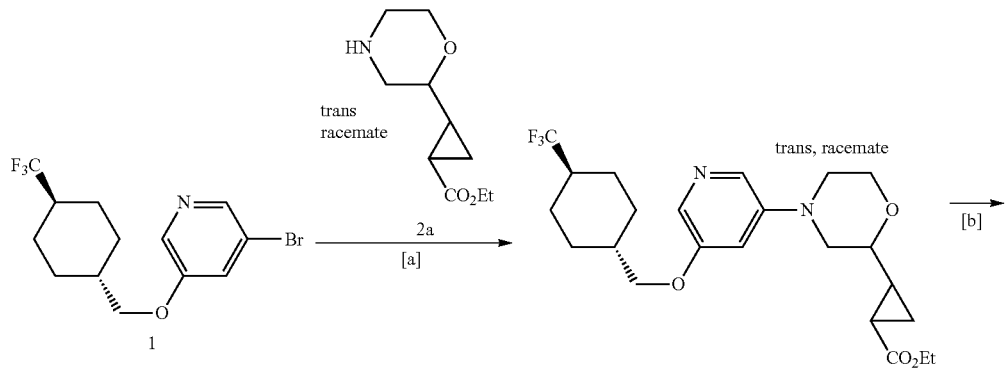

-continued
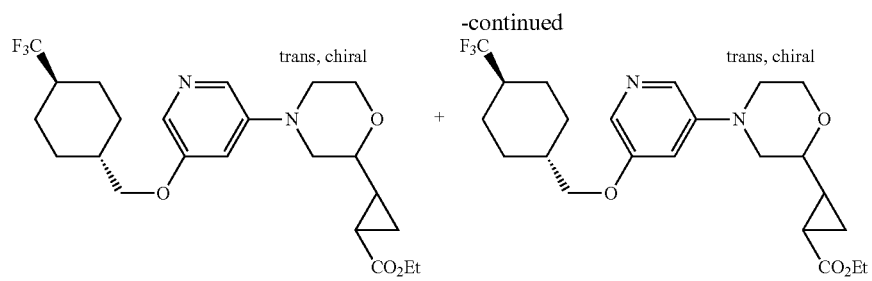
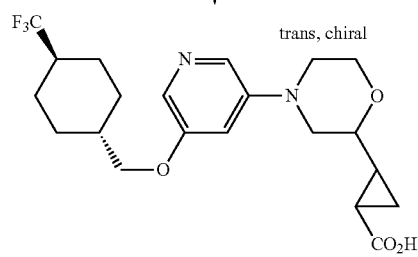
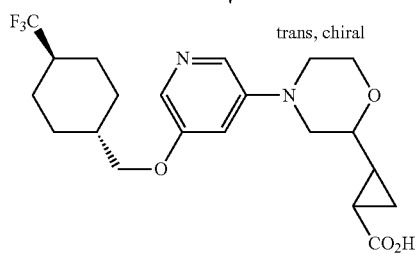
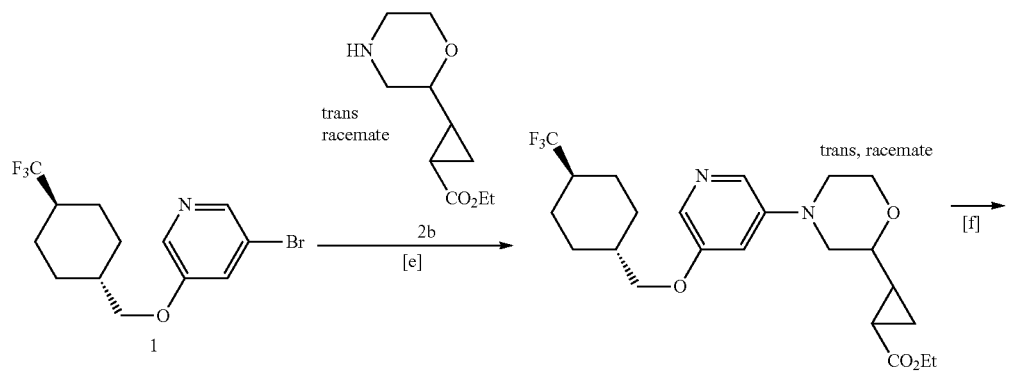
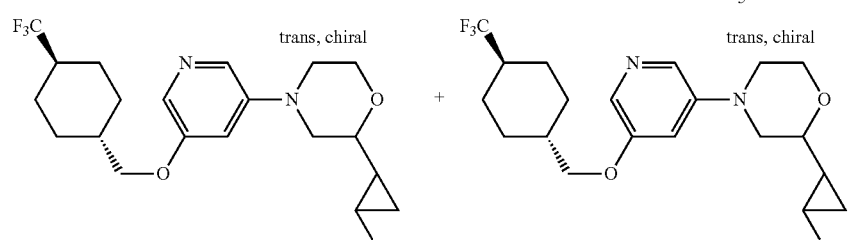
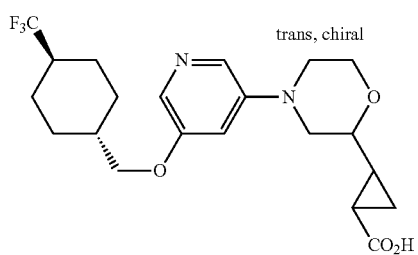
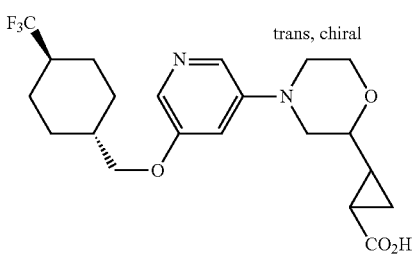

Step a

To a solution of compound 1 (463 mg, 1.37 mmol) obtained in Reference Example 42, Step b, and compound 2a (140 mg, 702 μmol, diastereomer of 2b) obtained in Reference Example 10, Step f, in 1,4-dioxane (3.5 mL) were added cesium carbonate (558 mg, 1.71 mmol), palladium(II) acetate (15 mg, 68 μmol) and 2-dicyclohexylphosphino-2',6'-diisopropoxybiphenyl (63.9 mg, 137 μmol), and the mixture was stirred in a nitrogen atmosphere under heating at 110° C. for 5 hr. The reaction mixture was allowed to cool to room temperature, water was added and the mixture was extracted with ethyl acetate. The organic layer was washed with saturated brine, dried over anhydrous sodium sulfate, filtered and concentrated. The residue was purified by silica gel chromatography to give compound 3 (220 mg, 65.5%). MS (ESI) m/z: 457 (M+1)$^+$.

Step b

Chiral resolution of compound 3 (220 mg) by chiral HPLC (CHIRAL PAK IA, 30×250, tert-butyl methyl ether:ethanol:diethylamine=85:15:0.1, 20 mL/min) gave compound 3a (95 mg, 99.9% ee, peak at retention time 12 min) and compound 3b (65 mg, 99.3% ee, peak at retention time 16 min).

Step c

To a mixed solution of compound 3a (95 mg, 0.21 mmol) in tetrahydrofuran (2.0 mL) and methanol (1.0 mL) was added 2 M-aqueous sodium hydroxide solution (1.0 mL, 2.0 mmol), and the mixture was stirred at room temperature overnight. The reaction solution was neutralized with 1 M-hydrochloric acid (2.1 mL), saturated brine (10 mL) was added, and the mixture was extracted with chloroform. The organic layer was washed with saturated brine, dried over anhydrous sodium sulfate, filtered and concentrated to give compound 4a (90 mg, 94%). This enantiomer was used as Example 19-1. MS(ESI) m/z: 429 (M+1)$^+$.

Step d

To a mixed solution of compound 3b (65 mg, 0.14 mmol) in tetrahydrofuran (2.0 mL) and methanol (1.0 mL) was added 2 M-aqueous sodium hydroxide solution (1.0 mL, 2.0 mmol), and the mixture was stirred at room temperature overnight. The reaction solution was neutralized with 1 M-hydrochloric acid (2.1 mL), saturated brine (10 mL) was added, and the mixture was extracted with chloroform. The organic layer was washed with saturated brine, dried over anhydrous sodium sulfate, filtered and concentrated to give compound 4b (55 mg, 90%). This enantiomer was used as Example 19-2. MS(ESI) m/z: 429 (M+1)$^+$.

Step e

To a solution of compound 1 (543 mg, 1.61 mmol) obtained in Reference Example 42, Step b, and compound 2b (160 mg, 803 μmol, diastereomer of 2a) obtained in Reference Example 10, Step g, in 1,4-dioxane (3.5 mL) were added cesium carbonate (654 mg, 2.01 mmol), palladium(II) acetate (18 mg, 80 μmol) and 2-dicyclohexylphosphino-2',6'-diisopropoxybiphenyl (74.9 mg, 161 μmol), and the mixture was stirred in a nitrogen atmosphere under heating at 110° C. for 5 hr. The reaction mixture was allowed to cool to room temperature, water was added and the mixture was extracted with ethyl acetate. The organic layer 1 was washed with saturated brine, dried over anhydrous sodium sulfate, filtered and concentrated. The residue was purified by silica gel chromatography to give compound 5 (26 mg, 64.5%). MS (ESI) m/z: 457 (M+1)$^+$.

Step f

Chiral resolution of compound 5 (260 mg) by chiral HPLC (CHIRAL PAK IC, 30×250, methanol:diethylamine=100:0.1, 20 mL/min) gave compound 5a (186 mg, 99.8% ee, peak at retention time 14 min) and compound 5b (140 mg, 97.7% ee, peak at retention time 19 min).

Step g

To a mixed solution of compound 5a (186 mg) in tetrahydrofuran (2.4 mL) and methanol (1.2 mL) was added 2 M-aqueous sodium hydroxide solution (1.2 mL, 2.4 mmol), and the mixture was stirred at room temperature overnight. The reaction solution was neutralized with 1 M-hydrochloric acid (2.5 mL), saturated brine (10 mL) was added, and the mixture was extracted with chloroform. The organic layer was washed with saturated brine, dried over anhydrous sodium sulfate, filtered and concentrated to give compound 6a (125 mg). This enantiomer was used as Example 19-3. MS(ESI) m/z: 429 (M+1)$^+$.

Step h

To a mixed solution of compound 5b (140 mg) in tetrahydrofuran (2.4 mL) and methanol (1.2 mL) was added 2 M-aqueous sodium hydroxide solution (1.2 mL, 2.4 mmol), and the mixture was stirred at room temperature overnight. The reaction solution was neutralized with 1 M-hydrochloric acid (2.5 mL), saturated brine (10 mL) was added, and the mixture was extracted with chloroform. The organic layer was washed with saturated brine, dried over anhydrous sodium sulfate, filtered and concentrated to give compound 6b (83 mg). This enantiomer was used as Example 19-4. MS(ESI) m/z: 429 (M+1)$^+$.

Example 20 trans-1-methyl-2-[(2S)-4-(5-{[trans-4-(trifluoromethyl)cyclohexyl]methoxy}pyridin-3-yl)morpholin-2-yl]cyclopropanecarboxylic acid

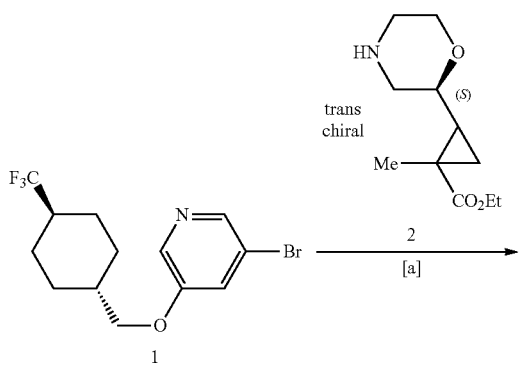

93

-continued

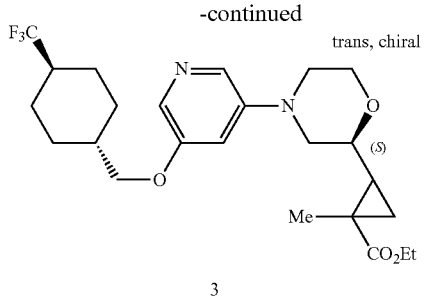

3

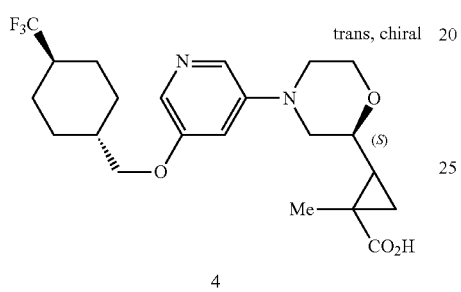

4

Step a

To a solution of compound 1 (289 mg, 855 μmol) obtained in Reference Example 42, Step b, and compound 2 (91.2 mg, 428 mol) obtained in Reference Example 11, Step g, in 1,4-dioxane (4.0 mL) were added cesium carbonate (348 mg, 1.07 mmol), palladium(II) acetate (14 mg, 64 μmol) and 2-dicyclohexylphosphino-2',6'-diisopropoxybiphenyl (59.9 mg, 128 μmol), and the mixture was stirred in a nitrogen atmosphere under heating at 110° C. for 8 hr. The reaction mixture was allowed to cool to room temperature, water was added, and the mixture was extracted with ethyl acetate. The organic layer was washed with saturated brine, dried over anhydrous sodium sulfate, filtered and concentrated. The residue was purified by NH silica gel chromatography and silica gel chromatography to give compound 3 (130 mg, 60.7%). MS(ESI) m/z: 471 (M+1)$^+$.

Step b

To a mixed solution of compound 3 (130 mg, 260 μmol) in tetrahydrofuran (1.3 mL) and methanol (1.3 mL) was added 4 M-aqueous sodium hydroxide solution (1.3 mL), and the mixture was stirred at room temperature for 5 hr. The reaction solution was diluted with water (7.0 mL) and washed with diisopropyl ether. The aqueous layer was neutralized with 4 M-hydrochloric acid (1.35 mL), saturated aqueous ammonium chloride solution (5 mL) was added, and the mixture was extracted with chloroform. The organic layer was washed with saturated brine, dried over anhydrous magnesium sulfate, filtered and concentrated to give compound 4 (103 mg, 85.1%). MS(ESI) m/z: 443 (M+1)$^+$.

94

Example 21

{[(3S)-4-(5-{[4-(trifluoromethoxy)benzyl]oxy}pyridin-3-yl)morpholin-3-yl]methoxy}acetic acid

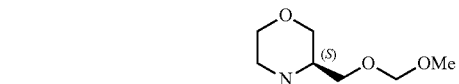

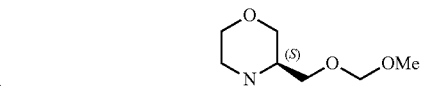

Step a

To a solution of compound 1 (368 mg, 1.06 mmol, Reference Example 49) and compound 2 (145 mg, 756 μmol, Reference Example 38) in 1,4-dioxane (4.0 mL) were added sodium tert-butoxide (182 mg, 1.89 mmol), palladium (II) acetate (17 mg, 76 μmol) and 2-dicyclohexylphosphino-2',6'-diisopropoxybiphenyl (70.5 mg, 151 μmol), and the mixture was stirred in a nitrogen atmosphere under heating at 105° C. for 3 hr. To the reaction mixture were further added palladium(II) acetate (17 mg, 76 μmol) and 2-dicyclohexylphosphino-2',6'-diisopropoxybiphenyl (70.5 mg, 151 μmol), and the mixture was stirred in a nitrogen atmosphere under heating at 105° C. for 3 hr. The reaction mixture was allowed to cool to room temperature, water and ethyl acetate were added and the mixture was filtered through celite. The filtrate was phase separated and the organic layer was washed with saturated brine, dried over anhydrous sodium sulfate, filtered and concentrated. The residue was purified by silica gel chromatography to give compound 3 (160 mg, 49.4%). MS (ESI) m/z: 429 (M+1)$^+$.

Step b

To a solution of compound 3 (155 mg, 362 μmol) in tetrahydrofuran (2.0 mL) was added 6 M-hydrochloric acid (2.0 mL, 12 mmol), and the mixture was stirred at room temperature for 10 hr. The reaction solution was neutralized with 2 M-aqueous sodium hydroxide solution (5.0 mL), and subjected to solid phase extraction purification using cation exchange resin column (Waters, PoraPak™, RxnCX) to give compound 4 (70 mg, 50%). MS(ESI) m/z: 385 (M+1)$^+$.

Step c

To a solution of compound 4 (60 mg, 156 μmol) in N,N-dimethylformamide (1.0 mL) was added under ice-cooling sodium hydride (60 wt %, 9.4 mg, 0.23 mmol), and the mixture was stirred under ice-cooling for 10 min. To the reaction solution was added dropwise under ice-cooling a solution of tert-butyl bromoacetate (33 mg, 0.17 mmol) in N,N-dimethylformamide (0.50 mL), and the mixture was stirred at room temperature for 4 hr. To the reaction mixture was added saturated aqueous ammonium chloride solution, and the mixture was extracted with ethyl acetate. The organic layer was washed with saturated brine, dried over anhydrous sodium sulfate, filtered and concentrated. The residue was purified by silica gel chromatography to give compound 5 (35 mg, 45%). MS(ESI) m/z: 499 (M+1)$^+$.

Step d

To a mixed solution of compound 5 (35 mg, 70 μmol) in tetrahydrofuran (1.0 mL) and methanol (0.50 mL) was added 4 M-aqueous sodium hydroxide solution (0.50 mL, 2.0 mmol), and the mixture was stirred at room temperature for 3 hr. The reaction solution was diluted with water (20 mL) and washed with diisopropyl ether-hexane. The aqueous layer was neutralized with 1 M-hydrochloric acid (2.1 mL) and extracted with chloroform. The organic layer was washed with saturated brine, dried over anhydrous magnesium sulfate, filtered and concentrated to give compound 6 (32 mg, 99%).

MS (ESI) m/z: 443 (M+1)$^+$

Example 22

(2E)-4-[(3R)-4-(5-{[4-(trifluoromethoxy)benzyl]oxy}pyridin-3-yl)morpholin-3-yl]-2-butenoic acid

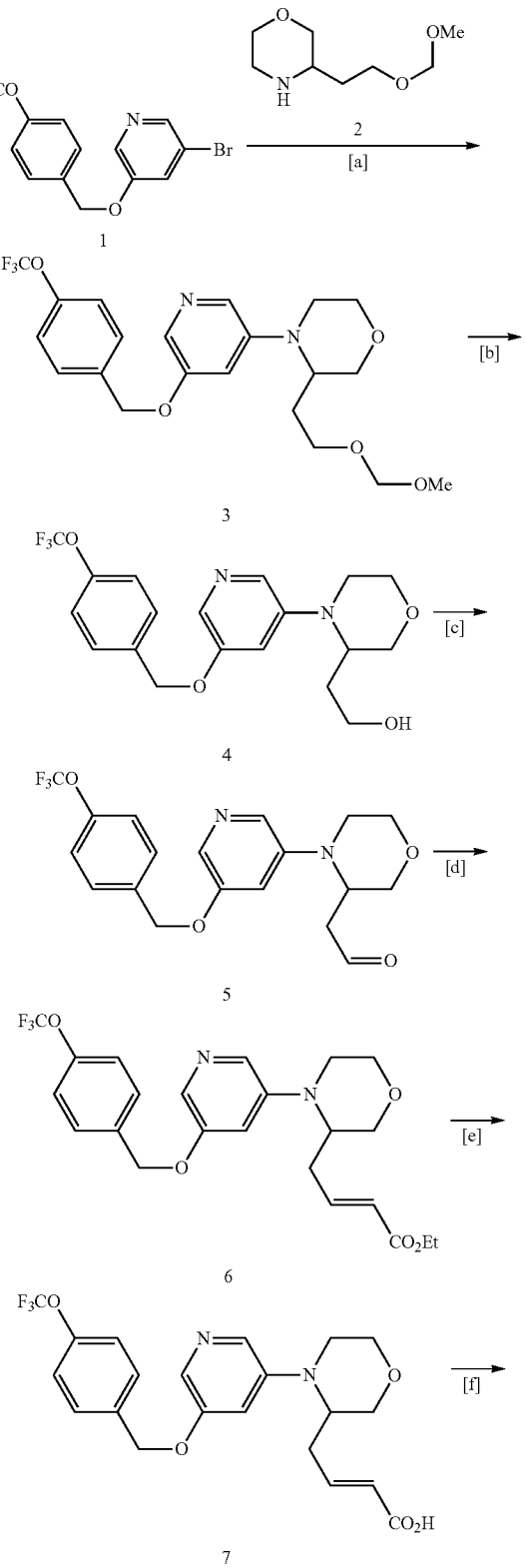

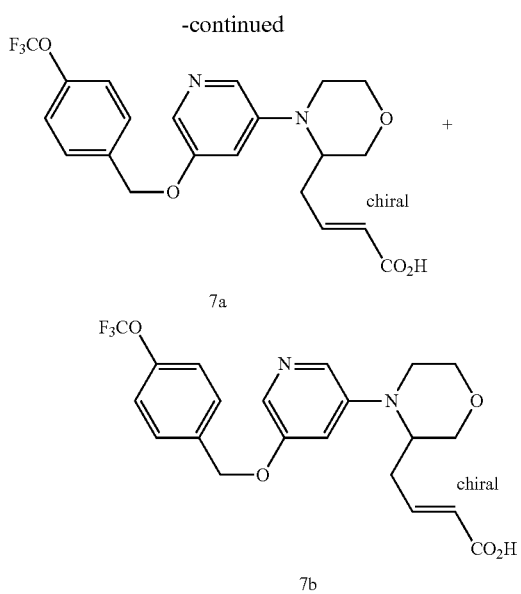

Step a

To a solution of compound 2 (594 mg, 3.39 mmol) obtained in Reference Example 12, Step c, and compound 1 (1.42 g, 4.07 mmol, Reference Example 49) in 1,4-dioxane (30 mL) were added cesium carbonate (2.76 g, 8.48 mmol), palladium(II) acetate (114 mg, 508 µmol) and 2-dicyclohexylphosphino-2',6'-diisopropoxybiphenyl (475 mg, 1.02 mmol), and the mixture was stirred in a nitrogen atmosphere with heating under reflux for 4 hr. The reaction mixture was allowed to cool to room temperature, diluted with ethyl acetate (200 mL) and filtered through celite. The filtrate was washed with water and saturated brine, dried over anhydrous sodium sulfate, filtered and concentrated. The residue was purified by silica gel chromatography to give compound 3 (731 mg, 48.7%).

MS (ESI) m/z: 443 (M+1)$^+$.

Step b

To a solution of compound 3 (731 mg, 1.65 mmol) in tetrahydrofuran (9.0 mL) was added 6 M-hydrochloric acid (9.0 mL, 54 mmol), and the mixture was stirred at room temperature overnight. The reaction solution was neutralized with 1 M-aqueous sodium hydroxide solution and extracted with ethyl acetate (240 mL). The organic layer was washed with saturated brine, dried over anhydrous sodium sulfate, filtered and concentrated. The residue was purified by silica gel chromatography to give compound 4 (404 mg, 61.4%).

MS (ESI) m/z: 399 (M+1)$^+$.

Step c

To a mixed solution of compound 4 (404 mg, 1.01 mmol) in dichloromethane (9.0 mL) and dimethyl sulfoxide (3.0 mL) were added triethylamine (705 µL, 5.07 mmol) and sulfur trioxide pyridine complex (526 mg, 3.04 mmol), and the mixture was stirred at room temperature for 6 hr. To the reaction solution was added water and the mixture was extracted with tert-butyl methyl ether. The organic layer was washed with water and saturated brine, dried over anhydrous sodium sulfate, filtered and concentrated. The residue was purified by silica gel chromatography to give compound 5 (334 mg, 83.1%).

MS (ESI) m/z: 397 (M+1)$^+$.

Step d

To a solution of ethyl diethylphosphonoacetate (682 mg, 3.04 mmol) in tetrahydrofuran (6.0 mL) was added under ice-cooling sodium hydride (60 wt %, 101 mg, 2.54 mmol), and the mixture was stirred under ice-cooling for 20 min. To the reaction solution was added dropwise under ice-cooling a solution of compound 5 (334 mg, 843 µmol) in tetrahydrofuran (6.0 mL), and the mixture was stirred while warming to room temperature for 1.5 hr. To the reaction solution was added water and the mixture was extracted with ethyl acetate. The organic layer was washed with water and saturated brine, dried over anhydrous sodium sulfate, filtered and concentrated under reduced pressure. The residue was purified by HPLC (Capcellpak C18 UG80, 30×250, 35 mL/min, 0.05% TFA aqueous solution/0.05% TFA acetonitrile solution=35%→55%, 15 min) to give compound 6 (212 mg, 44.8%). MS(ESI) m/z: 467 (M+1)$^+$.

Step e

To a mixed solution of compound 6 (50.0 mg, 107 µmol) in tetrahydrofuran (1.0 mL) and methanol (0.5 mL) was added 4 M-aqueous sodium hydroxide solution (0.5 mL, 2.0 mmol), and the mixture was stirred at room temperature for 60 hr. The reaction solution was concentrated under reduced pressure, and the residue was dissolved in water (2 mL), and neutralized with 1 M-hydrochloric acid (2.0 mL). The resulting solid was collected by filtration and washed with water to give compound 7 (30.0 mg, 63.8%). MS(ESI) m/z: 439 (M+1)$^+$.

Step f

Chiral resolution of compound 7 (21 mg) by chiral HPLC (CHIRAL PAK IA, 30×250, hexane:ethanol:tetrahydrofuran:acetic acid=60:30:10:0.1, 10 mL/min, separated after 0.5 recycle) gave compound 7a (4.1 mg, 99.8% ee, peak at retention time 27 min) and compound 7b (5.2 mg, 99.1% ee, peak at retention time 17 min). Compound 7a was used as Example 22-1 and compound 7b was used as Example 22-2.

Example 22-1: MS(ESI) m/z: 439 (M+1)$^+$

Example 22-2: MS(ESI) m/z: 439 (M+1)$^+$

Example 23

4-[1-(5-{[4-(trifluoromethoxy)benzyl]oxy}pyridin-3-yl)pyrrolidin-2-yl]butanoic acid

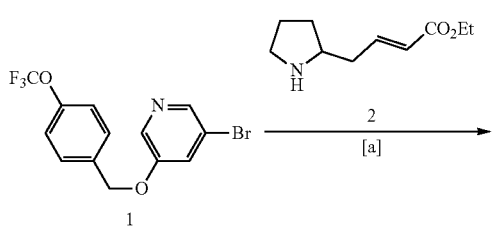

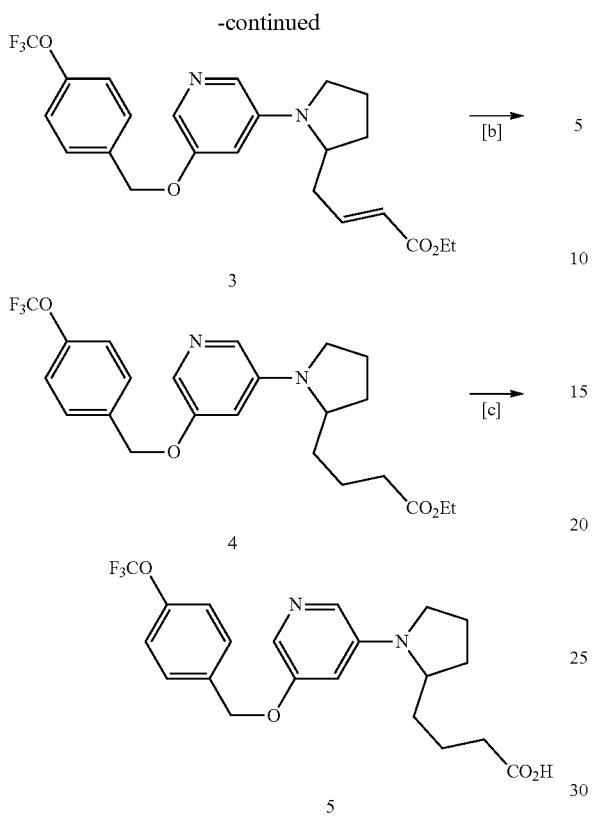

Step a

To a solution of compound 2 (197 mg, 1.08 mmol) obtained in Reference Example 14, Step c, and compound 1 (250 mg, 718 μmol, Reference Example 49) in 1,4-dioxane (7.2 mL) were added cesium carbonate (702 mg, 2.16 mmol), palladium(II) acetate (8.1 mg, 36 μmol) and 2-dicyclohexylphosphino-2',6'-diisopropoxybiphenyl (34 mg, 72 μmol), and the mixture was stirred in a nitrogen atmosphere under heating at 100° C. for 15 hr. The reaction mixture was allowed to cool to room temperature, water was added, and the mixture was extracted with chloroform. The organic layer was concentrated under reduced pressure, and the residue was purified by silica gel chromatography to give compound 3 (138 mg, 42.7%).

MS (ESI) m/z: 451 (M+1)$^+$.

Step b

To a solution of compound 3 (138 mg, 306 μmol) in ethanol (2.0 mL) was added 10%-palladium/carbon (30 mg), and the mixture was stirred in a hydrogen atmosphere at room temperature for 6 hr. The reaction mixture was filtered through celite and the filtrate was concentrated. The residue was dissolved in ethanol (2.0 mL), 10%-palladium/carbon (30 mg) was added, and the mixture was stirred in a hydrogen atmosphere at room temperature for 20 hr. The reaction mixture was filtered through celite and the filtrate was concentrated. The residue was purified by silica gel chromatography to give compound 4 (97.0 mg, 70.0%). MS(ESI) m/z: 453 (M+1)$^+$.

Step c

To a mixed solution of compound 4 (97.0 mg, 214 μmol) in tetrahydrofuran (1.0 mL) and methanol (1.0 mL) was added 4 M-aqueous sodium hydroxide solution (0.11 mL, 0.44 mmol), and the mixture was stirred at room temperature for 2 hr. The reaction solution was neutralized with 1 M-hydrochloric acid (0.44 mL), and the mixture was extracted with chloroform. The organic layer was concentrated under reduced pressure, and the residue was purified by silica gel chromatography to give compound 5 (81.0 mg, 89.0%). MS(ESI) m/z: 425 (M+1)$^+$.

Example 24

{[(2R)-1-(5-{[4-(trifluoromethoxy)benzyl]oxy}pyridin-3-yl)pyrrolidin-2-yl]methoxy}acetic acid

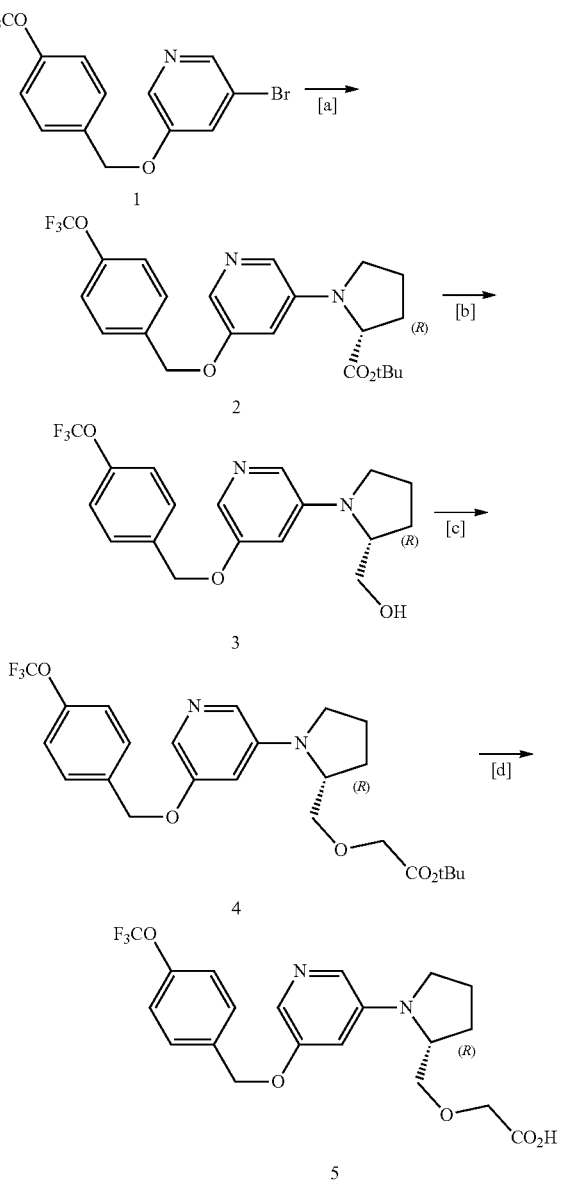

Step a

To a solution of compound 1 (1.89 g, 5.43 mmol, Reference Example 49) and tert-butyl D-prolinate (2.32 g, 13.5 mmol) in toluene (20 mL) were added sodium tert-butoxide (1.04 g, 10.9 mmol), tris(dibenzylideneacetone)dipalladium (0) (199 mg, 217 μmol) and 2,2'-bis(diphenylphosphino)-1,1'-binaphthalene (270 mg, 434 μmol), and the mixture was stirred in a nitrogen atmosphere under heating at 105° C. for 2.5 hr. The reaction mixture was allowed to cool to room temperature, saturated aqueous ammonium chloride solution and water were added, and the mixture was extracted with ethyl acetate. The organic layer was washed with water and saturated brine, dried over anhydrous sodium sulfate, filtered and concentrated. The residue was purified by silica gel chromatography to give compound 2 (1.74 g, 67.4%). MS(ESI) m/z: 439 (M+1)$^+$.

Step b

To a solution of compound 2 (830 mg, 1.52 mmol) in tetrahydrofuran (15 mL) was added under ice-cooling lithium aluminum hydride (86.2 mg, 2.27 mmol), and the mixture was stirred under ice-cooling for 3 hr. To the reaction mixture was further added under ice-cooling lithium aluminum hydride (57.5 mg, 1.52 mmol), and the mixture was stirred under ice-cooling for 5 hr. To the reaction mixture was added dropwise water (0.15 mL) under ice-cooling and the mixture was stirred at room temperature for 15 min. To the reaction suspension was added 4 M-aqueous sodium hydroxide solution (0.15 mL), and the mixture was stirred at room temperature for 15 min. Water (0.45 mL) was added and the mixture was stirred at room temperature overnight. The reaction suspension was filtered through celite and washed with tetrahydrofuran (60 mL). The filtrate was concentrated under reduced pressure, and the residue was purified by silica gel chromatography to give compound 3 (490 mg, 79.9%). MS(ESI) m/z: 369 (M+1)$^+$.

Step c

To a solution of compound 3 (240 mg, 593 μmol) in dimethyl sulfoxide (2.5 mL) was added under ice-cooling sodium hydride (60 wt %, 30.8 mg, 771 μmol), and the mixture was stirred under ice-cooling for 20 min. To the reaction solution was added dropwise under ice-cooling a solution of tert-butyl bromoacetate (127 mg, 652 μmol) in dimethyl sulfoxide (0.50 mL), and the mixture was stirred at room temperature for 10 hr. To the reaction mixture were added saturated aqueous ammonium chloride solution and water, and the mixture was extracted with ethyl acetate. The organic layer was washed with water and saturated brine, dried over anhydrous sodium sulfate, filtered and concentrated. The residue was purified by silica gel chromatography and NH silica gel chromatography to give compound 4 (120 mg, 42.0%). MS(ESI) m/z: 483 (M+1)$^+$.

Step d

To a solution of compound 4 (115 mg, 238 μmol) in dichloromethane (3.0 mL) was added trifluoroacetic acid (1.0 mL), and the mixture was stirred at room temperature for 3.5 hr. The reaction solution was concentrated under reduced pressure, and the residue was subjected to solid phase extraction purification using cation exchange resin column (Waters, PoraPak™, RxnCX). The residue was dissolved in tetrahydrofuran (2.0 mL) and methanol (1.0 mL), 2 M-aqueous sodium hydroxide solution (1.0 mL, 2.0 mmol) was added, and the mixture was stirred at room temperature for 1 hr. The reaction solution was neutralized with 0.5 M-hydrochloric acid (4.1 mL) and extracted with chloroform. The organic layer was washed with saturated brine, dried over anhydrous magnesium sulfate, filtered and concentrated to give compound 5 (95.0 mg, 93.5%). MS (ESI) m/z: 427 (M+1)$^+$.

The following compounds were produced according to Production Methods 1-6 and Examples 1-11.

TABLE 1

Example 25 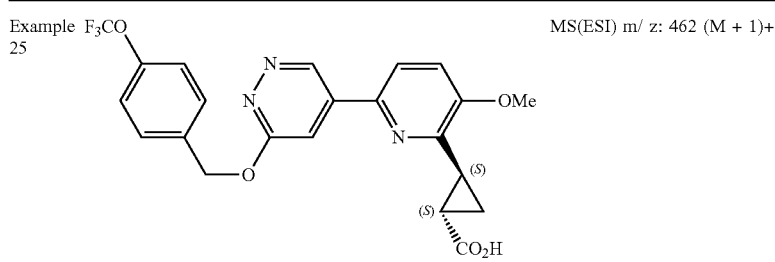 MS(ESI) m/z: 462 (M + 1)+

Example 26 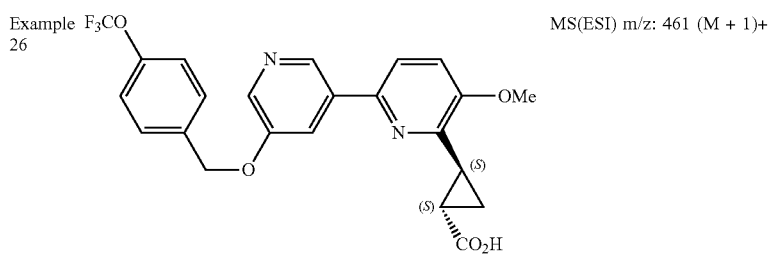 MS(ESI) m/z: 461 (M + 1)+

TABLE 1-continued
| | | |
|---|---|---|
| Example 27 | 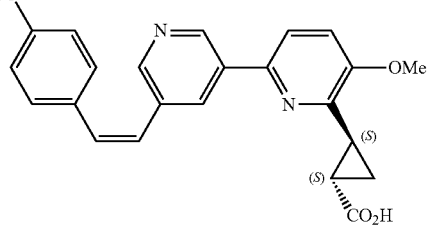 | MS(ESI) m/z: 457 (M + 1)+ |
| Example 28 | 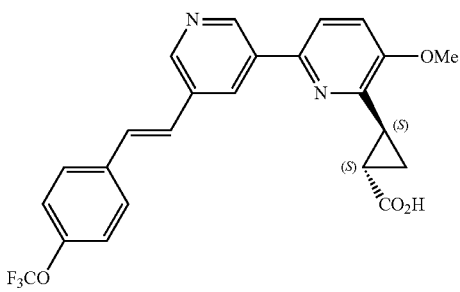 | MS(ESI) m/z: 457 (M + 1)+ |
TABLE 2
| | | |
|---|---|---|
| Example 29 | 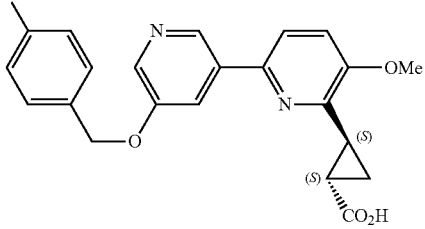 | MS(ESI) m/z: 445 (M + 1)+ |
| Example 30 | 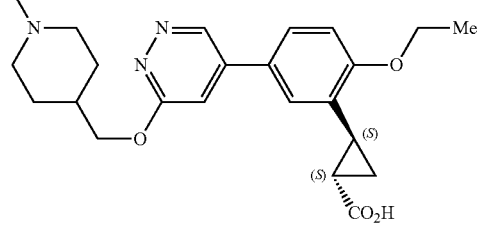 | MS(ESI) m/z: 480 (M + 1)+ |
| Example 31 | 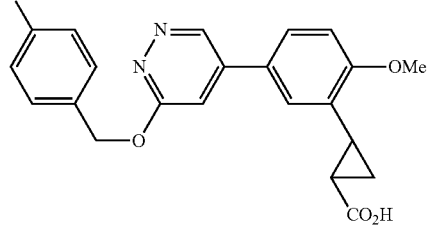<br>trans, racemate | MS(APCI) m/z: 461 (M + 1)+ |

TABLE 2-continued
| Example 32 | 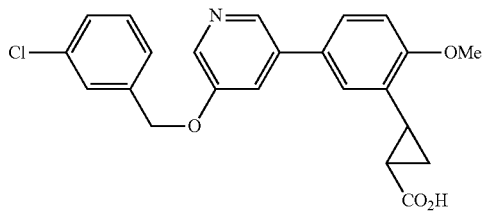 trans, racemate | MS(APCI) m/z: 410, 412 (M + 1)+ |
|---|---|---|
| Example 33 | 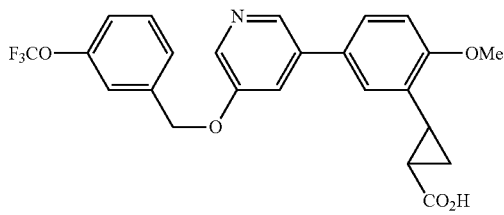 trans, racemate | MS(ESI) m/z: 460 (M + 1)+ |
| Example 34 | 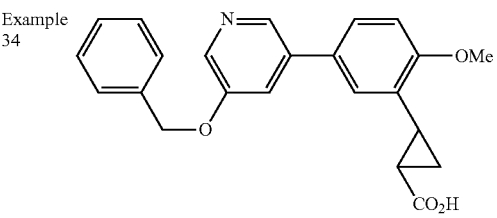 trans, racemate | MS(ESI) m/z: 376 (M + 1)+ |
The following compounds were produced according to Production Methods 7-8 and Examples 12-13.
TABLE 3
| Example 35 | 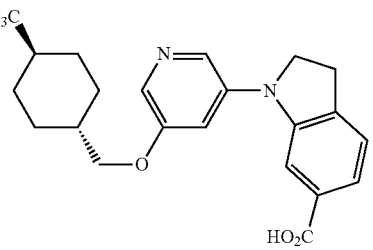 | MS(ESI) m/z: 421 (M + 1)+ |
|---|---|---|
| Example 36 | 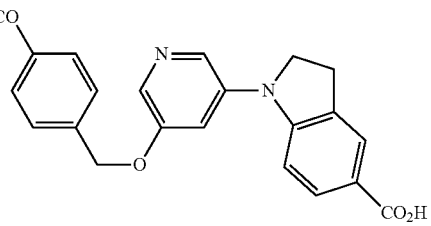 | MS(ESI) m/z: 431 (M + 1)+ |

TABLE 3-continued
| Example 37 | 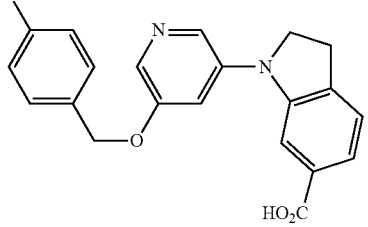 | MS(ESI) m/z: 431 (M + 1)+ |
| Example 38 | 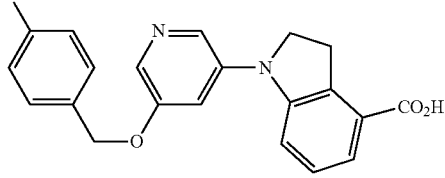 | MS(ESI) m/z: 431 (M + 1)+ |
| Example 39 | 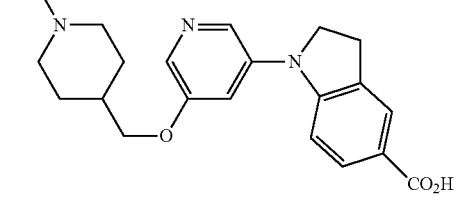 | MS(ESI) m/z: 436 (M + 1)+ |
| Example 40 | 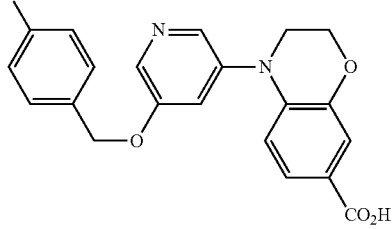 | MS(ESI) m/z: 447 (M + 1)+ |
| Example 41 | 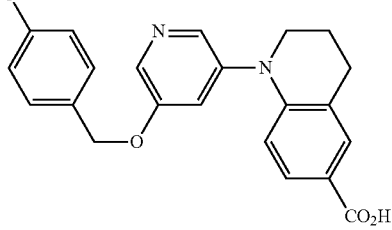 | MS(ESI) m/z: 445 (M + 1)+ |
TABLE 4
| Example 42 | 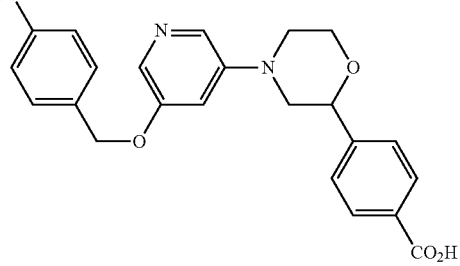 | MS (ESI) m/z: 475 (M + 1)+ |

TABLE 4-continued
| Example 43 | 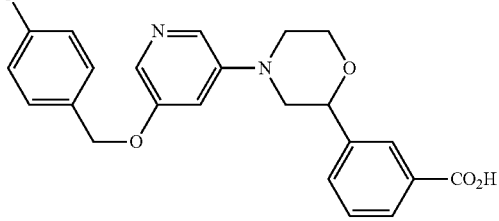 | MS (ESI) m/z: 475 (M + 1)+ |
| Example 44 | 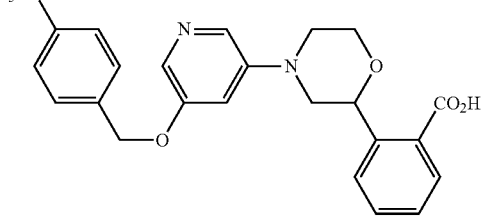 | MS (ESI) m/z: 475 (M + 1)+ |
| Example 45 | 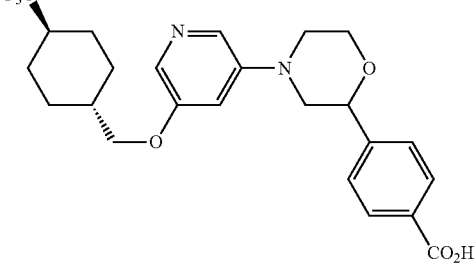 | MS (ESI) m/z: 465 (M + 1)+ |
| Example 46 | 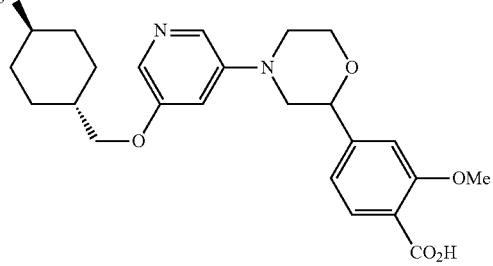 | MS (APCI) m/z: 495 (M + 1)+ |
| Example 47 | 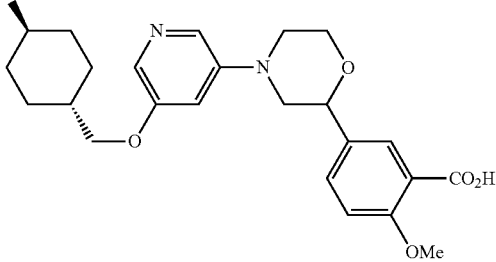 | MS (ESI) m/z: 495 (M + 1)+ |

TABLE 5
| Example 48 | 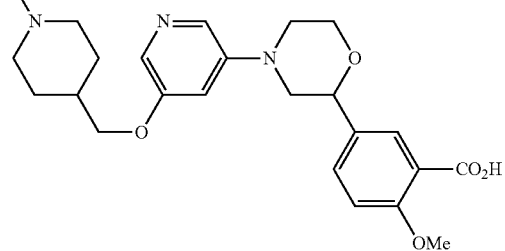 | MS (ESI) m/z: 510 (M + 1)+ |
| --- | --- | --- |
| Example 49 | 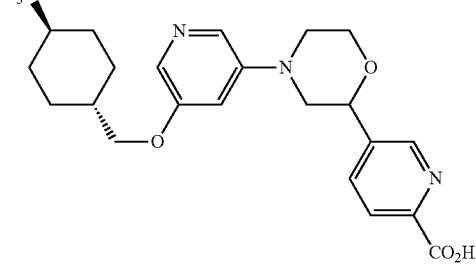 | MS (ESI) m/z: 466 (M + 1)+ |
| Example 50 | 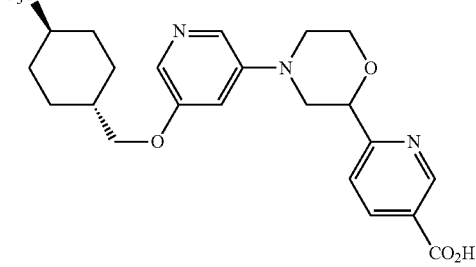 | MS (ESI) m/z: 466 (M + 1)+ |
| Example 51 | 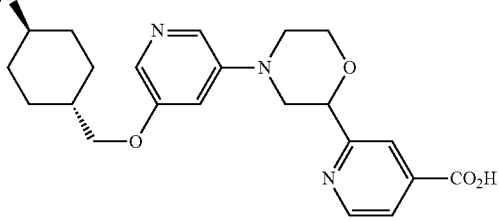 | MS (ESI) m/z: 466 (M + 1)+ |
| Example 52 | 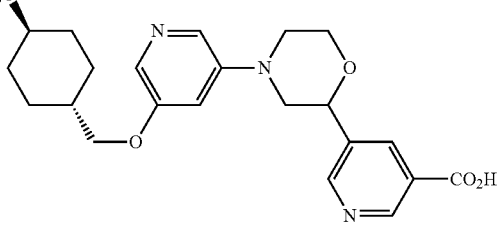 | MS (ESI) m/z: 466 (M + 1)+ |

TABLE 5-continued
| Example 53 | 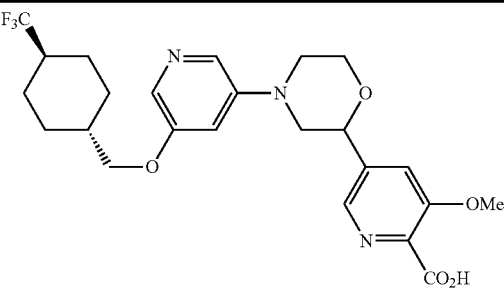 | MS (ESI) m/z: 496 (M + 1)+ |
TABLE 6
| Example 54 | 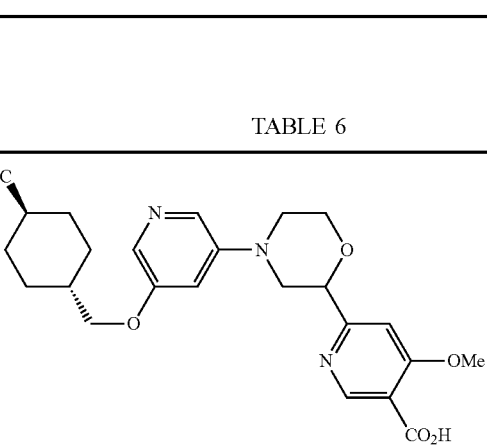 | MS (ESI) m/z: 496 (M + 1)+ |
| Example 55 | 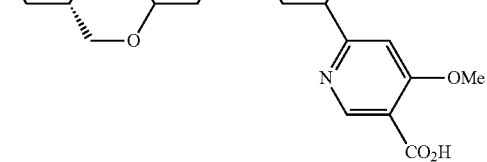 | MS (ESI) m/z: 480 (M + 1)+ |
| Example 56 | 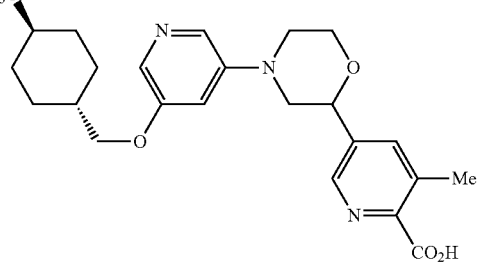 | MS (ESI) m/z: 480 (M + 1)+ |
| Example 57 | 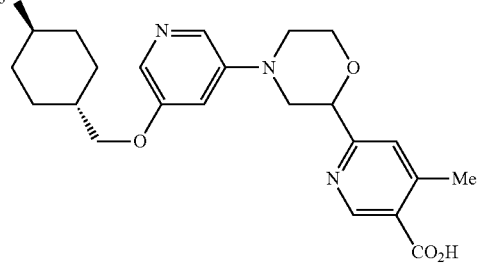 | MS (ESI) m/z: 480 (M + 1)+ |

TABLE 6-continued
| | | |
|---|---|---|
| Example 58 | 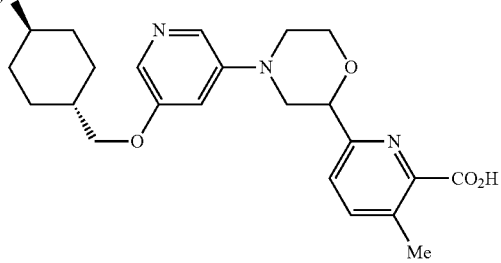 | MS (ESI) m/z: 480 (M + 1)+ |
| Example 59 | 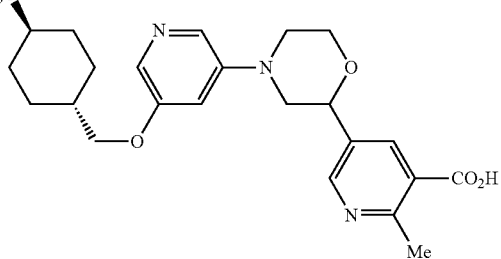 | MS (ESI) m/z: 480 (M + 1)+ |
TABLE 7
| | | |
|---|---|---|
| Example 60 | 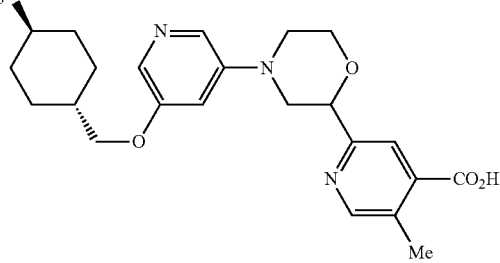 | MS (ESI) m/z: 480 (M + 1)+ |
| Example 61 | 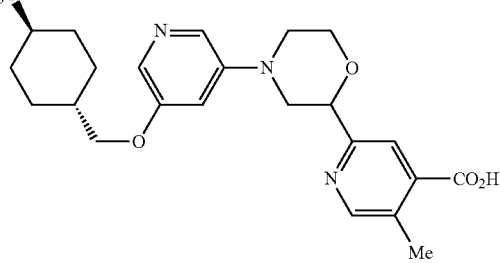 | MS (ESI) m/z: 480 (M + 1)+ |
| Example 62 | 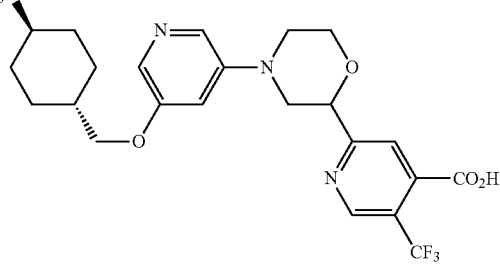 | MS (APCI) m/z: 534 (M + 1)+ |

TABLE 7-continued
| Example 63 | 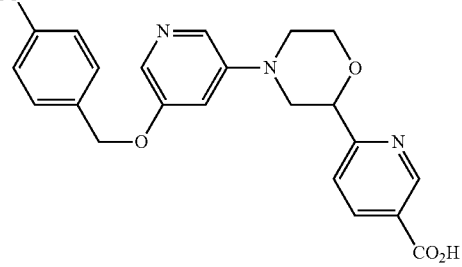 | MS (ESI) m/z: 476 (M + 1)+ |
| Example 64 | 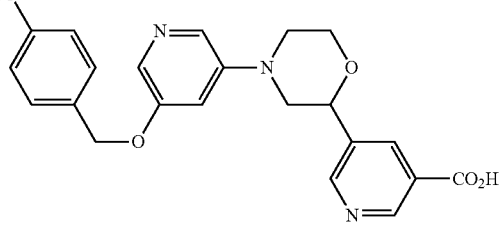 | MS (ESI) m/z: 476 (M + 1)+ |
| Example 65 | 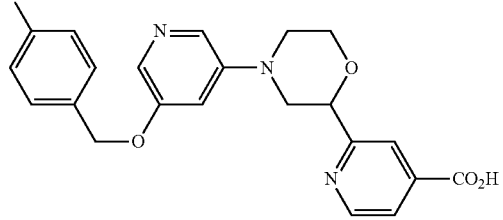 | MS (ESI) m/z: 476 (M + 1)+ |
TABLE 8
| Example 66 | 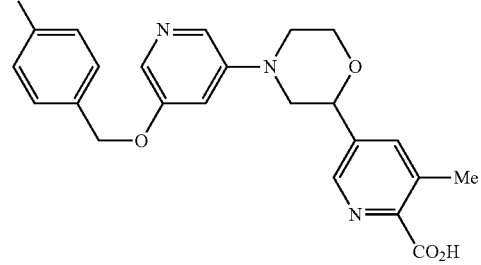 | MS (ESI) m/z: 490 (M + 1)+ |
| Example 67 | 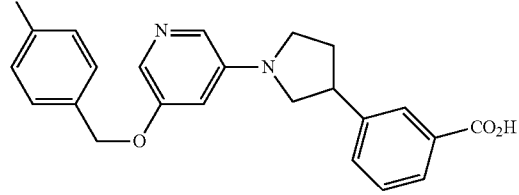 | MS (ESI) m/z: 459 (M + 1)+ |

TABLE 8-continued
| Example 68 | 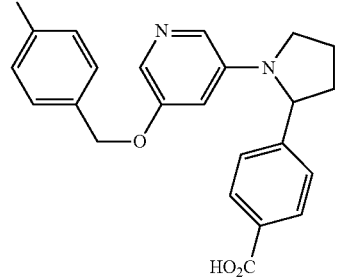 | MS (ESI) m/z: 459 (M + 1)+ |
The following compounds were produced according to Production Methods 7, 9-11 and Examples 14-16.
TABLE 9
| Example 69 | 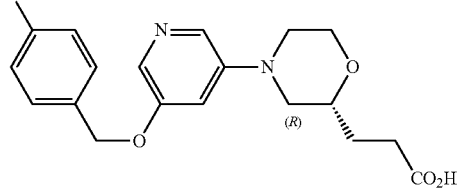 | MS (ESI) m/z: 427 (M + 1)+ |
| Example 70 | 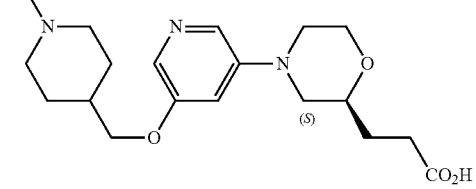 | MS (APCI) m/z: 432 (M + 1)+ |
| Example 71 | 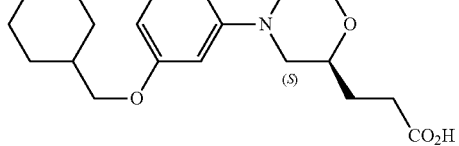 | MS (ESI) m/z: 349 (M + 1)+ |
| Example 72 | 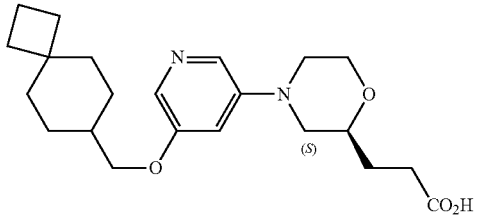 | MS (ESI) m/z: 389 (M + 1)+ |

TABLE 10
| Example 73 | 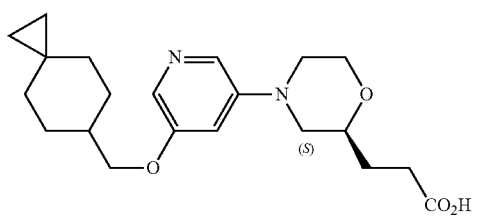 | MS (ESI) m/z: 375 (M + 1)+ |
| --- | --- | --- |
| Example 74 | 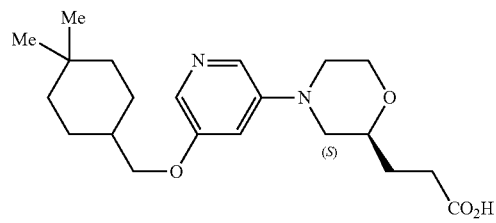 | MS (ESI) m/z: 377 (M + 1)+ |
| Example 75 | 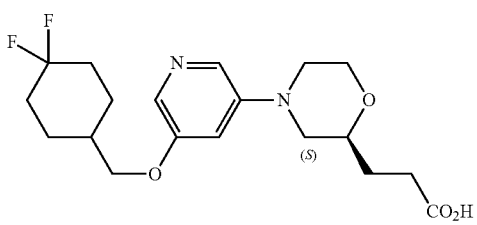 | MS (ESI) m/z: 385 (M + 1)+ |
| Example 76 | 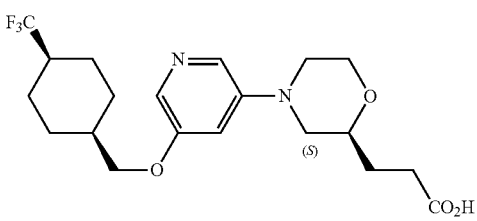 | MS (ESI) m/z: 417 (M + 1)+ |
| Example 77 | 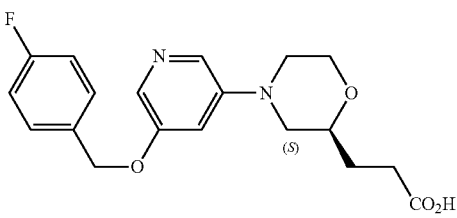 | MS (ESI) m/z: 361 (M + 1)+ |
| Example 78 | 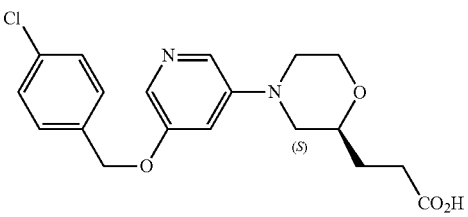 | MS (ESI) m/z: 377 (M + 1)+ |
| Example 79 | 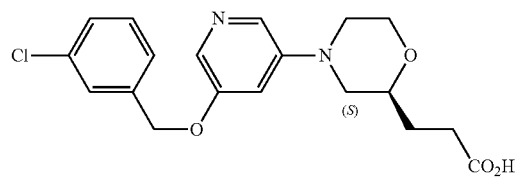 | MS (ESI) m/z: 377 (M + 1)+ |

TABLE 11
| Example 80 | 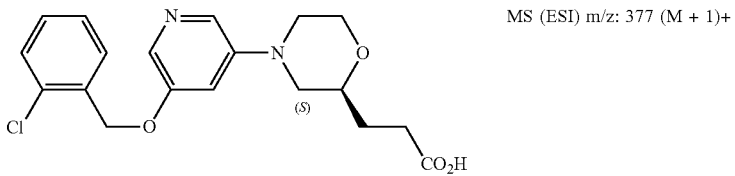 | MS (ESI) m/z: 377 (M + 1)+ |
| Example 81 | 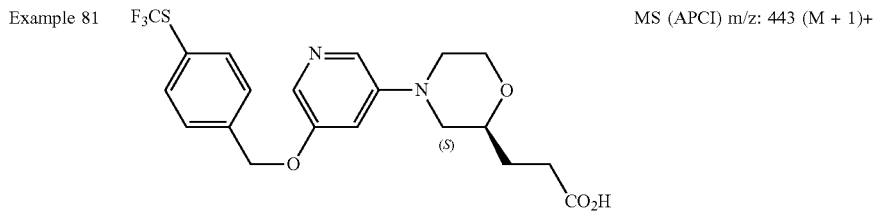 | MS (APCI) m/z: 443 (M + 1)+ |
| Example 82 | 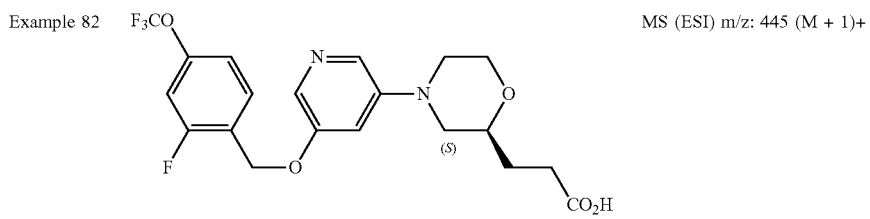 | MS (ESI) m/z: 445 (M + 1)+ |
| Example 83 | 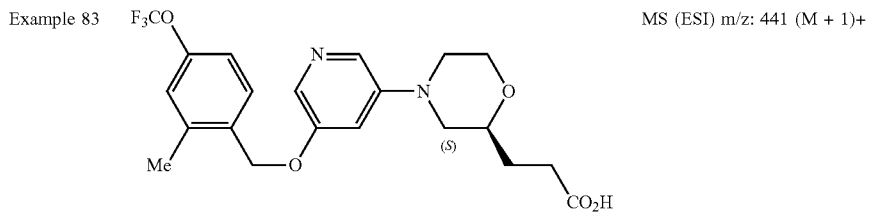 | MS (ESI) m/z: 441 (M + 1)+ |
| Example 84 | 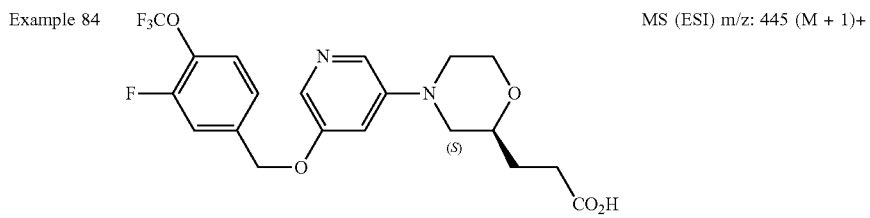 | MS (ESI) m/z: 445 (M + 1)+ |
| Example 85 | 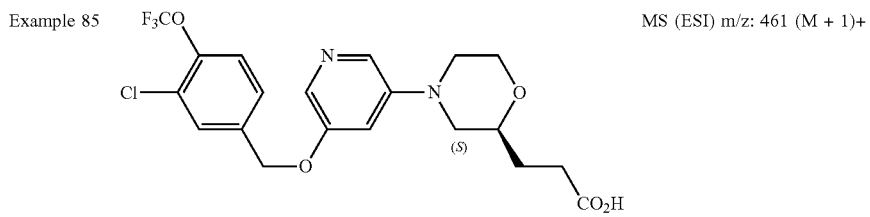 | MS (ESI) m/z: 461 (M + 1)+ |
| Example 86 | 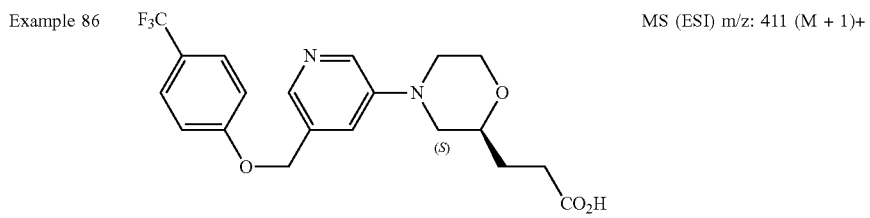 | MS (ESI) m/z: 411 (M + 1)+ |

TABLE 11-continued
| Example 87 | 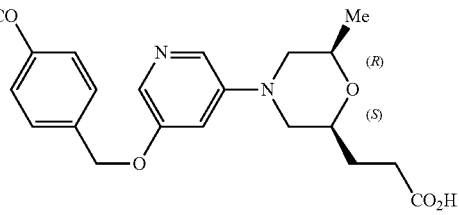 | MS (ESI) m/z: 441 (M + 1)+ |
| --- | --- | --- |
| Example 88 | 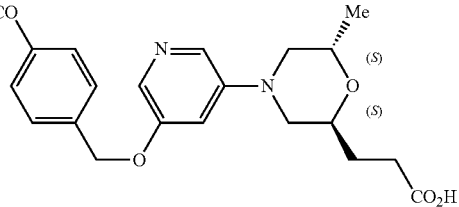 | MS (ESI) m/z: 441 (M + 1)+ |
The following compounds were produced according to Production Methods 7, 14-17 and Examples 19-24.
TABLE 12
| Example 89 | 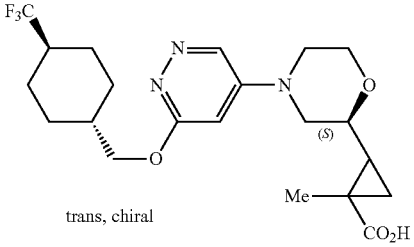 | MS (ESI) m/z: 444 (M + 1)+ |
| --- | --- | --- |
| Example 90 | 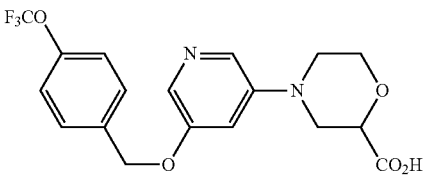 [SMILES: O=C(O)C1CN(c2cncc(OCc3ccc(OC(F)(F)F)cc3)c2)CCO1] | MS (APCI) m/z: 399 (M + 1)+ |
| Example 91 | 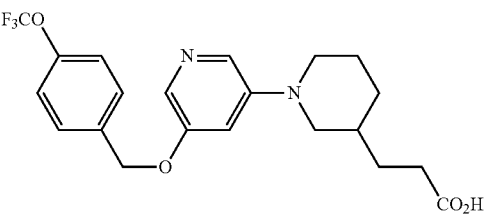 [SMILES: O=C(O)CCC1CCCN(c2cncc(OCc3ccc(OC(F)(F)F)cc3)c2)C1] | MS (ESI) m/z: 425 (M + 1)+ |
| Example 92 | 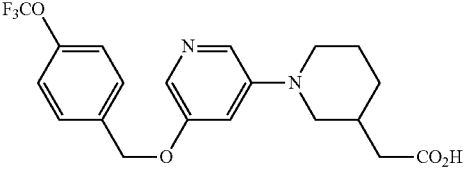 [SMILES: O=C(O)CC1CCCN(c2cncc(OCc3ccc(OC(F)(F)F)cc3)c2)C1] | MS (ESI) m/z: 411 (M + 1)+ |

TABLE 12-continued
| Example 93 | 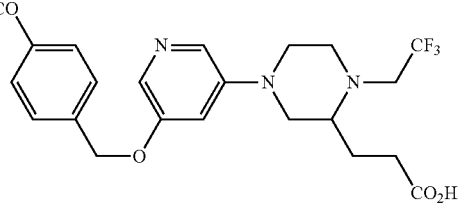 | MS (ESI) m/z: 508 (M + 1)+ |
| Example 94 | 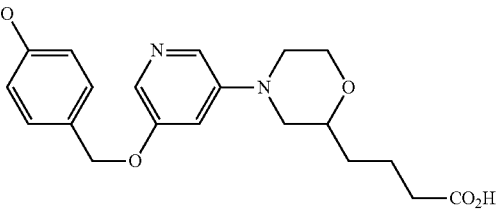 | MS (ESI) m/z: 441 (M + 1)+ |
| Example 95 | 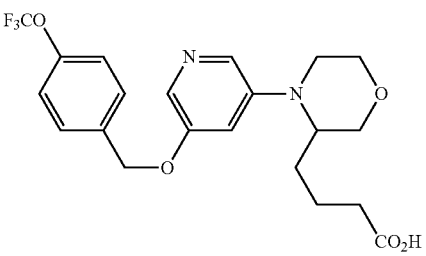 [SMILES: O=C(O)CCCC1COCCN1c1cncc(OCc2ccc(OC(F)(F)F)cc2)c1] | MS (ESI) m/z: 441 (M + 1)+ |
TABLE 13
| Example 96 | 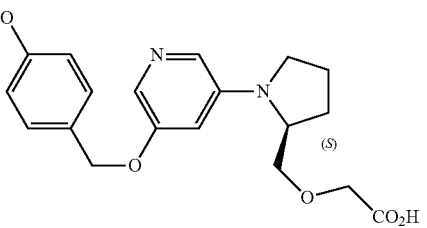 | MS (ESI) m/z: 427 (M + 1)+ |
| Example 97 | 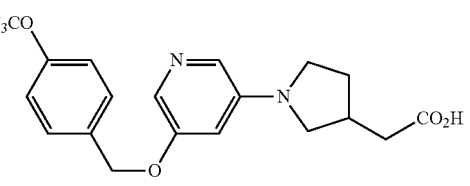 | MS (ESI) m/z: 397 (M + 1)+ |
| Example 98 | 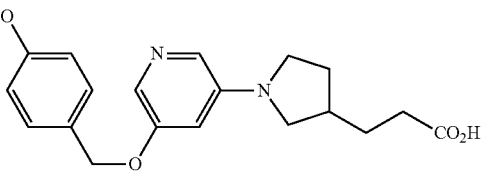 | MS (ESI) m/z: 411 (M + 1)+ |
| Example 99 | 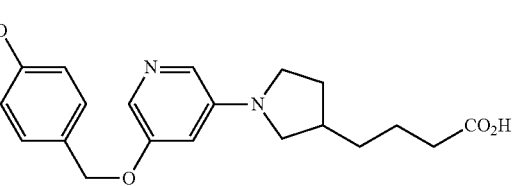 | MS (ESI) m/z: 425 (M + 1)+ |

TABLE 13-continued

| | | |
|---|---|---|
| Example 100 | 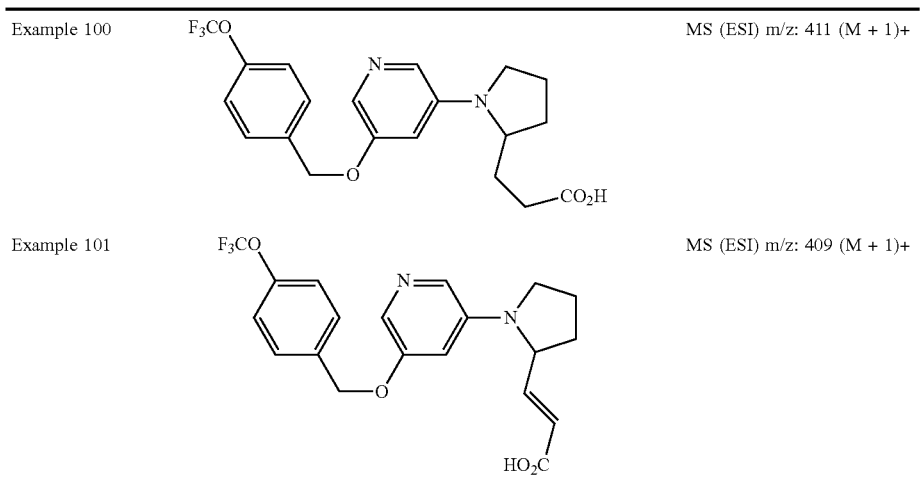 | MS (ESI) m/z: 411 (M + 1)+ |
| Example 101 | | MS (ESI) m/z: 409 (M + 1)+ |

Reference Example 1

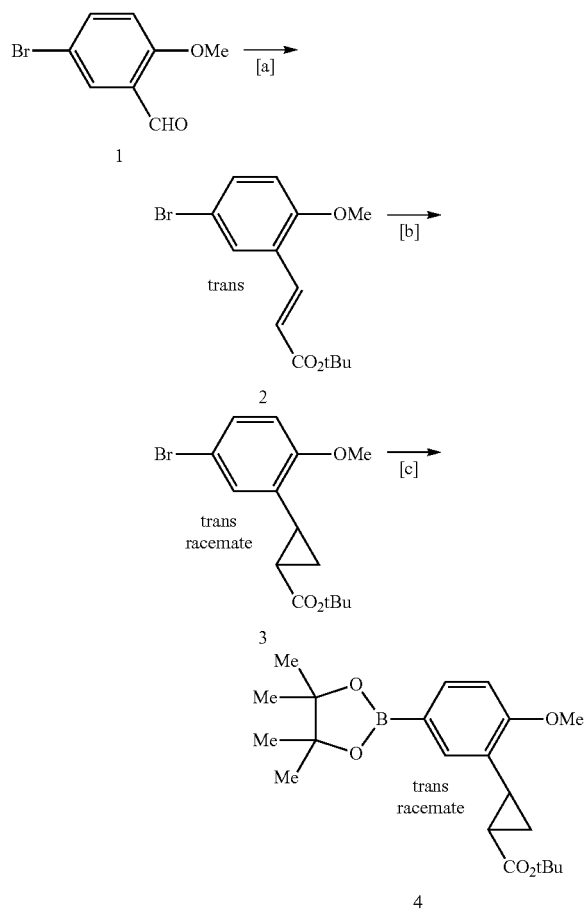

Step a

To a solution of tert-butyl diethylphosphonoacetate (14.1 g, 55.8 mmol) in tetrahydrofuran (200 mL) was added dropwise under ice-cooling a 1 M tetrahydrofuran solution (55.8 mL, 55.8 mmol) of potassium tert-butoxide, and the mixture was stirred for 30 min. To the reaction solution was added dropwise under ice-cooling a solution of compound 1 (10.0 g, 46.5 mmol) in tetrahydrofuran (100 mL), and the mixture was stirred under ice-cooling for 3 hr. To the reaction solution were added 1 M-hydrochloric acid (55 mL) and water (100 mL), and the mixture was extracted with ethyl acetate. The organic layer was washed with water and saturated brine, dried over anhydrous sodium sulfate, filtered and concentrated under reduced pressure. The residue was purified by silica gel chromatography to give compound 2 (14.8 g, 101%). MS(APCI) m/z: 257,259 (M-tBu+1)+.

Step b

To a solution of potassium tert-butoxide (1.75 g, 15.6 mmol) in dimethyl sulfoxide (40 mL) was added trimethylsulfoxonium iodide (3.43 g, 15.6 mmol) and the mixture was stirred for 30 min. To the reaction mixture was added a solution of compound 2 (4.07 g, 13.0 mmol) in dimethyl sulfoxide (40 mL), and the mixture was stirred at room temperature overnight. To the reaction mixture were added saturated aqueous ammonium chloride solution and water, and the mixture was extracted with ethyl acetate. The organic layer was washed with water and saturated brine, dried over anhydrous sodium sulfate, filtered and concentrated. The residue was purified by silica gel chromatography to give compound 3 (2.77 g, 65.2%). MS(APCI) m/z: 327,329 (M+1)+.

Step c

To a solution of compound 3 (2.72 g, 8.31 mmol) and bis(pinacolato)diborane (3.16 g, 12.5 mmol) in 1,4-dioxane (60 mL) were added potassium acetate (2.45 g, 24.9 mmol) and [1,1'-bis(diphenylphosphino)ferrocene]palladium(II) dichloride (243 mg, 333 μmol), and the mixture was stirred in a nitrogen atmosphere under heating at 80° C. overnight. The reaction mixture was allowed to cool to room temperature and filtered through celite. The filtrate was concentrated under reduced pressure, and the residue was purified by silica gel chromatography to give compound 4 (3.38 g, 109%).
MS(APCI) m/z: 319 (M-tBu+1)+.

Reference Example 2

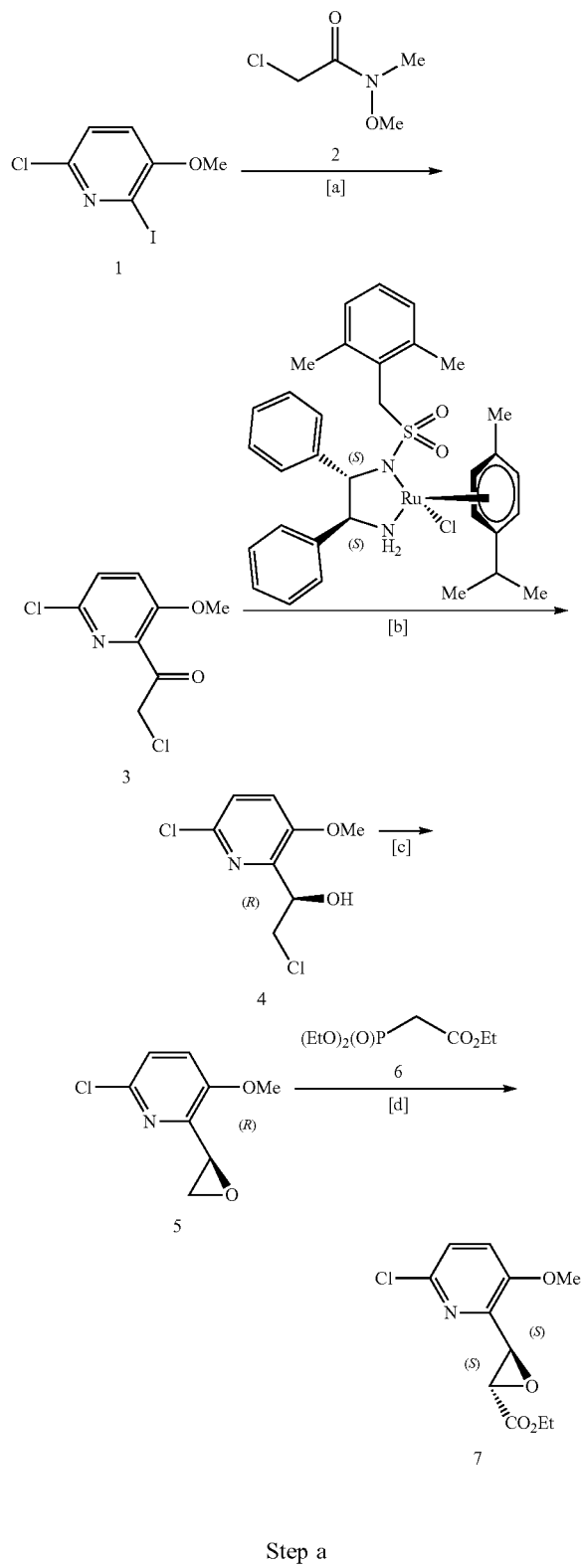

Step a

To a solution of 2 M tetrahydrofuran solution (24.5 mL, 49.0 mmol) of isopropylmagnesium chloride in tetrahydrofuran (30 mL) was added dropwise a solution of compound 1 (12.0 g, 44.5 mmol) in tetrahydrofuran (30 mL) in a nitrogen atmosphere at room temperature, and the mixture was stirred for 1 hr. To the reaction solution was further added dropwise a tetrahydrofuran solution (4.45 mL, 8.91 mmol) of 2 M-isopropylmagnesium chloride, and the mixture was stirred at room temperature for 1 hr. To the reaction solution were added under ice-cooling a solution of compound 2 (6.43 g, 46.8 mmol) in tetrahydrofuran (30 mL), and the mixture was stirred for 2 hr and stirred overnight while warming to room temperature. To the reaction mixture were added water (40 mL) and saturated aqueous ammonium chloride solution (160 mL), and the mixture was extracted with ethyl acetate. The organic layer was washed with saturated brine, dried over anhydrous sodium sulfate, filtered and concentrated. The residue was washed with chloroform (50 mL)-hexane (100 mL) to give compound 3 (5.84 g, 59.6%). MS(ESI) m/z: 220,222 (M+1)$^+$.

Step b

To a solution of compound 3 (14.2 g, 64.5 mmol) and chloro[(1S,2S)—N-(2',6'-dimethylbenzylsulfonyl)-1,2-diphenylethanediamine] (p-cymene) ruthenium (II) (777 mg, 1.29 mmol) in N-methylpyrrolidone (129 mL) was added dropwise a mixture of formic acid (12.2 mL, 323 mmol) and triethylamine (17.9 mL, 129 mmol) under ice-cooling, and the mixture was stirred under ice-cooling for 7 hr. To the reaction mixture was added water (700 mL) and the mixture was extracted with ethyl acetate (700 mL). The organic layer was washed with saturated aqueous sodium hydrogen carbonate (390 mL), water (520 mL) and saturated brine (260 mL), dried over anhydrous sodium sulfate, filtered and concentrated. The residue was purified by silica gel chromatography to give compound 4 (14.5 g, 95.3% ee). MS(ESI) m/z: 222,224 (M+1)$^+$.

Step c

To a solution of compound 4 (14.5 g, 65.3 mmol) in diethyl ether (140 mL) was added a solution of potassium hydroxide (85 wt %, 11.0 g, 166 mmol) in water (140 mL), and the mixture was stirred overnight. The reaction suspension was extracted with ethyl acetate (280 mL), the organic layer was washed with saturated brine, dried over anhydrous sodium sulfate, filtered and concentrated to give compound 5 (11.78 g, 99.2%, 90.1% ee). MS(ESI) m/z: 186,188 (M+1)$^+$.

Step d

To a solution of compound 6 (28.9 mL, 146 mmol) in tetrahydrofuran (40 mL) was added dropwise a 1 M tetrahydrofuran solution (127 mL, 127 mmol) of potassium tert-butoxide, a solution of compound 5 (11.8 g, 63.3 mmol) in tetrahydrofuran (19 mL) was added, and the mixture was stirred in a nitrogen atmosphere with heating under reflux for 1 day. The reaction mixture was allowed to cool to room temperature, water (740 mL) was added, and the resulting solid was collected by filtration and washed with water (185 mL). The obtained solid was recrystallized from ethanol (150 mL) to give compound 7 (11.8 g, 73.2%, 99.7% ee). MS(ESI) m/z: 256,258 (M+1)$^+$.

Reference Example 3

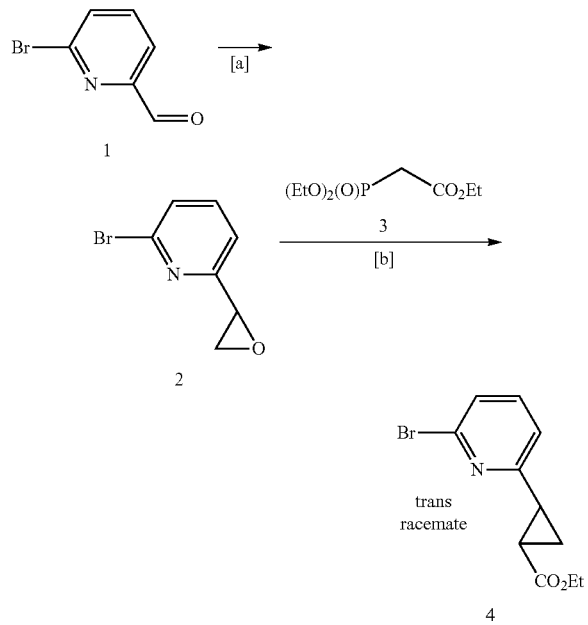

Step a

A suspension of sodium hydride (60 wt %, 421 mg, 10.5 mmol) in dimethyl sulfoxide (35 mL) was stirred in a nitrogen atmosphere under heating at 60° C. for 30 min. The reaction solution was allowed to cool to room temperature, trimethylsulfoxonium iodide (2.70 g, 12.3 mmol) was added, and the mixture was stirred for 30 min. To the reaction solution was added a solution of compound 1 (1.63 g, 8.76 mmol) in dimethyl sulfoxide (15 mL), and the mixture was stirred at room temperature for 2 hr. To the reaction mixture was added water (200 mL) and the mixture was extracted with tert-butyl methyl ether. The organic layer was washed with water and saturated brine, dried over anhydrous sodium sulfate, filtered and concentrated. The residue was purified by silica gel chromatography to give compound 2 (910 mg, 45.7%).

MS (ESI) m/z: 200,202 (M+1)$^+$.

Step b

To a solution of compound 3 (2.13 g, 9.50 mmol) in tetrahydrofuran (2.0 mL) was added dropwise under ice-cooling a 1 M tetrahydrofuran solution (7.92 mL, 7.92 mmol) of potassium tert-butoxide, compound 2 (900 mg, 3.96 mmol) was added to the reaction solution and the mixture was stirred in a nitrogen atmosphere with heating under reflux for 1 day. The reaction mixture was allowed to cool to room temperature, water (40 mL) was added, and the mixture was extracted with ethyl acetate (50 mL). The organic layer was washed with saturated brine, dried over anhydrous sodium sulfate, filtered and concentrated. The residue was purified by silica gel chromatography to give compound 4 (735 mg, 68.7%). MS(ESI) m/z: 270,272 (M+1)$^+$.

The following compounds were produced according to Production Methods 18-20 and Reference Examples 1-3.

TABLE 14

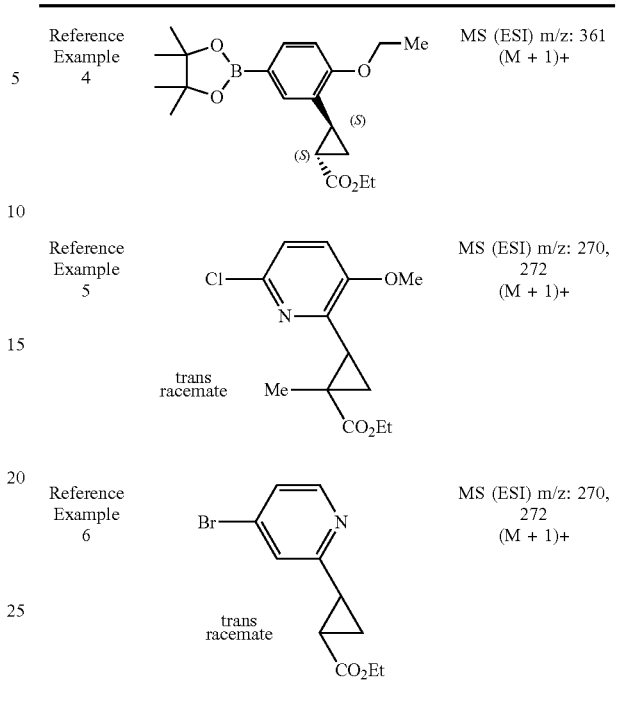

Reference Example 7

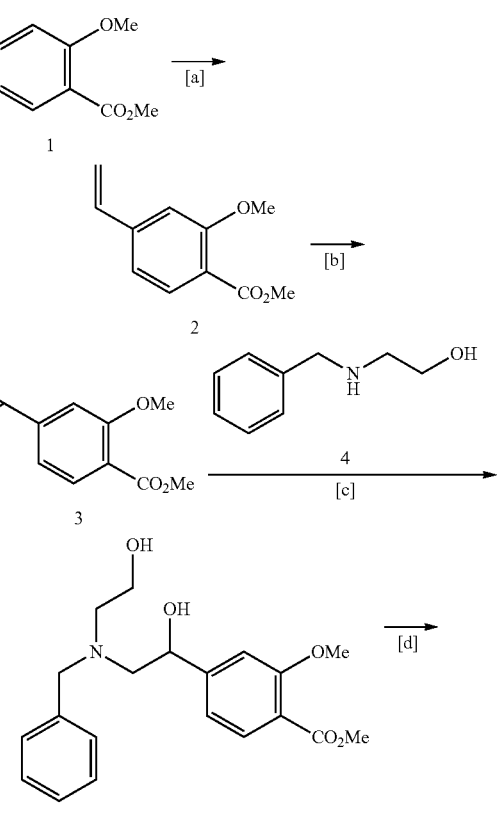

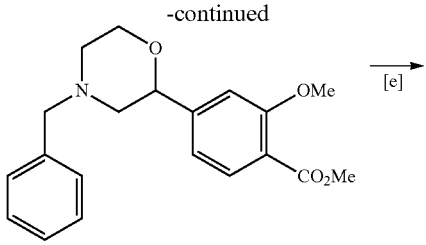

6

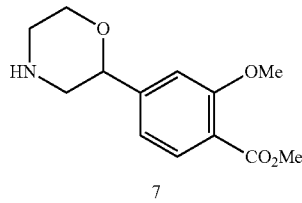

7

Step a

To a mixed solution of compound 1 (3.00 g, 12.2 mmol) and vinylboronic anhydride pyridine complex (2.36 g, 9.79 mmol) in 1,2-dimethoxyethane (122 mL) and water (10 mL) were added potassium carbonate (3.38 g, 24.5 mmol) and tetrakis(triphenylphosphine)palladium(0) (354 mg, 306 μmol), and the mixture was stirred in a nitrogen atmosphere with heating under reflux for 2 hr. The reaction mixture was allowed to cool to room temperature and filtered through celite. The filtrate was concentrated under reduced pressure, and the residue was purified by silica gel chromatography to give compound 2 (2.35 g, 99.9%). MS(ESI) m/z: 193 (M+1)$^+$.

Step b

To a mixed solution of compound 2 (2.35 g, 12.2 mmol) in tert-butyl alcohol (30 mL) and water (40 mL) was added N-bromosuccinimide (2.39 g, 13.4 mmol), and the mixture was stirred under heating at 45° C. for 2.5 hr. The reaction solution was allowed to cool to room temperature, 4 M-aqueous sodium hydroxide solution (23.06 mL, 12.2 mL) was added, and the mixture was stirred at room temperature for 10 min. To the reaction mixture was further added 4 M-aqueous sodium hydroxide solution (3.06 mL, 12.2 mL), and the mixture was stirred at room temperature overnight. Water was added to the reaction mixture, and the mixture was extracted with ethyl acetate. The organic layer was washed with water and saturated brine, dried over anhydrous magnesium sulfate, filtered and concentrated to give compound 3 (2.48 g, 97.4%).

$^1$H-NMR (400 MHz, CDCl$_3$) δ: 2.76 (1H, m), 3.17 (1H, m), 3.88 (1H, m), 3.88 (3H, s), 3.91 (3H, s), 6.87 (1H, d, J=1.5 Hz), 6.93 (1H, dd, J=8.2, 1.5 Hz), 7.78 (1H, d, J=8.2 Hz).

Step c

To a solution of compound 3 (2.48 g, 11.9 mmol) in 2-methyl-2-butanol (60 mL) was added compound 4 (1.89 g, 12.5 mmol), and the mixture was stirred under heating at 110° C. overnight. The reaction solution was concentrated under reduced pressure, and the residue was purified by silica gel chromatography to give compound 5 (2.17 g, 50.7%).

MS (APCI) m/z: 360 (M+1)$^+$.

Step d

To a solution of compound 5 (2.17 g, 6.04 mmol) in tetrahydrofuran (60 mL) were added tributylphosphine (2.23 mL, 9.06 mmol) and 1,1'-(azodicarbonyl)dipiperidine (2.29 g, 9.06 mmol), and the mixture was stirred at room temperature overnight. Insoluble material was filtered off from the reaction suspension, the filtrate was concentrated under reduced pressure and the residue was purified by silica gel chromatography to give compound 6 (1.18 g, 57.2%).

MS (APCI) m/z: 342 (M+1)$^+$.

Step e

To a solution of compound 6 (307 mg, 899 μmol) in methanol (45 mL) was added 10%-palladium/carbon (92 mg), and the mixture was stirred in a hydrogen atmosphere at room temperature overnight. The reaction mixture was filtered through celite, and the filtrate was concentrated under reduced pressure. The residue was purified by silica gel chromatography to give compound 7 (187 mg, 82.8%).

MS (APCI) m/z: 252 (M+1)$^+$.

Reference Example 8

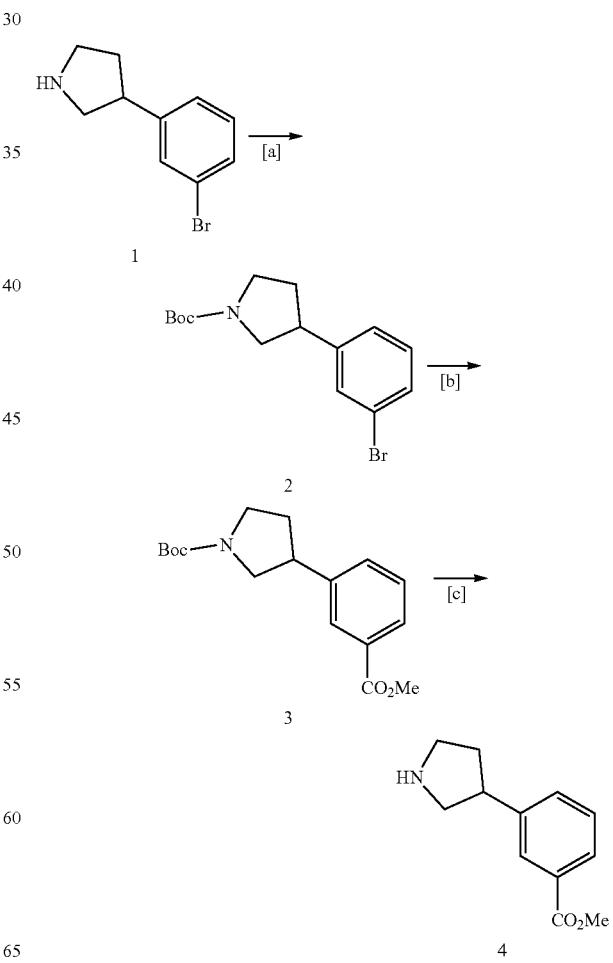

Step a

To a mixed solution of compound 1 (400 mg, 1.77 mmol) in tetrahydrofuran (18 mL) and methanol (3.0 mL) were added di-tert-butyl-dicarbonate (425 mg, 1.95 mmol) and triethylamine (377 μL, 2.65 mmol), and the mixture was stirred at room temperature for 15 hr. The reaction solution was concentrated under reduced pressure, and water and ethyl acetate were added to the residue for phase separation. The organic layer was washed with water and saturated brine, dried over anhydrous sodium sulfate, filtered and concentrated. The residue was purified by silica gel chromatography to give compound 2 (400 mg, 69.3%).

$^1$H-NMR (400 MHz, CDCl$_3$) δ: 1.48 (9H, s), 1.96 (1H, m), 2.25 (1H, m), 3.22-3.44 (3H, m), 3.53-3.66 (1H, m), 3.75-3.85 (1H, m), 7.15-7.21 (2H, m), 7.36-7.38 (1H, d, J=7 Hz), 7.38 (1H, s).

Step b

To a mixed solution of compound 2 (400 mg, 1.23 mmol) in N,N-dimethylformamide (5.0 mL) and ethanol (15 mL) were added sodium acetate (168 mg, 2.05 mmol), [1,1'-bis(diphenylphosphino)ferrocene]palladium(II) dichloride (289 mg, 354 μmol) and diisopropylethylamine (918 μL, 5.31 mmol), and the mixture was stirred in a carbon monoxide atmosphere under heating at 70° C. for 2 days. The reaction mixture was allowed to cool to room temperature, water and ethyl acetate were added, and the mixture was filtered through celite. The filtrate was phase separated, and the organic layer was washed with water and saturated brine, dried over anhydrous sodium sulfate, filtered and concentrated. The residue was purified by silica gel chromatography to give compound 3 (224 mg, 41.5%). MS(ESI) m/z: 250 (M-tBu+1)$^+$.

Step c

To a solution of compound 3 (224 mg, 724 μmol) in chloroform (2.0 mL) was added trifluoroacetic acid (0.56 mL), and the mixture was stirred at room temperature for 2 hr. The reaction solution was subjected to solid phase extraction purification using cation exchange resin column (Waters, PoraPak™, RxnCX) to give compound 4 (142 mg, 94.3%). MS(ESI) m/z: 206 (M+1)$^+$.

Reference Example 9

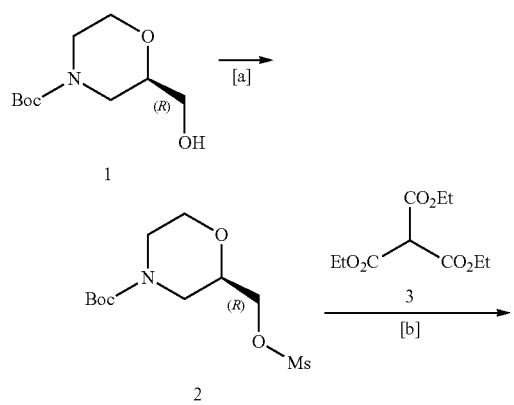

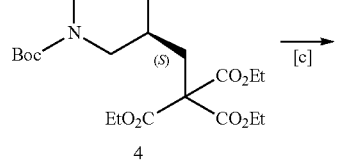

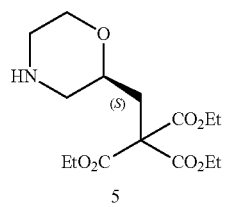

Step a

To a solution of compound 1 (20.0 g, 92.1 mmol) and triethylamine (16.6 mL, 120 mol) in dichloromethane (180 mL) was added dropwise a solution of mesyl chloride (7.84 mL, 101 mmol) in dichloromethane (8.0 mL) under ice-cooling, and the mixture was stirred under ice-cooling for 2 hr. To the reaction solution was added water (60 mL) under ice-cooling for phase separation. The organic layer was washed with saturated aqueous sodium hydrogen carbonate (40 mL) and saturated brine (60 mL), dried over anhydrous sodium sulfate, filtered and concentrated to give compound 2 (30.3 g). MS(ESI) m/z: 296 (M+1)$^+$.

Step b

To a solution of compound 2 (30.3 g, 92.3 mmol) and compound 3 (39.2 mL, 185 mmol) in N-methylpyrrolidone (230 mL) were added potassium carbonate (63.8 g, 462 mmol) and sodium iodide (4.15 g, 27.7 mmol), and the mixture was stirred under heating at 120° C. for 3.5 hr. The reaction mixture was allowed to cool to room temperature, water (500 mL) was added and the mixture was extracted with ethyl acetate (400 mL). The organic layer was washed with water (100 mL) and saturated brine (50 mL), dried over anhydrous sodium sulfate, filtered and concentrated. The residue was purified by silica gel chromatography to give compound 4 (41.6 g, 90.4%).

MS (ESI) m/z: 432 (M+1)$^+$.

Step c

To a solution of compound 4 (2.00 g, 4.17 mmol) in dichloromethane (20 mL) was added trifluoroacetic acid (4.0 mL), and the mixture was stirred at room temperature for 1 hr. To the reaction solution was added dropwise saturated aqueous sodium hydrogen carbonate (100 mL) and the mixture was extracted 3 times with chloroform (50 mL). The organic layer was dried over anhydrous sodium sulfate, filtered and concentrated to give compound 5 (1.40 g). MS(ESI) m/z: 332 (M+1)$^+$.

Reference Example 10

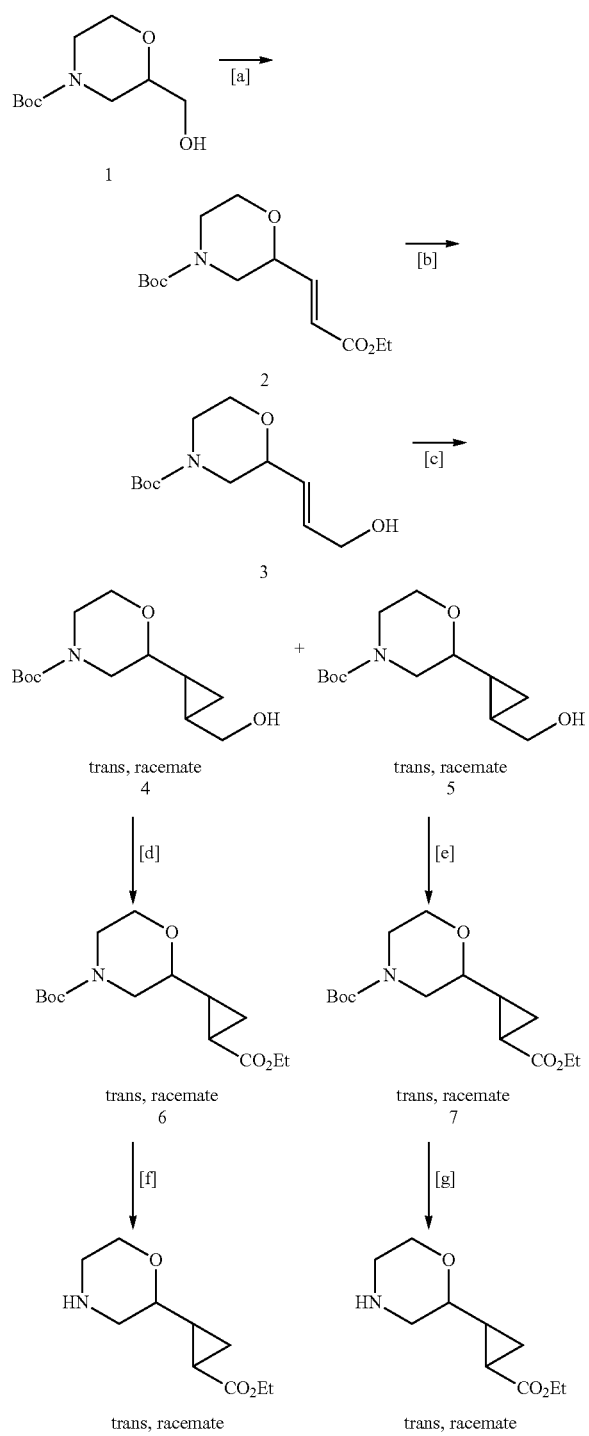

Step a

To a mixed solution of compound 1 (5.00 g, 23.0 mmol) in dichloromethane (60 mL) and dimethyl sulfoxide (20 mL) were added under ice-cooling triethylamine (19.2 mL, 138 mmol) and sulfur trioxide pyridine complex (11.0 g, 69.0 mmol), and the mixture was stirred at room temperature for 4 hr. To the reaction solution was added water (60 mL), and the mixture was extracted with chloroform (40 mL). The organic layer was washed with saturated aqueous sodium hydrogen carbonate (30 mL) and saturated brine (30 mL), dried over anhydrous magnesium sulfate, filtered and concentrated. The residue was dissolved in tetrahydrofuran (30 mL), added dropwise to a solution of ethyl diethylphosphonoacetate (7.73 g, 34.5 mmol) and sodium hydride (60 wt %, 1.20 g, 34.5 mmol) in tetrahydrofuran (30 mL) under ice-cooling and the mixture was stirred while warming to room temperature overnight. To the reaction solution was added water (60 mL) and the mixture was extracted with ethyl acetate (60 mL). The organic layer was dried over anhydrous sodium sulfate, filtered and concentrated under reduced pressure. The residue was purified by silica gel chromatography to give compound 2 (2.92 g, 38.3%). MS(ESI) m/z: 286 (M+1)$^+$.

Step b

To a solution of compound 2 (3.32 g, 10.2 mmol) in tetrahydrofuran (35 mL) was added dropwise under ice-cooling a 1 M dichloromethane solution (30.5 mL, 30.5 mmol) of diisobutylaluminum hydride, and the mixture was stirred under ice-cooling for 1.5 hr. To the reaction solution was added dropwise under ice-cooling a saturated aqueous Rochelle salt solution (30 mL), and the mixture was stirred at room temperature overnight and extracted 3 times with ethyl acetate (30 mL). The organic layer was dried over anhydrous sodium sulfate, filtered and concentrated under reduced pressure. The residue was purified by silica gel chromatography to give compound 3 (1.55 g, 57.7%). MS(ESI) m/z: 188 (M-tBu+1)$^+$.

Step c

To a solution of compound 3 (780 mg, 2.94 mmol) in 1,2-dichloroethane (15 mL) were added dropwise under ice-cooling a 1 M toluene solution (5.90 mL, 5.90 mmol) of diethylzinc and chloroiodomethane (860 μL, 11.8 mmol), and the mixture was stirred while warming to room temperature for 5 hr. To the reaction mixture were added saturated aqueous ammonium chloride solution (5.0 mL), saturated aqueous Rochelle salt solution (30 mL) and chloroform (30 mL) and the mixture was stirred at room temperature overnight and extracted twice with chloroform (30 mL). The organic layer was washed with saturated brine, dried over anhydrous sodium sulfate, filtered and concentrated. The residue was purified by silica gel chromatography to give compound 4 (145 mg, 19%) and compound 5 (140 mg, 18%). Compound 4 and compound 5 are diastereoisomers.
compound 4: MS(ESI) m/z: 258 (M+1)$^+$.
compound 5: MS(ESI) m/z: 258 (M+1)$^+$.

Step d

To a mixed solution of compound 4 (280 mg, 1.01 mmol) in acetonitrile (6.0 mL) and carbon tetrachloride (6.0 mL) were added a solution of sodium periodate (645 mg, 3.02 mmol) in water (9.0 mL) and ruthenium (IV) oxide hydrate (4.6 mg, 30 μmol), and the mixture was stirred at room temperature for 1 hr. To the reaction mixture was added 2-propanol (3.0 mL), and the mixture was stirred at room temperature for 1 hr and filtered through celite. To the filtrate was added saturated aqueous ammonium chloride solution (9.0 mL) and the mixture was extracted 3 times with chloroform. The organic layer was washed with saturated brine, dried over anhydrous sodium sulfate, filtered and concentrated. The residue was dissolved in N,N-dimethylformamide (4.0 mL), potassium carbonate (443 mg, 3.21 mmol) and iodoethane (257 μL, 3.21 mmol) were added, and the mixture was stirred at room temperature for 2 days. To the reaction mixture was added water (20 mL), and the mixture was extracted with ethyl acetate (40 mL). The organic layer was washed with saturated brine, dried over anhydrous sodium sulfate, filtered and concentrated under reduced pressure. The residue was purified by silica gel chromatography to give compound 6 (290 mg, 64.1%). MS(ESI) m/z: 300 (M+1)+.

Step e

To a mixed solution of compound 5 (260 mg, 900 μmol) in acetonitrile (5.0 mL) and carbon tetrachloride (5.0 mL) were added a solution of sodium periodate (578 mg, 2.70 mmol) in water (7.5 mL) and ruthenium (IV) oxide hydrate (4.1 mg, 27 μmol), and the mixture was stirred at room temperature for 1 hr. To the reaction mixture was added 2-propanol (2.5 mL), and the mixture was stirred at room temperature for 1 hr and filtered through celite. To the filtrate was added saturated aqueous ammonium chloride solution (7.5 mL) and the mixture was extracted 3 times with chloroform. The organic layer was washed with saturated brine, dried over anhydrous sodium sulfate, filtered and concentrated. The residue was dissolved in N,N-dimethylformamide (3.5 mL), potassium carbonate (377 mg, 2.73 mmol) and iodoethane (218 μL, 2.73 mmol) were added, and the mixture was stirred at room temperature for 4 days. To the reaction mixture was added water (20 mL) and the mixture was extracted with ethyl acetate (40 mL). The organic layer was washed with saturated brine, dried over anhydrous sodium sulfate, filtered and concentrated under reduced pressure. The residue was purified by silica gel chromatography to give compound 7 (210 mg, 77.2%). MS(ESI) m/z: 300 (M+1)+.

Step f

To a solution of compound 6 (205 mg, 685 μmol) in dichloromethane (3.5 mL) was added trifluoroacetic acid (1.0 mL), and the mixture was stirred at room temperature for 3 hr. The reaction solution was concentrated under reduced pressure, and the residue was dissolved in chloroform, washed with saturated aqueous sodium hydrogen carbonate and saturated brine, dried over anhydrous magnesium sulfate, filtered and concentrated to give compound 8 (140 mg).
$^1$H-NMR (400 MHz, CDCl$_3$) δ: 1.01 (1H, m), 1.15 (1H, m), 1.25 (3H, t, J=7.2 Hz), 1.50 (1H, m), 1.60 (1H, m), 2.68 (1H, m), 2.78 (1H, m), 2.85 (1H, m), 2.98 (1H, m), 3.09 (1H, m), 3.54 (1H, m), 3.85 (1H, m), 4.12 (2H, m).
MS(ESI) m/z: 200 (M+1)+.

Step g

To a solution of compound 7 (210 mg, 701 μmol) in dichloromethane (3.5 mL) was added trifluoroacetic acid (1.0 mL), and the mixture was stirred at room temperature for 3 hr. The reaction solution was concentrated under reduced pressure, and the residue was dissolved in chloroform, washed with saturated aqueous sodium hydrogen carbonate and saturated brine, dried over anhydrous magnesium sulfate, filtered and concentrated to give compound 9 (160 mg).
$^1$H-NMR (400 MHz, CDCl$_3$) δ: 0.87 (1H, m), 1.14 (1H, m), 1.25 (3H, t, J=7.2 Hz), 1.50 (1H, m), 1.70 (1H, m), 2.71 (1H, m), 2.79 (1H, m), 2.86 (1H, m), 2.94-2.99 (2H, m), 3.54 (1H, m), 3.86 (1H, m), 4.11 (2H, m).
MS(ESI) m/z: 200 (M+1)+.

Reference Example 11

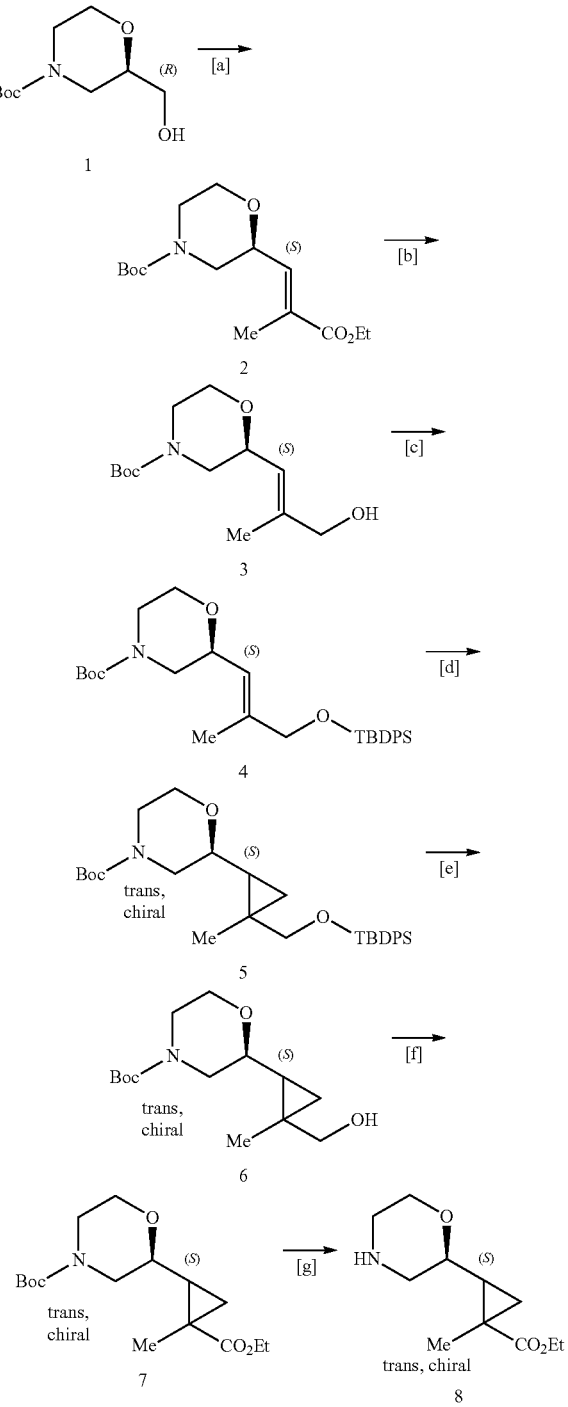

Step a

To a solution of compound 1 (2.50 g, 11.5 mmol) and 2,2,6,6-tetramethyl-1-piperidinyloxy free radical (36.0 mg, 230 μmol) in dichloromethane (35 mL) were added dropwise a solution of sodium bromide (118 mg, 1.15 mmol) in water (2.0 mL), saturated aqueous sodium hydrogen carbonate (5.5 mL) and 5% aqueous sodium hypochlorite solution (17.1 mL, 11.5 mmol) over 45 min under ice-cooling, and the mixture was stirred under ice-cooling for 30 min. To the reaction mixture was added saturated brine (30 mL), and the mixture was extracted 3 times with chloroform (30 mL). The organic layer was washed with saturated aqueous sodium hydrogen carbonate (30 mL) and saturated brine (30 mL), dried over anhydrous magnesium sulfate, filtered and concentrated. The residue was dissolved in tetrahydrofuran (20 mL) and added dropwise to a solution of ethyl diethylphosphonopropionate (3.47 g, 14.6 mmol) and sodium hydride (60 wt %, 499 mg, 12.5 mmol) in tetrahydrofuran (20 mL) under ice-cooling and the mixture was stirred while warming to room temperature overnight. To the reaction solution was added water (40 mL) and the mixture was extracted with ethyl acetate (80 mL). The organic layer was washed with saturated brine, dried over anhydrous sodium sulfate, filtered and concentrated under reduced pressure. The residue was purified by silica gel chromatography to give compound 2 (1.74 g, 53.6%).

MS (ESI) m/z: 300 (M+1)$^+$.

Step b

To a solution of compound 2 (1.74 g, 5.81 mmol) in tetrahydrofuran (20 mL) was added dropwise a 1 M dichloromethane solution (20.3 mL, 20.3 mmol) of diisobutylaluminum hydride at −50° C. over 40 min, and the mixture was stirred for 2 hr while warming to −30° C. To the reaction solution was added dropwise a mixture of methanol (1.0 mL) and tetrahydrofuran (10 mL) at −30° C., and the mixture was stirred for 1 hr while warming to −10° C. To the reaction solution was added saturated aqueous Rochelle salt solution (10 mL) at −10° C. and the mixture was stirred at room temperature overnight and extracted twice with ethyl acetate (40 mL). The organic layer was washed with saturated brine, dried over anhydrous sodium sulfate, filtered and concentrated under reduced pressure. The residue was purified by silica gel chromatography to give compound 3 (950 mg, 58.4%).

MS(ESI) m/z: 258 (M+1)$^+$.

Step c

To a solution of compound 3 (950 mg, 3.40 mmol) in dichloromethane (15 mL) were added imidazole (694 mg, 10.2 mmol) and tert-butylchlorodiphenylsilane (1.32 mL, 5.10 mmol), and the mixture was stirred at room temperature for 9 hr. To the reaction solution was added water, and the mixture was extracted with chloroform. The organic layer was washed with saturated brine, dried over anhydrous sodium sulfate, filtered and concentrated under reduced pressure. The residue was purified by silica gel chromatography to give compound 4 (2.20 g).

1H-NMR (400 MHz, CDCl$_3$) δ: 1.06 (9H, s), 1.48 (9H, s), 1.66 (3H, s), 2.71 (1H, m), 2.96 (1H, m), 3.57 (1H, m), 3.84-3.91 (3H, m), 4.05 (2H, s), 4.12 (1H, m), 5.52 (1H, d, J=8 Hz), 7.35-7.44 (6H, m), 7.64-7.68 (4H, m).

Step d

To a solution of compound 4 (2.20 g, 3.40 mmol) in 1,2-dichloroethane (35 mL) were added dropwise a 1 M toluene solution (11.1 mL, 11.1 mmol) of diethylzinc and chloroiodomethane (1.61 mL, 22.1 mmol) over 45 min under ice-cooling, and the mixture was stirred under ice-cooling for 4 hr. To the reaction mixture were added saturated aqueous ammonium chloride solution (5.0 mL), saturated aqueous Rochelle salt solution (10 mL) and chloroform (10 mL) and the mixture was stirred at room temperature overnight and extracted twice with chloroform (30 mL). The organic layer was washed with saturated aqueous Rochelle salt solution (10 mL) and saturated brine, dried over anhydrous sodium sulfate, filtered and concentrated. The residue was purified by silica gel chromatography to give compound 5 (1.35 g, 70.9%).

$^1$H-NMR (400 MHz, CDCl$_3$) δ: 0.36 (1H, t, J=5 Hz), 0.69-0.76 (2H, m), 1.06 (9H, s), 1.20 (3H, s), 1.46 (9H, s), 2.74 (1H, m), 2.93 (1H, m), 3.20 (1H, m), 3.45-3.56 (2H, m), 3.84-3.98 (3H, m), 7.35-7.44 (6H, m), 7.62-7.65 (4H, m).

Step e

To a solution of compound 5 (1.35 g, 2.41 mmol) in tetrahydrofuran (8.0 mL) was added a 1 M tetrahydrofuran solution (4.82 mL, 4.82 mmol) of tetrabutylammonium fluoride, and the mixture was stirred at room temperature overnight. To the reaction solution was added saturated aqueous ammonium chloride solution (10 mL), and the mixture was extracted with ethyl acetate. The organic layer was washed with saturated brine, dried over anhydrous sodium sulfate, filtered and concentrated under reduced pressure. The residue was purified by silica gel chromatography to give compound 6 (720 mg, 94.7%) MS (ESI) m/z: 272 (M+1)$^+$.

Step f

To a mixed solution of compound 6 (360 mg, 1.33 mmol) in acetonitrile (8.0 mL) and carbon tetrachloride (8.0 mL) were added a solution of sodium periodate (851 mg, 3.98 mmol) in water (12 mL) and ruthenium (IV) oxide hydrate (10 mg, 66 μmol), and the mixture was stirred at room temperature for 1.5 hr. To the reaction mixture was added 2-propanol (4.0 mL), and the mixture was stirred at room temperature for 1 hr and filtered through celite. To the filtrate were added saturated aqueous ammonium chloride solution (10 mL) and 10% aqueous citric acid solution (10 mL), and the mixture was extracted 3 times with chloroform. The organic layer was washed with saturated brine, dried over anhydrous sodium sulfate, filtered and concentrated. The residue was dissolved in N,N-dimethylformamide (5.0 mL), potassium carbonate (564 mg, 3.95 mmol) and iodoethane (316 μL, 3.95 mmol) were added, and the mixture was stirred at room temperature for 3 days. To the reaction mixture was added water (30 mL) and the mixture was extracted with ethyl acetate. The organic layer was washed with saturated brine, dried over anhydrous sodium sulfate, filtered and concentrated under reduced pressure. The residue was purified by silica gel chromatography to give compound 7 (270 mg, 62.8%).

MS (ESI) m/z: 314 (M+1)$^+$.

Step g

To a solution of compound 7 (270 mg, 827 μmol) in dichloromethane (4.5 mL) was added trifluoroacetic acid (1.5 mL), and the mixture was stirred at room temperature for 8 hr. The reaction solution was concentrated under reduced pressure, and the residue was dissolved in chloroform, washed with saturated aqueous sodium hydrogen carbonate and saturated brine, dried over anhydrous magnesium sulfate, filtered and concentrated to give compound 8 (195 mg). MS(ESI) m/z: 214 (M+1)⁺.

Reference Example 12

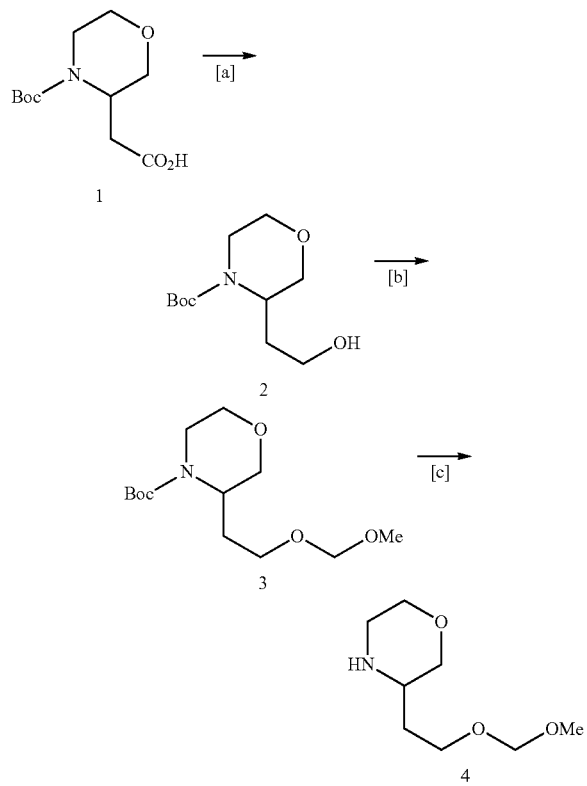

Step a

To a solution of compound 1 (1.00 g, 4.08 mmol) in 1,2-dimethoxyethane (6.0 mL) were added 4-methylmorpholine (493 μL, 4.48 mmol) and isobutyl chloroformate (586 μL, 4.48 mmol) under ice-cooling, and the mixture was stirred under ice-cooling for 2 hr. The reaction suspension was filtered, sodium borohydride (231 mg, 6.12 mmol) and water (3.0 mL) were added to the filtrate under ice-cooling, and the mixture was stirred under ice-cooling for 2 hr. To the reaction solution was added water and the mixture was extracted with ethyl acetate. The organic layer was washed with saturated brine, dried over anhydrous sodium sulfate, filtered and concentrated. The residue was purified by silica gel chromatography to give compound 2 (836 mg, 88.7%). MS(ESI) m/z: 176 (M-tBu+1)⁺.

Step b

To a solution of compound 2 (836 mg, 3.61 mmol) in dichloromethane (10 mL) were added dropwise under ice-cooling diisopropylethylamine (1.88 mL, 10.8 mmol) and chloromethyl methyl ether (851 μL, 11.21 mmol), and the mixture was stirred while warming to room temperature overnight. The reaction solution was concentrated under reduced pressure, and the residue was purified by silica gel chromatography to give compound 3 (926 mg, 93.1%). MS(ESI) m/z: 276 (M+1)⁺.

Step c

To a solution of compound 3 (926 mg, 3.36 mmol) in dichloromethane (20 mL) was added trifluoroacetic acid (2.6 mL), and the mixture was stirred at room temperature for 3 hr. The reaction solution was neutralized with 2 M-aqueous potassium carbonate solution and extracted 3 times with dichloromethane (30 mL). The organic layer was washed with saturated brine, dried over anhydrous sodium sulfate, filtered and concentrated to give compound 4 (594 mg). MS(ESI) m/z: 176 (M+1)⁺.

Reference Example 13

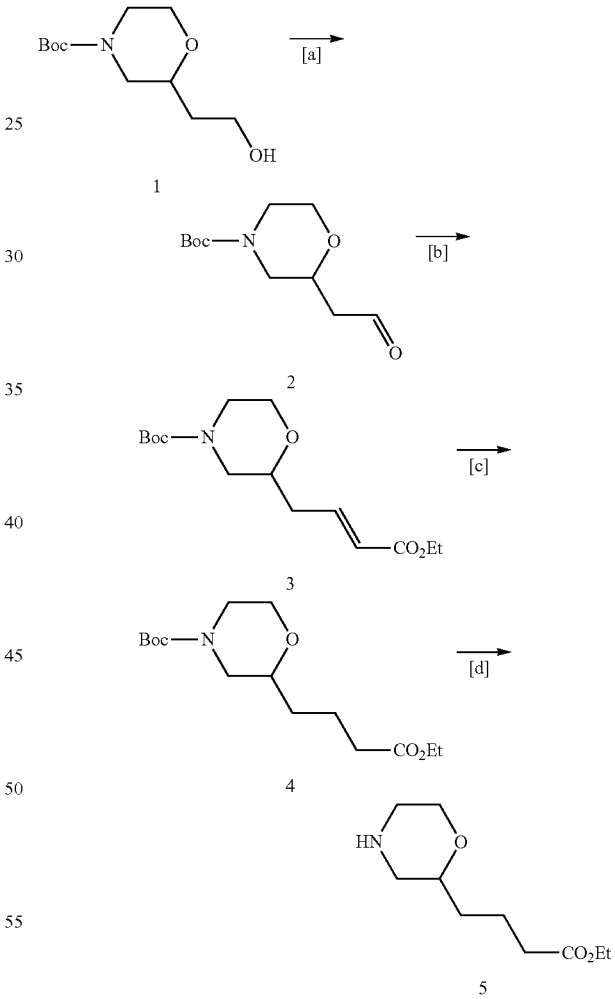

Step a

To a solution of compound 1 (400 mg, 1.73 mmol) in dichloromethane (12 mL) was added under ice-cooling Dess-Martin periodinane (1.10 g, 2.59 mmol), and the mixture was stirred at room temperature for 3 hr. To the reaction solution were added under ice-cooling saturated aqueous sodium hydrogen carbonate and saturated aqueous sodium sulfite solution, and the mixture was extracted with chloroform. The organic layer was dried over anhydrous sodium sulfate, filtered and concentrated. The residue was purified by silica gel chromatography to give compound 2 (399 mg). MS(ESI) m/z: 174 (M-tBu+1)$^+$.

Step b

To a solution of compound 2 (399 mg, 1.74 mmol) and ethyl diethylphosphonoacetate (587 mg, 2.62 mmol) in tetrahydrofuran (12.0 mL) was added under ice-cooling sodium hydride (60 wt %, 90.7 mg, 2.27 mmol), and the mixture was stirred for 15 min. The mixture was stirred while warming to room temperature overnight. To the reaction solution was added saturated aqueous ammonium chloride solution, and the mixture was extracted with chloroform. The organic layer was dried over anhydrous sodium sulfate, filtered and concentrated. The residue was purified by silica gel chromatography to give compound 3 (325 mg, 2.1%). MS(ESI) m/z: 244 (M-tBu+1)$^+$.

Step c

To a solution of compound 3 (320 mg, 1.07 mmol) in methanol (13 mL) was added 10%-palladium/carbon (64 mg), and the mixture was stirred in a hydrogen atmosphere at room temperature for 2 hr. The reaction mixture was diluted with chloroform (10 mL), filtered through celite, and the filtrate was concentrated under reduced pressure to give compound 4 (321 mg, 99.7%). MS(ESI) m/z: 302 (M+1)$^+$.

Step d

To a solution of compound 4 (130 mg, 431 μmol) in dichloromethane (2.6 mL) was added trifluoroacetic acid (0.26 mL), and the mixture was stirred at room temperature overnight. The reaction solution was subjected to solid phase extraction purification using cation exchange resin column (Waters, PoraPak™, RxnCX) to give compound 5 (81.6 mg, 94.0%).

MS(ESI) m/z: 202 (M+1)$^+$.

Reference Example 14

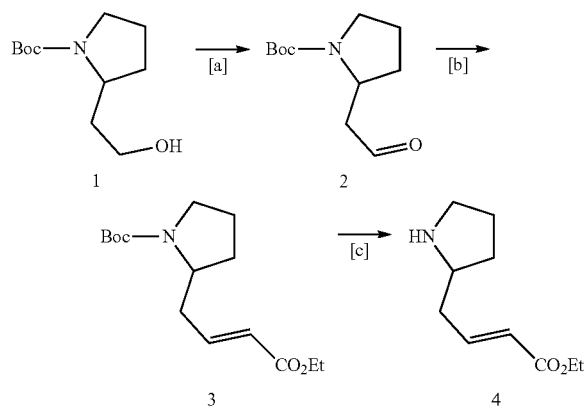

Step a

To a solution of compound 1 (450 mg, 2.09 mmol) in dichloromethane (21 mL) was added under ice-cooling Dess-Martin periodinane (1.33 g, 3.14 mmol), and the mixture was stirred at room temperature for 1.5 hr. To the reaction solution were added under ice-cooling saturated aqueous sodium hydrogen carbonate and saturated aqueous sodium sulfite solution, and the mixture was extracted with chloroform. The organic layer was washed with saturated brine, dried over anhydrous sodium sulfate, filtered and concentrated under reduced pressure. The residue was purified by silica gel chromatography to give compound 2 (295 mg, 66.2%). MS(ESI) m/z: 214 (M+1)$^+$.

Step b

To a solution of ethyl diethylphosphonoacetate (457 mg, 2.04 mmol) in tetrahydrofuran (14.0 mL) was added under ice-cooling sodium hydride (60 wt %, 70.7 mg, 1.77 mmol), and the mixture was stirred for 15 min. To the reaction solution was added dropwise under ice-cooling compound 2 (290 mg, 1.36 mmol), and the mixture was stirred under ice-cooling for 1.5 hr. To the reaction solution was added water and the mixture was extracted with ethyl acetate. The organic layer was dried over anhydrous sodium sulfate, filtered and concentrated to give compound 3 (612 mg). MS(ESI) m/z: 228 (M-tBu+1)$^+$.

Step c

To a solution of compound 3 (612 mg, 2.04 mmol) in chloroform (1.0 mL) was added trifluoroacetic acid (1.0 mL), and the mixture was stirred at room temperature for 1 hr. The reaction solution was subjected to solid phase extraction purification using cation exchange resin column (Waters, PoraPak™, RxnCX) to give compound 4 (220 mg, 88.2%).

MS (ESI) m/z: 184 (M+1)$^+$.

The following compounds were produced according to Production Methods 21-24 and Examples 7-14.

TABLE 15

| | | | |
|---|---|---|---|
| Reference Example 15 | | (structure) HCl | MS (ESI) m/z: 189 (M + 1)+ |
| Reference Example 16 | | (structure) HCl | MS (ESI) m/z: 189 (M + 1)+ |
| Reference Example 17 | | (structure) HCl | MS (ESI) m/z: 189 (M + 1)+ |
| Reference Example 18 | | (structure) | MS (APCI) m/z: 252 (M + 1)+ |

TABLE 15-continued

| Reference Example 19 | (morpholine-phenyl with CO2Me and OMe) | MS (ESI) m/z: 252 (M + 1)+ |
| --- | --- | --- |
| Reference Example 20 | (morpholine-pyridine-CO2Me) | MS (ESI) m/z: 223 (M + 1)+ |
| Reference Example 21 | (morpholine-pyridine-CO2Me) | MS (ESI) m/z: 223 (M + 1)+ |
| Reference Example 22 | (morpholine-pyridine-CO2Et) | MS (ESI) m/z: 237 (M + 1)+ |
| Reference Example 23 | (morpholine-pyridine-OMe-CO2iPr) | MS (ESI) m/z: 281 (M + 1)+ |
| Reference Example 24 | (morpholine-pyridine-OMe-CO2Me) | MS (ESI) m/z: 253 (M + 1)+ |
| Reference Example 25 | (morpholine-pyridine-Me-CO2iPr) | MS (ESI) m/z: 265 (M + 1)+ |
| Reference Example 26 | (morpholine-pyridine-Me-CO2Et) | MS (ESI) m/z: 251 (M + 1)+ |

TABLE 16

| Reference Example 27 | (morpholine-pyridine-Me-CO2Et) | MS (APCI) m/z: 251 (M + 1)+ |
| --- | --- | --- |
| Reference Example 28 | (morpholine-pyridine-CO2Et-Me) | MS (ESI) m/z: 251 (M + 1)+ |

TABLE 16-continued

| Reference Example 29 | (morpholine-pyridine-CO2Et-Me) | MS (ESI) m/z: 251 (M + 1)+ |
| --- | --- | --- |
| Reference Example 30 | (morpholine-pyridine-CO2Me-Me) | MS (ESI) m/z: 237 (M + 1)+ |
| Reference Example 31 | (morpholine-pyridine-CO2Et-CF3) | MS (ESI) m/z: 305 (M + 1)+ |
| Reference Example 32 | (pyrrolidine-phenyl-CO2Me) | MS (ESI) m/z: 206 (M + 1)+ |
| Reference Example 33 | (S)-morpholine-CH2-C(Me)(CO2Et)2 | MS (ESI) m/z: 274 (M + 1)+ |
| Reference Example 34 | (R)-morpholine-CH2-CH(CO2Et)2 with CO2Et | MS (ESI) m/z: 332 (M + 1)+ |
| Reference Example 35 | (R,S)-Me-morpholine-CH2-C(CO2Et)2 | MS (ESI) m/z: 346 (M + 1)+ |
| Reference Example 36 | (S)-morpholine-CH2-O-CH2-OMe | MS (ESI) m/z: 346 (M + 1)+ |

TABLE 17

| Reference Example 37 | (piperazine-CH2CF3, CH2-C(CO2Et)3) | MS (ESI) m/z: 413 (M + 1)+ |
| --- | --- | --- |
| Reference Example 38 | (S)-morpholine-CH2-O-CH2-OMe | MS (ESI) m/z: 162 (M + 1)+ |
| Reference Example 39 | morpholine-CH2CH2-CO2Et | MS (ESI) m/z: 188 (M + 1)+ |

TABLE 17-continued

| | | |
|---|---|---|
| Reference Example 40 | HN—⟨pyrrolidine⟩—CH₂CH₂—CO₂Et | MS (ESI) m/z: 172 (M + 1)+ |
| Reference Example 41 | HN—⟨pyrrolidine⟩—CH₂CH₂CH₂—CO₂Et | MS (ESI) m/z: 186 (M + 1)+ |

Reference Example 42

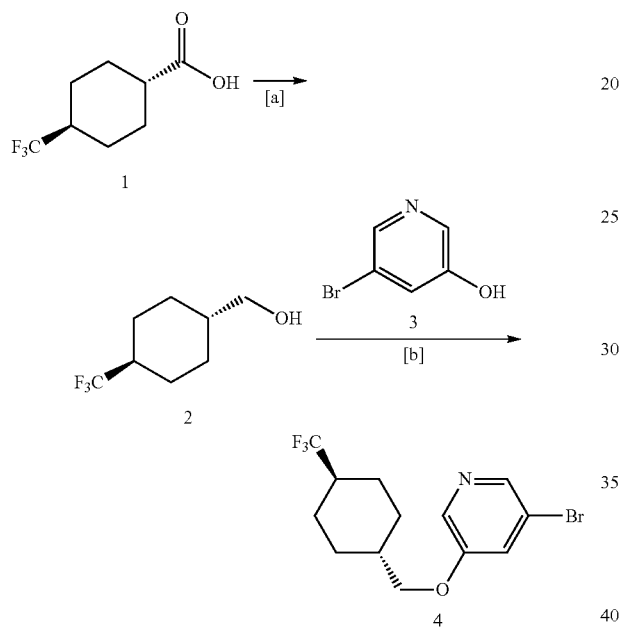

Step a

To a solution of lithium aluminum hydride (2.90 g, 76.5 mmol) in tetrahydrofuran (150 mL) were added under ice-cooling compound 1 (10.0 g, 51.0 mmol), and the mixture was stirred at room temperature for 4 hr. To the reaction mixture was added dropwise under ice-cooling a solution of water (3.0 mL) in tetrahydrofuran (150 mL), and the mixture was stirred at room temperature for 45 min. To the reaction suspension was added 4 M-aqueous sodium hydroxide solution (3.0 mL), and the mixture was stirred at room temperature for 30 min, water (3.0 mL) was added and the mixture was stirred at room temperature overnight. The reaction suspension was filtered through celite and washed with tetrahydrofuran (50 mL). The filtrate was concentrated under reduced pressure to give compound 2 (8.70 g, 93.7%).

1H-NMR (400 MHz, CDCl₃) δ: 0.94-1.05 (2H, m), 1.27-1.38 (3H, m), 1.49 (1H, m), 1.90-2.01 (5H, m), 3.48 (2H, t, J=6 Hz).

Step b

To a solution of compound 2 (678 mg, 3.72 mmol) and compound 3 (540 mg, 3.10 mmol) in tetrahydrofuran (20 mL) were added triphenylphosphine (1.22 g, 4.66 mmol) and diisopropyl azodicarboxylate (941 mg, 4.66 mmol), and the mixture was stirred at room temperature for 1.5 hr. The reaction solution was concentrated under reduced pressure, 50% aqueous N,N-dimethylformamide solution was added to the residue and the mixture was extracted with heptane. The organic phase was washed with 50% aqueous N,N-dimethylformamide solution and saturated brine, dried over anhydrous sodium sulfate, filtered and concentrated under reduced pressure. The residue was purified by silica gel chromatography to give compound 4 (972 mg, 92.6%). MS(ESI) m/z: 338,340 (M+1)+.

Reference Example 43

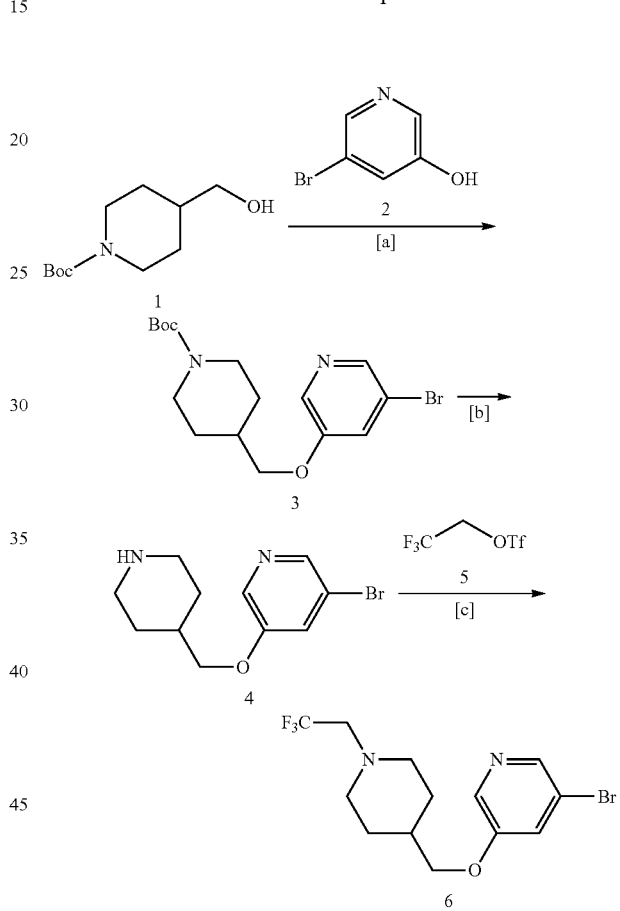

Step a

To a solution of compound 1 (2.04 g, 9.48 mmol) and compound 2 (1.50 g, 8.62 mmol) in tetrahydrofuran (15 mL) were added triphenylphosphine (2.71 g, 10.3 mmol) and diisopropyl azodicarboxylate (2.18 g, 10.8 mmol), and the mixture was stirred at room temperature for 5 hr. The reaction solution was concentrated under reduced pressure, and the residue was purified by silica gel chromatography to give compound 3 (2.90 g, 90.6%). MS(ESI) m/z: 371,373 (M+1)+.

Step b

To a solution of compound 3 (2.90 g, 7.81 mmol) in ethyl acetate (10 mL) was added a 4 M ethyl acetate solution (19.5 mL, 78.0 mmol) of hydrochloric acid, and the mixture was stirred at room temperature for 2 hr. The reaction mixture was neutralized with 2 M-aqueous sodium hydroxide solution and phase separation was performed. The organic layer was washed with saturated brine, dried over anhydrous sodium sulfate, filtered and concentrated under reduced pressure to give compound 4 (1.94 g, 91.5%). MS(ESI) m/z: 271,273 (M+1)+.

Step c

To a mixed solution of compound 4 (1.29 g, 4.76 mmol) in N,N-dimethylformamide (15 mL) and diisopropylethylamine (1.65 mL, 9.52 mmol) was added compound 5 (1.37 mL, 9.52 mmol), and the mixture was stirred at room temperature for 3 hr. To the reaction solution was added water and the mixture was extracted with ethyl acetate. The organic layer was washed with saturated brine, dried over anhydrous sodium sulfate, filtered and concentrated. The residue was purified by silica gel chromatography to give compound 6 (1.61 g, 95.5%).

MS (ESI) m/z: 353, 355 (M+1)+.

Reference Example 44

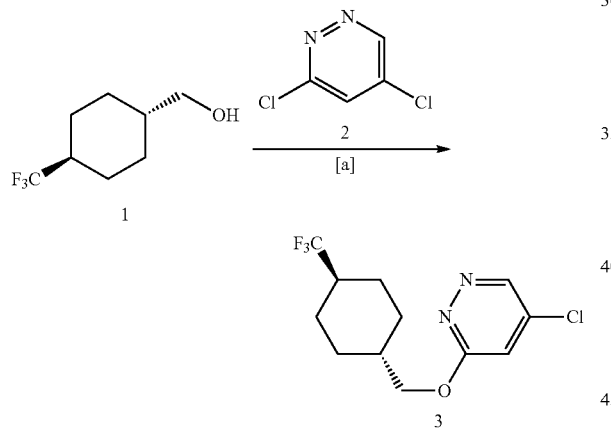

Step a

To a solution of compound 1 (12.6 g, 61.7 mmol) obtained in Reference Example 42, Step a, in tetrahydrofuran (225 mL) was added under ice-cooling sodium hydride (60 wt %, 2.69 g, 67.3 mmol) by small portions, and the mixture was stirred for 30 min. To the reaction solution was added dropwise under ice-cooling a solution of compound 2 (8.35 g, 56.1 mmol) in tetrahydrofuran (30 mL), and the mixture was stirred while warming to room temperature overnight. To the reaction solution was added water (150 mL) and the mixture was extracted with ethyl acetate (250 mL). The organic layer was washed with saturated brine, dried over anhydrous sodium sulfate, filtered and concentrated under reduced pressure. The residue was purified by silica gel chromatography to give compound 3 (4.95 g, 30.0%). MS(ESI) m/z: 295,297 (M+1)+.

Reference Example 45

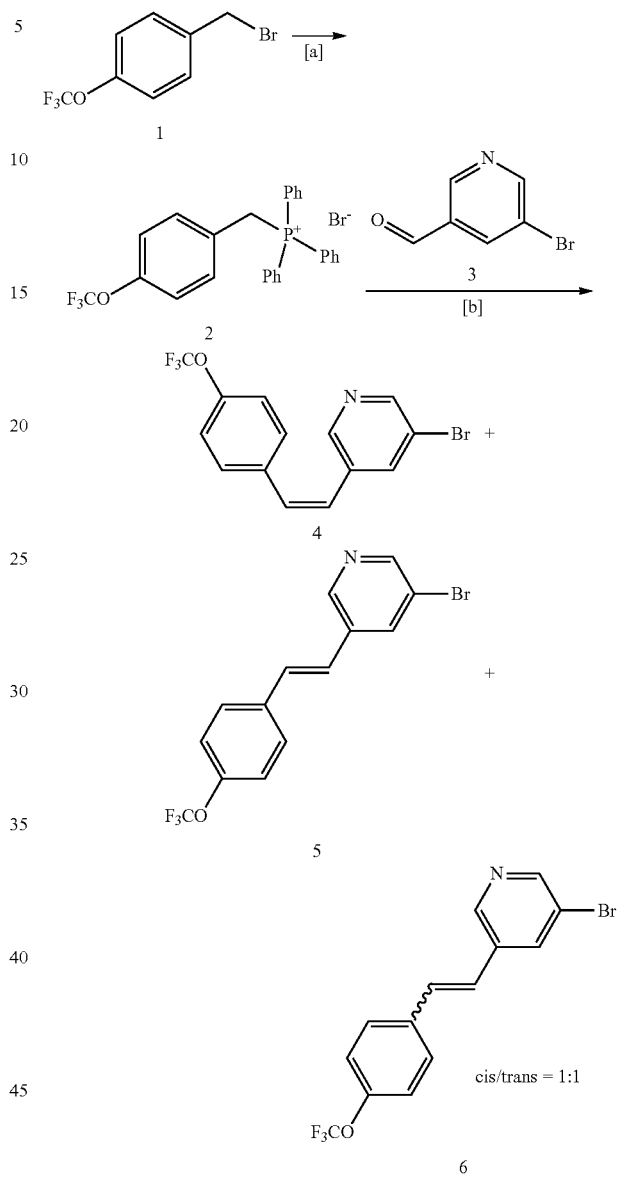

Step a

To a solution of compound 1 (5.00 g, 19.6 mmol) in toluene (100 mL) was added triphenylphosphine (5.66 g, 21.6 mmol), and the mixture was stirred with heating under reflux for 1 hr. The reaction mixture was diluted with toluene (50 mL) and the mixture was further stirred with heating under reflux for 1 hr. The reaction mixture was allowed to cool to room temperature, diluted with hexane (150 mL), and the resulting solid was collected by filtration and washed with hexane (100 mL) to give compound 2 (8.78 g, 86.6%).

MS (ESI) m/z: 437

Step b

To a mixed solution of compound 2 (3.62 g, 6.99 mmol) in tetrahydrofuran (40 mL) and N,N-dimethylformamide (10 mL) was added under ice-cooling sodium hydride (60 wt %, 155 mg, 6.45 mmol), and the mixture was stirred under ice-cooling for 30 min. To the reaction solution was added under ice-cooling compound 3 (1.00 g, 5.38 mmol) by small portions, and the mixture was stirred under ice-cooling for 30 min. The insoluble material was filtered off from the reaction suspension and washed with ethyl acetate (50 mL). The filtrate was diluted with ethyl acetate (50 mL), washed with water (100 mL) and saturated brine (100 mL), dried over anhydrous sodium sulfate, filtered and concentrated under reduced pressure. The residue was purified by silica gel chromatography to give compound 4 (864 mg, 46.7%), compound 5 (193 mg, 10.5%) and compound 6 (619 mg, 33.5%) as a cis/trans mixture.

compound 4: MS(ESI) m/z: 344,346 (M+1)$^+$.
compound 5: MS(ESI) m/z: 344,346 (M+1)$^+$.
Compound 6: MS(ESI) m/z: 344,346 (M+1)$^+$.

Reference Example 46

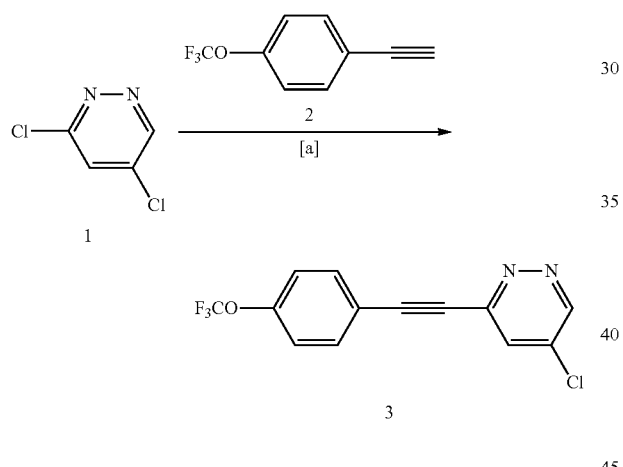

Step a

To a mixed solution of compound 1 (200 mg, 1.34 mmol) and compound 2 (250 mg, 1.34 mmol) in N,N-dimethylformamide (4.0 mL) and triethylamine (2.0 mL) were added bistriphenylphosphinepalladium(II) dichloride (94.2 mg, 134 µmol), triphenylphosphine (70.4 mg, 268 µmol) and copper iodide (25.6 mg, 134 µmol), and the mixture was stirred in a nitrogen atmosphere under heating at 50° C. for 6 hr. The reaction mixture was allowed to cool to room temperature, water (30 mL) was added and the mixture was extracted with ethyl acetate (50 mL). The organic layer was washed with water (30 mL) and saturated brine (30 mL), dried over anhydrous sodium sulfate, filtered and concentrated. The residue was purified by silica gel chromatography to give compound 3 (160 mg, 40.0%). MS(ESI) m/z: 299,301 (M+1)$^+$.

Reference Example 47

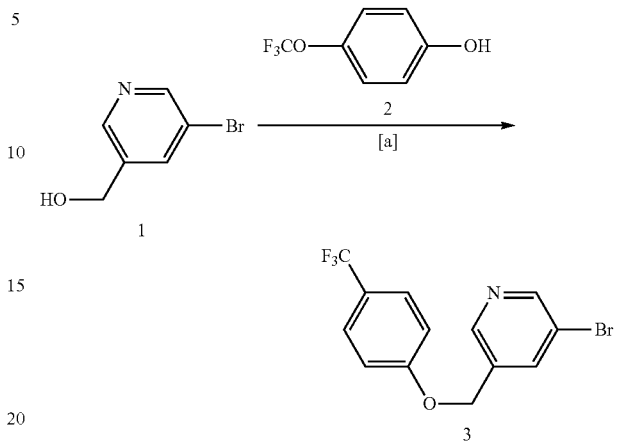

Step a

To a solution of compound 1 (200 mg, 1.06 mmol) and compound 2 (224 mg, 1.38 mmol) in tetrahydrofuran (6.0 mL) were added tributylphosphine (341 µL, 1.38 mmol) and 1,1'-(azodicarbonyl)dipiperidine (349 mg, 1.38 mmol) by small portions, and the mixture was stirred at room temperature overnight. The reaction suspension was diluted with hexane (6.0 mL), the insoluble material was filtered off and the filtrate was concentrated. The residue was purified by silica gel chromatography to give compound 3 (324 mg, 91.8%). MS (ESI) m/z: 332,334 (M+1)$^+$.

Reference Example 48

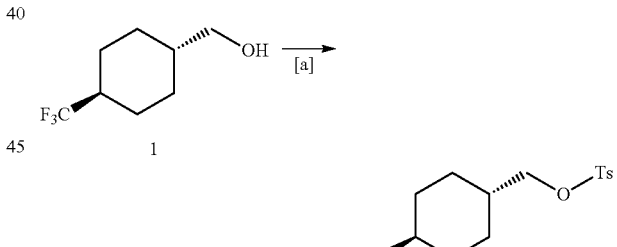

Step a

To a solution of compound 1 (100 mg, 549 µmol) obtained in Reference Example 42, Step a, in dichloromethane (2.0 mL) were added pyridine (133 µL, 1.65 mmol) and p-toluenesulfonyl chloride (126 mg, 659 µmol), and the mixture was stirred at room temperature for 6 hr. To the reaction solution was further added p-toluenesulfonyl chloride (62.8 mg, 329 µmol), and the mixture was stirred at room temperature overnight. The reaction solution was diluted with ethyl acetate (20 mL), washed with 1 M-hydrochloric acid (10 mL) and saturated aqueous sodium hydrogen carbonate (10 mL), and concentrated under reduced pressure to give compound 2 (176 mg, 95.2%).

¹H-NMR (400 MHz, CDCl$_3$) δ: 0.92-1.03 (2H, m), 1.22-1.33 (2H, m), 1.68 (1H, m), 1.81-1.86 (2H, m), 1.89-2.00 (3H, m), 2.46 (3H, s), 3.84 (2H, d, J=6.2 Hz), 7.35 (2H, d, J=8.2 Hz), 7.78 (2H, d, J=8.2 Hz).

The following compounds were produced according to Production Methods 25-29 and Examples 42-48.

TABLE 18

| | Structure | Data |
|---|---|---|
| Reference Example 49 | F$_3$CO-phenyl-CH$_2$-O-pyridine-Br | MS (ESI) m/z: 348, 350 (M + 1)+ |
| Reference Example 50 | F$_3$CO-phenyl-CH$_2$-O-pyridazine-Cl | MS (ESI) m/z: 305, 307 (M + 1)+ |
| Reference Example 51 | F$_3$C-piperidine-CH$_2$-O-pyridazine-Cl | MS (ESI) m/z: 310, 312 (M + 1)+ |
| Reference Example 52 | F$_3$C-cyclohexyl-CH$_2$-O-Ts | ¹H-NMR (400 MHz, CDCl$_3$) δ: 1.37-1.54 (4H, m), 1.56-1.66 (4H, m), 1.97-2.11 (2H, m), 2.45 (3H, s), 3.96 (2H, d, J = 7.2 Hz), 7.36 (2H, d, J = 8.5 Hz), 7.80 (2H, d, J = 8.5 Hz) |

Experimental Example 1

[Enzyme Inhibition Test Method]

A mixture (10 μL) of substrate and a set of choline quantification reagents (200 μM LPC (1-Oleoyl-sn-glycero-3-phosphocholine Sigma #L1881), 25 μM Amplex UltraRed reagent (Invitrogen), 0.1 U/mL Peroxidase (TOYOBO), 1 U/mL Choline oxidase (TOYOBO)), prepared with assay buffer (50 mM Tris (pH 8.0), 140 mM NaCl, 5 mM KCl, 1 mM CaCl$_2$), 1 mM MgCl$_2$, 0.1% BSA (Albumin from bovine serum, SIGMA), 0.0025% Triton X-100), enzyme (0.4 ng/μL human recombinant ATX) (10 μL), compound-containing solution (100 nL) were dispensed to a 384-well plate, incubated at room temperature for 1 hr and the fluorescence (Ex. 525 nm/Em. 598 nm) was measured. As the standard, choline chloride was used. With a blank free of enzyme was taken as inhibitory rate 100%, and a control free of inhibitor as inhibitory rate 0%, the inhibitory rate was calculated, and IC50 value was calculated from the inhibitory activity percentage at each concentration.

Experimental Example 2

[Measurement of ATX Activity in Plasma (Ex Vivo)]

A compound administration solution prepared by wet pulverization in a mixer mill (type: MM400) for 10 min and adjusting to a given concentration with 0.5% aqueous carboxymethylcellulose solution was orally administered to male Wistar rat (5-week-old when used) at 5 mL/kg. Blood samples were collected from the cervical vein over time at 8 to 24 hr after administration. The blood was heparin-treated using a micro blood collection tube Capiject (CJ-AL, TERUMO CORPORATION), and the plasma was separated by centrifugation (4° C., 12,000 rpm, for 2 min), and preserved at −80° C. The rats after blood sampling were euthanized by exsanguination from the caudal vena cava under isoflurane inhalation anesthesia. The measurement of ATX activity in plasma was evaluated using the concentration of choline in the plasma, which was liberated from lysophosphatidylcholine (substrate of ATX) by the lysophospholipase D activity of ATX, as an index. An equal amount of 2× assay buffer (200 mM Tris-HCl pH9.0, 10 mM MgCl$_2$, 1 M NaCl, 0.1% Triton X-100) is added to plasma (12 μL) and reacted at 37° C. for 6 hr. The reaction mixture (10 μL) after reaction for 6 hr and 45 μL of reagent R$^1$ solution (100 mM Tris-HCl pH 8.0, 0.5 mM TOOS, 10 U/mL peroxidase, 0.01% Triton X-100) were added and blended and absorbance at 550-700 nm was measured and used as a prevalue. As the standard, choline chloride was used. 1 mM choline chloride was diluted with 2× assay buffer up to 7 steps in 2-fold serial dilution, R$^1$ solution was treated similarly and the absorbance was measured. Furthermore, 15 μL of reagent R$^2$ solution (100 mM Tris-HCl pH 8.0, 1 mM 4-aminoantipyrine, 10 U/mL choline oxidase, 0.01% Triton X-100) was added, and the mixture was reacted at room temperature for 10 min, and absorbance at 550-700 nm was measured. The choline concentration per reaction time was calculated from the difference between the absorbance after R$^2$ solution addition and prevalue measured before R$^2$ addition and used as ATX activity value.

<Calculating Formula> inhibitory activity (%) =
$$100 \times \{1 - [\text{choline concentration } (\mu M) \text{ of test substance administration group/choline concentration } (\mu M) \text{ of solvent control group}]\}$$

The results obtained in Experimental Examples 1 and 2 are shown in the following Tables.

TABLE 19

| Example | Experimental Example 1 human ATX IC50 (nM) | Experimental Example 2 Rat single administration test (inhibitory activity (%) 8 hr after 1 mg/kg oral administration) |
|---|---|---|
| 1-1 | 1 | 94 |
| 1-2 | 5 | 93 |
| 2 | 9 | 72 |
| 3 | 35 | |
| 4 | 17 | |
| 5 | 1 | 92 |
| 6 | 4 | 71 |
| 7-1 | 1 | |
| 7-2 | 2 | |
| 8-1 | 2 | 92 |
| 8-2 | 20 | 47 |
| 9-1 | 2 | 94 |
| 9-2 | 3 | 94 |
| 10-1 | 1 | |
| 10-2 | 3 | |

TABLE 20

| | | |
|---|---|---|
| 11-1 | 10 | |
| 11-2 | 25 | |

TABLE 20-continued

| | | |
|---|---|---|
| 12 | 1 | 76 |
| 13 | 3 | 71 |
| 14 | 12 | 92 |
| 15 | 42 | 75 |
| 16 | 13 | 89 |
| 17 | 56 | |
| 18-1 | 133 | |
| 18-2 | 1042 | |
| 19-1 | 1 | |
| 19-2 | 31 | |
| 19-3 | 5 | |
| 19-4 | 49 | |
| 20 | 2 | |
| 21 | 56 | |
| 22-1 | 3 | 83 |
| 22-2 | 74 | not performed |
| 23 | 11 | 83 |
| 24 | 13 | |
| 25 | 1 | 91 |
| 26 | 5 | 82 |
| 27 | 56 | |
| 28 | 4 | |
| 29 | 3 | 80 |
| 30 | 2 | |
| 31 | 4 | 90 |
| 32 | 26 | |
| 33 | 57 | |
| 34 | 121 | |

TABLE 21

| | | |
|---|---|---|
| 35 | 1 | |
| 36 | 6 | |
| 37 | 8 | |
| 38 | 382 | |
| 39 | 7 | 84 |
| 40 | 12 | |
| 41 | 31 | |
| 42 | 8 | |
| 43 | 13 | |
| 44 | 350 | |
| 45 | 7 | 81 |
| 46 | 2 | 74 |
| 47 | 3 | |
| 48 | 35 | |
| 49 | 3 | |
| 50 | 10 | |
| 51 | 5 | |
| 52 | 7 | |
| 53 | 1 | |
| 54 | 5 | |
| 55 | 2 | |
| 56 | 7 | |
| 57 | 7 | |
| 58 | 4 | |
| 59 | 5 | |
| 60 | 5 | |
| 61 | 15 | |
| 62 | 1 | |
| 63 | 7 | |
| 64 | 1 | |
| 65 | 16 | |
| 66 | 5 | |

TABLE 22

| | | |
|---|---|---|
| 67 | 13 | |
| 68 | 14 | |
| 69 | 152 | |
| 70 | 135 | |
| 71 | 104 | |
| 72 | 8 | |
| 73 | 9 | |
| 74 | 10 | |
| 75 | 68 | |
| 76 | 78 | |
| 77 | 381 | |
| 78 | 91 | |
| 79 | 189 | |
| 80 | 493 | |
| 81 | 12 | |
| 82 | 19 | 89 |
| 83 | 8 | 89 |
| 84 | 21 | 89 |
| 85 | 29 | |
| 86 | 129 | |
| 87 | 16 | 95 |
| 88 | 133 | |
| 89 | 9 | |
| 90 | 419 | |
| 91 | 24 | |
| 92 | 57 | 73 |
| 93 | 39 | 70 |
| 94 | 32 | |
| 95 | 36 | |
| 96 | 19 | |
| 97 | 378 | |

TABLE 23

| | |
|---|---|
| 98 | 120 |
| 99 | 50 |
| 100 | 204 |
| 101 | 113 |

Experimental Example 3

[Consideration of Action of ATX Inhibitor on Mouse Bleomycin-Induced Lung Fibrosis Model]

Figure 2:
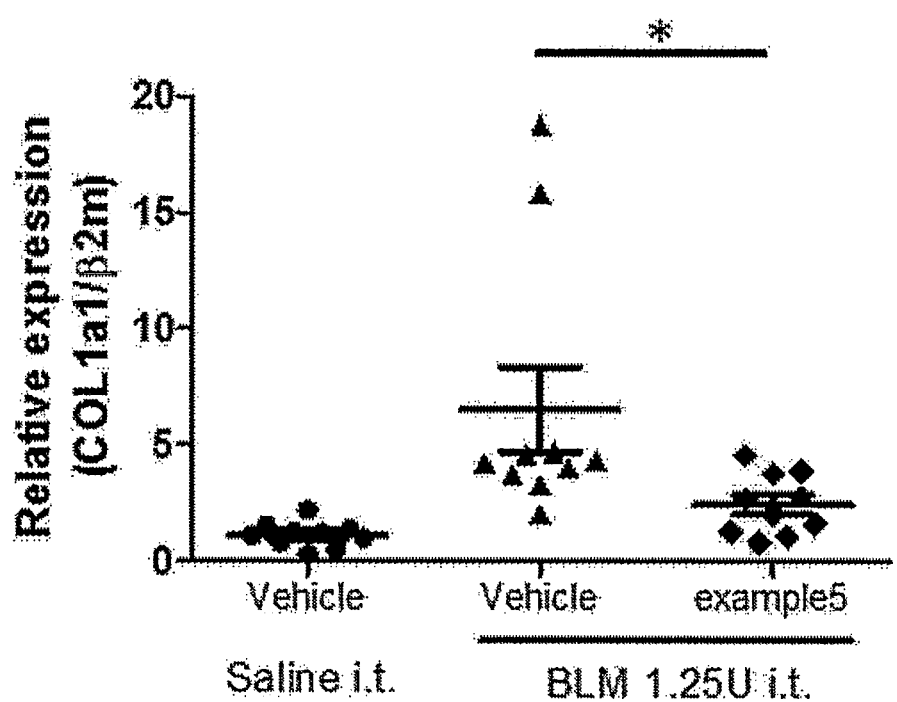
FIG. 2 is a graph showing the Col1a1 mRNA amount in lung tissue as the result of Experimental Example 3.
Figure 3:
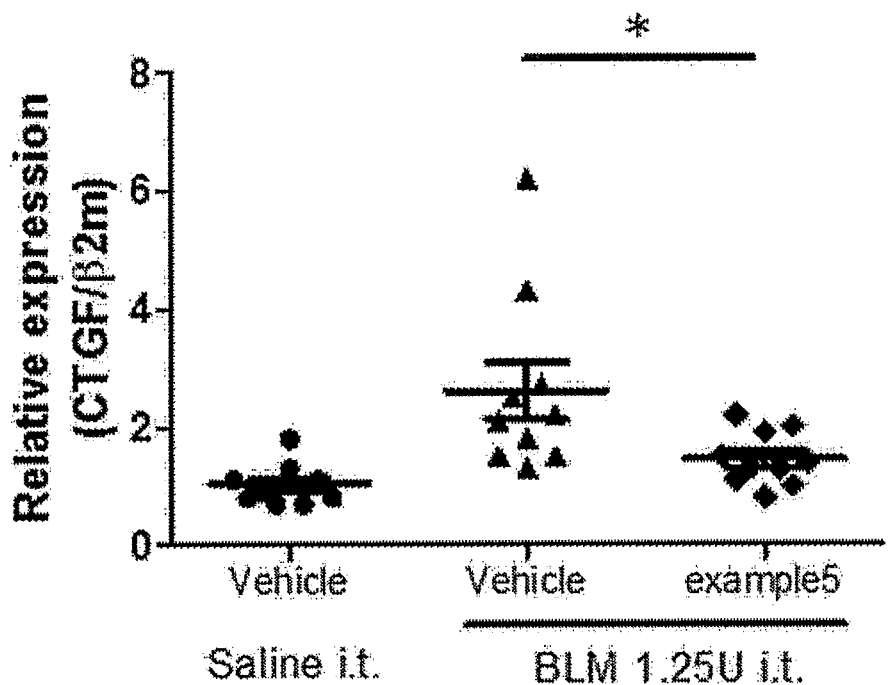
FIG. 3 is a graph showing the CTGF mRNA amount in lung tissue as the result of Experimental Example 3.
Figure 4:
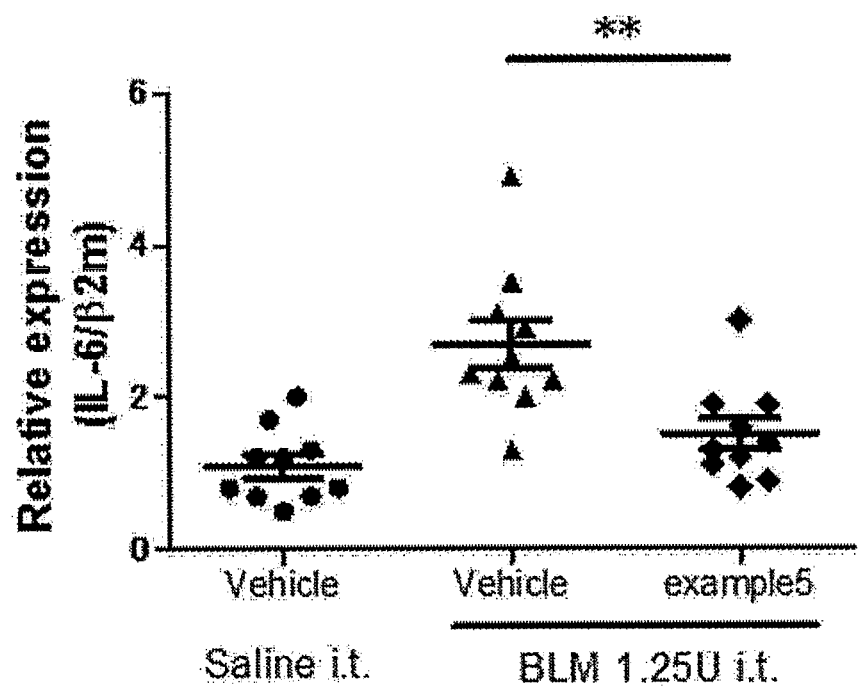
FIG. 4 is a graph showing the IL-6 mRNA amount in lung tissue as the result of Experimental Example 3.

The effectiveness of an ATX inhibitor (Example 5, hereinafter to be referred to as example 5 in the Figures) on bleomycin (BLM)-induced lung fibrosis model was evaluated using, as an index, variation of each fibrosis index marker in the plasma or BALF, or fibrosis related genes in the lung. As a result, the ATX inhibitor suppressed SP-D in the plasma (FIG. 1) and, as regards genes in the lung, showed an expression suppressive action on Colla1 (FIG. 2), CTGF (FIG. 3), IL-6 (FIG. 4). It also suppressed ATX activity in the plasma completely (FIG. 5), and also showed a suppressive action on the production of LPA (C18:2) in BALF (FIG. 6).

<Production of Bleomycin-Induced Lung Fibrosis Model>

8-Week-old mice were grouped in the group constitution shown in Table 24 using a simulation method such that the body weight would become uniform before the previous day of bleomycin administration (SOP/STA/PA-0003). The mice were anesthetized with isoflurane, 0.5 mg/mL of bleomycin solution was intratracheally administered at 50 μL/head to produce a bleomycin-induced lung fibrosis model (1.25 U/kg). In the saline group, physiological saline was administered instead of bleomycin. The ATX inhibitor (Example 5) was orally administered two times per day from the day of bleomycin administration. In addition, the body weight was measured once per day from the day of grouping.

TABLE 24

Group constitution of bleomycin-induced lung fibrosis model

| group No. | BLM | test substance | period (days) | n |
|---|---|---|---|---|
| 1 | none | vehicle | 14 | 10 |
| 2 | 1.25 U | vehicle | 14 | 10 |

TABLE 24-continued

Group constitution of bleomycin-induced lung fibrosis model

| group No. | BLM | test substance | period (days) | n |
|---|---|---|---|---|
| 3 | 1.25 U | ATX inhibitor (Example 5), 30 mg/kg, bid | 14 | 10 |

<ATX Inhibitor Preparation Method>

One equivalent of a mixture of 1N NaOH and 0.5% CMC solution (100 µL in total) relative to the ATX inhibitor (Example 5) was added, 10 zirconia beads ((φ3 mm) were added, and they were pulverized using a mixer mill MM400 (frequency 28.01/min, pulverization time 10 min). 0.5% CMC was added to 30 mg/mL to give a suspension and the suspension was sonicated for 10 min. The administration dose volume was 10 mL/Kg and the administration dose amount was 30 mg/kg. Administration was performed twice per day and the initial administration was performed 30 min before BLM administration.

<Reagent>

Bleomycin hydrochloride for injection (BLM, product name: Bleo (5 mg/ampoule), manufacturer: Nippon Kayaku Co., Ltd., manufacturing No.: 250590, preparation method: BLM was dissolved in physiological saline to a concentration of 1 mg/mL and then diluted with physiological saline to prepare a 0.5 mg/mL solution, and administered intratracheally at a rate of 50 µL/head.

Otsuka physiological saline (Otsuka Pharmaceutical Co., Ltd., preservation condition: preservation at room temperature). Sircol Soluble/Insoluble Collagen Assay kit (Biocolor, S1111). rat/mouse SP-D kit "YAMASA" EIA (YAMASA CORPORATION, 80072).

<Test Animal> animal species: female C57BL/6J mouse, supply company: CHARLES RIVER LABORATORIES JAPAN, INC., number of animals used: 10 per group (age at arrival: 7 weeks old).

<Rearing Environment> set temperature (allowable range): 23° C. (20-26° C.), set humidity (allowable range): 55% (30 to 70%), set contrast: 12 hr lighting (AM 7:00-PM 7:00 light), water, food: free intake.

<Sampling, and Measurement of Each Index>

At 14 days from the bleomycin administration, plasma, BALF and lung tissue were collected. BALF was recovered and the concentration of LPA (18:2) in BALF (FIG. 6) was measured. After blood was collected from the abdominal vena cava, whole blood was anticoagulated using heparin and centrifuged to collect plasma. Then, the ATX activity (FIG. 5) and SP-D (FIG. 1) in the plasma were measured. Furthermore, the chest was opened and whole lung tissue was collected, and gene expression of each of Col1a1 (FIG. 2), CTGF (FIG. 3) and IL-6 (FIG. 4) in the lung was analyzed. For the gene expression analysis, mRNA was extracted from the lung tissue using TRIzol, reverse transcription was performed using a kit of Life technologies, and qPCR was performed using Taqman probe.

<Measurement of LPA Concentration in BALF>

An organic solvent and LPA (17:0) solution as an internal standard substance were added to the collected BALF (200 µL), and the mixture was dried to solidness under reduced pressure at 35° C. To the residue after drying was added 50 µL of 50% aqueous ethanol solution, and the re-dissolved solution was used as an analysis sample. The analysis sample was separated by reversed-phase column and LPA (18:2) was detected by the QTRAP6500 system (ABSciex). In addition, LPA (18:2) synthesis reference standard was added to PBS buffer used for recovery of BALF and compared with the analytical curve sample that underwent a similar pre-treatment, whereby the concentration of LPA (18:2) contained in BALF was calculated (FIG. 6).

<Measurement of ATX Activity in Plasma>

Figure 5:
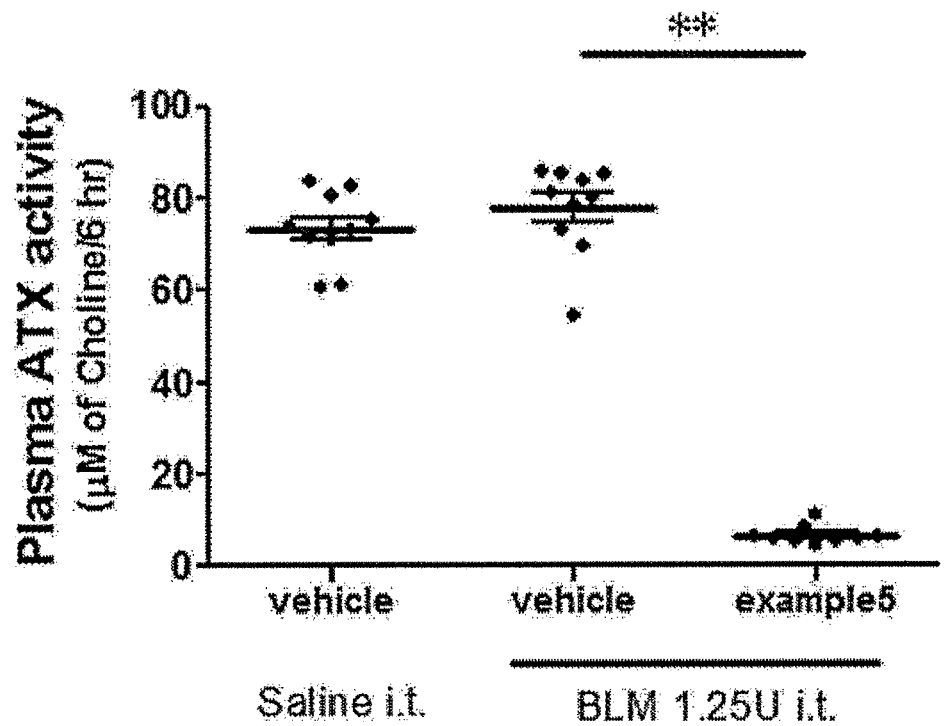
FIG. 5 is a graph showing the ATX activity in plasma as the result of Experimental Example 3.
Figure 6:
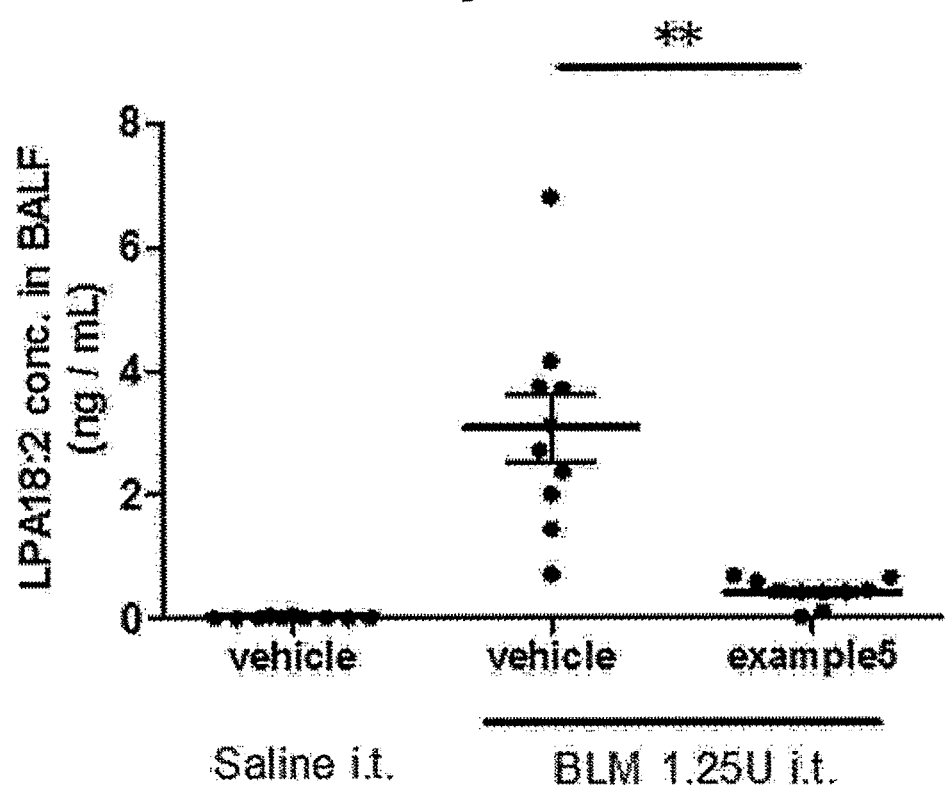
FIG. 6 is a graph showing the LPA (18:2) amount in BALF as the result of Experimental Example 3.

By measurement and calculation from the collected plasma by a method similar to Experimental Example 2, the ATX activity value was obtained (FIG. 5).

<Statistical Analysis>

The difference between the saline group and the BLM administration group and the difference between the BLM administration group and the compound administration group were analyzed by the Student's t-test wherein the significance level was 5% on both sides. The statistical analysis was performed using SAS.

Experimental Example 4

[Study of Action of ATX Inhibitor on *Macaca fascicularis* Intraocular Pressure]

Figure 7:
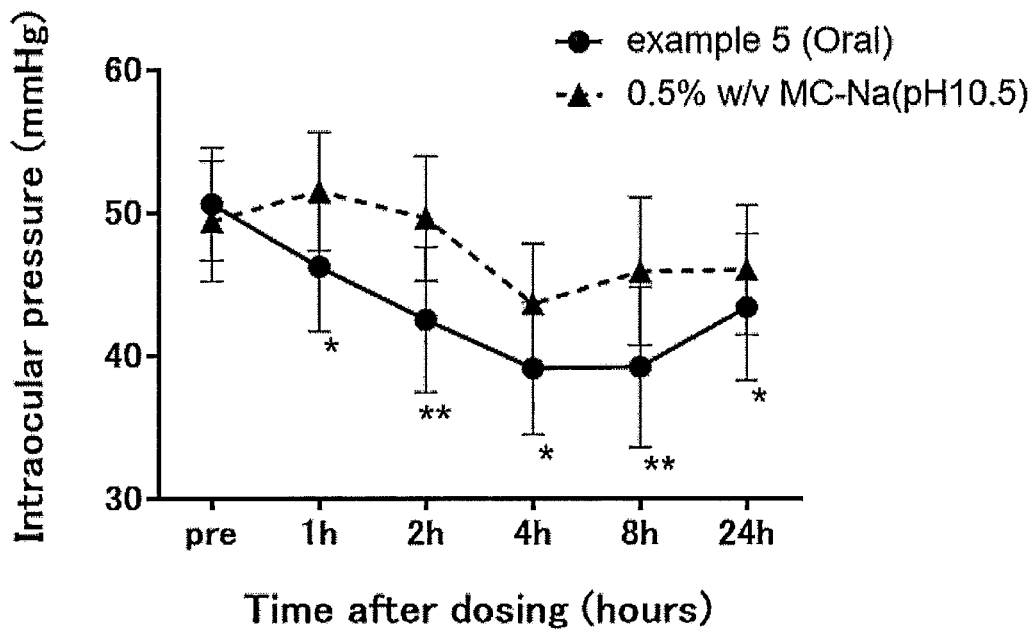
FIG. 7 is a graph showing the action of ATX inhibitor on intraocular pressure of *Macaca fascicularis* by oral administration as the result of Experimental Example 4.
Figure 8:
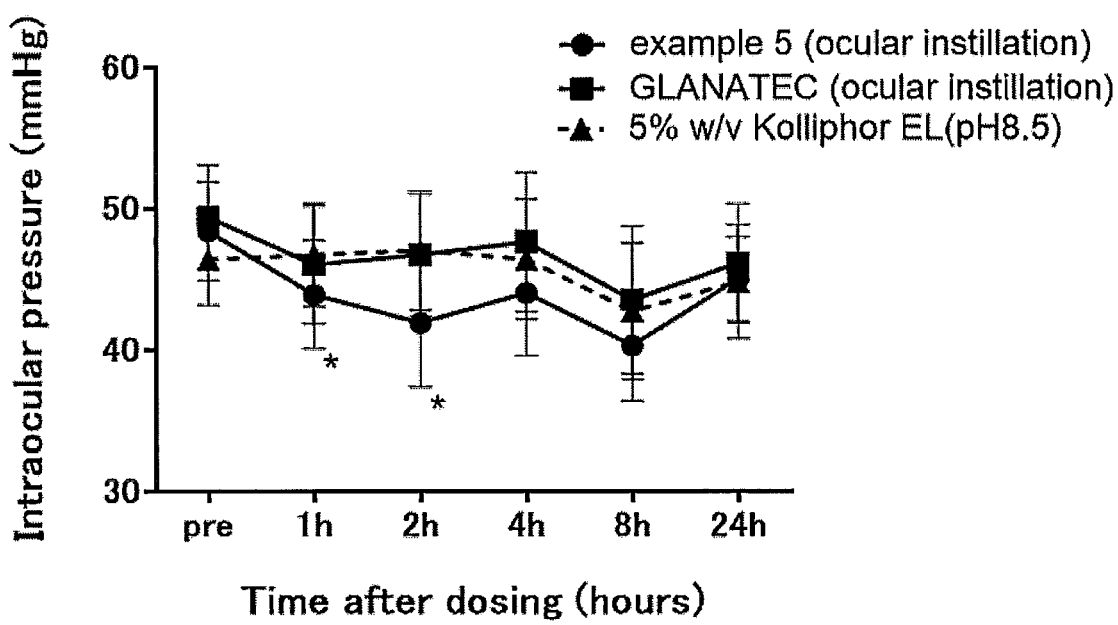
FIG. 8 is a graph showing the action of ATX inhibitor on intraocular pressure of *Macaca fascicularis* by instillation as the result of Experimental Example 4.

The efficacy of ATX inhibitor (Example 5, hereinafter indicated as in example 5 in the Figures) for *Macaca fascicularis* laser-induced high intraocular pressure model was evaluated using the intraocular pressure lowering action as an index. As a result, the ATX inhibitor (Example 5) showed a statistically significant intraocular pressure lowering action on both administration routes of single oral administration of test drug (FIG. 7) and single instillation administration of test drug (FIG. 8).

<Production of *Macaca fascicularis* Laser-Induced High Intraocular Pressure Model>

A green laser beam at wavelength 532 nm was uniformly irradiated to 3600 around of the trabecular meshwork, which is the excretory passage of the aqueous humor, of the left eye alone, whereby high intraocular pressure was induced. The right eye was maintained normal. After a 7-day acclimation period, the animals were grouped in the group constitution shown in Table 25. Administration was performed in a crossover test using the animals repeatedly for ATX inhibitor, vehicle and positive control substance as shown in Table 26.

TABLE 25

| group | test substance and control substance | administration route | dose | number of animals (animal No.)* |
|---|---|---|---|---|
| 1 | oral vehicle | oral | — | 10 ((1)-(10)) |
| 2 | instillation vehicle | instillation | — | |
| 3 | ATX inhibitor | oral | 100 mg/kg | |
| 4 | (Example 5) | instillation | 0.0135 mg/eye | |

TABLE 25-continued

| group | test substance and control substance | administration route | dose | number of animals (animal No.)* |
|---|---|---|---|---|
| 5 | GLANATEC ophthalmic solution 0.4% | instillation | 0.12 mg/eye | |

*Animals were used repeatedly.
positive control substance: GLANATEC ophthalmic solution 0.4%

TABLE 26

| administration schedule (administration date) | animal No. | | | | |
|---|---|---|---|---|---|
| | (1), (2) | (3), (4) | (5), (6) | (7), (8) | (9), (10) |
| 1st administration (day 0) | oral vehicle oral administration | ATX inhibitor oral administration | instillation vehicle administration by instillation | ATX inhibitor administration by instillation | GLANATEC ophthalmic solution 0.4% |
| 2nd administration (day 7) | ATX inhibitor oral administration | instillation vehicle administration by instillation | ATX inhibitor administration by instillation | GLANATEC ophthalmic solution 0.4% | oral vehicle oral administration |
| 3rd administration (day 14) | instillation vehicle administration by instillation | ATX inhibitor administration by instillation | GLANATEC ophthalmic solution 0.4% | oral vehicle oral administration | ATX inhibitor oral administration |
| 4th administration (day 21) | ATX inhibitor administration by instillation | GLANATEC ophthalmic solution 0.4% | oral vehicle oral administration | ATX inhibitor oral administration | instillation vehicle administration by instillation |
| 5th administration (day 28) | GLANATEC ophthalmic solution 0.4% | oral vehicle oral administration | ATX inhibitor oral administration | instillation vehicle administration by instillation | ATX inhibitor administration by instillation |

<Preparation Method of ATX Inhibitor Oral Administration Solution>

The required amount of ATX inhibitor (Example 5) was weighed, transferred to an agate mortar and lightly ground. Several drops of oral vehicle (0.5% w/v CMC-Na) was added dropwise and mixed with the ATX inhibitor (Example 5). Dropwise addition of the oral vehicle to the mixture and mixing were repeated to give a paste. The paste was transferred to a graduated glass and the oral vehicle was added to 60% of the final preparation amount. The vehicle (0.5 mol/L NaOH-containing 0.5% w/v CMC-Na) was added with stirring with a stirrer (NaOH was 0.75 mol relative to 1 mol in Example 5). The oral vehicle was added to increase the amount and the pH was confirmed to be not exceeding 11.0 (measured value: pH10.55-10.88).

<Preparation Method of ATX Inhibitor Instillation Administration Solution>

A 0.04 mol/L boric acid/phosphoric acid/acetic acid mixed solution (307 mL) was mixed with a 0.2 mol/L aqueous sodium hydroxide solution (193 mL) (pH about 8.4), pH was adjusted to 8.5 with 1 mol/L hydrochloric acid to prepare Britton-Robinson buffer (pH 8.5). 5% Kolliphor EL was dissolved in the above and the resulting solution was used as an instillation administration vehicle (5% w/v kolliphor EL solution (pH 8.5)). 4.5 mg of ATX inhibitor (Example 5) was measured in a 10 mL measuring flask, the instillation administration vehicle (9.6 mL) was added and the mixture was sonicated for 30 min in an ultrasonication washing machine set to about 40° C. After confirmation of uniform suspending, the instillation administration vehicle was used to fill up to the marked line of the measuring flask, and the mixture was sonicated for 40 min in the same manner as described above, and complete dissolution was confirmed by visual observation. When being suspension at this time point, sonication was continued until complete dissolution.

<Reagents>
CMC-Na (Sigma-Aldrich Co. LLC)
Kolliphor EL (Sigma-Aldrich Co. LLC, C5156)
boric acid (Sigma-Aldrich Co. LLC, B6768)
phosphoric acid (FUJIFILM Wako Pure Chemical Corporation, 162-20492)
acetic acid (FUJIFILM Wako Pure Chemical Corporation, 017-00256)
water for injection (Otsuka Pharmaceutical Factory, Inc.)
GLANATEC ophthalmic solution 0.4% (Kowa Company, Ltd.): positive control substance <Test Animal>
animal species: male *Macaca fascicularis*
Supply company: Shin Nippon Science Co., Ltd.
number of animals used: 10 (7 to 8 years old at the time of acclimation start)

<Breeding Environment>
temperature: measured: 25.4-27.5° C., allowable range 23-29° C.
humidity: measured: 47-74%, allowable range 30-70%
ventilation frequency: 15 times/hour
lighting: artificial lighting for 12 hours per day (from 07:00 to 19:00 lighting)

feed: solid feed (Purina Mills LLC, HF Primate J 12G 5K9J) about 108 g (about 12 g×9) was given once per day, 14:00 to 16:00, and the remaining food was collected by 11:00 on the next day (before administration in the case of the administration day).

drinking water: freely ingested using an automatic water supply system

<Measurement of Intraocular Pressure>

The animal was held under anesthesia and the intraocular pressure was measured three times using a recoil tonometer (TonoVet Tonometer TV01, Tiolat Oy). The adopted value was the median value of the three measurements. The surface anesthetic was not used in consideration of irritation to the cornea due to frequent administration of the surface anesthetic.

<Intraocular Pressure Measurement Point>

Before compound administration, about 1, 2, 4, 8 and 24 hr after administration (6 points on each administration day).

<Statistical Analysis>

As to the intraocular pressure of the left eye (eye with high intraocular pressure), the mean and standard error of the adopted value, the mean and standard error of change rate from before each administration, and the mean and standard error of the change amount from before each administration were calculated at each measurement time point.

[Instillation Administration]

1) To examine the presence or absence of the effect at each time point on the intraocular pressure lowering action after administration, covariance analysis using individual as a variable, administration group as a fixed factor, and intraocular pressure before administration as a covariate was performed at each time point after administration, and a comparison test was performed among the instillation vehicle (instillation administration) group, the test substance (instillation administration) group, and the positive control substance group (multiplicity was not adjusted).

2) As regards the change rate and change amount of the intraocular pressure from before each administration, variance analysis using individual as a variable, and administration group and administration day as fixed factors was performed at each time point after administration, and a comparison test was performed among the instillation vehicle (instillation administration) group, the test substance (instillation administration) group and the positive control substance group.

[Oral Administration]

1) To examine the presence or absence of the effect at each time point on the intraocular pressure lowering action after administration, covariance analysis using individual as a variable, administration group as a fixed factor, and intraocular pressure before administration as a covariate was performed at each time point after administration, and a comparison test was performed between the oral vehicle (oral administration) group and the test substance (oral administration) group.

2) As regards the change rate and change amount of the intraocular pressure from before each administration, variance analysis using individual as a variable, and administration group and administration day as fixed factors was performed at each time point after administration, and a comparison test was performed among the oral vehicle (oral administration) group and the test substance (oral administration) group.

SAS System for windows, Release 9.3 (SAS Institute Inc.) was used for these tests. The significance level of the tests was 5% on both sides.

INDUSTRIAL APPLICABILITY

The compound of the present invention has a superior autotaxin inhibitory action, and is useful as a prophylactic or therapeutic drug for diseases caused by autotaxin, for example, various diseases such as cancer or tumor (e.g., malignant melanoma, brain tumor, neuroblastoma, glioblastoma multiforme, EBV positive Hodgkin lymphoma, glioblastoma, non-small cell lung cancer, lung tumor, breast tumor, ovary tumor, pancreas tumor, prostate intraepithelial tumor, prostate tumor, thyroid gland tumor, follicular lymphoma, liver tumor, renal cell carcinoma and the like), fibrous disease (e.g., lung fibrosis, scleroderma, hepatic fibrosis, renal fibrosis, diabetic nephropathy, atherosclerosis and the like), inflammatory diseases (e.g., asthma, COPD, rheumatoid arthritis, arthritis deformans, NASH, NAFLD, type II diabetes-related obesity, acute coronary syndrome, inflammatory bowel disease, Crohn's disease, ulcerative colitis, neuropathic pain, pruritus and the like), ophthalmic diseases (e.g., glaucoma and the like), urological disease (e.g., prostatomegaly and the like) and the like.

This application is based on patent application No. 2018-141254 filed in Japan, the contents of which are incorporated in full herein by this reference.

The invention claimed is:

1. A method for treating a disease involving autotaxin, comprising:

administering an effective amount of a carboxylic acid compound of formula (1)

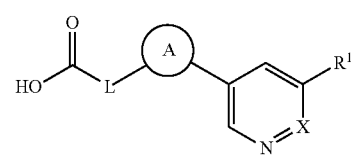

(1)

or a pharmacologically acceptable salt thereof to a patient in need thereof, wherein $R^1$ in the formula (1) is

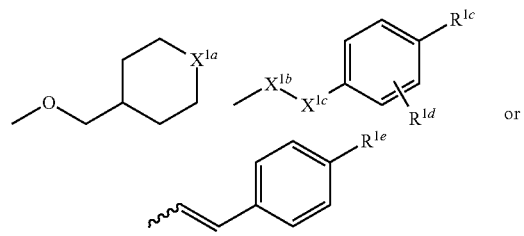

or where $X^{1a}$ is —C($R^{1a}$)$_2$— where plural $R^{1a}$ are the same or different and each $R^{1a}$ is a hydrogen atom, a halogen atom, $C_1$-$C_2$ perfluoroalkyl, $C_1$-$C_2$ perfluoroalkoxy or $C_1$-$C_6$ alkyl, or plural $R^{1a}$ are bonded to form 1,1-$C_3$-$C_6$ cycloalkylene or —N$R^{1b}$— where $R^{1b}$ is a hydrogen atom or $C_1$-$C_2$ perfluoroalkyl, $X^{1b}$ and $X^{1c}$ are the same or different and each of $X^{1b}$ and $X^{1c}$ is —O— or —CH$_2$— provided $X^{1b}$ and $X^{1c}$ are not simultaneously —O—, $R^{1c}$ is a hydrogen atom, a halogen atom, $C_1$-$C_2$ perfluoroalkyl, $C_1$-$C_2$ perfluoroalkoxy, $C_1$-$C_6$ alkyl or $C_1$-$C_2$ perfluoroalkylthio, $R^{1d}$ is a hydrogen atom, a halogen atom or $C_1$-$C_6$ alkyl, and $R^{1e}$ is a hydrogen atom, $C_1$-$C_2$ perfluoroalkyl or $C_1$-$C_2$ perfluoroalkoxy, X in the formula (1) is —N= or —CH=, ring A in the formula (1) is

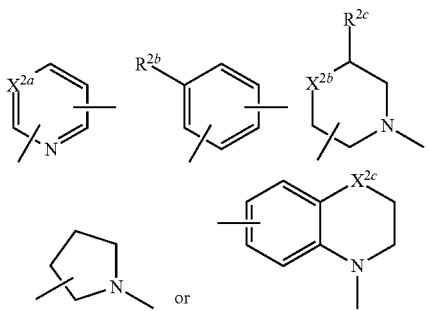

where $X^{2a}$ is —N= or —CR$^{2a}$= where R$^{2a}$ is a hydrogen atom, a halogen atom, $C_1$-$C_6$ alkyl or $C_1$-$C_6$ alkoxy, $R^{2b}$ is a hydrogen atom, a halogen atom, $C_1$-$C_6$ alkyl or $C_1$-$C_6$ alkoxy, $R^{2c}$ is a hydrogen atom or $C_1$-$C_6$ alkyl, $X^{2b}$ is —O—, —NR$^{2d}$— where R$^{2d}$ is a hydrogen atom or $C_1$-$C_2$ perfluoroalkyl or —CHR$^{2e}$— where R$^{2e}$ is a hydrogen atom or $C_1$-$C_6$ alkyl, $X^{2c}$ is —(CH$_2$)$_{n'}$— where n' is 0 or 1 or —O—, and L in the formula (1) is —(CHR$^{3a}$)$_n$— where n is 0, 1, 2 or 3, plural R$^{3a}$ are the same or different and each R$^{3a}$ is a hydrogen atom or a $C_1$-$C_6$ alkyl, —(CH$_2$)$_m$—O—(CH$_2$)$_{m'}$— where m and m' are the same or different and each of m and m' is 0, 1 or 2, $C_2$-$C_3$ alkenylene,

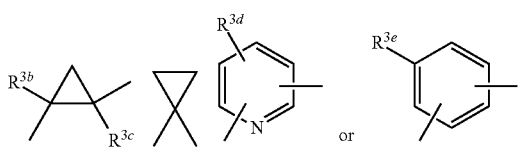

where R$^{3b}$ and R$^{3c}$ are the same or different and each of R$^{3b}$ and R$^{3c}$ is a hydrogen atom or $C_1$-$C_6$ alkyl, R$^{3d}$ is a hydrogen atom, $C_1$-$C_6$ alkoxy, $C_1$-$C_6$ alkyl or $C_1$-$C_2$ perfluoroalkyl, R$^{3e}$ is a hydrogen atom, $C_1$-$C_6$ alkoxy, $C_1$-$C_6$ alkyl or $C_1$-$C_2$ perfluoroalkyl, wherein the disease involving autotaxin is cancer or tumor, a fibrotic disease, an inflammatory disease, an ophthalmic disease, a urological disease, type II diabetes-related obesity or an acute coronary syndrome, the cancer or tumor is malignant melanoma, brain tumor, neuroblastoma, glioblastoma multiforme, EBV positive Hodgkin lymphoma, glioblastoma, non-small cell lung cancer, lung tumor, breast tumor, ovary tumor, pancreas tumor, prostate intraepithelial tumor, prostate tumor, thyroid gland tumor, follicular lymphoma, liver tumor or renal cell carcinoma, the fibrotic disease is lung fibrosis, scleroderma, hepatic fibrosis, renal fibrosis, diabetic nephropathy or atherosclerosis, the inflammatory disease is asthma, COPD, rheumatoid arthritis, arthritis deformans, NASH, NAFLD, inflammatory bowel disease, Crohn's disease, ulcerative colitis, neuropathic pain or pruritus, the acute coronary syndrome is angina pectoris or myocardial infarction, the ophthalmic disease is glaucoma, and the urological disease is prostatomegaly.

2. The method of claim 1, wherein the administering the carboxylic acid compound of formula (1) or a pharmacologically acceptable salt thereof includes administering a pharmaceutical composition comprising the carboxylic acid compound of formula (1) or a pharmacologically acceptable salt thereof, and a pharmaceutically acceptable carrier to the patient in need thereof.

3. The method of claim 1, wherein R$^1$ in the formula (1) is

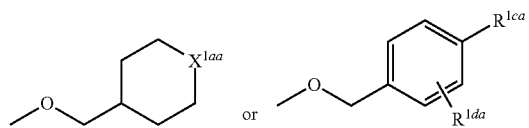

where $X^{1aa}$ is -C(R$^{1aa}$)$_2$- where plural R$^{1aa}$ are the same or different and each R$^{1aa}$ is a hydrogen atom, $C_1$-$C_2$ perfluoroalkyl or $C_1$-$C_6$ alkyl, or plural R$^{1aa}$ are bonded to form 1,1-$C_3$-$C_6$ cycloalkylene, or -NR$^{1ba}$- where R$^{1ba}$ is a hydrogen atom or $C_1$-$C_2$ perfluoroalkyl, R$^{1ca}$ is $C_1$-$C_2$ perfluoroalkyl, $C_1$-$C_2$ perfluoroalkoxy or $C_1$-$C_2$ perfluoroalkylthio, and R$^{1da}$ is a halogen atom or $C_1$-$C_6$ alkyl.

4. The method of claim 1, wherein the ring A in the formula (1) is

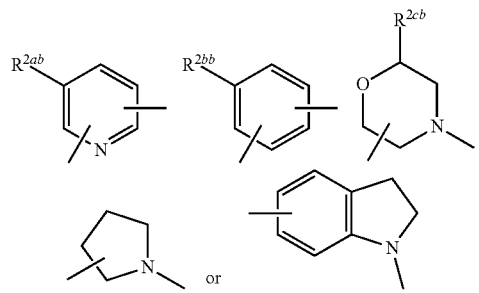

where R$^{2ab}$ is a hydrogen atom, $C_1$-$C_6$ alkoxy or $C_1$-$C_6$ alkyl, R$^{2bb}$ is a hydrogen atom, $C_1$-$C_6$ alkoxy or $C_1$-$C_6$ alkyl, and R$^{2cb}$ is a hydrogen atom or $C_1$-$C_6$ alkyl.

5. The method of claim 1, wherein the ring A in the formula (1) is

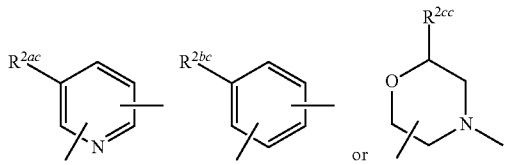

where R$^{2ac}$ is a hydrogen atom, $C_1$-$C_6$ alkoxy or $C_1$-$C_6$ alkyl, R$^{2bc}$ is a hydrogen atom, $C_1$-$C_6$ alkoxy or $C_1$-$C_6$ alkyl, and R$^{2cc}$ is a hydrogen atom or $C_1$-$C_6$ alkyl.

6. The method of claim 1, wherein the ring A in the formula (1) is

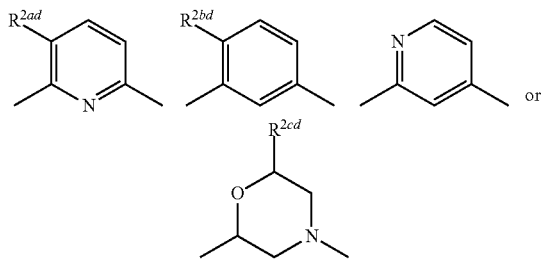 or where $R^{2ad}$ is a hydrogen atom, $C_1$-$C_6$ alkoxy or $C_1$-$C_6$ alkyl, $R^{2bd}$ is a hydrogen atom, $C_1$-$C_6$ alkoxy or $C_1$-$C_6$ alkyl, and $R^{2cd}$ is a hydrogen atom or $C_1$-$C_6$ alkyl.

7. The method of claim 1, wherein L in the formula (1) is —(CH$_2$)$_n$— where n is 1 or 2 or

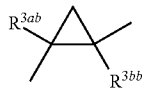

where $R^{3ab}$ and $R^{3bb}$ are the same or different and each of $R^{3ab}$ and $R^{3bb}$ is a hydrogen atom or $C_1$-$C_6$ alkyl.

8. The method of claim 1, wherein X in the formula (1) is —N=.

9. The method of claim 1, wherein the carboxylic acid compound of formula (1) is
trans-2-[2-methoxy-5-(5-{[4-(trifluoromethoxy) benzyl] oxy} pyridin-3-yl) phenyl] cyclopropanecarboxylic acid,
trans-2-[2-methoxy-5-(6-{[4-(trifluoromethoxy) benzyl] oxy} pyridazin-4-yl) phenyl] cyclopropanecarboxylic acid,
(1S,2S)-2-[2-methoxy-5-(6-{[trans-4-(trifluoromethyl) cyclohexyl] methoxy} pyridazin-4-yl) phenyl] cyclopropanecarboxylic acid,
(1R,2R)-2-[2-methoxy-5-(6-{[trans-4-(trifluoromethyl) cyclohexyl] methoxy} pyridazin-4-yl) phenyl] cyclopropanecarboxylic acid,
(1S,2S)-2-(5-methoxy-5'-{[4-(trifluoromethoxy) benzyl] oxy}-2,3'-bipyridin-6-yl) cyclopropanecarboxylic acid,
(1S,2S)-2-[3-methoxy-6-(6-{[4-(trifluoromethoxy) benzyl] oxy} pyridazin-4-yl) pyridin-2-yl] cyclopropanecarboxylic acid,
(1S,2S)-2-[3-methoxy-6-(6-{[trans-4-(trifluoromethyl) cyclohexyl] methoxy} pyridazin-4-yl) pyridin-2-yl] cyclopropanecarboxylic acid,
(1S,2S)-2-(5-{[4-(trifluoromethoxy) benzyl] oxy}-3,4'-bipyridin-2'-yl) cyclopropanecarboxylic acid,
(1R,2R)-2-(5-{[4-(trifluoromethoxy) benzyl] oxy}-3,4'-bipyridin-2'-yl) cyclopropanecarboxylic acid,
(1S,2S)-2-(5-{[trans-4-(trifluoromethyl) cyclohexyl] methoxy}-3,4'-bipyridin-2'-yl) cyclopropanecarboxylic acid,
(1R,2R)-2-(5-{[trans-4-(trifluoromethyl) cyclohexyl] methoxy}-3,4'-bipyridin-2'-yl) cyclopropanecarboxylic acid,
(1S,2S)-2-[4-(6-{[trans-4-(trifluoromethyl) cyclohexyl] methoxy} pyridazin-4-yl) pyridin-2-yl] cyclopropanecarboxylic acid,
(1R,2R)-2-[4-(6-{[trans-4-(trifluoromethyl) cyclohexyl] methoxy} pyridazin-4-yl) pyridin-2-yl] cyclopropanecarboxylic acid,
(1S,2S)-2-(5'-{[trans-4-(trifluoromethyl) cyclohexyl] methoxy}-2,3'-bipyridin-6-yl) cyclopropanecarboxylic acid,
(1R,2R)-2-(5'-{[trans-4-(trifluoromethyl) cyclohexyl] methoxy}-2,3'-bipyridin-6-yl) cyclopropanecarboxylic acid,
(1S,2S)-2-[3-methoxy-6-(6-{[trans-4-(trifluoromethyl) cyclohexyl] methoxy} pyridazin-4-yl) pyridin-2-yl]-1-methylcyclopropanecarboxylic acid,
(1R,2R)-2-[3-methoxy-6-(6-{[trans-4-(trifluoromethyl) cyclohexyl] methoxy} pyridazin-4-yl) pyridin-2-yl]-1-methylcyclopropanecarboxylic acid,
(1S,2S)-2-[2-ethoxy-5-(6-{[1-(2,2,2-trifluoroethyl) piperidin-4-yl] methoxy} pyridazin-4-yl) phenyl] cyclopropanecarboxylic acid,
3-[(2S)-4-(5-{[4-(trifluoromethoxy) benzyl] oxy} pyridin-3-yl) morpholin-2-yl] propanoic acid,
3-[(2S)-4-(5-{[trans-4-(trifluoromethyl) cyclohexyl] methoxy} pyridin-3-yl) morpholin-2-yl] propanoic acid,
3-[(2S)-4-(5-{[3-fluoro-4-(trifluoromethoxy) benzyl] oxy} pyridin-3-yl) morpholin-2-yl] propanoic acid,
3-[(2S)-4-(5-{[2-fluoro-4-(trifluoromethoxy) benzyl] oxy} pyridin-3-yl) morpholin-2-yl] propanoic acid,
3-[(2S)-4-(5-{[2-methyl-4-(trifluoromethoxy) benzyl] oxy} pyridin-3-yl) morpholin-2-yl] propanoic acid,
3-[(2S)-4-(5-{[3-chloro-4-(trifluoromethoxy) benzyl] oxy} pyridin-3-yl) morpholin-2-yl] propanoic acid,
3-[(2S,6R)-6-methyl-4-(5-{[4-(trifluoromethoxy) benzyl] oxy} pyridin-3-yl) morpholin-2-yl] propanoic acid,
(1S,2S)-2-[(2S)-4-(5-{[trans-4-(trifluoromethyl) cyclohexyl] methoxy} pyridin-3-yl) morpholin-2-yl] cyclopropanecarboxylic acid,
(1R,2R)-2-[(2S)-4-(5-{[trans-4-(trifluoromethyl) cyclohexyl] methoxy} pyridin-3-yl) morpholin-2-yl] cyclopropanecarboxylic acid,
(1R,2R)-2-[(2R)-4-(5-{[trans-4-(trifluoromethyl) cyclohexyl] methoxy} pyridin-3-yl) morpholin-2-yl] cyclopropanecarboxylic acid, or
(1S,2S)-2-[(2R)-4-(5-{[trans-4-(trifluoromethyl) cyclohexyl] methoxy} pyridin-3-yl) morpholin-2-yl] cyclopropanecarboxylic acid,
or a pharmacologically acceptable salt thereof.

10. The method of claim 1, wherein the fibrotic disease is lung fibrosis, scleroderma, hepatic fibrosis or renal fibrosis.

11. The method of claim 1, wherein the inflammatory disease is asthma or COPD.

12. The method of claim 1, wherein the inflammatory disease is rheumatoid arthritis or arthritis deformans.

13. The method of claim 1, wherein the inflammatory disease is NASH or NAFLD.

14. The method of claim 1, wherein the inflammatory disease is an inflammatory bowel disease, a Crohn's disease or ulcerative colitis.

15. The method of claim 1, wherein the inflammatory disease is neuropathic pain or pruritus.

16. The method of claim 1, wherein the carboxylic acid compound of the formula (1) is (1S,2S)-2-[3-methoxy-6-(6-{[trans-4-(trifluoromethyl) cyclohexyl] methoxy} pyridazin-4-yl) pyridin-2-yl] cyclopropanecarboxylic acid, or a pharmacologically acceptable salt thereof.

17. The method of claim 1, wherein the carboxylic acid compound of the formula (1) is (1S,2S)-2-[2-methoxy-5-(6-{[trans-4-(trifluoromethyl) cyclohexyl] methoxy} pyridazin-4-yl) phenyl] cyclopropanecarboxylic acid, or a pharmacologically acceptable salt thereof.

18. The method of claim 1, wherein the carboxylic acid compound of the formula (1) is (1S,2S)-2-[3-methoxy-6-(6-{[trans-4-(trifluoromethyl) cyclohexyl] methoxy} pyridazin-4-yl) pyridin-2-yl]-1-methylcyclopropanecarboxylic acid, or a pharmacologically acceptable salt thereof.

19. The method of claim 2, wherein the fibrotic disease is lung fibrosis, scleroderma, hepatic fibrosis or renal fibrosis.

20. The method of claim 2, wherein the inflammatory disease is asthma or COPD.

21. The method of claim 2, wherein the inflammatory disease is rheumatoid arthritis or arthritis deformans.

22. The method of claim 2, wherein the inflammatory disease is NASH or NAFLD.

* * * * *